US008470592B2

(12) United States Patent
Brevnova et al.

(10) Patent No.: US 8,470,592 B2
(45) Date of Patent: Jun. 25, 2013

(54) **ISOLATION AND CHARACTERIZATION OF *SCHIZOCHYTRIUM AGGREGATUM* CELLOBIOHYDROLASE I (CBH 1)**

(75) Inventors: Elena E. Brevnova, Lebanon, NH (US); Jim Flatt, Colorado Springs, CO (US); Chhayal Gandhi, Lebanon, NH (US); Vineet Rajgarhia, Lebanon, NH (US); John McBride, Lebanon, NH (US); Anne Warner, Lebanon, NH (US)

(73) Assignee: Mascoma Corporation, Lebanon, NH (US)

( * ) Notice: Subject to any disclaimer, the term of this patent is extended or adjusted under 35 U.S.C. 154(b) by 42 days.

(21) Appl. No.: 13/003,199

(22) PCT Filed: Jul. 7, 2009

(86) PCT No.: PCT/US2009/003972
§ 371 (c)(1),
(2), (4) Date: Sep. 1, 2011

(87) PCT Pub. No.: WO2010/005553
PCT Pub. Date: Jan. 14, 2010

(65) Prior Publication Data
US 2011/0312054 A1 Dec. 22, 2011

Related U.S. Application Data

(60) Provisional application No. 61/129,585, filed on Jul. 7, 2008.

(51) Int. Cl.
*C12N 15/00* (2006.01)
*C12N 9/00* (2006.01)
*C07H 21/04* (2006.01)
*C07K 14/00* (2006.01)

(52) U.S. Cl.
USPC ........ 435/320.1; 435/183; 536/23.1; 530/350

(58) Field of Classification Search
USPC ................ 435/320.1, 183; 536/23.1; 530/350
See application file for complete search history.

(56) References Cited

U.S. PATENT DOCUMENTS
2002/0138878 A1 9/2002 Sticklen et al.

FOREIGN PATENT DOCUMENTS
| EP | 1 482 033 A1 | 12/2004 |
| WO | WO 03/070939 A1 | 8/2003 |
| WO | WO 2007/115201 A2 | 10/2007 |

OTHER PUBLICATIONS

Bremer, G.B., "Lower marine fungi (labyrinthulomycetes) and the decay of mangrove leaf litter." *Hydrobiologia* 295(1-3):89-95, Kluwer Academic Publishers, Netherlands (1995).
Bremer, G.B and Talbot, G., "Cellulolytic enzyme activity in the marine protest *Schizochytrium aggregatum*," *Botanica Marina* 31(1):37-41, Verlag Walter de Gruyter & Co., Germany (1995).
Davies, G. and Henrissat, B., "Structures and mechanisms of glycosyl hydrolases," *Structure* 3(9):853-859, Current Biology Ltd., England (1995).
Den Haan, R., et al., "Functional expression of cellobiohydrolases in *Saccharomyces cerevisiae* towards one-step conversion of cellulose to ethanol," *Enzyme. Microb. Technol.* 40(5):1291-1299, Elsevier Inc., United States (2007).
Fujita, Y., et al., "Synergistic saccharification, and Direct Fermentation to Ethanol, of Amorphous Cellulose by Use of an Engineered Yeast Strain Codisplaying Three Types of cellulolytic enzyme" *Appl. Environ. Microbiol.* 70(2):1207-1212, The American Society for Microbiology, United States (2004).
Henrissat, B., et al., "Conserved catalytic machinery and the prediction of a common fold for several families of glycosyl hydrolases," *Proc. Natl. Acad. Sci. USA* 92(15):7090-7094,The National Academy of Sciences, United States (1995).
Kotula, L. and Curtis, P.J., "Evaluation of foreign gene codon optimization in yeast: expression of a mouse IG kappa chain," *Biotechnology (N Y)* 9(12):1386-1389, Nature Publishing Company, United States (1991).
McBride, J.E., et al., "Utilization of cellobiose by recombinant β-glucosidase-expressing strains of *Saccharomyces cerevisiae*: characterization and evaluation of the sufficiency of expression," *Enzyme. Microb. Technol.* 37(1):93-101, Elsevier Inc., United States (2005).
Nakamura, Y., et al.,"Codon Usage tabulated from the international DNA sequence databases: status for the year 2000," *Nuleic Acids Res.* 28(1):292 , Oxford University Press, England (2000).
Penttilä, M.E., et al.,"Efficient secretion of two fungal cellobiohydrolases by *Saccharomyces cerevisiae*," *Gene* 63(1):103-112, Elsevier Science Publishers B.V., Netherlands (1988).
Sasaguri, S., et al., "Codon optimization prevents premature polyadenylation of heterologously-expressed cellulases from termite-gut symbionts in *Aspergillus oryzae*," *J. Gen. Appl. Microbiol.* 54(6):343-351, Institute of Microbiology University of Tokyo, Japan (2008).

(Continued)

*Primary Examiner* — Karen Cochrane-Carlson
(74) *Attorney, Agent, or Firm* — Sterne, Kessler, Goldstein & Fox P.L.L.C.

(57) ABSTRACT

The present invention provides for the isolation and characterization of the cbh1 gene from *Schizochytrium aggregatum*. In particular, the present invention provides for the nucleic acid and amino acid sequences of *Schizochytrium aggregatum* cbh1, and domains, variants and derivatives thereof. The present invention further provides for the heterologous expression of *Schizochytrium aggregatum* Cbh1 in host cells, including yeast, e.g., *Saccharomyces cerevisiae*. Expression of *Schizochytrium aggregatum* Cbh1 in host cells will augment cellulose digestion and facilitate ethanol production by those host cells on cellulosic substrates. In certain embodiments, heterologous expression in *Saccharomyces cerevisiae* is in coordination with heterologous expression of other known, or newly identified saccharolytic enzymes. Therefore, the present invention also provides that the novel *Schizochytrium aggregatum* Cbh1 gene can utilized in a consolidated bioprocessing system.

21 Claims, 7 Drawing Sheets

OTHER PUBLICATIONS

Figure 1:
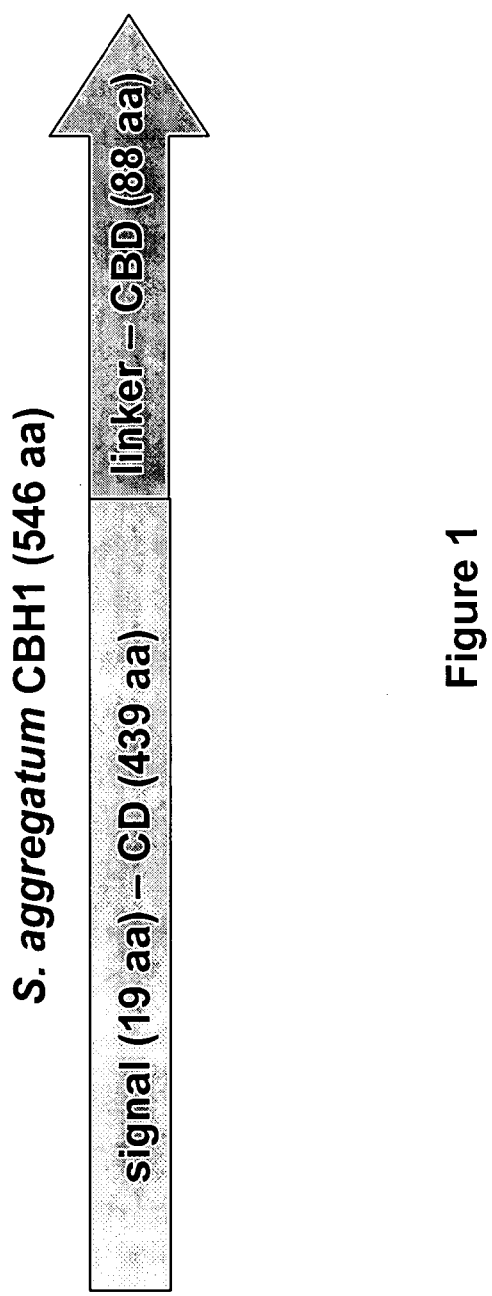

Sharp, P.M. and Li, W.-H., "The codon Adaptation Index—a measure of directional synonymous codon usage bias, and its potential applications," *Nuleic Acids Res.* 15(3):1281-1295, IRL Press Limited, England (1987).

Smith, D.B. and Johnson, K.S. "Single-step purification of polypeptides expressed in *Escherichia coli* as fusions with glutathione S-transferase," *Gene* 67(1):31-40, Elsevier Science Publishers B.V., Netherlands (1988).

Van Rensburg, P., et al., "Engineering yeast for efficient cellulose degradation," *Yeast* 14(1):67-76, John Wiley & Sons, Ltd., United States (1998).

Van Rooyen, R., et al., "Construction of cellobiose-growing and fermenting *Saccharomyces cerevisiae* strains," *J. Biotechnol.* 120(3):284-295, Elsevier B.V., Netherlands (2005).

Zhou, X., et al., "Correlation of cellulase gene expression and cellulolytic activity throughout the gut of the termite *Reticulitermes flavipes*," *Gene* 395(1-2):29-39, Elsevier B.V., Netherlands (2007).

English language abstract for International Application No. WO 03/03070939 A1, European Patent Office, espacenet database—Worldwide (2003) (listed as document FP1 on accompanying equivalent form PTO/SB/08A.

International Search Report with Written Opinion for International Application No. PCT/US2009/003972, European Patent Office, Netherlands, mailed on Nov. 17, 2009.

ISOLATION AND CHARACTERIZATION OF *SCHIZOCHYTRIUM AGGREGATUM* CELLOBIOHYDROLASE I (CBH 1)

This is the U.S. National Phase of International Appl. No. PCT/US2009/003972, filed Jul. 7, 2009, which claims the benefit of U.S. Provisional Appl. No. 61/129,585, filed Jul. 7, 2008, each of which is hereby incorporated by reference in its entirety.

BACKGROUND OF THE INVENTION

Lignocellulosic biomass is widely recognized as a promising source of raw material for production of renewable fuels and chemicals. The primary obstacle impeding the more widespread production of energy from biomass feedstocks is the general absence of low-cost technology for overcoming the recalcitrance of these materials to conversion into useful fuels. Lignocellulosic biomass contains carbohydrate fractions (e.g., cellulose and hemicellulose) that can be converted into ethanol. In order to convert these fractions, the cellulose and hemicellulose must ultimately be converted or hydrolyzed into monosaccharides; it is the hydrolysis that has historically proven to be problematic.

Biologically mediated processes are promising for energy conversion, in particular for the conversion of lignocellulosic biomass into fuels. Biomass processing schemes involving enzymatic or microbial hydrolysis commonly involve four biologically mediated transformations: (1) the production of saccharolytic enzymes (cellulases and hemicellulases); (2) the hydrolysis of carbohydrate components present in pretreated biomass to sugars; (3) the fermentation of hexose sugars (e.g., glucose, mannose, and galactose); and (4) the fermentation of pentose sugars (e.g., xylose and arabinose). These four transformations occur in a single step in a process configuration called consolidated bioprocessing (CBP), which is distinguished from other less highly integrated configurations in that it does not involve a dedicated process step for cellulase and/or hemicellulase production.

CBP offers the potential for lower cost and higher efficiency than processes featuring dedicated cellulase production. The benefits result in part from avoided capital costs, substrate and other raw materials, and utilities associated with cellulase production. In addition, several factors support the realization of higher rates of hydrolysis, and hence reduced reactor volume and capital investment using CBP, including enzyme-microbe synergy and the use of thermophilic organisms and/or complexed cellulase systems. Moreover, cellulose-adherent cellulolytic microorganisms are likely to compete successfully for products of cellulose hydrolysis with non-adhered microbes, e.g., contaminants, which could increase the stability of industrial processes based on microbial cellulose utilization. Progress in developing CBP-enabling microorganisms is being made through two strategies: engineering naturally occurring cellulolytic microorganisms to improve product-related properties, such as yield and titer; and engineering non-cellulolytic organisms that exhibit high product yields and titers to express a heterologous cellulase and hemicellulase system enabling cellulose and hemicellulose utilization.

Three major types of enzymatic activities are required for native cellulose degradation: The first type are endoglucanases (1, 4-β-D-glucan 4-glucanohydrolases; EC 3.2.1.4). Endoglucanases cut at random in the cellulose polysaccharide chain of amorphous cellulose, generating oligosaccharides of varying lengths and consequently new chain ends. The second type are exoglucanases, including cellodextrinases (1, 4-β-D-glucan glucanohydrolases; EC 3.2.1.74) and cellobiohydrolases (1,4-β-D-glucan cellobiohydrolases; EC 3.2.1.91). Exoglucanases act in a processive manner on the reducing or non-reducing ends of cellulose polysaccharide chains, liberating either glucose (glucanohydrolases) or cellobiose (cellobiohydrolase) as major products. Exoglucanases can also act on microcrystalline cellulose, presumably peeling cellulose chains from the microcrystalline structure. The third type are (β-glucosidases (β-glucoside glucohydrolases; EC 3.2.1.21). β-Glucosidases hydrolyze soluble cellodextrins and cellobiose to glucose units.

A variety of plant biomass resources are available as lignocellulosics for the production of biofuels, notably bioethanol. The major sources are (i) wood residues from paper mills, sawmills and furniture manufacturing, (ii) municipal solid wastes, (iii) agricultural residues and (iv) energy crops. Preconversion of particularly the cellulosic fraction in these biomass resources (using either physical, chemical or enzymatic processes) to fermentable sugars (glucose, cellobiose and cellodextrins) would enable their fermentation to bioethanol, provided the necessary fermentative micro-organism with the ability to utilize these sugars is used.

On a world-wide basis, $1.3 \times 10^{10}$ metric tons (dry weight) of terrestrial plants are produced annually (Demain, A. L., et al., *Microbiol. Mol. Biol. Rev.* 69, 124-154 (2005)). Plant biomass consists of about 40-55% cellulose, 25-50% hemicellulose and 10-40% lignin, depending whether the source is hardwood, softwood, or grasses (Sun, Y. and Cheng, J., *Bioresource Technol.* 83, 1-11 (2002)). The major polysaccharide present is water-insoluble, cellulose that contains the major fraction of fermentable sugars (glucose, cellobiose or cellodextrins).

Bakers' yeast (*Saccharomyces cerevisiae*) remains the preferred micro-organism for the production of ethanol (Hahn-Hägerdal, B., et al., *Adv. Biochem. Eng. Biotechnol.* 73, 53-84 (2001)). Attributes in favor of this microbe are (i) high productivity at close to theoretical yields (0.51 g ethanol produced/g glucose used), (ii) high osmo- and ethanol tolerance, (iii) natural robustness in industrial processes, (iv) being generally regarded as safe (GRAS) due to its long association with wine and bread making, and beer brewing. Furthermore, *S. cerevisiae* exhibits tolerance to inhibitors commonly found in hydrolyzaties resulting from biomass pretreatment. The major shortcoming of *S. cerevisiae* is its inability to utilize complex polysaccharides such as cellulose, or its break-down products, such as cellobiose and cellodextrins.

Genes encoding cellobiohydrolases in *T. reseei* (cbh1 and cbh2), *A. niger* (cbhA and cbhB) and *P. chrysosporium* (cbh1-4) have been cloned and described. The proteins encoded by these genes are all modular enzymes containing a catalytic domain linked via a flexible liner sequence to a cellulose-binding molecule. Cbh1, CbhB and Cbh1-4 are family 7 glycosyl hydrolases. Glycosyl hydrolases are a widespread group of enzymes that hydrolyse the glycosidic bond between two or more carbohydrates, or between a carbohydrate and a non-carbohydrate moiety. A classification system for glycosyl hydrolases, based on sequence similarity, has led to the definition of 85 different families (Henrissat, B. et al., *Proc. Natl. Acad. Sci.* 92:7090-7094 (1995); Davies, G. and Henrissat, B., *Structure* 3: 853-859 (1995)). Glycoside hydrolase family 7 (GHF7) comprises enzymes with several known activities including endoglucanase (EC:3.2.1.4) and cellobiohydrolase (EC:3.2.1.91). These enzymes were formerly known as cellulase family C.

Exoglucanases such as cellobiohydrolases play a role in the conversion of cellulose to glucose by cutting a dissaccharide cellobiose from the reducing or nonreducing end of the cellulose polymer chain. Structurally, cellulases and xylanases generally consist of a catalytic domain joined to a cellulose-binding domain (CBD) via a linker region that is rich in proline and/or hydroxy-amino acids. In type I exoglucanases, the CBD domain is found at the C-terminal extremity of these enzyme (this short domain forms a hairpin loop structure stabilised by 2 disulphide bridges).

Glycosyl hydrolase family 7 enzymes usually have at least 50 to 60% homology at the amino acid level, but the homology between any of these enzymes and the glycosyl hydrolase family 6 CBH2 is less than about 15%.

With the aid of recombinant DNA technology, several of these heterologous cellulases from bacterial and fungal sources have been transferred to *Saccharomyces cerevisiae*, enabling the degradation of cellulosic derivatives (Van Rensburg, P., et al., *Yeast* 14, 67-76 (1998)), or growth on cellobiose (Van Rooyen, R., et al., *J. Biotech.* 120, 284-295 (2005)); McBride, J. E., et al., *Enzyme Microb. Techol.* 37, 93-101 (2005)).

Related work was described by Fujita, Y., et al., (*Appl. Environ. Microbiol.* 70, 1207-1212 (2004)) where cellulases immobilised on the yeast cell surface had significant limitations. First, Fujita et al. were unable to achieve fermentation of amorphous cellulose using yeast expressing only recombinant BGL1 and EGII. A second limitation of the Fujita et al. approach was that cells had to be pre-grown to high cell density on standard carbon sources before the cells were useful for ethanol production using amorphous cellulose (e.g., Fujita et al. teach high biomass loadings of ~15 g/L to accomplish ethanol production).

As noted above, ethanol producing yeast such as *S. cerevisiae* require addition of external cellulases when cultivated on cellulosic substrates such as pre-treated wood because this yeast does not produce endogenous cellulases. Expression of fungal cellulases such as *T. reesei* Cbh1, Cbh2 in yeast *S. cerevisiae* have been shown to be functional (Den Haan, R., et al., *Enzyme and Microbial Technology* 40:1291-1299 (2007)). However current levels of expression and specific activity of cellulases heterologously expressed in yeast are still not sufficient to enable growth and ethanol production by yeast on cellulosic substrates without externally added enzymes. While studies have shown that perhaps recombinant fungal Cbh1 has specific activity comparable to that of the native protein, there remains a significant need for improvement in the amount of Cbh activity expressed in order to attain the goal of achieving a consolidated bioprocessing (CBP) system capable of efficiently and cost-effectively converting cellulosic substrates to ethanol.

Therefore it would be very beneficial to isolate other cellulases from cellulolytic organisms with higher specific activity and higher expression levels in host organisms, such as the yeast *S. cerevisiae*. Since Cbh1 activity seems to be the most limiting in terms of expression level in yeast (Pennilä M E et al., *Gene* 63:103-12 (1988)), it would be advantageous to isolate a novel cbh1 gene and demonstrate its functional expression in yeast.

In order to address the limitations of heterologous Cbh1 expression in consolidated bioprocessing systems, the present invention provides for the identification of novel cellulases that facilitate cellulose digestion and ethanol production in host cells. In particular, the present invention is directed to the isolation of novel cellulases that are capable of being heterologously expressed in yeast, e.g., *Saccharomyces cerevisiae*.

BRIEF SUMMARY OF THE INVENTION

The present invention provides for the isolation and characterization of the cbh1 gene from *Schizochytrium aggregatum*. In particular, the present invention provides for the nucleic acid and amino acid sequences of *Schizochytrium aggregatum* cbh1, and domains, variants and derivatives thereof. The present invention further provides for the heterologous expression of *Schizochytrium aggregatum* Cbh1 in host cells, including yeast, e.g., *Saccharomyces cerevisiae*. Expression of *Schizochytrium aggregatum* Cbh1 in host cells augments cellulose digestion and facilitates ethanol production by those host cells on cellulosic substrates. In certain embodiments, heterologous expression in *Saccharomyces cerevisiae* is in coordination with heterologous expression of other known, or newly identified saccharolytic enzymes. Therefore, the present invention also provides that the novel *Schizochytrium aggregatum* cbh1 gene can be utilized in a consolidated bioprocessing system.

BRIEF DESCRIPTION OF THE DRAWINGS/FIGURES

FIG. 1 depicts a schematic diagram of *Schizochytrium aggregatum* Cbh1, illustrating the conserved domains of the Cbh1 protein. One domain is referred to as the catalytic domain (CD). A second domain is referred to as the cellulose binding domain (CBD). These two domains are connected via a linker sequence. Two regions are depicted in the diagram, one corresponding to the CD having a signal sequence at the N-terminus, the second corresponding to a linker-CBD, where the linker connects the CD to the CBD.

Figure 2:
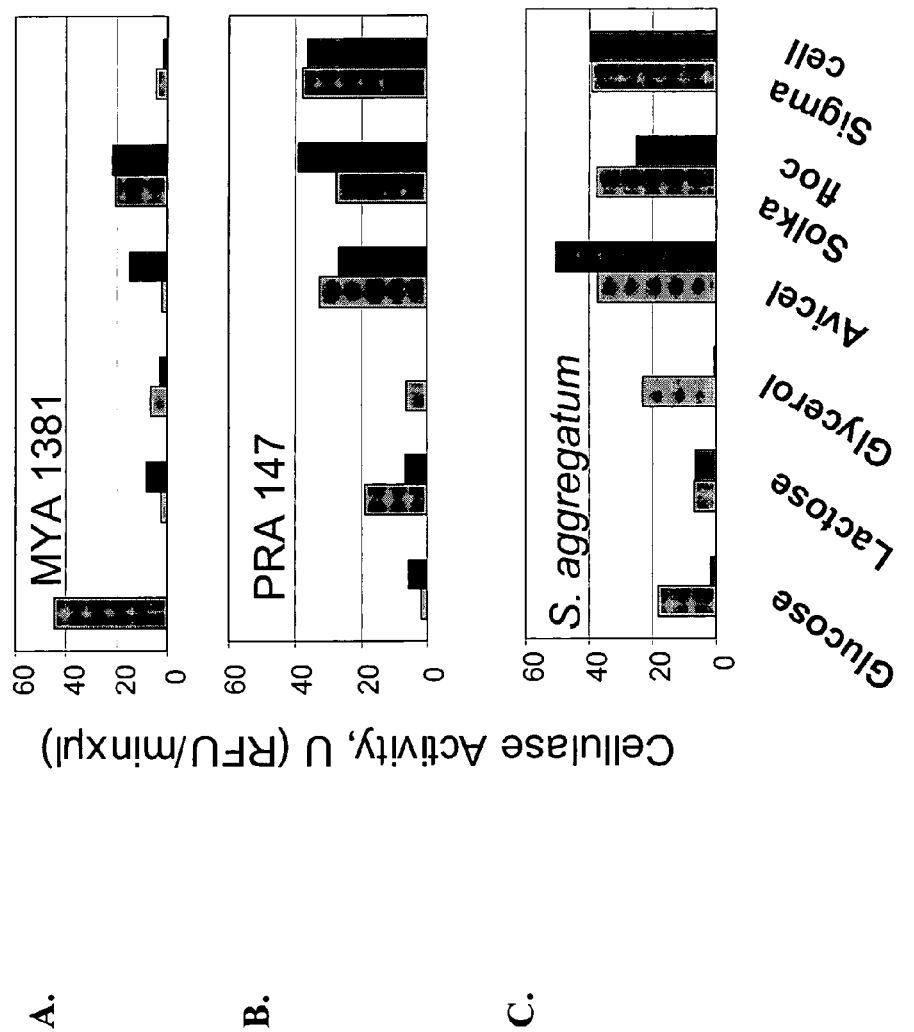

FIG. 2 depicts a bar graph showing secreted and cell associated cellulase activity of three different Thraustochytrid family strains (*Schizochytrium aggregatum*, ATCC-PRA 147, and ATCC-MYA 1381) grown on media with different carbon sources, measured by a resorufin-cellobioside assay. The carbon sources are glucose, Sigma cell, Avicel, Solka floc, lactose, and glycerol. The dark grey bar corresponds to the cell associated cellulose activity; the light grey bar corresponds to the secreted activity.

Figure 3:
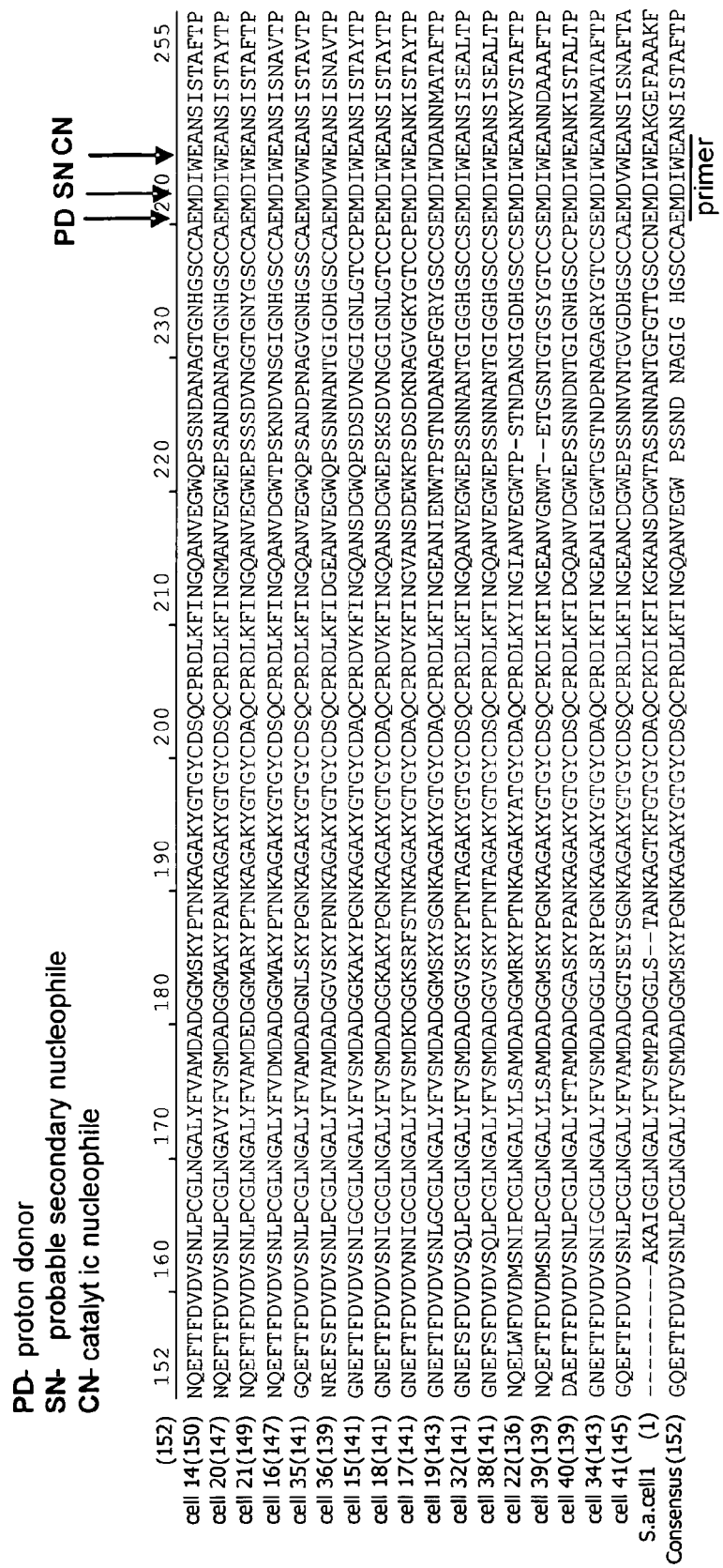

FIG. 3 depicts a sequence alignment between the amino acid sequence of a fragment of *Schizochytrium aggregatum* Cbh1 and the amino acid sequences of several other fungal Cbh1's. The various fungal sequences represented in the alignment are described infra in Example 2.

Figure 4:
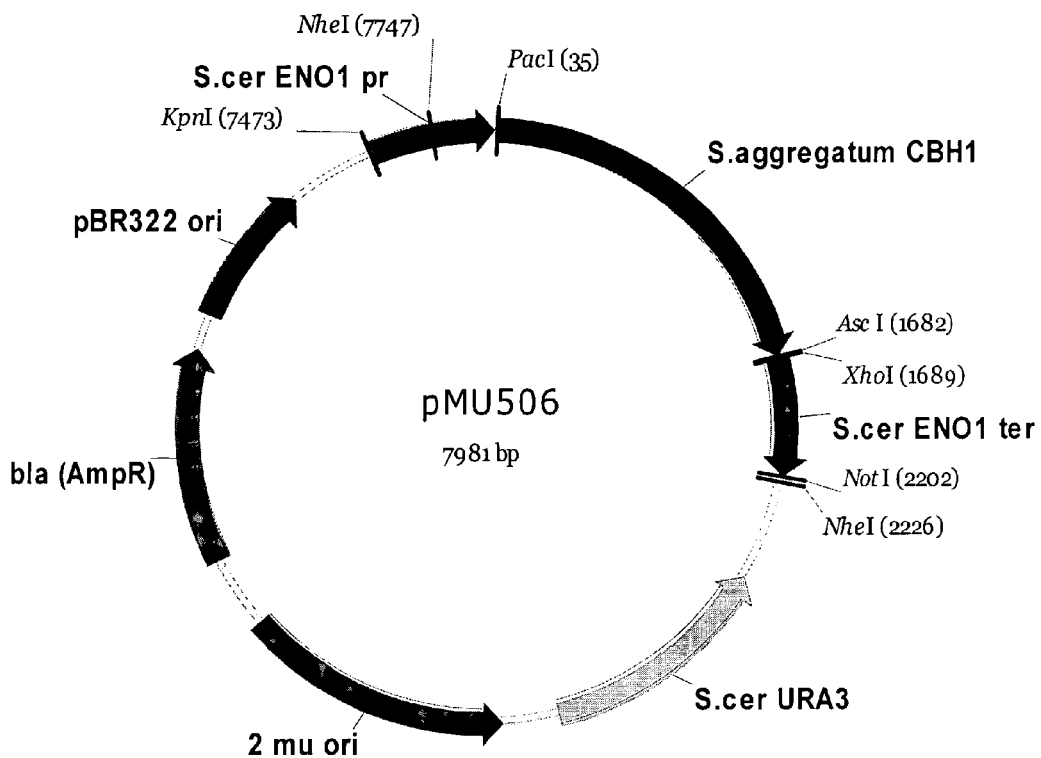

FIG. 4 depicts a map of the *Schizochytrium aggregatum* cbh1 episomal yeast expression construct. S. cer ENO1 pr=*Saccharomyces cerevisiae* ENO1 promoter; S. cer ENO1 ter=*Saccharomyces cerevisiae* ENO1 terminator; *Schizochytrium aggregatum* CBH1=the native sequence of *Schizochytrium aggregatum* cbh1 gene with its native signal sequence; S. cer. URA3=cURA3 auxotrophic marker; 2 mu ori=2 micron *Saccharomyces cerevisiae* origin of replication; bla(AmpR)=ampicillin resistance marker; pBR322=*E. coli* pB322 plasmid origin of replication.

Figure 5:
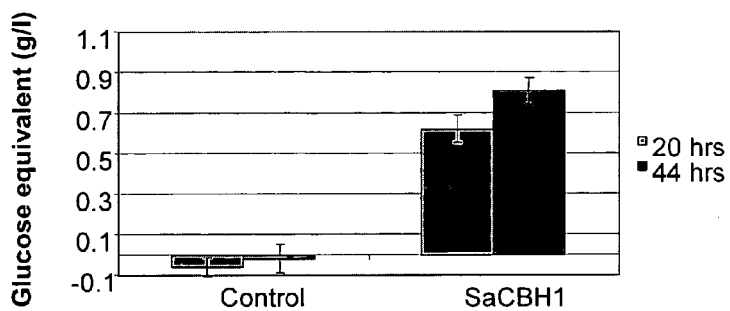

FIG. 5 depicts a bar graph showing *Schizochytrium aggregatum* Cbh1 cellulase activity on phosphoric acid swollen cellulose (PASC). Yeast strain MO430 is transformed with *Schizochytrium aggregatum* cbh1 and yeast strain MO419 is the control transformed with empty vector. Cellulase activity was measured at 20 and 44 hours.

Figure 6:
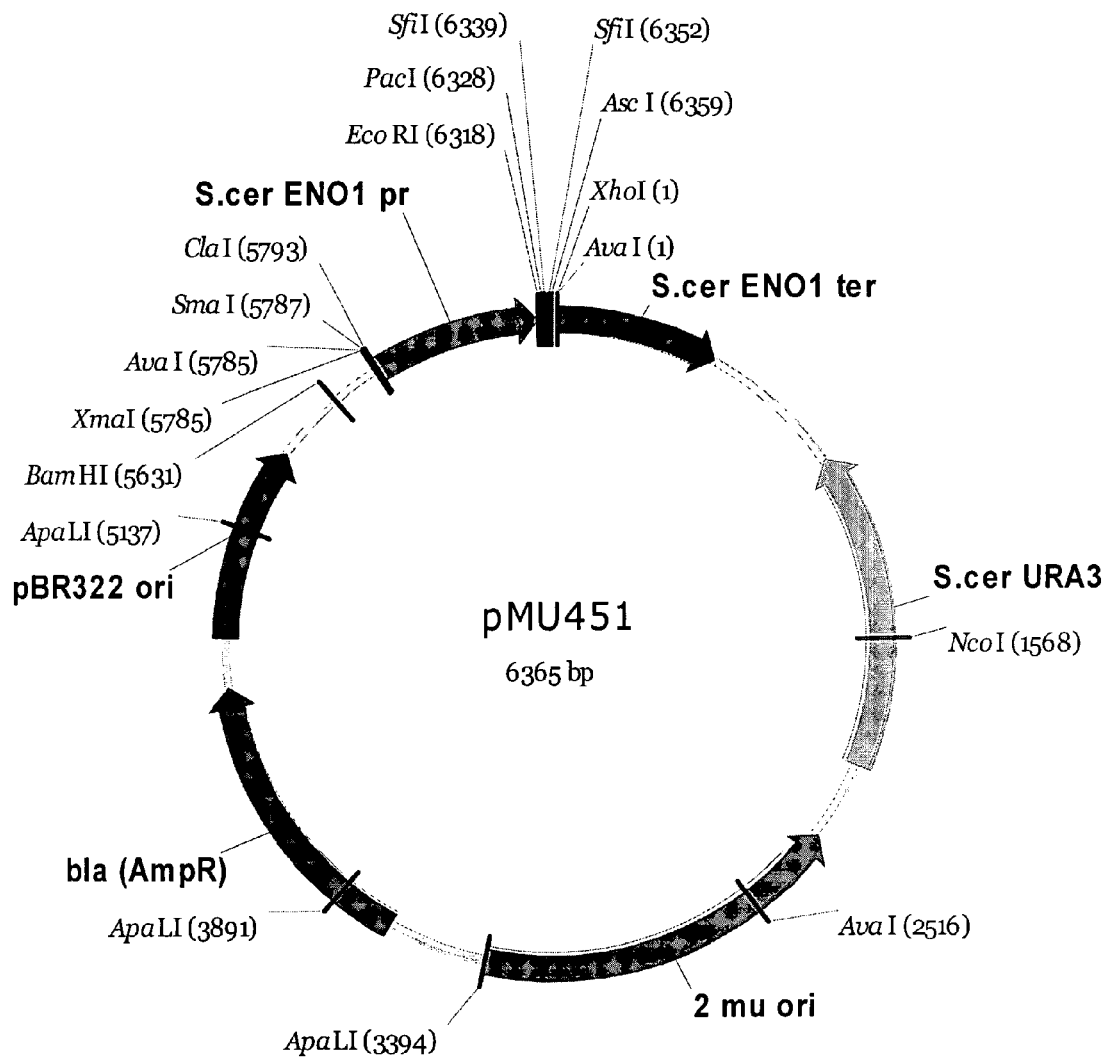

FIG. 6 depicts a map y of the pMU451 episomal expression vector. Genes of cellulases attached to the *Saccharomyces cerevisiae* alpha mating factor pre signal sequence were inserted into PacI/AscI sites of pMU451. S. cer. ENO1 pr=the *Saccharomyces cerevisiae* ENO1 promoter; S. cer. ENO1 ter=the *Saccharomyces cerevisiae* ENO1 terminator; S. cer. URA3=*Saccharomyces cerevisiae* URA3 auxotrophic marker; 2 mu ori—2 mu S. cer. plasmid origin of replication;

bla(AmpR)—Amp resistance marker; pBR322 —E. coli pB322 plasmid origin of replication.

Figure 7:
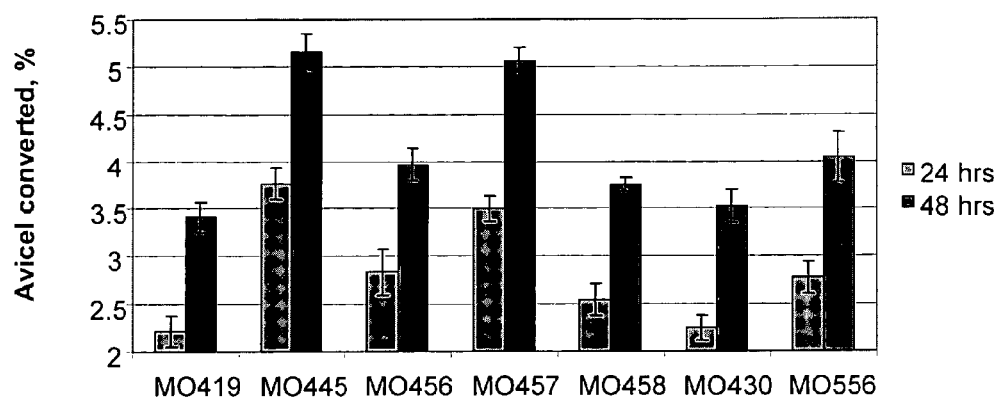

FIG. 7 is a bar graph showing secreted activity on Avicel of codon-optimized *Schizochytrium aggregatum* Cbh1 expressed in yeast (MO556). Strain MO419 transformed with empty vector used as a negative control; strains MO445, MO456, MO457 and MO458 expressing codon optimized genes of fungal Cbh1s (Table 8) used as a positive control. Strain MO430 expresses native (cDNA copy) *Schizochytrium aggregatum* Cbh1. All cellulases except the native *Schizochytrium aggregatum* CBH1 are attached to *Saccharomyces cerevisiae* alpha mating factor pre signal sequence.

Figure 8:
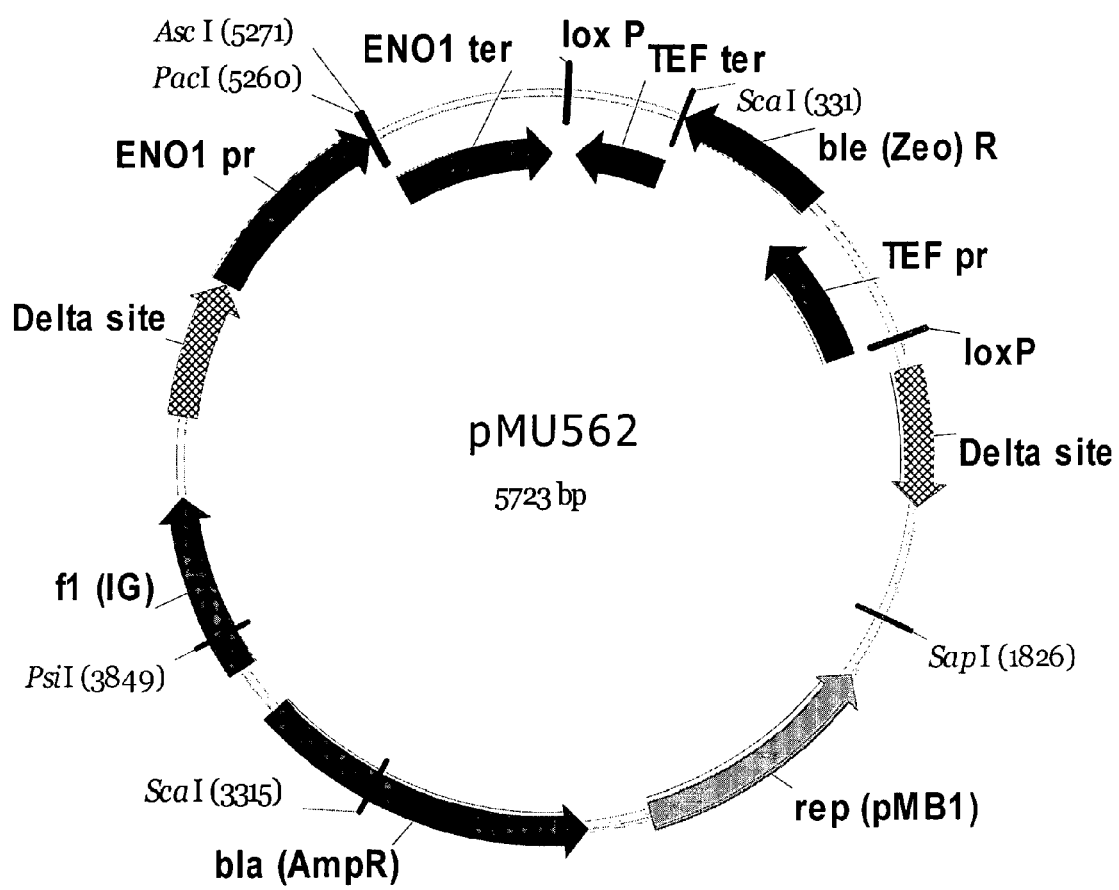

FIG. 8 depicts a map of the pMU562 integrative yeast expression vector. f1 (IG)=the intergenic region of phage f1; rep (pMB1)=the pMB1 replicon responsible for the replication of phagemid; bla (ApR)=gene, coding for beta-lactamase that confers resistance to ampicillin; Delta site=*Saccharomyces cerevisiae* delta integration sites; ENO1 pr=*Saccharomyces cerevisiae* ENO1 promoter; ENO1 ter=*Saccharomyces cerevisiae* ENO1 terminator; TEF pr=*Saccharomyces cerevisiae* TEF1 promoter; TEF1 ter=*Saccharomyces cerevisiae* TEF1 terminator; ble (Zeo)= *Streptoalloteichus hindustanus* ble Zeocin resistance gene; lox P=Cre recombinase recognition site.

DETAILED DESCRIPTION OF THE INVENTION

The present invention relates to, inter alia, the isolation and use of a novel cellulase gene, cbh1 from *Schizochytrium aggregatum*, a cellulolytic marine fungoid organism.

The invention further relates to expression systems in yeast, such as *Saccharomyces cerevisiae*, using this novel gene. The present invention provides important tools to enable growth of host such cells such as yeast on cellulosic substrates for ethanol production.

Definitions

A "vector," e.g., a "plasmid" or "YAC" (yeast artificial chromosome) refers to an extrachromosomal element often carrying one or more genes that are not part of the central metabolism of the cell, and is usually in the form of a circular double-stranded DNA molecule. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. Preferably, the plasmids or vectors of the present invention are stable and self-replicating.

An "expression vector" is a vector that is capable of directing the expression of genes to which it is operably associated.

The term "heterologous" as used herein refers to an element of a vector, plasmid or host cell that is derived from a source other than the endogenous source. Thus, for example, a heterologous sequence could be a sequence that is derived from a different gene or plasmid from the same host, from a different strain of host cell, or from an organism of a different taxonomic group (e.g., different kingdom, phylum, class, order, family genus, or species, or any subgroup within one of these classifications). The term "heterologous" is also used synonymously herein with the term "exogenous."

The term "domain" as used herein refers to a part of a molecule or structure that shares common physical or chemical features, for example hydrophobic, polar, globular, helical domains or properties, e.g., a DNA binding domain or an ATP binding domain. Domains can be identified by their homology to conserved structural or functional motifs. Examples of cellobiohydrolase (CBH) domains include the catalytic domain (CD) and the cellulose binding domain (CBD).

A "nucleic acid," "polynucleotide," or "nucleic acid molecule" is a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes cDNA, genomic DNA, synthetic DNA, and semi-synthetic DNA.

An "isolated nucleic acid molecule" or "isolated nucleic acid fragment" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA).

A "gene" refers to an assembly of nucleotides that encode a polypeptide, and includes cDNA and genomic DNA nucleic acids. "Gene" also refers to a nucleic acid fragment that expresses a specific protein, including intervening sequences (introns) between individual coding segments (exons), as well as regulatory sequences preceding (5' non-coding sequences) and following (3' non-coding sequences) the coding sequence. "Native gene" refers to a gene as found in nature with its own regulatory sequences.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified, e.g., in Sambrook, J., Fritsch, E. F. and Maniatis, T. MOLECULAR CLONING: A LABORATORY MANUAL, Second Edition, Cold Spring Harbor Laboratory Press, Cold Spring Harbor (1989), particularly Chapter 11 and Table 11.1 therein (hereinafter "Maniatis", entirely incorporated herein by reference). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. For more stringent conditions, washes are performed at higher temperatures in which the washes are identical to those above except for the temperature of the final two 30 min washes in 0.2×SSC, 0.5% SDS are increased to 60° C. Another set of highly stringent conditions uses two final washes in 0.1×SSC, 0.1% SDS at 65° C. An additional set of highly stringent conditions are defined by hybridization at 0.1×SSC, 0.1% SDS, 65° C. and washed with 2×SSC, 0.1% SDS followed by 0.1×SSC, 0.1% SDS.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see, e.g., Maniatis at 9.50-9.51). For hybridizations with shorter nucleic acids, i.e., oligonucleotides, the position of mismatches becomes more important, and the length of the oligonucleotide determines its specificity (see, e.g., Maniatis, at 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences.

As known in the art, "similarity" between two polypeptides is determined by comparing the amino acid sequence and conserved amino acid substitutes thereto of the polypeptide to the sequence of a second polypeptide.

Suitable nucleic acid sequences or fragments thereof (isolated polynucleotides of the present invention) encode polypeptides that are at least about 70% to 75% identical to the amino acid sequences reported herein, at least about 80%, 85%, or 90% identical to the amino acid sequences reported herein, or at least about 95%, 96%, 97%, 98%, 99%, or 100% identical to the amino acid sequences reported herein. Suitable nucleic acid fragments are at least about 70%, 75%, or 80% identical to the nucleic acid sequences reported herein, at least about 80%, 85%, or 90% identical to the nucleic acid sequences reported herein, or at least about 95%, 96%, 97%, 98%, 99%, or 100% identical to the nucleic acid sequences reported herein. Suitable nucleic acid fragments not only have the above identities/similarities but typically encode a polypeptide having at least 50 amino acids, at least 100 amino acids, at least 150 amino acids, at least 200 amino acids, or at least 250 amino acids.

The term "probe" refers to a single-stranded nucleic acid molecule that can base pair with a complementary single stranded target nucleic acid to form a double-stranded molecule.

The term "complementary" is used to describe the relationship between nucleotide bases that are capable to hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing as well as those substantially similar nucleic acid sequences.

As used herein, the term "oligonucleotide" refers to a nucleic acid, generally of about 18 nucleotides, that is hybridizable to a genomic DNA molecule, a cDNA molecule, or an mRNA molecule. Oligonucleotides can be labeled, e.g., with $^{32}$P-nucleotides or nucleotides to which a label, such as biotin, has been covalently conjugated. An oligonucleotide can be used as a probe to detect the presence of a nucleic acid according to the invention. Similarly, oligonucleotides (one or both of which may be labeled) can be used as PCR primers, either for cloning full length or a fragment of a nucleic acid of the invention, or to detect the presence of nucleic acids according to the invention. Generally, oligonucleotides are prepared synthetically, preferably on a nucleic acid synthesizer. Accordingly, oligonucleotides can be prepared with non-naturally occurring phosphoester analog bonds, such as thioester bonds, etc.

A DNA or RNA "coding region" is a DNA or RNA molecule which is transcribed and/or translated into a polypeptide in a cell in vitro or in vivo when placed under the control of appropriate regulatory sequences. "Suitable regulatory regions" refer to nucleic acid regions located upstream (5' non-coding sequences), within, or downstream (3' non-coding sequences) of a coding region, and which influence the transcription, RNA processing or stability, or translation of the associated coding region. Regulatory regions may include promoters, translation leader sequences, RNA processing site, effector binding site and stem-loop structure. The boundaries of the coding region are determined by a start codon at the 5' (amino) terminus and a translation stop codon at the 3' (carboxyl) terminus. A coding region can include, but is not limited to, prokaryotic regions, cDNA from mRNA, genomic DNA molecules, synthetic DNA molecules, or RNA molecules. If the coding region is intended for expression in a eukaryotic cell, a polyadenylation signal and transcription termination sequence will usually be located 3' to the coding region.

"Open reading frame" is abbreviated ORF and means a length of nucleic acid, either DNA, cDNA or RNA, that comprises a translation start signal or initiation codon, such as an ATG or AUG, and a termination codon and can be potentially translated into a polypeptide sequence.

"Promoter" refers to a DNA fragment capable of controlling the expression of a coding sequence or functional RNA. In general, a coding region is located 3' to a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity. A promoter is generally bounded at its 3' terminus by the transcription initiation site and extends upstream (5' direction) to include the minimum number of bases or elements necessary to initiate transcription at levels detectable above background. Within the promoter will be found a transcription initiation site (conveniently defined for example, by mapping with nuclease S1), as well as protein binding domains (consensus sequences) responsible for the binding of RNA polymerase.

A coding region is "under the control" of transcriptional and translational control elements in a cell when RNA polymerase transcribes the coding region into mRNA, which is then trans-RNA spliced (if the coding region contains introns) and translated into the protein encoded by the coding region.

"Transcriptional and translational control regions" are DNA regulatory regions, such as promoters, enhancers, terminators, and the like, that provide for the expression of a coding region in a host cell. In eukaryotic cells, polyadenylation signals are control regions.

The term "operably associated" refers to the association of nucleic acid sequences on a single nucleic acid fragment so that the function of one is affected by the other. For example, a promoter is operably associated with a coding region when it is capable of affecting the expression of that coding region (i.e., that the coding region is under the transcriptional control of the promoter). Coding regions can be operably associated to regulatory regions in sense or antisense orientation.

The term "expression," as used herein, refers to the transcription and stable accumulation of sense (mRNA) or antisense RNA derived from the nucleic acid fragment of the invention. Expression may also refer to translation of mRNA into a polypeptide.

Polynucleotides of the Invention

The present invention is directed to a novel cbh1 nucleic acid sequence isolated from the celluloytic marine fungoid organism *Schizochytrium aggregatum*. The *Schizochytrium aggregatum* cbh1 gene is contained within a 7422 base pair region corresponding to a fragment of the *Schizochytrium aggregatum* chromosomal DNA, represented below as SEQ ID NO:1. The ATG start site and TAG termination site of the *Schizochytrium aggregatum* cbh1 gene are indicated in bold, with introns of cbh1 indicated by double underlining.

(SEQ ID NO: 1)
GTAATACGACTCACTATAGGGCACGCGTGGTCGACGGCCCGGGCTGG

TATCTTGCTGGAGGCGTTGCGACAGGCCTCACAGCAGGACTTGCCGC

TTGTGGAGTAGGACGCGGTCTCTTGTTGCCTGGCTCTTTTCCAGGAG

GCGCATCCTGATAGCTTCGCTTCGATGGCCGTTCATCACTGTCTTCG

CTCCATGGCTTGGAGCCTTTTTGAGACTGGCTGTATGGGTTCCATCT

CGCATATTCGTCCCTTTTTCGTTTCATGCCTACCTGGACCTTTTCGT

ACCCCTCTCTTTGCCGTTTCCACTTCTCTGCCCTCCGTTTCTTTTCT

TCTTTCTCGGTGGCGTTGGTGCGTTCTTGCTCGGCGGCGTCGGTTCG

TTCTTTCTCGGCGGCTTTGGCCTGTGCCTCCTGGTACCACTTTCTTT

CCTGTCTCTCTTGATGCCTTCCGCTCCATCTCTTCCTCTTTCGAA

GTGACATGTATCTCATCCCTGACTCCATGGAACTGCGGGCAACCAGC

TCGCTCACAATTGGTTTTGGCTTCTTCGAACGACGCTGACTTCGTAG

CAGATTTCTGTTTGGCCGCTTCGAGTTTGGCTTCAGCTTCCTTGAGC

AGAGCGTCTTGCTCGCGAAGGCCAATTTCTGCATTGCTAAGGTCTTT

TGAGAGCAACAGATCTCCTTCCTTGGCCGCTTGGGAGAGGTTGTTAA

AAGCCGTGTTCGCCTTGTTCCTGGCTTTGATGCGCTCCTCCAACAGA

TATTCTGCCATACCCTCAGCCTTGGAAGCGAGATGCATGTTTTTGCG

AGCGTCTAGGAACACCTTGTGAAAAATGTCATGGCGACCGGTCCCGC

TAGGACGACTCTTGGCTTTCGTGTTGGGAGGCATCTTGCGGTGTTCG

TCTTGGATGCGATGATGTTCGAGGAATCGTCTTGTTGCACGGCGGGA

GTATATGTGGTTTTTCGACACAGGCGTACGAGTTTGTCGTGTAGCTC

GGTCGGCACAATTTCCGAAGAATGACTTCGTGGACCTTTTGTCGCGT

CTATTTGGCGATGGCTGGCGCTTGACGCGGGTTGCCAGTGACTTTCT

ACCAGTGAATAAAGGGCTTGTCTAGCTAGCCTTTGTTCTCGGTCCAT

ATTCATGACCATAATTCACGGGTTATCTGCCATCCAACATGTTAATG

TGAGCACTGCAGATAATTTGCTTCCGTTAATTAGTTGTGTGAGTGCT

ATCGCTGGGTCAAGATTTAGCTCAATTATTCTTTGGTACCCGGGTGT

TCTCAAAGCTGGTGAGCTTCAAGGGGCAACGCGCTTGTGACACTGCC

ATCGAAGGGAGGAATTTCTGTATGCTCATAATCCATGAGTACTCTTT

ATATGCTTCTCGTAAACATGTATGCATGTCAGCGTTCTGGTTGTTCT

CTCATCCACTTGCAACTGCGAATCACTCTTCTCCCGGGACAGCGACA

TTCGATATGTCTCGGCATATCTTCATCAGCTCCTCTTGTTTTTTAAC

ATTGTCGGCTGCTCCATGCGGAGCCTGTTCACCACCAGTGGTGAAGA

ATGCTCCGGAGGCCAGTTTGGCGGCGAATCCTTCACCAGAGGACCAC

TCTGTCAAAACCTGGGATGACTTGTCTGTGGTTCCAGGAGCAGACGA

ACCGCCCATCTTTGTTTTCAGCCAGCCAGGATGCATGCTGACGCTCT

GCACATCAGTCCAGCGTCTCGCGAAAGCCTTCGAGAGCATGGTGTCC

TGCAGTTTGCTATTGGCGTACGAGAAAGAAGTTGTACAGTTCTTGAG

GGATTCGTCACCCCCAAAGTGACTGTCAGAGCTCATGAAGAGAATCC

TGGACTTCGGTTTGTTCATGAGACATGTCAAGATGTATGGTGCAAGT

GTGTTGACGGCGAAGACGGCGGAAACTCCGTCTGAAGTGATCTCCTG

CGAAGATGTAGCACCGTAGCCGATGCCGGCATTGTCTGCAAAAGTAT

ATGTATCAGCATAGCATCTAGCATGACCTATACATGGTGACTTACGA

ATGATGGCATCGAAGGTACCAGTCTTGTTTGCCTCTTCGGCCAATCG

TTTAGTCTCGTTGATCGAAGAGAGATTTCCAATCAAGCATCCTTCAG

CTTTGGGCACAGCCTTGCTGGCCTGCTTTGCTCGCTCTGAGTTACGT

GCGTGAAGAGTGACTTGGTGCCCCTTTTCGGAAAGCGCCTTGGCTGC

GGCCAAACCAATACCGTCGCTGGATCCTGTGATGAAGACGCGCACCA

TCTTGGAAAGTAAGGTGTATGTACAAGGACGTGATGTAGCTACAATG

GTCGAAGAACTACAAATGCTCAGAAATCATGAGAACGAGGAGCAAGC

ACAGCTGTCGTTGCTAGAGTGGACATGAGGCCATCCGGTTGTCGGTT

ATGCGTTCTCGCCTCGACAGATGGAGCAAAAGAAATGGAGATGTTCG

TGATGACGTCATTGGACGTAAACATTCCAAGGAGGCAGAATGCCCTG

TTCGATGTTTACGTGTATATGTTTCGATGTATGTTCGAAACCAAATT

GCTAGTGGTGAACATATCCGATGATGGCTGCAGCATTTCCATGTTTC

GTCTGCGTTCTCAATCGTTCTCAATCGCCCAGGTTTCTGCGCGTGTG

ACACGTGATCCTAGATCCGTGACCTTCGGCAAGGGGAGCCGTTCTTG

TTAACTGGGGATGGTGTTGACACGAACGAAGAAATGGTTTGAAAGAG
ATGGAAAGCCAGGAAAGCTGACGAAGCTGATAGGTGGAAGATACGAT
TCTCTCCTGCCTTCAATCTTACAGTATGGTCACCTTTCCAGGACAGC
TGGATCTGAGGACCGTAATGCCCGTCGTCGCGGATCGTATGCGGCTC
TTCCAGCCAAATGCACGCCCAAACTACACTGCCTCCGTGGAAGGTCT
CCATTCTCATGCCTTTGAGTTGCAGCGCTAGCTATCAGAAACACCAA
AGGGAAGTTTATCCGGTTGTACCACGAGACCACAAAGGCGTCCGGAG
CCACAGGCGAGATTGGACCGCGTCCAGGAACCTGGTAATTTGAAGGT
TGCAGCAGTGCGAACATTGCTCGCTGTAAAAGCTACGTCTGCTCGAC
TTCGGAATGTCATCGATATGTGCAGTTTGCCGCAATCGTCACTCATC
TTGGCGGTGGTTCTTCGAATTATCGCTTCACGCCAACTCCAGATCTA
CCATCTAGTGCAGAAGGTATTGCTGGTGGTAAGCCCAAAGAGTGGCG
AGGACTCCGAGGAGGCTGGAGGCAAACGTTGCATGGCTTTGGTACAA
AGGAAAATTGATTAATTATGCAGGGCAAGCTGCACGGGGAAGAGCTT
GGCGACGCCTTACCATTCTGGCCCGGACTCTTGACTTCTTTGGCTAA
CAACATGTGCTGCTCCGGGCTACTTTCTGCTATATTGCTCGTTAAAC
CAGGAGGCTTAAGCTATACCCACAAATTGCTTCATGTGTTCATTGTC
CAGCACTTCCCTGCATGTCCGCGTGTCACCAGGACATACCACAAGCC
AGACCGGACCATGAGCAGGATACTGGCATACATCGGCAACTGCTGGC
GTAGATCTTGACTCGTCGTGCGACGACGGGCTCAGCCCTCCGTAGCC
CACAATCTGCCTAAGCAGGACAGAACATCTTCTGTCCGTCGGACCGT
CCAACGAGGGCAATCAGTGGATCCCACAATGCTGGACAGGCCTCAGA
ACAGCCATGAGCAAGATTTGTGTTTTGCGCGAAGGCCATGATTGCAA
GTGGAAGTGAGGATGACGAACTATATAACGACGAAGACGCCATCCAC
AGTTCATTCTCATCAACCAACAAAGCAAGCAGTTTAAATCTACCTTA
CAGAACAACCTGCAAGCATGTCTGCCATTACCCTCGCCCTGGGTGCT
CTTGCCCTCAGCTCTGTTGTCAACGCTCAGCAGGCTGGAACCCTTAC
TCCTGAAAAACACCCTGCTTTTTCTGTGTCTACTTGCTCTGCCGGCG
GCACTTGCACGTCCAAGACCCAGAGCATTGTGCTCGATGGCAACTGG
CGCTGGCTCCACTCTACTTCCGGCTCCACCAACTGCTACACAGGTAA
CACCTTCGACAAGACTTTGTGCCCTGATGGAGTGACTTGCGCCGCAA
ACTGCGCCCTCGATGGTGCTGACTACACCGGCACTTACGGTATCAAG
GCATCCGGCAACTCTCTGAGCCTTCAGCTCAAGACTGGCAGCAACGT
TGGCTCCAGAGTCTACCTCATGGACGAGCAGGACAAGAACTACCAGC
TCTTCAACCTGAAGAACCAGGAGTTTACGTTCGACGTCGACGTCAGC
AAGATCGGATG<u>TAAGTACTCTACATGACAGGGCAGTAGATTAAATGCT
TAAGCAAAGGCAATAGG</u>TGGTCTCAACGGCGCTCTGTACTTCGTGTCC
ATGCCCGCAGATGGTGGACTTTCTACCACTAACAAGGCCGGCACCAA
GTTCGGAACAGGATATTGTGATGCTCAGTGTCCTAAAGACATCAAGT
TTATCAAGGGCAAGGCAAACAGCGATGGCTGGACAGCATCTTCCAAC

AACGCAAACACCGGTTTCGGTACGACCGGCTCCTGCTGCAACGAGAT
GGATATCTGGGAGGCAAACGGGATCTCCAACGCTGTGACTCCTCACT
CCTGCAGTCCCGGCAACGCCGCTTGCACTTCTGACACAACTTGTGGC
TCTGGCGACGGTAACCGCTACAAAGGCTACTGTGACAAGGACGGTTG
CGATTTCAACCCCTTCAGGATGGGCAACCAGACCTTCTACGGCCCCG
GCAAGACTATCGACACCACCAAGCCTCTCACTGTGGTCACCCAATTC
ATTACCTCTGACAACACTGCTAGTGGCGATCTTGTTGAGATCCGTCG
CAAGTACGTCCAGGGCGGCAAGGTCTTCGATCAGCCCACATCCAACG
TTGCTGGCGTTAGCGGCAACTCGATCACCGACACCTTCTGCAAAAAC
CAGAAGTCCGTCTTCGGTGACACTAACGACTTCGCTGCGAAGGGTGG
CTTGAAGGCTATGGGCGACGCCTTCGCTGATGGCATGGTCCTTGTCA
TGTCTCTGTGGGATGATTACGATGTCAACATGCACTGGCTCAACTCT
CCTTACCCAACTGACGCCGACCCAACAAAGCCTGGTGTTGCCCGTGG
AACTTGCTCTATCACCTCTGGTAAGCCCGCCGACGTCGAGAGCCAGA
CTCCTGGTGCCACCGTTGTCTACTCGAACATCAAGACTGGTCCCATT
GGCTCCACCTTCTCTGGCGCCCAACAGCCCGGTGGCCCCGGCAGTGG
TTCTTCATCTTCCAGCTCAGCGGGAGGCTCAAGCACCACCTCCAGGT
CTTCTTCTACCACCTCCAGGGCTACCACCACGAGTGTCGGGACCACT
ACCACCACCACTAGCTCTCGCACGACCACAACCAGCGCTGCTGGCGG
CGTCGTCCAGAAGTACGGACAGTGCGGT<u>GTAAGTGTTCCCTATCTGTC
CCTATCTGTCCAATTTTTACTACTCTCCATGTATACTGACTCG
CGTGACAGG</u>GCCTGAC
ATACACTGGTCCTACTACTTGTGTGAGCGGAACCACTTGCACCAAGG
CCAACGACTACTACTCGCAGTGCTTGTAGATACAGTTACTTGGCGGC
ACGACCAACATGACGTGAAAACGATGACGAACACACGTGCTAGGCAG
GAAAAGGACGTTGCAGCTGTCTGGAGAACTTTGATAGTTACATTCGT
TAACCGACAATTTGAATTACCACGTTTGTAGATCCTCATGGTTTCCC
ACTGACTTCTCGTGGTGAGGTTGCGTGACCTGCAGATTCGTGCAACT
TCTTTCTCGTGGTGTTAACGGTGCAACGGCTGAGTCGCAAATTTTTCG
GTCCTTGTACGAGCACTATTGGCAACACCACCGACACCAAGAAAGCT
AGAGACGCCAATCATGTTTCAGATCGATGCAACGATCATCCGTCGCC
AGGCGTCCAGCGATCACGATATCACAGCTATAGTAGGCGACGACCAC
GCCGTGGGAACCGAGAACATGGGGATTAGCAACCAAAATCAGACAGT
ATGCTTACCTTGTTAAGCGGATAGCTATCTAATGCTTGCATGAACGG
TCGTCACTATAGGACAATTAATGGTTCATTATGGAACCTGCTGCAAT
AGAACATGGGCACGCTATTGGCGGGAGCAAGCGCGGCGATCTCGCGG
CGATGTAGAATTCACCTTTGACTTCAACCAGGACCCGCTGGTTCTCG
CCTAGCTAAAGGATAAGATGGGGGAATAAACCAGTCGTTCCGGACTC
ACCAACGGCCAGGACGACATGACTCTCACGTCCGACAATACTCCGTT
ACAATATCATAAACGAGAGTTCAAGACCAGCAATTTTGCAACATGGG
ACATCGATGGCTGATTTCAGCTTACAATTTGAAGCATGCTCAGGGCT

-continued
CACAAGCCCGGAATGAACCATTTATGCGATTGACGGAGTCGTTGTCC

GATAGCCAAACTGCCCTGAGACGCTTTGGTGTGGCTAACACGTTCTA

CAGTGCAGATCCTTAGCGGGTCTTCGGGCAAAGCCCTGATTGGGACA

AACTTCATCTGTCACGACTAGACCCGAACTCACCTGCTCCGACTTCC

ACACACGCTCGCCCGTACCTGGCCCCCGGTACCGATATTATGCAGGA

ACTTCTGTGATATAGAATCCACACTGAGCTTGATCAAACTGCCCGCC

ACGGGGCACGATATGTCCTAGCCGCGTCTGACTTGGGTTGCATGTTG

GGTATTACGGCACAGCATCCATGGAGGGTTACTGCTCAACCATGCTG

ACGCAATGAAAAAAGTCCTGGCCGAGACCAGGGTGCTTGCGTGTGAC

AAGCAATAACGCCACCGCATTGGTCACATCGCGTGTCTTCACACCTT

CTTTGAGCCGGCTCAACGTGTGCCGCGTATCTCAAACACGCGATGCC

CTGCGCGAGGAAACGCCTAGAGAAATACTACCGTCACAAACCCTGGA

TCATCGATACTAGGCTGGCTTAAGTAATTAGTGTAAGGCCACCGACC

GACCCGTTCACCCCTGACCATCTGGAGTGCATGGAGAATCACTCCAT

GTGTAGATCATCGTTGCCGGCGCATGTTAGATCGATTATGGCGCGCT

GCATTATGCACTAATGACTTGAGCTGCCCTCTCTCCTTACCGGGCGC

GTGAACGGGTTCCTCAGGGCCGGTTACTACAAGTGCCCATCGTCGTG

CACATTTGCTGCGCTCMGCCGTGCGCTTTGCGGGTCGTTCTTGCGTC

CTGTACAGTTGTTGAGGAGACGACTATATACCATTACCGCCAACATG

GAAGGCACGTTTGAAGGCATCAATCTTGCTGATAGGACCAGCCCGGG

CCGTCGACCACGCGTGCCCTATAGTGAGTCGTATTAC

The start codon, ATG, begins at position 3872 of SEQ ID NO: 1, followed by exon 1 (extending from position 3872 to 4345 of SEQ ID NO:1), intron 1 (extending from position 4346 to 4488 of SEQ ID NO:1), exon 2 (extending from position 4489 to 5542 of SEQ ID NO:1), intron 2 (extending from position 5543 to 5593 of SEQ ID NO:1), exon 3 (extending from position 5594 to 5626 of SEQ ID NO:1), and the termination codon TAG, ending at position 5626 of SEQ ID NO:1.

Also encompassed by the invention is the corresponding cDNA encoding the *Schizochytrium aggregatum* cbh1, 1638 base pairs in length, represented by SEQ ID NO:2, and encoding for a protein of 546 amino acid residues:

(SEQ ID NO: 2)
ATGTCTGCCATTACCCTCGCCCTGGGTGCTCTTGCCCTCAGCTCTGT

TGTCAACGCTCAGCAGGCTGGAACCCTTACTCCTGAAAAACACCCTG

CTTTTTCTGTGTCTACTTGCTCTGCCGGCGGCACTTGCACGTCCAAG

ACCCAGAGCATTGTGCTCGATGGCAACTGGCGCTGGCTCCACTCTAC

TTCCGGCTCCACCAACTGCTACACAGGTAACACCTTCGACAAGACTT

TGTGCCCTGATGGAGTGACTTGCGCCGCAAACTGCGCCCTCGATGGT

GCTGACTACACCGGCACTTACGGTATCAAGGCATCCGGCAACTCTCT

GAGCCTTCAGCTCAAGACTGGCAGCAACGTTGGCTCCAGAGTCTACC

TCATGGACGAGCAGGACAAGAACTACCAGCTCTTCAACCTGAAGAAC

CAGGAGTTTACGTTCGACGTCGACGTCAGCAAGATCGGATGTGGTCT

CAACGGCGCTCTGTACTTCGTGTCCATGCCCGCAGATGGTGGACTTT

CTACCACTAACAAGGCCGGCACCAAGTTCGGAACAGGATATTGTGAT

GCTCAGTGTCCTAAAGACATCAAGTTTATCAAGGGCAAGGCAAACAG

CGATGGCTGGACAGCATCTTCCAACAACGCAAACACCGGTTTCGGTA

CGACCGGCTCCTGCTGCAACGAGATGGATATCTGGGAGGCAAACGGG

ATCTCCAACGCTGTGACTCCTCACTCCTGCAGTCCCGGCAACGCCGC

TTGCACTTCTGACACAACTTGTGGCTCTGGCGACGGTAACCGCTACA

AAGGCTACTGTGACAAGGACGGTTGCGATTTCAACCCCTTCAGGATG

GGCAACCAGACCTTCTACGGCCCCGGCAAGACTATCGACACCACCAA

GCCTCTCACTGTGGTCACCCAATTCATTACCTCTGACAACACTGCTA

GTGGCGATCTTGTTGAGATCCGTCGCAAGTACGTCCAGGGCGGCAAG

GTCTTCGATCAGCCCACATCCAACGTTGCTGGCGTTAGCGGCAACTC

GATCACCGACACCTTCTGCAAAAACCAGAAGTCCGTCTTCGGTGACA

CTAACGACTTCGCTGCGAAGGGTGGCTTGAAGGCTATGGGCGACGCC

TTCGCTGATGGCATGGTCCTTGTCATGTCTCTGTGGGATGATTACGA

TGTCAACATGCACTGGCTCAACTCTCCTTACCCAACTGACGCCGACC

CAACAAAGCCTGGTGTTGCCCGTGGAACTTGCTCTATCACCTCTGGT

AAGCCCGCCGACGTCGAGAGCCAGACTCCTGGTGCCACCGTTGTCTA

CTCGAACATCAAGACTGGTCCCATTGGCTCCACCTTCTCTGGCGCCC

AACAGCCCGGTGGCCCCGGCAGTGGTTCTTCATCTTCCAGCTCAGCG

GGAGGCTCAAGCACCACCTCCAGGTCTTCTTCTACCACCTCCAGGGC

TACCACCACGAGTGTCGGGACCACTACCACCACCACTAGCTCTCGCA

CGACCACAACCAGCGCTGCTGGCGGCGTCGTCCAGAAGTACGGACAG

TGCGGTGGCCTGACATACACTGGTCCTACTACTTGTGTGAGCGGAAC

CACTTGCACCAAGGCCAACGACTACTACTCGCAGTGCTTG

The present invention also encompasses an isolated polynucleotide comprising a nucleic acid at least about 60%, 65%, 70%, 75%, or 80% identical, at least about 90% to about 95% identical, or at least about 96%, 97%, 98%, 99% or 100% identical to SEQ ID NO:1, an intron or exon of SEQ ID NO:1, SEQ ID NO:2, or fragments, variants, or derivatives thereof.

In certain aspects, the present invention encompasses a polynucleotide comprising a nucleic acid encoding a functional or structural domain of *Schizochytrium aggregatum* cbh1, e.g., as represented schematically in FIG. 1. The domains of *Schizochytrium aggregatum* Cbh1 include, without limitation: (1) a signal sequence, from amino acid 1 to about 19 of SEQ ID NO:3; (2) a catalytic domain (CD) from about amino acid 20 to about amino acid 456 of SEQ ID NO:3; (3) a linker sequence from about amino acid 457 to about 506 of SEQ ID NO:3; and (4) a cellulose binding domain from about amino acid 507 to about amino acid 546 of SEQ ID NO:3. Particular amino acids important for catalytic function include those corresponding to the proton donor, the probable secondary nucleophile, and the catalytic nucleophile, as indicated in FIG. 3. Thus, the present invention encompasses a polynucleotide comprising a nucleic acid encoding the region from 1 to about 19 of SEQ ID NO:3, from about amino acid 20 to about amino acid 456 of SEQ ID NO:3, from about amino acid 457 to about amino acid 506 and/or from about amino acid 507 to about amino acid 546 of SEQ ID NO:3. In addition, the present invention encompasses a polynucleotide comprising a nucleic acid encoding the region from amino acid 1 to about 546 of SEQ ID NO:3, from about amino acid 2 to about amino acid 546 of SEQ ID NO:3, and from about amino acid 20 to about amino acid 546 of SEQ ID NO:3.

The present invention also encompasses an isolated polynucleotide comprising a nucleic acid that is about 60%, 65%, 70%, 75%, or 80% identical, at least about 90% to about 95% identical, or at least about 96%, 97%, 98%, 99% or 100% identical to a nucleic acid encoding a Cbh1 *Schizochytrium aggregatum* domain, as described above.

By a nucleic acid having a nucleotide sequence at least, for example, 95% "identical" to a reference nucleotide sequence of the present invention, it is intended that the nucleotide sequence of the nucleic acid is identical to the reference sequence except that the nucleotide sequence may include up to five point mutations per each 100 nucleotides of the reference nucleotide sequence encoding the *S. aggregatum* polypeptide. In other words, to obtain a nucleic acid having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence shown of SEQ ID NO:2 or any fragment specified as described herein.

As a practical matter, whether any particular nucleic acid molecule or polypeptide is at least 60%, 65%, 70%, 75%, 80%, 85%, 90%, 95%, 96%, 97%, 98% or 99% identical to a nucleotide sequence or polypeptide of the present invention can be determined conventionally using known computer programs. A method for determining the best overall match between a query sequence (a sequence of the present invention) and a subject sequence, also referred to as a global sequence alignment, can be determined using the FASTDB computer program based on the algorithm of Brutlag et al. (*Comp. App. Biosci*. (1990) 6:237-245.) In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to be made for the purposes of the present invention.

Some embodiments of the invention encompass a nucleic acid molecule comprising at least 10, 20, 30, 35, 40, 50, 60, 70, 80, 90, 100, 200, 300, 400, 500, 600, 700, or 800 consecutive nucleotides or more of SEQ ID NO:1, SEQ ID NO:2, or fragments thereof. In certain aspects, fragments of SEQ ID NO:1 or SEQ ID NO:2 encode a Cbh1 *Schizochytrium aggregatum* domain, as set forth above.

The polynucleotide of the present invention may be in the form of RNA or in the form of DNA, which DNA includes cDNA, genomic DNA, and synthetic DNA. The DNA may be double stranded or single-stranded, and if single stranded may be the coding strand or non-coding (anti-sense) strand. The coding sequence which encodes the mature polypeptide may be identical to the coding sequence encoding SEQ ID NO:3 or may be a different coding sequence which coding sequence, as a result of the redundancy or degeneracy of the genetic code, encodes the same mature polypeptide as the DNA of SEQ ID NO:2.

In certain embodiments, the present invention provides an isolated polynucleotide comprising a nucleic acid fragment which encodes at least 10, at least 20, at least 30, at least 40, at least 50, at least 60, at least 70, at least 80, at least 90, at least 95, or at least 100 or more contiguous amino acids of SEQ ID NO:3.

The polynucleotide encoding for the mature polypeptide of SEQ ID NO:3 may include: only the coding sequence for the mature polypeptide; the coding sequence of any domain of the mature polypeptide; and the coding sequence for the mature polypeptide (or domain-encoding sequence) together with non-coding sequence, such as introns or non-coding sequence 5' and/or 3' of the coding sequence for the mature polypeptide.

Thus, the term "polynucleotide encoding a polypeptide" encompasses a polynucleotide which includes only sequences encoding for the polypeptide as well as a polynucleotide which includes additional coding and/or non-coding sequences.

In further aspects of the invention, nucleic acid molecules having sequences at least 60%, 65%, 70%, 75%, 80%, 85%, 90%, 95%, 96%, 97%, 98% or 99% identical to the nucleic acid sequences disclosed herein, encode a polypeptide having *Schizochytrium aggregatum* Cbh1 functional activity. By "a polypeptide having *Schizochytrium aggregatum* Cbh1 functional activity" is intended polypeptides exhibiting activity similar, but not necessarily identical, to a functional activity of the *Schizochytrium aggregatum* Cbh1 polypeptides of the present invention, as measured, for example, in a particular biological assay. For example, a *Schizochytrium aggregatum* Cbh1 functional activity can routinely be measured by determining the ability of a *Schizochytrium aggregatum* Cbh1 polypeptide with respect to cellulase activity.

Of course, due to the degeneracy of the genetic code, one of ordinary skill in the art will immediately recognize that a large portion of the nucleic acid molecules having a sequence at least 60%, 65%, 70%, 75%, 80%, 85%, 90%, 95%, 96%, 97%, 98%, or 99% identical to the nucleic acid sequence of SEQ ID NO:1 or SEQ ID NO:2, or fragments thereof, will encode polypeptides "having *Schizochytrium aggregatum* Cbh1 functional activity." In fact, since degenerate variants of any of these nucleotide sequences all encode the same polypeptide, in many instances, this will be clear to the skilled artisan even without performing the above described comparison assay. It will be further recognized in the art that, for such nucleic acid molecules that are not degenerate variants, a reasonable number will also encode a polypeptide having *Schizochytrium aggregatum* Cbh1 functional activity.

Fragments of the full length gene of the present invention may be used as a hybridization probe for a cDNA library to isolate the full length cDNA and to isolate other cDNAs which have a high sequence similarity to the *Schizochytrium aggregatum* cbh1 gene, or a gene encoding for a protein with similar biological activity. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

In certain embodiments, a hybridization probe may have at least 30 bases and may contain, for example, 50 or more bases. The probe may also be used to identify a cDNA clone corresponding to a full length transcript and a genomic clone or clones that contain the complete gene including regulatory and promoter regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of bacterial or fungal cDNA, genomic DNA or mRNA to determine which members of the library the probe hybridizes to.

The present invention further relates to polynucleotides which hybridize to the hereinabove-described sequences if there is at least 60%, at least 70%, at least 80%, at least 90%, or at least 95% identity between the sequences. The present invention particularly relates to polynucleotides which hybridize under stringent conditions to the hereinabove-described polynucleotides. As herein used, the term "stringent conditions" means hybridization will occur only if there is at least 95% or at least 97% identity between the sequences. In certain aspects of the invention, the polynucleotides which hybridize to the hereinabove described polynucleotides encode polypeptides which either retain substantially the same biological function or activity as the mature polypeptide encoded by the DNAs of SEQ ID NO:1, SEQ ID NO:2.

Alternatively, polynucleotides which hybridize to the hereinabove-described sequences may have at least 20 bases, at least 30 bases, or at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, or SEQ ID NO:2, for example, for recovery of the polynucleotide or as a diagnostic probe or as a PCR primer.

Hybridization methods are well defined and have been described above. Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

For example, genes encoding similar proteins or polypeptides to those of the instant invention could be isolated directly by using all or a portion of the instant nucleic acid fragments as DNA hybridization probes to screen libraries from any desired bacteria using methodology well known to those skilled in the art. Specific oligonucleotide probes based upon the instant nucleic acid sequences can be designed and synthesized by methods known in the art (see, e.g., Maniatis, 1989). Moreover, the entire sequences can be used directly to synthesize DNA probes by methods known to the skilled artisan such as random primers DNA labeling, nick translation, or end-labeling techniques, or RNA probes using available in vitro transcription systems.

In certain aspects of the invention, polynucleotides which hybridize to the hereinabove-described sequences having at least 20 bases, at least 30 bases, or at least 50 bases which hybridize to a polynucleotide of the present invention may be employed as PCR primers. Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art. Generally two short segments of the instant sequences may be used in polymerase chain reaction (PCR) protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding microbial genes. Alternatively, the second primer sequence may be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., *PNAS USA* 86:5673 (1989); Loh et al., *Science* 243:217 (1989)).

In addition, specific primers can be designed and used to amplify a part of or full-length of the instant sequences. The resulting amplification products can be labeled directly during amplification reactions or labeled after amplification reactions, and used as probes to isolate full length DNA fragments under conditions of appropriate stringency.

Therefore, the nucleic acid sequences and fragments thereof of the present invention may be used to isolate genes encoding homologous proteins from the same or other fungal species or bacterial species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, Mullis et al., U.S. Pat. No. 4,683,202; ligase chain reaction (LCR) (Tabor, S. et al., Proc. Acad. Sci. USA 82, 1074, (1985)); or strand displacement amplification (SDA, Walker, et al., *Proc. Natl. Acad. Sci. U.S.A.*, 89, 392, (1992)).

The polynucleotides of the present invention also comprise nucleic acids encoding *Schizochytrium aggregatum* Cbh1, a domain of *Schizochytrium aggregatum* Cbh1, or a fragment of *Schizochytrium aggregatum* Cbh1 fused in frame to a marker sequence which allows for detection of the polypeptide of the present invention. The marker sequence may be a yeast selectable marker selected from the group consisting of URA3, HIS3, LEU2, TRP1, LYS2 or ADE2. Additional marker sequences include other auxotrophic markers or dominant markers known to one of ordinary skill in the art such as ZEO (zeocin), NEO (G418), hygromycin, arsenite, HPH, NAT, and the like.

The present invention also encompasses variants of the *Schizochytrium aggregatum* cbh1 gene. Variants may contain alterations in the coding regions, non-coding regions, or both. Examples are polynucleotide variants containing alterations which produce silent substitutions, additions, or deletions, but do not alter the properties or activities of the encoded polypeptide. In certain embodiments, nucleotide variants are produced by silent substitutions due to the degeneracy of the genetic code. In further embodiments, *Schizochytrium aggregatum* cbh1 polynucleotide variants can be produced for a variety of reasons, e.g., to optimize codon expression for a particular host (change codons in the bacterial mRNA to those preferred by a lower eukaryotic host such as the yeast *Saccharomyces cerevisiae*).

Also provided in the present invention are allelic variants, orthologs, and/or species homologs. Procedures known in the art can be used to obtain full-length genes, allelic variants, splice variants, full-length coding portions, orthologs, and/or species homologs of genes corresponding to SEQ ID NO:1 or SEQ ID NO:2, using information from the sequences disclosed herein. For example, allelic variants and/or species homologs may be isolated and identified by making suitable probes or primers from the sequences provided herein and screening a suitable nucleic acid source for allelic variants and/or the desired homologue.

Codon Optimization

As used herein the term "codon optimized coding region" means a nucleic acid coding region that has been adapted for expression in the cells of a given vertebrate by replacing at least one, or more than one, or a significant number, of codons with one or more codons that are more frequently used in the genes of that vertebrate.

In general, highly expressed genes in an organism are biased towards codons that are recognized by the most abundant tRNA species in that organism. One measure of this bias is the "codon adaptation index" or "CAI," which measures the extent to which the codons used to encode each amino acid in a particular gene are those which occur most frequently in a reference set of highly expressed genes from an organism.

The CAI of codon optimized sequences of the present invention corresponds to between about 0.8 and 1.0, between about 0.8 and 0.9, or about 1.0. A codon optimized sequence may be further modified for expression in a particular organism, depending on that organism's biological constraints. For example, large runs of "As" or "Ts" (e.g., runs greater than 4, 4, 5, 6, 7, 8, 9, or 10 consecutive bases) can be removed from the sequences if these are known to effect transcription negatively. Furthermore, specific restriction enzyme sites may be removed for molecular cloning purposes. Examples of such restriction enzyme sites include PacI, AscI, BamHI, BglII, EcoRI and XhoI. Additionally, the DNA sequence can be checked for direct repeats, inverted repeats and mirror repeats with lengths of ten bases or longer, which can be modified manually by replacing codons with "second best" codons, i.e., codons that occur at the second highest frequency within the particular organism for which the sequence is being optimized.

Deviations in the nucleotide sequence that comprise the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 1. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the proteins encoded by the DNA.

TABLE 1

| The Standard Genetic Code | | | | |
|---|---|---|---|---|
| | T | C | A | G |
| T | TTT Phe (F) | TCT Ser (S) | TAT Tyr (Y) | TGT Cys (C) |
| | TTC Phe (F) | TCC Ser (S) | TAC Tyr (Y) | TGC |
| | TTA Leu (L) | TCA Ser (S) | TAA Ter | TGA Ter |
| | TTG Leu (L) | TCG Ser (S) | TAG Ter | TGG Trp (W) |
| C | CTT Leu (L) | CCT Pro (P) | CAT His (H) | CGT Arg (R) |
| | CTC Leu (L) | CCC Pro (P) | CAC His (H) | CGC Arg (R) |
| | CTA Leu (L) | CCA Pro (P) | CAA Gln (Q) | CGA Arg (R) |
| | CTG Leu (L) | CCG Pro (P) | CAG Gln (Q) | CGG Arg (R) |
| A | ATT Ile (I) | ACT Thr (T) | AAT Asn (N) | AGT Ser (S) |
| | ATC Ile (I) | ACC Thr (T) | AAC Asn (N) | AGC Ser (S) |
| | ATA Ile (I) | ACA Thr (T) | AAA Lys (K) | AGA Arg (R) |
| | ATG Met (M) | ACG Thr (T) | AAG Lys (K) | AGG Arg (R) |
| G | GTT Val (V) | GCT Ala (A) | GAT Asp (D) | GGT Gly (G) |
| | GTC Val (V) | GCC Ala (A) | GAC Asp (D) | GGC Gly (G) |
| | GTA Val (V) | GCA Ala (A) | GAA Glu (E) | GGA Gly (G) |
| | GTG Val (V) | GCG Ala (A) | GAG Glu (E) | GGG Gly (G) |

Many organisms display a bias for use of particular codons to code for insertion of a particular amino acid in a growing peptide chain. Codon preference or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Given the large number of gene sequences available for a wide variety of animal, plant and microbial species, it is possible to calculate the relative frequencies of codon usage. Codon usage tables are readily available, for example, at http://phenotype.biosci.umbc.edu/codon/sgd/index.php (visited May 7, 2008) or at http://www.kazusa.or.jp/codon/ (visited Mar. 20, 2008), and these tables can be adapted in a number of ways. See Nakamura, Y., et al. "Codon usage tabulated from the international DNA sequence databases: status for the year 2000" Nucl. Acids Res. 28:292 (2000). Codon usage tables for yeast, calculated from GenBank Release 128.0 [15 Feb. 2002], are reproduced below as Table 2. This Table uses mRNA nomenclature, and so instead of thymine (T) which is found in DNA, the Table uses uracil (U) which is found in RNA. The Table has been adapted so that frequencies are calculated for each amino acid, rather than for all 64 codons.

TABLE 2

Codon Usage Table for *Saccharomyces cerevisiae* Genes

| Amino Acid | Codon | Number | Frequency per thousand |
|---|---|---|---|
| Phe | UUU | 170666 | 26.1 |
| Phe | UUC | 120510 | 18.4 |
| Total | | | |
| Leu | UUA | 170884 | 26.2 |
| Leu | UUG | 177573 | 27.2 |
| Leu | CUU | 80076 | 12.3 |
| Leu | CUC | 35545 | 5.4 |
| Leu | CUA | 87619 | 13.4 |
| Leu | CUG | 68494 | 10.5 |
| Total | | | |
| Ile | AUU | 196893 | 30.1 |
| Ile | AUC | 112176 | 17.2 |
| Ile | AUA | 116254 | 17.8 |
| Total | | | |
| Met | AUG | 136805 | 20.9 |
| Total | | | |
| Val | GUU | 144243 | 22.1 |
| Val | GUC | 76947 | 11.8 |
| Val | GUA | 76927 | 11.8 |
| Val | GUG | 70337 | 10.8 |
| Total | | | |
| Ser | UCU | 153557 | 23.5 |
| Ser | UCC | 92923 | 14.2 |
| Ser | UCA | 122028 | 18.7 |
| Ser | UCG | 55951 | 8.6 |
| Ser | AGU | 92466 | 14.2 |
| Ser | AGC | 63726 | 9.8 |
| Total | | | |
| Pro | CCU | 88263 | 13.5 |
| Pro | CCC | 44309 | 6.8 |
| Pro | CCA | 119641 | 18.3 |
| Pro | CCG | 34597 | 5.3 |
| Total | | | |
| Thr | ACU | 132522 | 20.3 |
| Thr | ACC | 83207 | 12.7 |
| Thr | ACA | 116084 | 17.8 |
| Thr | ACG | 52045 | 8.0 |
| Total | | | |
| Ala | GCU | 138358 | 21.2 |
| Ala | GCC | 82357 | 12.6 |
| Ala | GCA | 105910 | 16.2 |
| Ala | GCG | 40358 | 6.2 |
| Total | | | |
| Tyr | UAU | 122728 | 18.8 |
| Tyr | UAC | 96596 | 14.8 |
| Total | | | |
| His | CAU | 89007 | 13.6 |
| His | CAC | 50785 | 7.8 |
| Total | | | |

TABLE 2-continued

Codon Usage Table for *Saccharomyces cerevisiae* Genes

| Amino Acid | Codon | Number | Frequency per thousand |
|---|---|---|---|
| Gln | CAA | 178251 | 27.3 |
| Gln | CAG | 79121 | 12.1 |
| Total | | | |
| Asn | AAU | 233124 | 35.7 |
| Asn | AAC | 162199 | 24.8 |
| Total | | | |
| Lys | AAA | 273618 | 41.9 |
| Lys | AAG | 201361 | 30.8 |
| Total | | | |
| Asp | GAU | 245641 | 37.6 |
| Asp | GAC | 132048 | 20.2 |
| Total | | | |
| Glu | GAA | 297944 | 45.6 |
| Glu | GAG | 125717 | 19.2 |
| Total | | | |
| Cys | UGU | 52903 | 8.1 |
| Cys | UGC | 31095 | 4.8 |
| Total | | | |
| Trp | UGG | 67789 | 10.4 |
| Total | | | |
| Arg | CGU | 41791 | 6.4 |
| Arg | CGC | 16993 | 2.6 |
| Arg | CGA | 19562 | 3.0 |
| Arg | CGG | 11351 | 1.7 |
| Arg | AGA | 139081 | 21.3 |
| Arg | AGG | 60289 | 9.2 |
| Total | | | |
| Gly | GGU | 156109 | 23.9 |
| Gly | GGC | 63903 | 9.8 |
| Gly | GGA | 71216 | 10.9 |
| Gly | GGG | 39359 | 6.0 |
| Total | | | |
| Stop | UAA | 6913 | 1.1 |
| Stop | UAG | 3312 | 0.5 |
| Stop | UGA | 4447 | 0.7 |

By utilizing this or similar tables, one of ordinary skill in the art can apply the frequencies to any given polypeptide sequence, and produce a nucleic acid fragment of a codon-optimized coding region which encodes the polypeptide, but which uses codons optimal for a given species. Codon-optimized coding regions can be designed by various different methods.

In one method, a codon usage table is used to find the single most frequent codon used for any given amino acid, and that codon is used each time that particular amino acid appears in the polypeptide sequence. For example, referring to Table 2 above, for leucine, the most frequent codon is UUG, which is used 27.2% of the time. Thus all the leucine residues in a given amino acid sequence would be assigned the codon UUG.

In another method, the actual frequencies of the codons are distributed randomly throughout the coding sequence. Thus, using this method for optimization, if a hypothetical polypeptide sequence had 100 leucine residues, referring to Table 2 for frequency of usage in the *S. cerevisiae*, about 5, or 5% of the leucine codons would be CUC, about 11, or 11% of the leucine codons would be CUG, about 12, or 12% of the leucine codons would be CUU, about 13, or 13% of the leucine codons would be CUA, about 26, or 26% of the leucine codons would be UUA, and about 27, or 27% of the leucine codons would be UUG.

These frequencies would be distributed randomly throughout the leucine codons in the coding region encoding the hypothetical polypeptide. As will be understood by those of ordinary skill in the art, the distribution of codons in the sequence can vary significantly using this method; however, the sequence always encodes the same polypeptide.

Codon-optimized sequences of the present invention include SEQ ID NO: 4 as follows, where the *Schizochytrium aggregatum* cbh1 cDNA sequence has been codon optimized for *Saccharomyces cerevisiae*. The native *Schizochytrium aggregatum* cbh1 signal sequence is exchanged by replacing it with a slightly modified (one amino acid different) *Saccharomyces cerevisiae* alpha mating factor pre signal sequence (underlined); STOP-codon is double underlined:

(SEQ ID NO: 4)
<u>ATGAGATTTCCATCTATTTTCACTGCTGTTTTGTTCGCAGCCTCATC</u>

<u>GAGTCTAGCT</u>CAACAGGCCGGTACTCTAACGCCTGAGAAACATCCCG

CCTTCTCCGTTAGTACATGTTCCGCTGGAGGCACGTGCACTAGTAAG

ACACAAAGCATAGTCTTAGATGGCAACTGGAGATGGCTTCACAGCAC

ATCCGGTTCAACGAACTGTTATACTGGCAATACATTCGACAAGACGC

TTTGTCCCGATGGTGTCACTTGTGCCGCTAATTGTGCTTTGGACGGT

GCAGACTATACCGGAACGTATGGCATAAAGGCTTCAGGAAATTCCTT

ATCCCTACAGCTTAAAACTGGAAGTAATGTGGGTTCTAGAGTTTACT

TGATGGACGAGCAAGATAAGAATTATCAATTATTCAACTTGAAGAAT

CAGGAGTTCACTTTTGATGTAGACGTGTCAAAGATCGGCTGTGGTTT

AAACGGCGCCTTGTACTTCGTGTCCATGCCAGCAGACGGAGGTTTGT

CCACAACTAACAAAGCTGGTACGAAGTTCGGCACGGGATATTGTGAC

GCCCAATGCCCAAAAGATATTAAGTTCATCAAAGGAAAGGCAAATTC

TGATGGCTGGACAGCTTCCTCAAATAATGCCAACACAGGATTCGGCA

CAACCGGTAGTTGTTGCAATGAAATGGATATATGGGAAGCAAACGGA

ATTAGTAATGCTGTTACACCTCATTCATGTTCTCCTGGAAATGCCGC

ATGTACGTCCGATACGACTTGCGGTAGTGGTGACGGAAACAGATACA

AAGGCTATTGCGATAAGGATGGATGCGACTTTAATCCATTCAGAATG

GGAAATCAAACTTTCTACGGCCCCGGAAAGACGATAGATACTACGAA

GCCACTAACGGTGGTGACACAGTTCATAACGTCAGACAATACAGCTT

CTGGCGACTTAGTTGAAATTAGAAGAAAGTATGTGCAAGGAGGTAAA

GTGTTTGATCAGCCCACCAGCAACGTAGCCGGTGTCAGTGGCAATTC

AATTACAGACACTTTTTGCAAGAACCAGAAATCTGTGTTTGGAGATA

CGAATGACTTCGCAGCTAAGGGCGGATTAAAAGCAATGGGAGATGCA

TTTGCTGATGGTATGGTCCTAGTAATGTCCTTATGGGACGATTACGA

CGTCAATATGCATTGGCTTAATTCACCTTATCCAACCGATGCCGACC

CTACAAAGCCAGGTGTTGCTAGAGGTACATGCAGTATCACTAGTGGA

AAGCCCGCTGATGTGGAGAGCCAAACCCCTGGTGCTACAGTTGTATA

CTCAAACATTAAGACTGGTCCAATTGGCTCTACGTTCAGTGGAGCCC

AGCAACCTGGAGGCCCCGGATCTGGTTCCTCAAGTAGTTCATCCGCA

GGCGGTTCATCCACTACGTCAAGGTCCAGTAGCACTACCTCTAGAGC

TACAACTACCAGCGTCGGAACAACCACTACGACAACCTCTAGTAGGA

CGACCACTACAAGCGCCGCAGGCGGTGTAGTTCAGAAATATGGCCAG

TGTGGAGGTCTAACTTACACAGGACCAACGACTTGCGTATCTGGTAC

AACGTGCACGAAGGCTAATGATTATTACTCCCAATGTTTA<u><u>TAA</u></u>

In one method, a codon usage table is used to find the single most frequent codon used for any given amino acid, and that codon is used each time that particular amino acid appears in the polypeptide sequence. For example, referring to Table 2 above, for leucine, the most frequent codon is UUG, which is used 27.2% of the time. Thus all the leucine residues in a given amino acid sequence would be assigned the codon UUG. The *Saccharomyces cerevisiae* codon-optimized nucleotide sequence encoding *Schizochytrium aggregatum* cbh 1 which has been optimized using this method is presented herein as SEQ ID NO 5:

(SEQ ID NO: 5)
ATG TCA GCC ATT ACT CTT GCC TTA GGT GCT TTA GCC

CTT TCC TCT GTT GTA AAT GCT CAA CAG GCA GGT ACC

TTG ACA CCA GAG AAA CAT CCA GCT TTT AGC GTA TCT

ACC TGT AGT GCA GGT GGA ACT TGT ACT TCT AAG ACC

CAA AGC ATT GTG TTG GAC GGA AAT TGG AGA TGG TTA

CAC TCT ACA AGT GGT TCT ACA AAT TGT TAC ACT GGT

AAC ACT TTT GAC AAG ACT CTA TGC CCC GAT GGT GTA

ACT TGC GCA GCT AAT TGC GCA TTA GAC GGA GCC GAC

TAC ACA GGT ACA TAT GGC ATA AAG GCT TCA GGC AAT

TCT CTG AGT CTA CAA CTT AAG ACA GGT AGC AAC GTT

GGC TCC AGA GTT TAT TTA ATG GAC GAA CAA GAT AAA

AAC TAC CAA CTA TTC AAT CTG AAA AAT CAA GAA TTC

ACA TTT GAT GTC GAT GTT TCC AAA ATC GGC TGT GGT

TTG AAC GGT GCA TTA TAT TTT GTT TCA ATG CCC GCA

GAT GGA GGT TTA TCC ACT ACA AAT AAG GCT GGA ACC

AAA TTT GGA ACG GGA TAT TGT GAC GCT CAA TGT CCT

AAG GAT ATT AAA TTT ATA AAA GGA AAG GCT AAC TCT

GAT GGT TGG ACA GCC TCC AGT AAC AAT GCT AAT ACG

GGC TTC GGT ACC ACA GGA TCC TGT TGC AAT GAA ATG

GAT ATT TGG GAA GCA AAC GGT ATC AGT AAC GCA GTA

ACG CCA CAT TCG TGC TCT CCT GGT AAT GCT GCC TGC

ACC TCT GAT ACA ACT TGT GGT TCT GGC GAC GGT AAC

AGG TAT AAA GGT TAT TGT GAT AAG GAC GGT TGT GAT

TTC AAT CCT TTC AGG ATG GGC AAT CAG ACC TTC TAT

GGT CCC GGT AAA ACA ATT GAT ACT ACG AAA CCT TTA

ACT GTC GTA ACG CAA TTT ATA ACA TCT GAT AAT ACC

GCC TCA GGC GAT CTG GTT GAG ATT CGT AGA AAA TAT

GTC CAA GGA GGT AAA GTG TTT GAT CAA CCA ACC AGC

AAC GTC GCA GGT GTG AGC GGC AAC TCT ATA ACT GAT

ACT TTT TGT AAG AAC CAA AAA TCG GTT TTC GGT GAT

ACT AAT GAT TTC GCA GCT AAG GGT GGC TTG AAA GCT

ATG GGT GAT GCA TTT GCT GAT GGT ATG GTC CTA GTT

ATG TCC TTG TGG GAT GAC TAC GAT GTC AAT ATG CAT

```
TGG TTA AAT TCA CCA TAC CCT ACA GAC GCT GAC CCA

ACA AAG CCA GGT GTT GCT AGA GGA ACA TGC TCT ATT

ACC AGC GGT AAG CCA GCT GAT GTT GAA TCC CAA ACT

CCA GGA GCA ACT GTG GTT TAT AGC AAT ATC AAA ACA

GGT CCT ATC GGA TCA ACT TTT TCA GGT GCC CAG CAA

CCA GGT GGC CCA GGA AGT GGT TCC TCT TCA TCT TCG

TCA GCT GGT GGC TCT TCG ACT ACA TCA AGA TCG TCC

TCA ACG ACT AGT AGA GCC ACG ACA ACC TCA GTT GGT

ACC ACT ACG ACC ACT ACA TCA AGT AGA ACA ACT ACC

ACT AGT GCT GCT GGA GGC GTG GTA CAG AAA TAC GGT

CAG TGC GGT GGT TTG ACG TAT ACT GGT CCA ACC ACA

TGT GTG AGT GGT ACG ACT TGT ACC AAA GCT AAC GAC

TAC TAC TCG CAG TGT TTG
```

In another method, the actual frequencies of the codons are distributed randomly throughout the coding sequence. Thus, using this method for optimization, if a hypothetical polypeptide sequence had 100 leucine residues, referring to Table 2 for frequency of usage in the *S. cerevisiae*, about 5, or 5% of the leucine codons would be CUC, about 11, or 11% of the leucine codons would be CUG, about 12, or 12% of the leucine codons would be CUU, about 13, or 13% of the leucine codons would be CUA, about 26, or 26% of the leucine codons would be UUA, and about 27, or 27% of the leucine codons would be UUG.

These frequencies would be distributed randomly throughout the leucine codons in the coding region encoding the hypothetical polypeptide. As will be understood by those of ordinary skill in the art, the distribution of codons in the sequence can vary significantly using this method, however, the sequence always encodes the same polypeptide. A different *Saccharomyces cerevisiae* codon-optimized nucleotide sequences encoding *Schizochytrium aggregatum* cbh1 which has been optimized using this method is presented herein as SEQ ID NO: 6:

```
                                         (SEQ ID NO: 6)
ATG TCA GCC ATT ACT CTT GCC TTA GGT GCT TTA GCC

CTT TCC TCT GTT GTA AAT GCT CAA CAG GCA GGT ACC

TTG ACA CCA GAG AAA CAT CCA GCT TTT AGC GTA TCT

ACC TGT AGT GCA GGT GGA ACT TGT ACT TCT AAG ACC

CAA AGC ATT GTG TTG GAC GGA AAT TGG AGA TGG TTA

CAC TCT ACA AGT GGT TCT ACA AAT TGT TAC ACT GGT

AAC ACT TTT GAC AAG ACT CTA TGC CCC GAT GGT GTA

ACT TGC GCA GCT AAT TGC GCA TTA GAC GGA GCC GAC

TAC ACA GGT ACA TAT GGC ATA AAG GCT TCA GGC AAT

TCT CTG AGT CTA CAA CTT AAG ACA GGT AGC AAC GTT

GGC TCC AGA GTT TAT TTA ATG GAC GAA CAA GAT AAA

AAC TAC CAA CTA TTC AAT CTG AAA AAT CAA GAA TTC

ACA TTT GAT GTC GAT GTT TCC AAA ATC GGC TGT GGT

TTG AAC GGT GCA TTA TAT TTT GTT TCA ATG CCC GCA

GAT GGA GGT TTA TCC ACT ACA AAT AAG GCT GGA ACC

AAA TTT GGA ACG GGA TAT TGT GAC GCT CAA TGT CCT

AAG GAT ATT AAA TTT ATA AAA GGA AAG GCT AAC TCT

GAT GGT TGG ACA GCC TCC AGT AAC AAT GCT AAT ACG

GGC TTC GGT ACC ACA GGA TCC TGT TGC AAT GAA ATG

GAT ATT TGG GAA GCA AAC GGT ATC AGT AAC GCA GTA

ACG CCA CAT TCG TGC TCT CCT GGT AAT GCT GCC TGC

ACC TCT GAT ACA ACT TGT GGT TCT GGC GAC GGT AAC

AGG TAT AAA GGT TAT TGT GAT AAG GAC GGT TGT GAT

TTC AAT CCT TTC AGG ATG GGC AAT CAG ACC TTC TAT

GGT CCC GGT AAA ACA ATT GAT ACT ACG AAA CCT TTA

ACT GTC GTA ACG CAA TTT ATA ACA TCT GAT AAT ACC

GCC TCA GGC GAT CTG GTT GAG ATT CGT AGA AAA TAT

GTC CAA GGA GGT AAA GTG TTT GAT CAA CCA ACC AGC

AAC GTC GCA GGT GTG AGC GGC AAC TCT ATA ACT GAT

ACT TTT TGT AAG AAC CAA AAA TCG GTT TTC GGT GAT

ACT AAT GAT TTC GCA GCT AAG GGT GGC TTG AAA GCT

ATG GGT GAT GCA TTT GCT GAT GGT ATG GTC CTA GTT

ATG TCC TTG TGG GAT GAC TAC GAT GTC AAT ATG CAT

TGG TTA AAT TCA CCA TAC CCT ACA GAC GCT GAC CCA

ACA AAG CCA GGT GTT GCT AGA GGA ACA TGC TCT ATT

ACC AGC GGT AAG CCA GCT GAT GTT GAA TCC CAA ACT

CCA GGA GCA ACT GTG GTT TAT AGC AAT ATC AAA ACA

GGT CCT ATC GGA TCA ACT TTT TCA GGT GCC CAG CAA

CCA GGT GGC CCA GGA AGT GGT TCC TCT TCA TCT TCG

TCA GCT GGT GGC TCT TCG ACT ACA TCA AGA TCG TCC

TCA ACG ACT AGT AGA GCC ACG ACA ACC TCA GTT GGT

ACC ACT ACG ACC ACT ACA TCA AGT AGA ACA ACT ACC

ACT AGT GCT GCT GGA GGC GTG GTA CAG AAA TAC GGT

CAG TGC GGT GGT TTG ACG TAT ACT GGT CCA ACC ACA

TGT GTG AGT GGT ACG ACT TGT ACC AAA GCT AAC GAC

TAC TAC TCG CAG TGT TTG
```

When using the latter method, the term "about" is used precisely to account for fractional percentages of codon frequencies for a given amino acid. As used herein, "about" is defined as one amino acid more or one amino acid less than the value given. The whole number value of amino acids is rounded up if the fractional frequency of usage is 0.50 or greater, and is rounded down if the fractional frequency of use is 0.49 or less. Using again the example of the frequency of usage of leucine in human genes for a hypothetical polypeptide having 62 leucine residues, the fractional frequency of codon usage would be calculated by multiplying 62 by the frequencies for the various codons. Thus, 7.28 percent of 62 equals 4.51 UUA codons, or "about 5," i.e., 4, 5, or 6 UUA codons, 12.66 percent of 62 equals 7.85 HUG codons or "about 8," i.e., 7, 8, or 9 UUG codons, 12.87 percent of 62 equals 7.98 CUU codons, or "about 8," i.e., 7, 8, or 9 CUU codons, 19.56 percent of 62 equals 12.13 CUC codons or "about 12," i.e., 11, 12, or 13 CUC codons, 7.00 percent of 62 equals 4.34 CUA codons or "about 4," i.e., 3, 4, or 5 CUA codons, and 40.62 percent of 62 equals 25.19 CUG codons, or "about 25," i.e., 24, 25, or 26 CUG codons.

Randomly assigning codons at an optimized frequency to encode a given polypeptide sequence, can be done manually by calculating codon frequencies for each amino acid, and then assigning the codons to the polypeptide sequence randomly. Additionally, various algorithms and computer software programs are readily available to those of ordinary skill in the art. For example, the "EditSeq" function in the Lasergene Package, available from DNAstar, Inc., Madison, Wis., the backtranslation function in the VectorNTI Suite, available from InforMax, Inc., Bethesda, Md., and the "backtranslate" function in the GCG—Wisconsin Package, available from Accelrys, Inc., San Diego, Calif. In addition, various resources are publicly available to codon-optimize coding region sequences, e.g., the "backtranslation" function at http://www.entelechon.com/bioinformatics/backtranslation.php?lang=eng (visited Apr. 15, 2008) and the "backtranseq" function available at http://bioinfo.pbi.nrc.ca:8090/EMBOSS/index.html (visited Jul. 9, 2002). Constructing a rudimentary algorithm to assign codons based on a given frequency can also easily be accomplished with basic mathematical functions by one of ordinary skill in the art.

A further *Saccharomyces cerevisiae* codon-optimized polynucleotide sequence of the present invention, corresponding to SEQ ID NO: 7 is as follows:

```
                                            (SEQ ID NO: 7)
ATG TCA GCC ATT ACT CTT GCC TTA GGT GCT TTA GCC

CTT TCC TCT GTT GTA AAT GCT CAA CAG GCA GGT ACC

TTG ACA CCA GAG AAA CAT CCA GCT TTT AGC GTA TCT

ACC TGT AGT GCA GGT GGA ACT TGT ACT TCT AAG ACC

CAA AGC ATT GTG TTG GAC GGA AAT TGG AGA TGG TTA

CAC TCT ACA AGT GGT TCT ACA AAT TGT TAC ACT GGT

AAC ACT TTT GAC AAG ACT CTA TGC CCC GAT GGT GTA

ACT TGC GCA GCT AAT TGC GCA TTA GAC GGA GCC GAC

TAC ACA GGT ACA TAT GGC ATA AAG GCT TCA GGC AAT

TCT CTG AGT CTA CAA CTT AAG ACA GGT AGC AAC GTT

GGC TCC AGA GTT TAT TTA ATG GAC GAA CAA GAT AAA

AAC TAC CAA CTA TTC AAT CTG AAA AAT CAA GAA TTC

ACA TTT GAT GTC GAT GTT TCC AAA ATC GGC TGT GGT

TTG AAC GGT GCA TTA TAT TTT GTT TCA ATG CCC GCA

GAT GGA GGT TTA TCC ACT ACA AAT AAG GCT GGA ACC

AAA TTT GGA ACG GGA TAT TGT GAC GCT CAA TGT CCT

AAG GAT ATT AAA TTT ATA AAA GGA AAG GCT AAC TCT

GAT GGT TGG ACA GCC TCC AGT AAC AAT GCT AAT ACG

GGC TTC GGT ACC ACA GGA TCC TGT TGC AAT GAA ATG
```

-continued

```
GAT ATT TGG GAA GCA AAC GGT ATC AGT AAC GCA GTA

ACG CCA CAT TCG TGC TCT CCT GGT AAT GCT GCC TGC

ACC TCT GAT ACA ACT TGT GGT TCT GGC GAC GGT AAC

AGG TAT AAA GGT TAT TGT GAT AAG GAC GGT TGT GAT

TTC AAT CCT TTC AGG ATG GGC AAT CAG ACC TTC TAT

GGT CCC GGT AAA ACA ATT GAT ACT ACG AAA CCT TTA

ACT GTC GTA ACG CAA TTT ATA ACA TCT GAT AAT ACC

GCC TCA GGC GAT CTG GTT GAG ATT CGT AGA AAA TAT

GTC CAA GGA GGT AAA GTG TTT GAT CAA CCA ACC AGC

AAC GTC GCA GGT GTG AGC GGC AAC TCT ATA ACT GAT

ACT TTT TGT AAG AAC CAA AAA TCG GTT TTC GGT GAT

ACT AAT GAT TTC GCA GCT AAG GGT GGC TTG AAA GCT

ATG GGT GAT GCA TTT GCT GAT GGT ATG GTC CTA GTT

ATG TCC TTG TGG GAT GAC TAC GAT GTC AAT ATG CAT

TGG TTA AAT TCA CCA TAC CCT ACA GAC GCT GAC CCA

ACA AAG CCA GGT GTT GCT AGA GGA ACA TGC TCT ATT

ACC AGC GGT AAG CCA GCT GAT GTT GAA TCC CAA ACT

CCA GGA GCA ACT GTG GTT TAT AGC AAT ATC AAA ACA

GGT CCT ATC GGA TCA ACT TTT TCA GGT GCC CAG CAA

CCA GGT GGC CCA GGA AGT GGT TCC TCT TCA TCT TCG

TCA GCT GGT GGC TCT TCG ACT ACA TCA AGA TCG TCC

TCA ACG ACT AGT AGA GCC ACG ACA ACC TCA GTT GGT

ACC ACT ACG ACC ACT ACA TCA AGT AGA ACA ACT ACC

ACT AGT GCT GCT GGA GGC GTG GTA CAG AAA TAC GGT

CAG TGC GGT GGT TTG ACG TAT ACT GGT CCA ACC ACA

TGT GTG AGT GGT ACG ACT TGT ACC AAA GCT AAC GAC

TAC TAC TCG CAG TGT TTG
```

A number of options are available for synthesizing codon optimized coding regions designed by any of the methods described above, using standard and routine molecular biological manipulations well known to those of ordinary skill in the art. In one approach, a series of complementary oligonucleotide pairs of 80-90 nucleotides each in length and spanning the length of the desired sequence are synthesized by standard methods. These oligonucleotide pairs are synthesized such that upon annealing, they form double stranded fragments of 80-90 base pairs, containing cohesive ends, e.g., each oligonucleotide in the pair is synthesized to extend 3, 4, 5, 6, 7, 8, 9, 10, or more bases beyond the region that is complementary to the other oligonucleotide in the pair. The single-stranded ends of each pair of oligonucleotides is designed to anneal with the single-stranded end of another pair of oligonucleotides. The oligonucleotide pairs are allowed to anneal, and approximately five to six of these double-stranded fragments are then allowed to anneal together via the cohesive single stranded ends, and then they ligated together and cloned into a standard bacterial cloning vector, for example, a TOPO® vector available from Invitrogen Corporation, Carlsbad, Calif. The construct is then sequenced by standard methods. Several of these constructs consisting of 5 to 6 fragments of 80 to 90 base pair fragments ligated together, i.e., fragments of about 500 base pairs, are prepared, such that the entire desired sequence is represented in a series of plasmid constructs. The inserts of these plasmids are then cut with appropriate restriction enzymes and ligated together to form the final construct. The final construct is then cloned into a standard bacterial cloning vector, and sequenced. Additional methods would be immediately apparent to the skilled artisan. In addition, gene synthesis is readily available commercially.

In certain embodiments, an entire polypeptide sequence, or fragment, variant, or derivative thereof is codon optimized by any of the methods described herein. Various desired fragments, variants or derivatives are designed, and each is then codon-optimized individually. In addition, partially codon-optimized coding regions of the present invention can be designed and constructed. For example, the invention includes a nucleic acid fragment of a codon-optimized coding region encoding a polypeptide in which at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 100% of the codon positions have been codon-optimized for a given species. That is, they contain a codon that is preferentially used in the genes of a desired species, e.g., a yeast species such as *Saccharomyces cerevisiae*, in place of a codon that is normally used in the native nucleic acid sequence.

In additional embodiments, a full-length polypeptide sequence is codon-optimized for a given species resulting in a codon-optimized coding region encoding the entire polypeptide, and then nucleic acid fragments of the codon-optimized coding region, which encode fragments, variants, and derivatives of the polypeptide are made from the original codon-optimized coding region. As would be well understood by those of ordinary skill in the art, if codons have been randomly assigned to the full-length coding region based on their frequency of use in a given species, nucleic acid fragments encoding fragments, variants, and derivatives would not necessarily be fully codon optimized for the given species. However, such sequences are still much closer to the codon usage of the desired species than the native codon usage. The advantage of this approach is that synthesizing codon-optimized nucleic acid fragments encoding each fragment, variant, and derivative of a given polypeptide, although routine, would be time consuming and would result in significant expense.

The codon-optimized coding regions can be versions encoding a cbh1 gene from any strain of *Schizochytrium aggregatum*, or fragments, variants, or derivatives thereof. The present invention therefore encompasses nucleic acid fragments of codon-optimized coding regions encoding the *Schizochytrium aggregatum* Cbh1, the nucleic acid fragments encoding the complete polypeptide, as well as various fragments, variants, and derivatives thereof, although other Cbh1-encoding nucleic acid sources are not excluded.

Codon optimization is carried out for a particular vertebrate species by methods described herein, for example, in certain embodiments codon-optimized coding regions encoding polypeptides of *Schizochytrium aggregatum* Cbh1, or nucleic acid fragments of such coding regions encoding fragments, variants, or derivatives thereof are optimized according to yeast codon usage, e.g., *Saccharomyces cerevisiae*. In particular, the present invention relates to codon-optimized coding regions encoding polypeptides of *Schizochytrium aggregatum* Cbh1, or nucleic acid fragments of such coding regions fragments, variants, or derivatives thereof which have been optimized according to yeast codon usage, for example, *Saccharomyces cerevisiae* codon usage. For example, yeast codon-optimized coding regions encoding polypeptides of *Schizochytrium aggregatum* Cbh1, or nucleic acid fragments of such coding regions encoding fragments, variants, or derivatives thereof, are prepared by incorporating codons preferred for use in yeast genes into the DNA sequence encoding the *Schizochytrium aggregatum* Cbh1 polypeptide. Also provided are polynucleotides, vectors, and other expression constructs comprising codon-optimized coding regions encoding polypeptides of *Schizochytrium aggregatum* Cbh1, or nucleic acid fragments of such coding regions encoding fragments, variants, or derivatives thereof, and various methods of using such polynucleotides, vectors and other expression constructs.

The present invention is further directed towards polynucleotides comprising codon-optimized coding regions encoding polypeptides of *Schizochytrium aggregatum* Cbh1. The invention is also directed to polynucleotides comprising codon-optimized nucleic acid fragments encoding fragments, variants and derivatives of these polypeptides.

The present invention provides isolated polynucleotides comprising codon-optimized coding regions of *Schizochytrium aggregatum* Cbh1, or fragments, variants, or derivatives thereof. In certain embodiments described herein, a codon-optimized coding region encoding SEQ ID NO:3 is optimized according to codon usage in yeast (*Saccharomyces cerevisiae*). Alternatively, a codon-optimized coding region encoding SEQ ID NO:3 may be optimized according to codon usage in any plant, animal, or microbial species.

Polypeptides of the Invention

The present invention is further directed to a novel isolated *Schizochytrium aggregatum* Cbh1 polypeptide. The *Schizochytrium aggregatum* Cbh1 polypeptide is 546 amino acid residues in length. The amino acid sequence of the *Schizochytrium aggregatum* Cbh1 polypeptide corresponds to SEQ ID NO: 3 as follows:

```
                                          (SEQ ID NO: 3)
MSAITLALGALALSSVVNAQQAGTLTPEKHPAFSVSTCSAGGTCTSKT

QSIVLDGNWRWLHSTSGSTNCYTGNTFDKTLCPDGVTCAANCALDGAD

YTGTYGIKASGNSLSLQLKTGSNVGSRVYLMDEQDKNYQLFNLKNQEF

TFDVDVSKIGCGLNGALYFVSMPADGGLSTINKAGTKFGTGYCDAQCP

KDIKFIKGKANSDGWTASSNNANTGFGTTGSCCNEMDIWEANGISNAV

TPHSCSPGNAACTSDTTCGSGDGNRYKGYCDKDGCDFNPFRMGNQTFY

GPGKTIDTTKPLTVVTQFITSDNTASGDLVEIRRKYVQGGKVFDQPTS

NVAGVSGNSITDTFCKNQKSVFGDTNDFAAKGGLKAMGDAFADGMVLV

MSLWDDYDVNMHWLNSPYPTDADPTKPGVARGTCSITSGKPADVESQT

PGATVVYSNIKTGPIGSTFSGAQQPGGPGSGSSSSSSAGGSSTTSRSS

STTSRATTTSVGTTTTTTTSSRTTTTSAAGGVVQKYGQCGGLTYTGPTT

CVSGTTCTKANDYYSQCL
```

The *Schizochytrium aggregatum* Cbh1 protein exhibits the highest degree of homology to a *Botryotinia fuckeliana* Cbh1 cellulase (SEQ ID NO:77) (Accession No. XP_001555330), with 57% identity over the 546 amino acid stretch.

(SEQ ID NO: 77)
MISKVLAFTSLLAAARAQQAGTLTTETHPPLSVSQCTASGCTTSAQSI

VVDANVVRWLHSTTGSTNCYTGNTWDKTLCPDGATCAANCALDGADYS

GVYGITTSGNSIKLNFVTKGANTNVGSRTYLMAAGSTTQYQMLKLLNQ

EFTFDVDVSNLPCGLNGALYFAAMDADGGLSRFPTNKAGAKYGTGYCD

AQCPQDIKFINGVANSVGWTPSSNDVNAGAGQYGSCCSEMDIWEANKI

SAAYTPHPCSVDTQTRCTGTDCGIGARYSSLCDADGCDFNSYRQGNTS

FYGAGLTVNTNKVFTVVTQFITNDGTASGTLKEIRRFYVQNGVVIPNS

QSTIAGVPGNSITDSFCAAQKTAFGDTNEFATKGGLATMSKALAKGMV

LVMSIWDDHTANMLWLDAPYPATKSPSAPGVTRGSCSATSGNPVDVEA

NSPGSSVTFSNIKWGPINSTYTGSGAAPSVPGTTTVSSAPASTATSGA

GGVAKYAQCGGSGYSGATACVSGSTCVALNPYYSQCQ

The present invention further encompasses polypeptides which comprise, or alternatively consist of, an amino acid sequence which is at least about 80%, 85%, 90%, 95%, 96%, 97%, 98%, or 99% identical to, for example, the polypeptide sequence shown in SEQ ID NO:3 and/or polypeptide fragments of any of these polypeptides (e.g., those fragments described herein, or domains of SEQ ID NO:3).

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 95%, 96%, 97%, 98% or 99% identical to, for instance, the amino acid sequence of SEQ ID NO:3 can be determined conventionally using known computer programs. As discussed above, a method for determining the best overall match between a query sequence (a sequence of the present invention) and a subject sequence, also referred to as a global sequence alignment, can be determined using the FASTDB computer program based on the algorithm of Brutlag et al. (*Comp. App. Biosci.* 6:237-245 (1990)). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. Also as discussed above, manual corrections may be made to the results in certain instances.

In certain aspects of the invention, the polypeptides and polynucleotides of the present invention are provided in an isolated form, e.g., purified to homogeneity.

The present invention also encompasses polypeptides which comprise; or alternatively consist of, an amino acid sequence which is at least 80%, 85%, 90%, 95%, 96%, 97%, 98%, 99% similar to a polypeptide comprising the amino acid sequence of SEQ ID NO:3, and to portions of such a polypeptide, with such portion of the polypeptide generally containing at least 30 amino acids and more preferably at least 50 amino acids.

As known in the art "similarity" between two polypeptides is determined by comparing the amino acid sequence and conserved amino acid substitutes thereto of the polypeptide to the sequence of a second polypeptide.

The present invention further relates to a fragment, variant, derivative, or analog of the polypeptide comprising the amino acid sequence of SEQ ID NO:3.

Fragments or portions of the polypeptides of the present invention may be employed for producing the corresponding full-length polypeptide by peptide synthesis, therefore, the fragments may be employed as intermediates for producing the full-length polypeptides.

Fragments of *Schizochytrium aggregatum* Cbh1 polypeptides of the present invention encompass domains, proteolytic fragments, deletion fragments and in particular, fragments of *Schizochytrium aggregatum* Cbh1 polypeptides which retain any specific biological activity of the *Schizochytrium aggregatum* Cbh1 protein. Polypeptide fragments further include any portion of the polypeptide which comprises a catalytic activity of the Cbh1 protein.

The variant, derivative or analog of the polypeptide comprising the amino acid sequence of SEQ ID NO:3, can be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide for purification of the polypeptide or (v) one in which a fragment of the polypeptide is soluble, i.e., not membrane bound, yet still binds ligands to the membrane bound receptor. Such variants, derivatives and analogs are deemed to be within the scope of those skilled in the art from the teachings herein.

The present invention also encompasses variants of the polynucleotide sequence disclosed in SEQ ID NO:1 or SEQ ID NO:2, the complementary strand thereto, and variants of the polypeptide sequence disclosed in SEQ ID NO:3. Variants include one or several nucleic acid/amino acid deletions, substitutions and/or additions, where the variant retains cellobiohydrolase activity. Preferably, the variants (including derivatives) encode less than 50 amino acid substitutions and/or additions and/or deletions, less than 40 amino acid substitutions and/or additions and/or deletions, less than 30 amino acid substitutions and/or additions and/or deletions, less than 25 amino acid substitutions and/or additions and/or deletions, less than 20 amino acid substitutions and/or additions and/or deletions, less than 15 amino acid substitutions and/or additions and/or deletions, less than 5 amino acid substitutions and/or additions and/or deletions, less than 4 amino acid substitutions and/or additions and/or deletions, less than 3 amino acid substitutions and/or additions and/or deletions or less than 2 amino acid substitutions and/or additions and/or deletions relative to the reference Cbh1 polypeptide, domain, fragment or derivative thereof.

The polypeptides of the present invention further include variants of the polypeptides. A "variant" of the polypeptide can be a conservative variant, or an allelic variant. As used herein, a conservative variant refers to alterations in the amino acid sequence that do not adversely affect the biological functions of the protein. A substitution, insertion or deletion is said to adversely affect the protein when the altered sequence prevents or disrupts a biological function associated with the protein. For example, the overall charge, structure or hydrophobic-hydrophilic properties of the protein can be altered without adversely affecting a biological activity. Accordingly, the amino acid sequence can be altered, for example to render the peptide more hydrophobic or hydrophilic, without adversely affecting the biological activities of the protein.

A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., cellobiohydrolase activity).

By an "allelic variant" is intended alternate forms of a gene occupying a given locus on a chromosome of an organism. Genes II, Lewin, B., ed., John Wiley & Sons, New York (1985). Non-naturally occurring variants may be produced using art-known mutagenesis techniques. Allelic variants, though possessing a slightly different amino acid sequence than those recited above, will still have the same or similar biological functions associated with the *Schizochytrium aggregatum* Cbh1 protein.

The allelic variants, the conservative substitution variants, and members of the Cbh1 protein family, will have an amino acid sequence having at least 75% amino acid sequence identity with the *Schizochytrium aggregatum* Cbh1 amino acid sequence set forth in SEQ ID NO:3, at least 80%, at least 90%, at least 95%. Identity or homology with respect to such sequences is defined herein as the percentage of amino acid residues in the candidate sequence that are identical with the known peptides, after aligning the sequences and introducing gaps, if necessary, to achieve the maximum percent homology, and not considering any conservative substitutions as part of the sequence identity. N terminal, C terminal or internal extensions, deletions, or insertions into the peptide sequence shall not be construed as affecting homology.

Standard techniques known to those of skill in the art can be used to introduce mutations in the nucleotide sequence encoding a molecule of the invention, including, for example, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the *Schizochytrium aggregatum* Cbh1 amino acid sequence of the present invention.

Thus, the proteins and peptides of the present invention include molecules comprising the amino acid sequence of SEQ ID NO: 3 or fragments thereof having a consecutive sequence of at least about 3, 4, 5, 6, 10, 15, 20, 25, 30, 35, 40, 50, 60, 70, 80, 90, 100, 200, 300, 400 or more amino acid residues of the *Schizochytrium aggregatum* Cbh1 polypeptide sequence; amino acid sequence variants of such sequences wherein at least one amino acid residue has been inserted N- or C terminal to, or within, the disclosed sequence; amino acid sequence variants of the disclosed sequences, or their fragments as defined above, that have been substituted by another residue. Contemplated variants further include those containing predetermined mutations by, e.g., homologous recombination, site-directed or PCR mutagenesis, and the corresponding proteins of other animal species, including but not limited to rabbit, rat, porcine, bovine, ovine, equine and non-human primate species, the alleles or other naturally occurring variants of the family of proteins; and derivatives wherein the protein has been covalently modified by substitution, chemical, enzymatic, or other appropriate means with a moiety other than a naturally occurring amino acid (for example, a detectable moiety such as an enzyme or radioisotope).

Using known methods of protein engineering and recombinant DNA technology, variants may be generated to improve or alter the characteristics of the *Schizochytrium aggregatum* Cbh1 polypeptides. For instance, one or more amino acids can be deleted from the N-terminus or C-terminus of the secreted protein without substantial loss of biological function.

Thus, the invention further includes *Schizochytrium aggregatum* Cbh1 polypeptide variants which show substantial biological activity. Such variants include deletions, insertions, inversions, repeats, and substitutions selected according to general rules known in the art so as have little effect on activity.

The skilled artisan is fully aware of amino acid substitutions that are either less likely or not likely to significantly effect protein function (e.g., replacing one aliphatic amino acid with a second aliphatic amino acid), as further described below.

For example, guidance concerning how to make phenotypically silent amino acid substitutions is provided in Bowie et al., "Deciphering the Message in Protein Sequences: Tolerance to Amino Acid Substitutions," *Science* 247:1306-1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, *Science*

244:1081-1085 (1989).) The resulting mutant molecules can then be tested for biological activity.

As the authors state, these two strategies have revealed that proteins are often surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

The terms "derivative" and "analog" refer to a polynucleotide or polypeptide differing from the *Schizochytrium aggregatum* Cbh1 polynucleotide or polypeptide, but retaining essential properties thereof. Generally, derivatives and analogs are overall closely similar, and, in many regions, identical to the *Schizochytrium aggregatum* Cbh1 polynucleotide or polypeptide. The term "derivative" and "analog" when referring to *Schizochytrium aggregatum* polypeptides of the present invention include any polypeptides which retain at least some of the activity of the corresponding native polypeptide, e.g., the endoglucanase activity, or the activity of the its catalytic domain.

Derivatives of *Schizochytrium aggregatum* Cbh1 polypeptides of the present invention are polypeptides which have been altered so as to exhibit additional features not found on the native polypeptide. Derivatives can be covalently modified by substitution, chemical, enzymatic, or other appropriate means with a moiety other than a naturally occurring amino acid (for example, a detectable moiety such as an enzyme or radioisotope). Examples of derivatives include fusion proteins.

An analog is another form of a *Schizochytrium aggregatum* Cbh1 polypeptide of the present invention. An "analog" also retains substantially the same biological function or activity as the polypeptide of interest, i.e., functions as a *Schizochytrium aggregatum* Cbh1. An analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

Tethered and Secreted *Schizochytrium aggregatum* Cbh1 Polypeptides

In certain aspects of the invention, the *Schizochytrium aggregatum* Cbh1 is prepared as a tethered fusion polypeptide.

As used herein, a protein is "tethered" to an organism's cell surface if at least one terminus of the protein is bound, covalently and/or electrostatically for example, to the cell membrane or cell wall. It will be appreciated that a tethered protein may include one or more enzymatic regions that may be joined to one or more other types of regions at the nucleic acid and/or protein levels (e.g., a promoter, a terminator, an anchoring domain, a linker, a signaling region, etc.). While the one or more enzymatic regions may not be directly bound to the cell membrane or cell wall (e.g., such as when binding occurs via an anchoring domain), the protein is nonetheless considered a "tethered enzyme" according to the present specification.

Tethering can, for example, be accomplished by incorporation of an anchoring domain into a recombinant protein that is heterologously expressed by a cell, or by prenylation, fatty acyl linkage, glycosyl phosphatidyl inositol anchors or other suitable molecular anchors which may anchor the tethered protein to the cell membrane or cell wall of the host cell. A tethered protein can be tethered at its amino terminal end or optionally at its carboxy terminal end.

Such tethered polypeptides can provide an advantage for cell growth, where saccharified substrate is unable to diffuse away from the cell before being metabolized. In addition, a portion of a population of cells expressing a *Schizochytrium aggregatum* tethered Cbh1 can exhibit enhanced expression of the tethered enzyme relative to the overall population. This portion may exhibit enhanced binding to the substrate and improved growth characteristics.

In other aspects of the invention, the *Schizochytrium aggregatum* Cbh1 is a secreted polypeptide.

As used herein, "secreted" means released into the extracellular milieu, for example into the media. Although tethered proteins may have secretion signals as part of their immature amino acid sequence, they are maintained as attached to the cell surface, and do not fall within the scope of secreted proteins as used herein.

As used herein, "flexible linker sequence" refers to an amino acid sequence which links a cell wall anchoring amino acid sequence with an amino acid sequence that contains the desired enzymatic activity. The flexible linker sequence allows for necessary freedom for the amino acid sequence that contains the desired enzymatic activity to have reduced steric hindrance with respect to proximity to the cell and may also facilitate proper folding of the amino acid sequence that contains the desired enzymatic activity.

Homology of *Schizochytrium aggregatum* Cbh1 Polypeptides to GHF7 Family Members Using BLAST analysis, SEQ ID NO:3, corresponding to the amino acid sequence of the *Schizochytrium aggregatum* Cbh1, was found to be homologous to several members of the glycosyl hydrolase, family 7 (FIG. 3). As noted above, glycosyl hydrolases, or O-glycosyl hydrolases, are a widespread group of enzymes that hydrolyse the glycosidic bond between two or more carbohydrates, or between a carbohydrate and a non-carbohydrate moiety. A classification system for glycosyl hydrolases, based on sequence similarity, has led to the definition of 85 different families. Because the folding of certain families is better conserved than their sequences, some of the families can be grouped in "clans".

Glycoside hydrolase family 7 (also referred to as GH7 or GHF7) comprises enzymes with several known activities including endoglucanase activity and cellobiohydrolase (CBH) activity. These enzymes were formerly known as cellulase family C. Exoglucanases such as cellobiohydrolases play a role in the conversion of cellulose to glucose by cutting the dissaccharide cellobiose from the reducing or nonreducing end of the cellulose polymer chain. Cbh1 s generally cut reducing ends, while Cbh2s cut nonreducing ends. See http://www.cazy.org/fam/GH7.html (last updated May 23, 2008). Structurally, cellulases and xylanases generally consist of a catalytic domain (CD) joined to a cellulose-binding domain (CBD) via a linker region that is rich in proline and/or hydroxy-amino acids. In type I exoglucanases, the CBD domain is found at the C-terminal extremity of these enzyme (this short domain forms a hairpin loop structure stabilised by 2 disulphide bridges).

The "catalytic domain" is also referred to as the active site. The structure and chemical properties of the active site allow the recognition and binding of the substrate. The active site is usually a small pocket at the surface of the enzyme that contains residues responsible for the substrate specificity (charge, hydrophobicity, steric hindrance) and catalytic residues which often act as proton donors or acceptors or are responsible for binding a cofactor such as PLP, TPP or NAD. The active site is also the site of inhibition of enzymes. In the case of *Schizochytrium aggregatum* Cbh1, the catalytic domain contains residues that allow the recognition and binding of the Cbh1 exoglucanase to the cellulose substrate. Examples of such amino acid residues include the proton donor, probable secondary nucleophile, and catalytic nucleophile as shown in FIG. 3.

A "cellulose-binding domain" is a domain that naturally binds to cellulose. It is thought that CBDs concentrate the catalytic domains on the surface of the insoluble cellulose substrate. The CBD of the present invention is comprised of three folded anti-parallel β-sheets. It is wedge-shaped, with a hydrophobic flat face that interacts with the cellulose surface via two tyrosine residues and a glutamine, and a hydrophilic face. The CBD binds to both amorphous and crystalline cellulose.

"Cellulose" is an unbranched homopolymer of β(1-4) linked glucose subunits. Crystalline cellulose presents a surface array of parallel, closely-packed cellulose chains to a CBD. Amorphous cellulose presents antiparallel or disordered chains to a CBD. The binding site of a CBD is adapted to binding to a surface.

Vectors and Host Cells

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which can be, for example, a cloning vector or an expression vector. The vector can be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; and yeast plasmids. However, any other appropriate vector known to one of ordinary skill in the art may be used.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively associated with an appropriate expression control sequence(s) (promoter) to direct mRNA synthesis. Representative examples of such promoters are as follows:

| Gene | Organism | Systematic name | Reason for use/benefits |
|------|----------|-----------------|-------------------------|
| PGK1 | S. cerevisiae | YCR012W | Strong constitutive promoter |
| ENO1 | S. cerevisiae | YGR254W | Strong constitutive promoter |
| TDH3 | S. cerevisiae | YGR192C | Strong constitutive promoter |
| TDH2 | S. cerevisiae | YJR009C | Strong constitutive promoter |
| TDH1 | S. cerevisiae | YJL052W | Strong constitutive promoter |
| ENO2 | S. cerevisiae | YHR174W | Strong constitutive promoter |
| GPM1 | S. cerevisiae | YKL152C | Strong constitutive promoter |
| TPI1 | S. cerevisiae | YDR050C | Strong constitutive promoter |

Additionally, promoter sequences from stress and starvation response genes are useful in the present invention. In some embodiments, promoter regions from the *S. cerevisiae* genes GAC1, GET3, GLC7, GSH1, GSH2, HSF1, HSP12, LCB5, LRE1, LSP1, NBP2, PIL1, PIM1, SGT2, SLG1, WHI2, WSC2, WSC3, WSC4, YAP1, YDC1, HSP104, HSP26, ENA1, MSN2, MSN4, SIP2, SIP4, SIP5, DPL1, IRS4, KOG1, PEP4, HAP4, PRB1, TAX4, ZPR1, ATG1, ATG2, ATG10, ATG11, ATG12, ATG13, ATG14, ATG15, ATG16, ATG17, ATG18, and ATG19 can be used. Any suitable promoter to drive gene expression in the host cells of the invention can be used.

Additionally, the *E. coli*, lac or trp, and other promoters known to control expression of genes in prokaryotic or lower eukaryotic cells can be used. The expression vector also contains a ribosome binding site for translation initiation and a transcription terminator. The vector can also include appropriate sequences for amplifying expression, or can include additional regulatory regions.

In addition, the expression vectors may contain one or more selectable marker genes to provide a phenotypic trait for selection of transformed host cells such as URA3, HIS3, LEU2, TRP1, LYS2 or ADE2, dihydrofolate reductase, neomycin (G418) resistance or zeocin resistance for eukaryotic cell culture, or tetracycline or ampicillin resistance in *E. coli*.

The vector containing the appropriate DNA sequence as herein, as well as an appropriate promoter or control sequence, can be employed to transform an appropriate host to permit the host to express the protein.

Thus, in certain aspects, the present invention relates to host cells containing the above-described constructs. The host cell can be a higher eukaryotic cell, such as a mammalian cell, or a lower eukaryotic cell, such as a yeast cell, e.g., *Saccharomyces cerevisiae*, or the host cell can be a prokaryotic cell, such as a bacterial cell.

Representative examples of appropriate hosts include bacterial cells, such as *E. coli, Streptomyces, Salmonella typhimurium*; thermophilic or mesophlic bacteria; fungal cells, such as yeast; and plant cells, etc. The selection of an appropriate host is deemed to be within the scope of those skilled in the art from the teachings herein.

Appropriate fungal hosts include yeast. In certain aspects of the invention the yeast is *Saccharomyces cerevisiae, Kluveromyces lactus, Schizzosaccharomyces pombe, Candida albicans, Pichia pastoris, Pichia stipitis, Yarrowia lipolytica, Hansenula polymorpha, Phaffia rhodozyma, Candida utilis, Arxula adeninivorans, Debaryomyces hansenii, Debaryomyces polymorphus, Schwanniomyces occidentalis, Issatchenkia orientalis*, or *Kluveromyces marxianus*.

Major groups of thermophilic bacteria include eubacteria and archaebacteria. Thermophilic eubacteria include: phototropic bacteria, such as cyanobacteria, purple bacteria, and green bacteria; Gram-positive bacteria, such as *Bacillus, Clostridium*, Lactic acid bacteria, and *Actinomyces*; and other eubacteria, such as *Thiobacillus*, Spirochete, *Desulfotomacu-*

*lum*, Gram-negative aerobes, Gram-negative anaerobes, and *Thermotoga*. Within archaebacteria are considered Methanogens, extreme thermophiles (an art-recognized term), and *Thermoplasma*. In certain embodiments, the present invention relates to Gram-negative organotrophic thermophiles of the genera *Thermus*, Gram-positive eubacteria, such as genera *Clostridium*, and also which comprise both rods and cocci, genera in group of eubacteria, such as *Thermosipho* and *Thermotoga*, genera of Archaebacteria, such as *Thermococcus, Thermoproteus* (rod-shaped), *Thermofilum* (rod-shaped), *Pyrodictium, Acidianus, Sulfolobus, Pyrobaculum, Pyrococcus, Thermodiscus, Staphylothermus, Desulfurococcus, Archaeoglobus*, and *Methanopyrus*. Some examples of thermophilic microorganisms (including bacteria, prokaryotic microorganisms such as fungi), which may be suitable for the present invention include, but are not limited to: *Clostridium thermosulfurogenes, Clostridium cellulolyticum, Clostridium thermocellum, Clostridium thermohydrosulfuricum, Clostridium thermoaceticum, Clostridium thermosaccharolyticum, Clostridium tartarivorum, Clostridium thermocellulaseum, Thermoanaerobacterium thermosaccarolyticum, Thermoanaerobacterium saccharolyticum, Thermobacteroides acetoethylicus, Thermoanaerobium brockii, Methanobacterium thermoautotrophicum, Pyrodictium occultum, Thermoproteus neutrophilus, Thermofilum librum, Thermothrix thioparus, Desulfovibrio thermophilus, Thermoplasma acidophilum, Hydrogenomonas thermophilus, Thermomicrobium roseum, Thermus flavas, Thermus ruber, Pyrococcus furiosus, Thermus aquaticus, Thermus thermophilus, Chloroflexus aurantiacus, Thermococcus litoralis, Pyrodictium abyssi, Bacillus stearothermophilus, Cyanidium caldarium, Mastigocladus laminosus, Chlamydothrix calidissima, Chlamydothrix penicillata, Thiothrix carnea, Phormidium tenuissimum, Phormidium geysericola, Phormidium subterraneum, Phormidium bijahensi, Oscillatoria filiformis, Synechococcus lividus, Chloroflexus aurantiacus, Pyrodictium brockii, Thiobacillus thiooxidans, Sulfolobus acidocaldarius, Thiobacillus thermophilica, Bacillus stearothermophilus, Cercosulcifer hamathensis, Vahlkampfia reichi, Cyclidium citrullus, Dactylaria gallopava, Synechococcus lividus, Synechococcus elongatus, Synechococcus minervae, Synechocystis aquatilus, Aphanocapsa thermalis, Oscillatoria terebriformis, Oscillatoria amphibia, Oscillatoria germinata, Oscillatoria okenii, Phormidium laminosum, Phormidium parparasiens, Symploca thermalis, Bacillus acidocaldarias, Bacillus coagulans, Bacillus thermocatenalatus, Bacillus licheniformis, Bacillus pamilas, Bacillus macerans, Bacillus circulars, Bacillus laterosporus, Bacillus brevis, Bacillus subtilis, Bacillus sphaericus, Desulfotomaculum nigrificans, Streptococcus thermophilus, Lactobacillus thermophilus, Lactobacillus bulgaricus, Bifidobacterium thermophilum, Streptomyces fragmentosporus, Streptomyces thermonitrificans, Streptomyces thermovulgaris, Pseudonocardia thermophila, Thermoactinomyces vulgaris, Thermoactinomyces sacchari, Thermoactinomyces candidas, Thermomonospora curvata, Thermomonospora viridis, Thermomonospora citrina, Microbispora thermodiastatica, Microbispora aerata, Microbispora bispora, Actinobifida dichotomica, Actinobifida chromogena, Micropolyspora caesia, Micropolyspora faeni, Micropolyspora cectivugida, Micropolyspora cabrobrunea, Micropolyspora thermovirida, Micropolyspora viridinigra, Methanobacterium thermoautothropicum*, variants thereof, and/or progeny thereof.

In certain embodiments, the present invention relates to thermophilic bacteria of the genera *Thermoanaerobacterium* or *Thermoanaerobacter*, including, but not limited to, species selected from the group consisting of: *Thermoanaerobacterium thermosulfurigenes, Thermoanaerobacterium aotearoense, Thermoanaerobacterium polysaccharolyticum, Thermoanaerobacterium zeae, Thermoanaerobacterium xylanolyticum, Thermoanaerobacterium saccharolyticum, Thermoanaerobium brockii, Thermoanaerobacterium thermosaccharolyticum, Thermoanaerobacter thermohydrosulfuricus, Thermoanaerobacter ethanolicus, Thermoanaerobacter brockii*, variants thereof, and progeny thereof.

In certain embodiments, the present invention relates to microorganisms of the genera *Geobacillus, Saccharococcus, Paenibacillus, Bacillus*, and *Anoxybacillus*, including, but not limited to, species selected from the group consisting of: *Geobacillus thermoglucosidasius, Geobacillus stearothermophilus, Saccharococcus caldoxylosilyticus, Saccharoccus thermophilus, Paenibacillus campinasensis, Bacillus flavothermus, Anoxybacillus kamchatkensis, Anoxybacillus gonensis*, variants thereof, and progeny thereof.

The present invention also includes recombinant constructs comprising one or more of the sequences as broadly described above. The constructs comprise a vector, such as a plasmid or viral vector, into which a sequence of the invention has been inserted, in a forward or reverse orientation. In one aspect of this embodiment, the construct further comprises regulatory sequences, including, for example, a promoter, operably associated to the sequence. Large numbers of suitable vectors and promoters are known to those of skill in the art, and are commercially available. The following vectors are provided by way of example only.

Yeast: Yeast vectors include those of five general classes, based on their mode of replication in yeast: YIp (yeast integrating plasmids), YRp (yeast replicating plasmids), YCp (yeast replicating plasmids with centromere (CEN) elements incorporated), YEp (yeast episomal plasmids), and YLp (yeast linear plasmids). With the exception of the YLp plasmids, all of these plasmids can be maintained in *E. coli* as well as in *Saccharomyces cerevisiae* and thus are also referred to as yeast shuttle vectors.

In certain aspects, these plasmids contain types of selectable genes including plasmid-encoded drug-resistance genes and/or cloned yeast genes, where the drug resistant gene and/or cloned yeast gene can be used for selection. Drug-resistance genes include, e.g., ampicillin, kanamycin, tetracycline, neomycin, hygromycin, zeocin, NAT, arsentied and sulfometuron methyl. Cloned yeast genes include HIS3, LEU2, LYS2, TRP1, URA3, TRP1 and SMR1. Other yeast genes that may be used correspond to different appropriate auxotrophic or dominant markers known to one of ordinary skill in the art. pYAC vectors may also be utilized to clone large fragments of exogenous DNA on to artificial linear chromosomes.

In certain aspects of the invention, YCp plasmids, which have high frequencies of transformation and increased stability to due the incorporated centromere elements, are utilized. In certain other aspects of the invention, YEp plasmids, which provide for high levels of gene expression in yeast, are utilized. In additional aspects of the invention, YRp plasmids are utilized.

In particular embodiments, the vector of the present invention is a plasmid selected from the group consisting of the pMU506 or the pMU562 plasmid.

Representative examples of bacterial plasmids include pQE70, pQE60, pQE-9 (Qiagen), pbs, pD10, phagescript, psiX174, pBluescript SK, pbsks, pNH8A, pNH16a, pNH18A, pNH46A (Stratagene); ptrc99a, pKK223 3, pKK233-3, pDR540, pRIT5 (Pharmacia).

However, any other appropriate plasmid or vector known to one of ordinary skill in the art may be used.

Promoter regions can be selected from any desired gene. Particular named yeast promoters include the constitute promoter ENO1, the PGK1 promoter, the TEF1 promoter and the HXT7 promoter. Particular named bacterial promoters include lad, lacZ, T3, T7, gpt, lambda PR, PL and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

Introduction of the construct into a host yeast cell, e.g., *Saccharomyces cerevisiae*, can be effected by, e.g., lithium acetate transformation, spheroplast transformation, or transformation by electroporation, as described in Current Protocols in Molecular Biology, 13.7.1-13.7.10.

Introduction of the construct in host cells can also be effected by calcium phosphate transfection, DEAE-Dextran mediated transfection, or electroporation. (Davis, L., et al., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Following creation of a suitable host cell and growth of the host cell to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Yeast cells, e.g., *Saccharomyces cerevisiae*, employed in expression of proteins can be manipulated as follows. The Cbh polypeptides can be recovered and purified from recombinant cell cultures by methods including spheroplast preparation and lysis, cell disruption using glass beads, and cell disruption using liquid nitrogen for example.

Various mammalian cell culture systems can also be employed to express recombinant protein. Expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences.

Additional methods include ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The Cbh polypeptides can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

Cbh polypeptides are provided in an isolated form, and, in certain aspects, are substantially purified. A recombinantly produced version of a Cbh polypeptide, including the secreted polypeptide, can be substantially purified using techniques described herein or otherwise known in the art, such as, for example, by the one-step method described in Smith and Johnson, Gene 67:31-40 (1988). Cbh polypeptides also can be purified from natural, synthetic or recombinant sources using techniques described herein or otherwise known in the art.

The Cbh polypeptides of the present invention can be in the form of the secreted protein, including the mature form, or may be a part of a larger protein, such as a fusion protein. It is often advantageous to include an additional amino acid sequence which contains secretory or leader sequences, prosequences, sequences which aid in purification, such as multiple histidine residues, or an additional sequence for stability during recombinant production.

Secretion of desired proteins into the growth media has the advantages of simplified and less costly purification procedures. It is well known in the art that secretion signal sequences are often useful in facilitating the active transport of expressible proteins across cell membranes. The creation of a transformed host capable of secretion may be accomplished by the incorporation of a DNA sequence that codes for a secretion signal which is functional in the host production host. Methods for choosing appropriate signal sequences are well known in the art (see for example EP 546049; WO 9324631). The secretion signal DNA or facilitator may be located between the expression-controlling DNA and the instant gene or gene fragment, and in the same reading frame with the latter.

Heterologous Expression of *Schizochytrium aggregatum* Cbh1 in Host Cells

In order to address the limitations of the previous systems, the present invention provides a novel cbh1 gene and Cbh1 polypeptide that can be effectively and efficiently utilized in a consolidated bioprocessing system.

One aspect of the invention is thus related to the efficient production of saccharolytic enzymes (cellulases and hemicellulases) to aid in the digestion of cellulose and generation of ethanol.

A "saccharolytic enzyme" is also referred to as a cellulase, and can correspond to any enzyme involved in cellulase digestion, metabolism and/or hydrolysis, including an endoglucananse, exoglucanase, or β-glucosidase. An exoglucanase can be, for example, a cellobiohydrolase.

In particular, the invention relates to the production of *Schizochytrium aggregatum* Cbh1 in a host organism. In certain embodiments, this host organism is yeast, such as *Saccharomyces cerevisiae*.

In certain embodiments of the present invention, a host cell comprising a vector which encodes and expresses *Schizochytrium aggregatum* Cbh1 that is utilized for consolidated bioprocessing is co-cultured with additional host cells expressing one or more additional endoglucanases, cellobiohydrolases and/or β-glucosidases. In other embodiments of the invention, a host cell transformed with *Schizochytrium aggregatum* Cbh1 is transformed with and expresses one or more heterologous endoglucanases, cellobiohydrolases or β-glucosidases. The endoglucanase, cellobiohydrolase and/or β-glucosidase can be any suitable endoglucanase, cellobiohydrolase and β-glucosidase derived from, for example, a fungal or bacterial source. Furthermore, the endoglucanase, cellobiohydrolase and/or β-glucosidase can be either tethered or secreted.

In certain embodiments of the invention, the endoglucanase(s) can be an endoglucanase I or an endoglucanase II isoform, paralogue or orthologue. In another embodiment, the endoglucanase expressed by the host cells of the present invention can be recombinant endo-1,4-β-glucanase. In certain embodiments of the present invention, the endoglucanase is an endoglucanase I from *Trichoderma reesei*. In another embodiment, the endoglucanase is encoded by the polynucleotide sequence of SEQ ID NO:59 (Accession No. M15665), as follows:

```
                                         (SEQ ID NO: 59)
MAPSVTLPLTTAILAIARLVAAQQPGTSTPEVHPKLTTYKCTKSGGCV

AQDTSVVLDWNYRWMHDANYNSCTVNGGVNTTLCPDEATCGKNCFIEG

VDYAASGVTTSGSSLTMNQYMPSSSGGYSSVSPRLYLLDSDGEYVMLK

LNGQELSFDVDLSALPCGENGSLYLSQMDENGGANQYNTAGANYGSGY

CDAQCPVQTWRNGTLNTSHQGFCCNEMDILEGNSRANALTPHSCTATA

CDSAGCGFNPYGSGYKSYYGPGDTVDTSKTFTIITQFNTDNGSPSGNL

VSITRKYQQNGVDIPSAQPGGDTISSCPSASAYGGLATMGKALSSGMV

LVFSIWNDNSQYMNWLDSGNAGPCSSTEGNPSNILANNPNTHVVFSNI

RWGDIGSTTNSTAPPPPPASSTTFSTTRRSSTTSSSPSCTQTHWGQCG

GIGYSGCKTCTSGTTCQYSNDYYSQCL
```

In certain embodiments of the present invention the (β-glucosidase is derived from *Saccharomycopsis fibuligera*. In certain embodiments, the β-glucosidase is a β-glucosidase I or a β-glucosidase II isoform, paralogue or orthologue. In certain other embodiments, the β-glucosidase expressed by the cells of the present invention can be recombinant β-glucanase I from a *Saccharomycopsis fibuligera* source, corresponding to SEQ ID NO: 60 (Accession No. M22475), as follows:

```
                                         (SEQ ID NO: 60)
MLMIVQLLVFALGLAVAVPIQNYTQSPSQRDESSQWVSPHYYPTPQGG

RLQDVWQEAYARAKAIVGQMTIVEKVNLTTGTGWQLDPCVGNTGSVPR

FGIPNLCLQDGPLGVRFADFVTGYPSGLATGATFNKDLFLQRGQALGH

EFNSKGVHIALGPAVGPLGVKARGGRNFEAGSDPYLQGTAAAATIKGL

QENNVMACVKHFIGNEQEKYRQPDDINPATNQTTKEAISANIPDRAMH

ALYLWPFADSVRAGVGSVMCSYNRVNNTYACENSYMMNHLLKEELGFQ

GFVVSDWGAQLSGVYSAISGLDMSMPGEVYGGWNTGTSFWGQNLTKAI

YNETVPIERLDDMATRILAALYATNSFPTEDHLPNFSSWTTKEYGNKY

YADNTTEIVKVNYNVDPSNDFTEDTALKVAEESIVLLKNENNTLPISP

EKAKRLLLSGIAAGPDPIGYQCEDQSCTNGALFQGWGSGSVGSPKYQV

TPFEEISYLARKNKMQFDYIRESYDLAQVTKVASDAHLSIVVVSAASG

EGYITVDGNQGDRKNLTLWNNGDKLIETVAENCANTVVVVTSTGQINF

EGFADHPNVTAIVWAGPLGDRSGTAIANILFGKANPSGHLPFTIAKTD

DDYIPIETYSPSSGEPEDNHLVENDLLVDYRYFEEKNIEPRYAFGYGL

SYNEYEVSNAKVSAAKKVDEELPEPATYLSEFSYQNAKDSKNPSDAFA

PADLNRVNEYLYPYLDSNVTLKDGNYEYPDGYSTEQRTTPNQPGGGLG

GNDALWEVAYNSTDKFVPQGNSTDKFVPQLYLKHPEDGKFETPIQLRG

FEKVELSPGEKKTVDLRLLRRDLSVWDTTRQSWIVESGTYEALIGVAV

NDIKTSVLFTI
```

In certain embodiments of the invention, the cellobiohydrolase(s) can be an cellobiohydrolase I and/or an cellobiohydrolase II isoform, paralogue or orthologue. In certain embodiments of the present invention the cellobiohydrolases are cellobiohydrolase I and II, or a domain of a Cbh1 or Cbh2 as set forth in the Table below:

TABLE 3

Synthetic cellobiohydrolase (CBH) genes

| Donor organism/ Gene | DNA sequence used | Accession number and amino acid sequence |
|---|---|---|
| *Humicola grisea* cbh1 | GAATTCATGAGAACCGCTAAGTTCGCTACCTTGGCTGCCTTGGTTGCCTCTGCTGCTGC TCAACAAGCCTGTTCCTTGACTACTGAACGTCACCCATCTTTGTCTTGGAACAAGTGTA CTGCTGGTGGTCAATGTCAAACTGTCCAAGCCTCCATCACTTTGGACTCTAATTGGAG ATGGACCCACCAAGTCTCTGGTAGTACTAACTGTTACACCGGTAATAAGTGGGACACT TCTATTTGTACTGACGCTAAGTCTTGTGCTCAAAATTGTTGTTGATGGTGCTGATTA CACCTCCACTTATGGTATTACCACCAACGGTGACTCTTTGTCCTTGAAGTTCGTTACTA AAGGTCAACATTCCACCAACGTCGGTTCTAGAACCTACTTAATGGACGGTGAAGACAA GTACCAAACCTTCGAATTGTTGGGTAATGAATTTACCTTCGATGTCGATGTGTCTAACA TCGGTTGTGGTTTGAACGGTGCTTTTATACTTCGTTTCTATGGACGCCGACGGTGGTTTG TCTCGTTACCCAGGTAATAAGGCTGGTGCCAAGTATGGTACCGGTTACTGTGATGCTC AATGCCCAAGAGACATTAAGTTCATCAACGGTGAAGCTAACATTGAAGGTTGGACTG GTTCTACCAACGACCCAAACGCTGGCGCCGGTAGATACGGTACCTGTTGTTCCGAAAT GGACATTTGGGAAGCCAACAACATGGCTACTGCTTTTACTCCACACCCATGTACCATC ATTGGTCAATCCAGATGTGAAGGTGACTCCTGTGGCGGTACCTACTCCAACGAAAGAT ACGCTGGTGTTTGTGATCCAGACGGTTGTGACTTCAACTCCTACAGACAAGGTAACAA GACTTTCTATGGTAAGGGTATGACTGTCGATACCACCAAGAAGATCACCGTCGTCACC CAATTCTTGAAGGACGCTAACGGTGATTTAGGTGAAATTAAAAGATTCTACGTCCAAG ATGGTAAGATCATCCCAAACTCTGAATCTACCATTCCAGGTGTTGAAGGTAATTCCAT CACTCAAGACTGGTGTGACAGACAAAAGGTTGCCTTCGGTGATATTGACGACTTCAAC AGAAAGGGTGGTATGAAGCAAATGGGTAAGGCTTTGGCCGGTCCAATGGTCTTGGTTA TGTCTATTTGGGACGATCACGCTTCCAACATGTTGTGGTTGGACTCCACCTTCCCAGTT GATGCTGCTGGTAAGCCAGGTGCCGAAAGAGGTGCTTGTCCAACTACTTCCGGTGTCC CAGCTGAAGTTGAAGCCGAAGCTCCAAATTCTAACGTTGTCTTCTCTAACATCAGATT | Accession No.: CAA35159 MRTAKFATLAALVASAAAQQACSL TTERHPSLSWNKCTAGGQCQTVQA SITLDSNWRWTHQVSGSTNCYTGN KWDTSICTDAKSCAQNCCVDGADY TSTYGITTNGDSLSLKFVTKGQHSTN VGSRTYLMDGEDKYQTFELLGNEFT FDVDVSNIGCGLNGALYFVSMDAD GGLSRYPGNKAGAKYGTGYCDAQC PRDIKFINGEANIEGWTGSTNDPNAG AGRYGTCCSEMDIWEANNMATAFT PHPCTIIGQSRCEGDSCGGTYSNERY AGVCDPDGCDFNSYRQGNKTFYGK GMTVDTTKKITVVTQFLKDANGDL GEIKRFYVQDGKIIPNSESTIPGVEGN SITQDWCDRQKVAFGDIDDFNRKGG MKQMGKALAGPMVLVMSIWDDHA SNMLWLDSTFPVDAAGKPGAERGA CPTTSGVPAEVEAEAPNSNVVFSNIR FGPIGSTVAGLPGAGNGGNNGGNPP PPTTTTSSAPATTTTASAGPKAGRW QQCGGIGFTGPTQCEEPYICTKLND WYSQCL |

TABLE 3-continued

Synthetic cellobiohydrolase (CBH) genes

| Donor organism/ Gene | DNA sequence used | Accession number and amino acid sequence |
|---|---|---|
| | CGGTCCAATCGGTTCCACAGTCGCTGGTTTGCCAGGTGCTGGTAATGGTGGTAATAAC GGTGGTAACCCACCACCACCAACCACTACCACTTCTTCTGCCCCAGCTACTACCACCA CCGCTTCTGCTGGTCCAAAGGCTGGTAGATGGCAACAATGTGGTGGTATTGGTTTCAC CGGTCCAACCCAATGTGAAGAACCATACATCTGTACCAAGTTGAACGACTGGTACTCT CAATGTTTATAACTCGAG (SEQ ID NO: 47) | (SEQ ID NO: 53) |
| Thermoascus aurantiacus cbh1 | GAATTCATGTACCAAAGAGCTCTATTGTTCTCCTTCTTCTTGGCCGCCGCTAGAGCTCA TGAAGCCGGTACTGTCACCGCCGAAAACCACCCATCCTTGACTTGGCAACAATGTTCC TCTGGTGGTTCTTGTACTACTCAAAACGGGAAGGTTGTTATTGACGCTAACTGGAGAT GGGTTCACACTACCTCCGGTTACACCAACTGTTACACTGGTAACACTTGGGATACTTCC ATCTGTCCAGACGACGTTACCTGTGCTCAAAACTGTGCTTTGGACGGTGCTGACTACTC CGGTACTTACGGTGTCACTACCTCTGGCAACGCGTTGAGATTGAACTTCGTCACCCAA TCTTCTGGTAAGAACATCGGTTCTAGATTGTACTTGTTGCAAGACGATACTACTTACCA AATCTTCAAGTTGTTGGGTCAAGAATTCACTTTCGACGTTGATGTTGATGTTGACTTGCCTT GTGGTTTGAACGGTGCTTTGTACTTCGTTGCTATGGACGCCGACGGTAACTTATCCAAG TACCCAGGTAACAAGGCCGGTGCCAAGTACGGTACCGGTTACTGTGATTCTCAATGTC CAAGAGACCTAAAATTCATTAACGGTCAAGCTAACGTCGAAGGTTGGCAACCATCTGC TAACGATCCAAACGCCGGTGTCGGTAATCACGGTTCCTCTCTGTGCTGAAATGGACGTT TGGGAAGCTAACTCTATCTCCACCGCCGTCACTCCACATCCATGTGATACCCCAGGTC AAACCATGTGTCAAGGTGATGATTGTGGTGGTACCTACTCTTCCACTAGATACGCTGG TACCTGTGACACCGACGGTTGTGATTTCAACCCATACCAACCAGGTAACCACTCTTTCT ACGGTCCAGGTAAGATTGTCGATACTTCTTCTAAGTTCACTGTTGTCACTCAATTCATT ACCGACGATGGTACCCCATCTGACCTAACTGAAATTAAGAGATTCTACGTCCAAA ACGGTAAAGTCATTCCACAATCCGAAAGCACCATTTCCGGTGTTACCGGTAACTCCAT CACCACTGAATACTGTACCGCTCAAAAGGCCGCCTTTGACAACACCGGTTTCTTCACC CATGGTGGTTTGCAAAAGATTTCTCAAGCCTTGGCTCAAGGTATGGTTTTGGTCATGTC CTTGTGGGATGACCACGCTGCTAACATGTTGTGGTTGGATTCTACTTACCCAACTGACG CTGATCCAGACACCCCAGGTGTTGCTAGAGGTACTTGTCCAACCACTTCTGGTGTTCCA GCTGACGTCGAATCTCAAAACCCTAACTCTTACGTTATCTACTCTAACATCAAGGTGG GTCCAATTAACTCCACCTTCACTGCTAACTAACTCGAG (SEQ ID NO: 48) | Accession No.: AAL16941 MYQRALLFSFFLAAARAHEAGTVT AENHPSLTWQQCSSGGSCTTQNGK VVIDANWRWVHTTSGYTNCYTGNT WDTSICPDDVTCAQNCALDGADYS GTYGVTTSGNALRLNFVTSSGKNI GSRLYLLQDDTTYQIFKLLGQEFTFD VDVSNLPCGLNGALYFVAMDADGN LSKYPGNKAGAKYGTGYCDSQCPR DLKFINGQANVEGWQPSANDPNAG VGNHGSSCAEMDVWEANSISTAVTP HPCDTPGQTMCQGDDCGGTYSSTR YAGTCDTDGCDFNPYQPGNHSFYGP GKIVDTSSKFTVVTQFITDDGTPSGT LTEIKRFYVQNGKVIPQSESTISGVT GNSITTEYCTAQKAAFDNTGFFTHG GLQKISQALAQGMVLVMSLWDDHA ANMLWLDSTYPTDADPDTPGVARG TCPTTSGVPADVESQNPNSYVIYSNI KVGPINSTFTAN (SEQ ID NO: 54) |
| Talaromyces emersonii cbh1 | GAATTCATGCTAAGAAGAGCTTTACTATTGAGCTCTTCTGCTATCTTGGCCGTTAAGGC TCAACAAGCCGGTACCGCTACTGCTGAAAACCACCCTCCATTGACCTGGCAAGAATGT ACCGCTCCAGGTTCTTGTACCACCCAAAACGGTGCTGTCTTGGACGCTAACTGGAGA GATGGGTCCACGACGTCAACGGTTACACTAACTGTTACACCGGTAACACCTGGGACCC AACTTACTGTCCAGACGACGAAACTTGCGCTCAAAACTGTGCCTTGGACGGTGCTGAC TACGAAGGTACTTACGGTGTTACCTCCTCTGGTTCTTCCTTGAAGTTGAACTTCGTCAC TGGTTCTAACGTCGGTTCCAGATTGTATTTGTTGCAAGATGACTCCACTTACCAAATCT TCAAGTTGTTGAACAGAGAATTTTCTTTCGACGTCGATGTGTCCAACTTGCCTTGTGGT TTGAACGGTGCTCTATACTTCGTTGCTATGGACGCTGATGGTGGTGTTTCCAAGTACCC AAACAACAAGGCTGGTGCCAAATACGGTACTGGTTACTGTGACTCTCAATGTCCACGT GACTTGAAGTTTATTGATGGTGAAGCTAATGTCGAAGGTTGGCAACCATCTTCTAACA ACGCTAACACTGGCATCGGTGACCACGGTTCTTGCTGTGCCGAAATGGACGTTTGGGA AGCCAACTCCATTTCCAACGCCGTCACTCCACACCCATGTGACACTCCAGGTCAAACT ATGTGTTCCGGCGATGACTGTGGTGGTACTTACTCTAACGATAGATACGCTGGTACCT GTGATCCAGACGGTTGCGACTTCAACCCATACAGAATGGGTAACACTTCCTTTTACGG TCCAGGCAAGATCATCGACACTACTAAGCCATTCACTGTTGTCACCCAATTCTTGACC GACGATGGTACTGATACCGGTACTTTGTCCGAAATCAAGAGATTCTACATCCAAAACT CTAACGTCATCCCACAACCAAATTCCGACATCTCTGGTGTCACTGGTAACTCCATTACC ACCGAATTTTGTACCGCCCAAAAGCAAGCTTTCGGTGACCACCAGCGGCTTCTCTCAAC ACGGTGGTTTGGCTAAGATGGGTGCTGCTATGCAACAAGGTATGGTTTTGGTCATGTC TTTGTGGGACGACTACGCTGCTCAAATGTTGTGGTTGGACTCCGATTACCCAACCGAT GCCGACCCAACCACCCCTGGTATCGCTAGAGGTACCTGTCCAACTGACTCTGGTGTTC CATCTGACGTCGAATCCCAATCTCCAAACTCCTACGTCACTTACTCCAACATTAAATT GGTCCAATCAACTCCACTTTCACTGCTTCTTAACTCGAG (SEQ ID NO: 49) | Accession No.: AAL89553 MLRRALLLSSSAILAVKAQQAGTAT AENHPPLTWQECTAPGSCTTQNGAV VLDANWRWVHDVNGYTNCYTGNT WDPTYCPDDETCAQNCALDGADYE GTYGVTSSGSSLKLNFVTGSNVGSR LYLLQDDSTYQIFKLLNREFSFDVDV SNLPCGLNGALYFVAMDADGGVSK YPNNKAGAKYGTGYCDSQCPRDLK FIDGEANVEGWQPSSNNANTGIGDH GSSCAEMDVWEANSISNAVTPHPCD TPGQTMCSGDDCGGTYSNDRYAGT CDPDGCDFNPYRMGNTSFYGPGKII DTTKPFTVVTQFLTDDGTDTGTLSEI KRFYIQNSNVIPQPNSDISGVTGNSIT TEFCTAQKQAFGDTDDFSQHGGLA KMGAAMQQGMVLVMSLWDDYAA QMLWLDSDYPTDADPTTPGIARGTC PTDSGVPSDVESQSPNSYVTYSNIKF GPINSTFTAS (SEQ ID NO: 55) |
| Talaromyces emersonii cbh2 | GAATTCATGCGTAACTTGTTGGCCTTGGCTCCAGCCGCTTTGTTGGTTGGTGCTGCCGA AGCTCAACAATCCTTGTGGGGTCAATGCGGTGGTTCTTCCTGGACTGGTGCAACTTCCT GTGCCGCTGGTCCACCTGTTCCACCATTAACCCATACTACGCTCAATGTGTTCCAGCC ACTGCCACTCCAACTACCTTGACTACCACCACTAAGCCAACCTCCACCGGTGGTGCTG CTCCAACCACTCCACCACCAACTACTACCGGTACTACCACCTCTCCAGTCGTCACCAG ACCTGCCTCGGCTCCGGTAACCCCTTCGAAGGTTACCAATTGTACGCTAACCCATACT ACGCTTCTGAAGTCATTTCCCTTGGCTATCCCATCTTTGAGCTCCGAGTTGGTTCCCAAAG GCCTCCGAAGTTGCTAAGGTCCCTTCATTTGTCTGGTTAGATCAAGCTGCCAAGGTTCC ATCTATGGGTGATTACTTGAAGGATATTCAATCTCAAAACGCTGCTGGTGCTGATCCA CCAATCGCCGGTATTTTTGTTGTTTACGATCTTCCAGATAGAGACTGTGCCGCCGCTTC TTCTAACGGTGAATTTTCTATCGCCAACAACGGTGTCGCTTTATACAAACAATATATCG ATTCCATTAGAGAACAATTAACCACTTACTCCGACGTCCATACCATCTTGGTTATCGAA CCAGACTCTTTGGCTAACGTTGTCACTAACTTGAACGTTCCAAAATGTGCTAACGCTCA AGATGCTTACTTGGAATGTATCAACTACGCTATTACCCAATTGGACTTGCCAAACGTT GCTATGTACTTGGACGCTGGTCACGCCGGTTGGTTGGGTTGGCAAGCCAACTTGGCCC | Accession No.: AAL78165 MRNLLALAPAALLVGAAEAQQSLW GQCGGSSWTGATSCAAGATCSTINP YYAQCVPATATPTTLTTTKPTSTG GAAPTTPPPTTGTTTSPVVTRPASA SGNPFEGYQLYANPYYASEVISLAIP SLSSELVPKASEVAKVPSFVWLDQA AKVPSMGDYLKDIQSQNAAGADPPI AGIFVVYDLPDRDCAAAASNGEFSI ANNGVALYKQYIDSIREQLTTYSDV HTILVIEPDSLANVVTNLNVPKCAN AQDAYLECINYAITQLDLPNVAMYL DAGHAGWLGWQANLAPAAQLFAS VYKNASSPASVRGLATNVANYNAW SISRCPSYTQGDANCDEEDYVNALG |

TABLE 3-continued

Synthetic cellobiohydrolase (CBH) genes

| Donor organism/ Gene | DNA sequence used | Accession number and amino acid sequence |
|---|---|---|
| | CAGCTGCTCAATTATTCGCTTCTGTTTACAAGAACGCCTCTTCCCCAGCCTCTGTTAGA<br>GGTTTGGCTACCAACGTGGCTAACTACAACGCCTGGTCCATTTCTAGATGTCCATCCTA<br>CACTCAAGGTGACGCTAACTGTGATGAAGAAGATTACGTTAACGCTTTGGGTCCATTG<br>TTCCAAGAACAAGGTTTCCCAGCTTACTTCATCATCGACACTTCCCGTAACGGTGTCAG<br>ACCAACTAAGCAATCTCAATGGGGTGACTGGTGTAACGTTATTGGTACCGGTTTCGGT<br>GTTAGACCAACCACCGACACTGGTAACCCATTGGAAGACGCTTTCGTTTGGGTCAAGC<br>CAGGTGGTGAATCCGACGGTACCTCCAACACTACTAGCCCACGTTACGATTACCACTG<br>TGGTTTGTCTGACGCTTTGCAACCAGCTCCAGAAGCTGGTACCTGGTTCCAAGCCTACT<br>TCGAACAATTGTTGACTAACGCCAACCCATTGTTCTAACTCGAG<br>(SEQ ID NO: 50) | PLFQEQGFPAYFIIDTSRNGVRPTKQ<br>SQWGDWCNVIGTGFGVRPTTDTGN<br>PLEDAFVWVKPGGESDGTSNTTSPR<br>YDYHCGLSDALQPAPEAGTWFQAY<br>FEQLLTNANPLF<br>(SEQ ID NO: 56) |
| Trichoderma reesei cbh1 | <u>ATGGTCTCCTTCACCTCCC</u>TGCTGGCCGGCGTTGCCGCTATCTCTGGTGTCCTAGCAGC<br>CCCTGCCGCAGAAGTTGAACCTGTCGCAGTTGAGAAACGTGAGGCCGAAGCAGAAGC<br>TCAATCCGCTTGTACCCTACAATCCGAAACTCACCCACCATTGACCTGGCAAAAGTGT<br>TCTAGCGGTGGAACTTGTACTCAACAAACTGGTTCTGTTGTTATCGACGCTAACTGGA<br>GATGGACACACGCCACTAACTCTTCTACCAACTGTTACGACGGTAACACTTGGTCTTC<br>CACTTTATGTCCAGATAACGAAACTTGTGCTAAGAATTGCTGTTTGGACGGTGCCGCC<br>TACGCTTCTACCTACGGTGTTACCACCTCCGGTAACTCCTTGTCTATTGGTTTCGTCACT<br>CAATCCGCTCAAAAGAACGTTGGTGCTAGATTGTACTTGATGGCTTCTGACACTACTT<br>ATCAAGAATTTACTTTGTTGGGTAACGAATTTTCTTTCGATGTTGACGTTTCCCAATTG<br>CCATGTGGCTTGAACGGTGCTTTGTACTTTGTCTCTATGGATGCTGACGGTGGTGTTTC<br>TAAGTACCCAACTAACACTGCCGGTGCTAAGTACGGTACTGGTTACTGTGATTCTCAA<br>TGTCCACGTGACTTGAAGTTCATTAACGGTCAAGCCAACGTCGAAGGTTGGGAACCAT<br>CCTCCAACAACGCTAACACCGGTATCGGTGGTCACGGTTCCTGTTGTTCCGAAATGGA<br>CATCTGGGAAGCTAACAGTATTTCTGAAGCTTTGACACCACACCCATGCACCACTGTC<br>GGTCAAGAAATTTGTGAAGGTGATGGATGTGGTGGAACCTACTCTGATAACAGATACG<br>GTGGTACTTGTGACCCAGACGGTTGTGACTGGAACCCATACAGATTGGGTAACACTTC<br>TTTCTATGGTCCAGGTTCTTCTTTCACCTTGGATACCACCAAGAAGTTGACTGTTGTTA<br>CCCAATTCGAAACTTCTGGTGCTATCAACAGATACTACGTTCAAAACGGTGTCACCTT<br>CCAACAACCAAACGCTGAATTGGGTTCTTACTCTGGTAATGAATTGAACGACGACTAC<br>TGTACCGCTGAAGAAGCTGAATTTGGTGGTTCCTCTTCTCCGACAAGGGTGGTTTGAC<br>CCAATTCAAGAAGGCTACCTCCGGTGGTATGGTTTTGGTTATGTCCTTGTGGGATGATT<br>ACTACGCAAACATGTTATGGTTAGACAGTACTTACCCAACTAACGAAACCTCCTCTAC<br>TCCAGGTGCTGTCAGAGGTTCCTGTTCTACCTCTTCTGGTGTTCCAGCTCAAGTTGAAT<br>CTCAATCTCCAAACGCTAAGGTCACTTTCTCAACATCAAGTTCGGTCCAATCGGTTCC<br>ACTGGTAATCCATCTGGTGGAAACCCTCCAGGTGGTAACGAGGTACTACCACTACTC<br>GTAGGCCAGCTACTACAACTGGTTCTTCCCCAGGCCCAACCCAATCCCACTACGGTCA<br>ATGTGGTGGTATCGGTTACTCTGGTCCAACCGTCTGTGCTTCTGGTACTACCTGTCAAG<br>TTTTTAAAC<u>CCATACTACTCTCAATGTTTGTAA</u><br>(SEQ ID NO: 51) | Accession No.: CAA49596<br>MVSFTSLLAGVAAISGVLAAPAAEV<br>EPVAVEKREAEAEAQSACTLQSETH<br>PPLTWQKCSSGGTCTQQTGSVVIDA<br>NWRWTHATNSSTNCYDGNTWSSTL<br>CPDNETCAKNCCLDGAAYASTYGV<br>TTSGNSLSIGFVTQSAQKNVGARLY<br>LMASDTTYQEFTLLGNEFSFDVDVS<br>QLPCGLNGALYFVSMDADGGVSKY<br>PTNTAGAKYGTGYCDSQCPRDLKFI<br>NGQANVEGWEPSSNNANTGIGGHG<br>SCCSEMDIWEANSISEALTPHPCTTV<br>GQEICEGDGCGGTYSDNRYGGTCDP<br>DGCDWNPYRLGNTSFYGPSSFTLD<br>TTKKLTVVTQFETSGAINRYYVQNG<br>VTFQQPNAELGSYSGNELNDDYCTA<br>EEAEFGGSSFSDKGGLTQFKKATSG<br>GMVLVMSLWDDYYANMLWLDSTY<br>PTNETSSTPGAVRGSCSTSSGVPAQV<br>ESQSPNAKVTFSNIKFGPIGSTGNPSG<br>GNPPGGNRGTTTTRRPATTTGSSPGP<br>TQSHYGQCGGIGYSGPTVCASGTTC<br>QVLNPYYSQCL<br>(SEQ ID NO: 57)<br>Secretion signal: 1-33<br>catalytic domain: 41-465<br>cellulose-binding domain: 503-535 |
| Trichoderma reesei cbh2 | <u>ATGGTCTCCTTCACCTCCC</u>TGCTGGCCGGCGTTGCCGCTATCTCTGGTGTCCTAGCAGC<br>CCCTGCCGCAGAAGTTGAACCTGTCGCAGTTGAGAAACGTGAGGCCGAAGCAGAAGC<br>TGTCCCATTAGAAGAAAGACAAGCCTGCTCCTCTGTTTGGGGTCAATGTGGTGGTCAA<br>AACTGGTCTGGTCCAACTTGTTGTGCTTCAGGTTCTACCTGTGTTTACTCCAACGACTA<br>CTATTCCCAATGTTTGCCAGGTGCTGCTTCCTCTTCCTCTTCAACTAGAGCTGCTTCTAC<br>AACTTCTAGGGTCTCCCCAACCACTTCCAGATCCTCTTCTGCTACTCCACCACCAGGTT<br>CTACTACCACTAGAGTTCCACCAGTCGGTTCCGGTACTGCTACTTACTCTGGTAACCCT<br>TTCGTCGGTGTTACTCCATGGGCTAACGCTTACTACGCTTCTGAAGTTTCTTCTTTGGCT<br>ATCCCATCTTTGACTGGTGCTATGGCTACAGCTGCTGCTGTCGCCAAAGTTCCATC<br>CTTCATGTGGTTGGACACCTTGGACAAAACTCCATTAATGGAACAAACCTTGGCAGAC<br>ATAAGGACTGCTAACAAGAACGGCGGTAACTACGCTGGTCAATTTGTTGTGTACGACT<br>TGCCAGACAGAGACTGTGCTGCTTTGGCTTCCAACGGTGAATACTCCATCGCTGACGG<br>TGGTGTCGCCAAGTACAAGAACTACATTGATACCATTAGACAAATCGTTGTCGAATAC<br>TCTGACATCAGAACCTTGTTAGTCATCGAACCAGATTCTTTAGCCAATGTTACTCACCAA<br>CTTGGGTACTCCAAAGTGTGCTAACGCTCAATCTGCCTACTTAGAATGTATCAATTATG<br>CAGTTACCCAATTGAACTTGCCAAACGTTGCTATGTACTTGGACGCTGGTCACGCCGG<br>TTGGTTGGGTTGGCCAGCTAACCAAGACCCAGCCGCTCAATTATTCGCAACGTTTAC<br>AAGAATGCCTCTTCTCCTAGAGCCTTGCGTGGTTTGGCTACTAACGTCGCTAACTACAA<br>CGGTTGGAACATCACTTCTCCACCATCTTACACCCAAGGTAACGCTGTTTACAACGAA<br>AAGTTGTACATTCACGCTATCGGTCGTCTTGCTAATCATGGTTGGTCTAACGCCTT<br>CTTCATCACCGACCAAGGTAGATCCGGTAAACAACCAACTGGTCAACAACAATGGGG<br>TGATTGGTGTAACGTCATCGGTACTGGTTTCGGTATCAGACCATCCGCTAACACTGGT<br>GATTCCTTGTTGGATTCCTTCGTCTGGGTTAAGCAGGTGGTGAATGTGATGGCACCTC<br>TGATTCCTCTGCTCCAAGATTCGATTCCCACTGCGCCTTGCCAGACGCTTTGCAACCAG<br>CCGCCCAAGCTGGTGCATGGTTCCAAGCTTACTTTGTCCAATTGTTGACCAACGCTAAC<br><u>CCATCTTTCTTGTAA</u><br>(SEQ ID NO: 52) | Accession No.: AAA34210<br>MIVGILTTLATLATLAASVPLEERQA<br>CSSVWGQCGGQNWSGPTCCASGST<br>CVYSNDYYSQCLPGAASSSSSTRAA<br>STTSRVSPTTSRSSSATPPPGSTTTRV<br>PPVGSGTATYSGNPFVGVTPWANA<br>YYASEVSSLAIPSLTGAMATAAAAV<br>AKVPSFMWLDTLDKTPLMEQTLADI<br>RTANKNGGNYAGQFVVYDLPDRDC<br>AALASNGEYSIADGGVAKYKNYIDT<br>IRQIVVEYSDIRTLLVIEPDSLANLVT<br>NLGTPKCANAQSAYLECINYAVTQL<br>NLPNVAMYLDAGHAGWLGWPANQ<br>DPAAQLFANVYKNASSPRALRGLAT<br>NVANYNGWNITSPPSYTQGNAVYN<br>EKLYIHAIGRLLANHGWSNAFFITDQ<br>GRSGKQPTGQQWGDWCNVIGTGF<br>GIRPSANTGDSLLDSFVWVKPGGEC<br>DGTSDSSAPRFDSHCALPDALQPAA<br>QAGAWFQAYFVQLLTNANPSFL<br>(SEQ ID NO: 58) |

In other embodiments, the cellobiohydrolases can be encoded by the polynucleotide sequences of SEQ ID NOs: 47-52.

In further embodiments, the one or more additional endoglucanases, cellobiohydrolases and/or βglucosidases can be from a termite or termite-associated symbiont. For example, the endogluconase can be a *Coptotermes formosanus* endogluconase (SEQ ID NO: 78) (Accession No. AB058671) as follows:

(SEQ ID NO: 78)
MRVFVCLLSALALCQAAYDYKTVLKNSLLFYEAQRSGKLPADQKVTWR

KDSALNDKGQKGEDLTGGYYDAGDFVKFGFPMAYTVTVLAWGLVDYES

AYSTAGALDDGRKALKWGTDYFLKAHTAANEFYGQVGQGDVDHAYWGR

PEDMTMSRPAYKIDTSKPGSDLAAETAAALAATAIAYKSADSTYSNNL

ITHAKQLFDFANNYRGKYSDSITDAKNFYASGDYKDELVWAAAWLYRA

TNDNTYLTKAESLYNEFGLGSWNGAFNWDNKISGVQVLLAKLTSKQAY

KDKVQGYVDYLVSSQKKTPKGLVYIDQWGTLRHAANSALIALQAADLG

INAASYRQYAKKQIDYALGDGGRSYVVGFGTNPPVRPHHRSSSCPDAP

AACDWNTYNSAGPNAHVLTGALVGGPDSNDSYTDSRSDYISNEVATDY

NAGFQSAVAGLLKAGV

The nucleic acids encoding the termite or termite-associated symbiont cellulases can be codon-optimized for expression in a yeast strain.

The transformed host cells or cell cultures, as described above, are measured for endoglucanase, cellobiohydrolase and/or β-glucosidase protein content. Protein content can be determined by analyzing the host (e.g., yeast) cell supernatants. In certain embodiments, the high molecular weight material is recovered from the yeast cell supernatant either by acetone precipitation or by buffering the samples with disposable de-salting cartridges. The analysis methods include the traditional Lowry method or protein assay method according to BioRad's manufacturer's protocol. Using these methods, the protein content of saccharolytic enzymes can be estimated.

The transformed host cells or cell cultures, as described above, can be further analyzed for cellulase activity (cellulose utilization), e.g., by measuring the individual cellulase (endoglucanase, cellobiohydrolase or β-glucosidase) or by measuring total cellulase activity. Endoglucanase activity can be measured based on a reduction in cellulosic substrate viscosity and/or an increase in reducing ends determined by a reducing sugar assay. Cellobiohydrolase activity can be measured, for example, by using Avicel as a substrate and determining its hydrolysis. β-glucosidase activity can be measured by a variety of assays, e.g., using cellobiose.

A total cellulase activity, which includes the activity of endoglucanase, cellobiohydrolase and β-glucosidase, will hydrolyze crystalline cellulose synergistically. Total cellulase activity can thus be measured using insoluble substrates including pure cellulosic substrates such as Whatman No. 1 filter paper, cotton linter, microcrystalline cellulose, bacterial cellulose, algal cellulose, and cellulose-containing substrates such as dyed cellulose, alpha-cellulose or pretreated lignocellulose.

It will be appreciated that suitable lignocellulosic material can be any feedstock that contains soluble and/or insoluble cellulose, where the insoluble cellulose can be in a crystalline or non-crystalline form. In various embodiments, the lignocellulosic biomass comprises, for example, wood, corn, corn stover, sawdust, bark, leaves, agricultural and forestry residues, grasses such as switchgrass, ruminant digestion products, municipal wastes, paper mill effluent, newspaper, cardboard or combinations thereof.

Specific activity of cellulases can also be detected by methods known to one of ordinary skill in the art, such as by the Avicel assay (described supra) that would be normalized by protein (cellulase) concentration measured for the sample. To accurately measure protein concentration, *Schizochytrium aggregatum* Cbh1 can be expressed with a His-taq or HA-tag and purified by a standard nickel resin purification technique or similar approach.

In additional embodiments, the transformed host cells or cell cultures are assayed for ethanol production. Ethanol production can be measured by techniques known to one of ordinary skill in the art, e.g., by a standard HPLC refractive index method.

EXAMPLES

Example 1

Isolation of *Schizochytrium Aggregatum* cbh1

The isolation of genes for saccharolytic enzymes from cellulolytic marine fungoid organisms of the Thraustochytrid family was considered. Thraustochytrids are important mangrove decomposers on decaying cellulose-rich materials such as macroalgae and mangrove leaves. Thus, Thraustochytrid family organisms are potential candidates from which novel cellulases can be isolated. Cellulase production has been detected in the Thraustochytrid family marine fungoid protist *Schizochytrium aggregatum* (Bremer GB, 1995). Given the production of cellulase in this organism, it was determined that isolation of a cellobiohydrolase I (cbh1) gene from *Schizochytrium aggregatum* would be advantageous, as the encoded protein could serve as a potential exoglucanase for use in a consolidated bioprocessing system.

Secreted and cell associated cellulase activity was measured for three cellulolytic marine fungoid Thraustochytrid strains, obtained from ATCC. The three marine fungoid strains utilized are as follows: (1) *Schizochytrium aggregatum* 16, ATCC #28209; (2) unidentified Thraustochytrid ATCC #PRA-147; and (3) *Schizochytrium limacinum* SR21, ATCC #MYA-1381. PCR analysis of 18S ribosomal RNA was carried out on these strains to confirm their identity. A Table summarizing the three strains is as follows:

TABLE 4

| Original strain name or ATCC designation | Family | Genus | Species |
| --- | --- | --- | --- |
| *Schizochytrium aggregatum* | Thraustochytriaceae | *Schizochytrium* | *Aggregatum* |
| ATCC PRA 147 | Thraustochytriaceae | *Aurantiochytrium* | Unknown |
| ATCC MYA 1381 | Thraustochytriaceae | *Schizochytrium* | Unknown |

The three strains were grown in shaker flasks for 10 days in media using six different carbon sources: glucose, Sigma cell, Avicel, Solka floc, lactose, and glycerol. The media composition was as follows: every 1 Liter (L) of media contained the following: yeast extract—1 g; peptone—1 g; carbon source—5 g; bacto agar—20 g; and sea water—to 1 L. The sea water was prepared by combining the following ingredients: every 2 Liters of sea water contained the following: NaCl—40 g; $MgCl_2 \times 6H_2O$—6 g; $CaCl_2 \times 2\ H_2O$—0.3 g; KCl—1 g; and, water—to 2 L.

Cellulase activity of the three strains was measured by the resorufin-cellobioside assay (MarkerGene Fluorecent Cellulase Assay Kit, MGT Inc.). As shown in FIG. 2, the *Schizochytrium aggregatum* strain demonstrated higher cellulase activity on cellulosic substrates. The *Schizochytrium aggregatum* strain was thus chosen to isolate its cbh1 cellulase gene.

As an initial step to isolate the cbh1 gene from the *Schizochytrium aggregatum* strain, thirty four degenerate primers having homology to conservative regions of fungal and protist Cbh's were designed. The fungal and protist Cbh sequences that were analyzed to find conservative regions within Cbh sequences are set forth in Table 5 as follows:

TABLE 5

| Cell # | Family | Organism | Protein | Activity | Genbank Acc. No. | Sequence |
|---|---|---|---|---|---|---|
| 14 | Fungi | Neosartorya fischeri | | Exo | XM_001258277 | MLASTFSYRMYKTALILAALLGSGQAQQVGTSQAEVHP SMTWQSCTAGGSCTTNNGKVVIDANWRWVHKVGDYT NCYTGNTWDKTLCPDDATCASNCALEGANYQSTYGATT SGDSLRLNFVTTSQQKNIGSRLYMMKDDTTYEMFKLLQ EFTFDVDVSNLPCGLNGALYFVAMDADGGMSKYPTNK AGAKYGTGYCDSQCPRDLKFINGQANVEGWQPSSNDAN AGTGNHGSCCAEMDIWEANSISTAFTPHPCDTPGQVMCT GDACGGTYSSDRYGGTCDPDGCDFNSFRQGNKTFYGPG MTVDTKSKFTVVTQFITDDGTASGTLKEIKRFYVQNGKV IPNSESTWSGVGGNSITNDYCTAQKSLFKDQNVFAKHGG MEGMGAALAQGMVLVMSLWDDHAANMLWLDSNYPT TASSSTPGVARGTCDISSGVPADVEANHPDASVVYSNIK VGPIGSTFNSGGSNPGGGTTTTAKPTTTTTTAGSPGGTGV AQHYGQCGGNGWQGPTTCASPYTCQKLNDFYSQCL (SEQ ID NO: 61) |
| 15 | Fungi | Gibberella zeae | F9 | Exo | AY196784 | MYRAIATASALIAAVRAQQVCSLTQESKPSLNWSKCTSS GCSNVKGSVTIDANWRWTHQVSGSTNCYTGNKWDTSV CTSGKVCAEKCCLDGADYASTYGITSSGDQLSLSFVTKG PYSTNIGSRTYLMEDENTYQMFQLLGNEFTFDVDVSNIG CGLNGALYFVSMDADGGKAKYPGNKAGAKYGTGYCD AQCPRDVKFINGQANSDGWQPSDSDVNGGIGNLGTCCP EMDIWEANSISTAYTPHPCTKLTQHSCTGDSCGGTYSND RYGGTCDADGCDFNSYRQGNKTFYGPGSGFNVDTTKKV TVVTQFHKGSNGRLSEITRLYVQNGKVIANSESKIAGVPG NSLTADFCTKQKKVFNDPDDFTKKGAWSGMSDALEAP MVLVMSLWHDHHSNMLWLDSTYPTDSTKLGSQRGSCS TSSGVPADLEKNVPNSKVAFSNIKFGPIGSTYKSDGTTPT NPTNPSEPSNTANPNPGTVDQWGQCGGSNYSGPTACKS GFTCKKINDFYSQCQ (SEQ ID NO: 62) |
| 16 | Fungi | Penicillium janthinellum | | exo | X59054 | MKGSISYQIYKGALLLSALLNSVSAQQVGTLTAETHPAL TWSKCTAGXCSQVSGSVVIDANWPXVHSTSGSTNCYTG NTWDATLCPDDVTCAANCAVDGARRQHLRVTTSGNSL RINFVTTASQKNIGSRLYLLENDTTYQKFNLLNQEFTFDV DVSNLPCGLNGALYFVDMDADGGMAKYPTNKAGAKY GTGYCDSQCPRDLKFINGQANVDGWTPSKNDVNSGIGN HGSCCAEMDIWEANSISNAVTPHPCDTPSQTMCTGQRCG GTYSTDRYGGTCDPDGCDFNPYRMGVTNFYGPGETIDT KSPFTVVTQFLTNDGTSTGTLSEIKRFYVQGGKVIGNPQS TIVGVSGNSITDSWCNAQKSAFGDTNEFSKHGGMAGMG AGLADGMVLVMSLWDDHASDMLWLDSTYPTNATSTTP GAKRGTCDISRRPNTVESTYPNAYVIYSNIKTGPLNSTFT GGTTSSSSTTTTTSKSTSTSSSSKTTTTVTTTTTSSGSSGTG ARDWAQCGGNGWTGPTTCVSPYTCTKQNDWYSQCL (SEQ ID NO: 63) |
| 17 | Fungi | Nectria haematococca | | exo | AY502070 | MYRAIATASALLATARAQQVCTLNTENKPALTWAKCTS SGCSNVRGSVVVDANWRWAHSTSSSTNCYTGNTWDKT LCPDGKTCADKCCLDGADYSGTYGVTSSGNQLNLKFVT VGPYSTNVGSRLYLMEDENNYQMFDLLGNEFTFDVDVN NIGCGLNGALYFVSMDKDGGKSRFSTNKAGAKYGTGYC DAQCPRDVKFINGVANSDEWKPSDSDKNAGVGKYGTCC PEMDIWEANKISTAYTPHPCKSLTQQSCEGDACGGTYSA TRYAGTCDPDGCDFNPYRQGNKTFYGPGSGFNVDTTKK VTVVTQFIKGSDGKLSEIKRLYVQNGKVIGNPQSEIANNP GSSVTDSFCKAQKVAFNDPDDFNKKGGWSGMSDALAK PMVLVMSLWHDHYANMLWLDSTYPKGSKTPGSARGSC PEDSGDPDTLEKEVPNSGVSFSNIICFGPIGSTYTGTGGSNP DPEEPEEPEEPVGTVPQYGQCGGINYSGPTACVSPYKCN KINDFYSQCQ (SEQ ID NO: 83) |

TABLE 5-continued

| Cell # | Family | Organism | Protein | Activity | Genbank Acc. No. | Sequence |
|---|---|---|---|---|---|---|
| 18 | Fungi | *Fusarium poae* | | exo | AY706934 | MYRAIATASALIAAVRAQQVCSLTTETKPALTWSKCTSS GCSNVQGSVTIDANWRWTHQVSGSTNCHTGNKWDTSV CTSGKVCAEKCCVDGADYASTYGITSSGNQLSLSFVTKG SYGTNIGSRTYLMEDENTYQMFQLLGNEFTFDVDVSNIG CGLNGALYFVSMDADGGKAKYPGNKAGAKYGTGYCD AQCPRDVKFINGQANSDGWEPSKSDVNGGIGNLGTCCPE MDIWEANSISTAYTPHPCTKLTQHACTGDSCGGTYSNDR YGGTCDADGCDFNAYRQGNKTFYGPGSGFNVDTTKKV TVVTQFHKGSNGRLSEITRLYVQNGKVIANSESKIAGNPG SSLTSDFCTTQKKVFGDIDDFAKKGAWNGMSDALEAPM VLVMSLWHDHHSNMLWLDSTYPTDSTALGSQRGSCSTS SGVPADLEKNVPNSKVAFSNIKFGPIGSTYNKEGTQPQPT NPTNPNPTNPTNPGTVDQWGQCGGTNYSGPTACKSPFTC KKINDFYSQCQ (SEQ ID NO: 64) |
| 19 | Fungi | *Chaetomium thermophilum* | | exo | AY861347 | MMYKKFAALAALVAGAAAQQACSLTTETHPRLTWKRC TSGGNCSTVNGAVTIDANWRWTHTVSGSTNCYTGNEW DTSICSDGKSCAQTCCVDGADYSSTYGITTSGDSLNLKFV TKHQHGTNVGSRVYLMENDTKYQMFELLGNEFTFDVD VSNLGCGLNGALYFVSMDADGGMSKYSGNKAGAKYGT GYCDAQCPRDLKFINGEANIENWTPSTNDANAGFGRYGS CCSEMDIWDANNMATAFTPHPCTIIGQSRCEGNSCGGTY SSERYAGVCDPDGCDFNAYRQGDKTFYGKGMTVDTTK KMTVVTQFHKNSAGVLSEIKRFYVQDGKIIANAESKIPG NPGNSITQEWCDAQKVAFGDIDDFNRKGGMAQMSKALE GPMVLVMSVWDDHYANMLWLDSTYPIDKAGTPGAERG ACPTTSGVPAEIEAQVPNSNVIFSNIRFGPIGSTVPGLDGS TPSNPTATVAPPTSTTTSVRSSTTQISTPTSQPGGCTTQKW GQCGGIGYTGCTNCVAGTTCTELNPWYSQCL (SEQ ID NO: 65) |
| 20 | Fungi | *Aspergillus terreus* | | exo | XM_001214180 | MPSTYDIYKKLLLLASFLSASQAQQVGTSKAEVHPSLTW QTCTSGGSCTTVNGKVVVDANWRWVHNVDGYNNCYT GNTWDTTLCPDDETCASNCALEGADYSGTYGVTTSGNS LRLNFVTQASQKNIGSRLYLMEDDSTYKMFKLLNQEFTF DVDVSNLPCGLNGAVYFVSMDADGGMAKYPANKAGA KYGTGYCDSQCPRDLKFINGMANVEGWEPSANDANAG TGNHGSCCAEMDIWEANSISTAYTPHPCDTPGQVMCTG DSCGGTYSSDRYGGTCDPDGCDFNSYRQGNKTFYGPGM TVDTKSKITVVTQFLTNDGTASGTLSEIKRFYVQNGKVIP NSESTWSGVSGNSITTAYCNAQKTLFGDTDVFTKHGGM EGMGAALAEGMVLVLSLWDDHHNSNMLWLDSNYPTDKP STTPGVARGSCDISSGDPKDVEANDANAYVVYSNIKVGP IGSTFSGSTGGGSSSSTTATSKTTTTSATKTTTTTKTTTT TSASSTSTGGAQHWAQCGGIGWTGPTTCVAPYTCQKQN DYYSQCL (SEQ ID NO: 66) |
| 21 | Fungi | *Penicillium chrysogenum* | cbhI | exo | AY790330 | MASTLSFKIYKNALLLAAFLGAAQAQQVGTSTAEVHPSL TWQKCTAGGSCTSQSGKVVIDSNWRWVHNTGGYTNCY TGNDWDRTLCPDDVTCATNCALDGADYKGTYGVTASG SSLRLNFVTQASQKNIGSRLYLMADDSKYEMFQLLNQEF TFDVDVSNLPCGLNGALYFVAMDEDGGMARYPTNKAG AKYGTGYCDAQCPRDLKFINGQANVEGWEPSSSDVNGG TGNYGSCCAEMDIWEANSISTAFTPHPCDDPAQTRCTGD SCGGTYSSDRYGGTCDPDGCDFNPYRMGNQSFYGPSKIV DTESPFTVVTQFITNDGTSTGTLSEIKRFYVQNGKVIPQSV STISAVTGNSITDSFCSAQKTAFKDTDVFAKHGGMAGMG AGLAEGMVLVMSLWDDHAANMLWLDSTYPTSASSTTP GAARGSCDISSGEPSDVEANHSNAYVVYSNIKVGPLGST FGSTDSGSGTTTTKVTTTATKTTTTTGPSTTGAAHYAQ CGGQNWTGPTTCASPYTCQRQGDYYSQCL (SEQ ID NO: 67) |
| 22 | Fungi | *Neurospora crassa* | | exo | X77778 | MRASLLAFSLAAAVAGGQQAGTLTAKRHPSLTWQKCTR GGCPTLNTTMVLDANWRWTHATSGSTKCYTGNKWQAT LCPDGKSCAANCALDGADYTGTYGITGSGWSLTLQFVT DNVGARAYLMADDTQYQMLELLNQELWFDVDMSNIPC GLNGALYLSAMDADGGMRKYPTNKAGAKYATGYCDA QCPRDLKYINGIANVEGWTPSTNDANGIGDHGSCCSEMD IWEANKVSTAFTPHPCTTIEQHMCEGDSCGGTYSDDRYG VLCDADGCDFNSYRMGNTTFYGEGKTVDTSSKFTVVTQ FIKDSAGDLAEIKAFVQNGKVIENSQSNVDGVSGNSITQ SFCKSQKTAFGDIDDFNKKGGLKQMGKALAQAMVLVM SIWDDHAANMLWLDSTYPVPKVPGAYRGSGPTTSGVPA EVDANAPNSKVAFSNIKFGHLGISPFSGGSSGTPPSNPSSS |

TABLE 5-continued

| Cell # | Family | Organism | Protein | Activity | Genbank Acc. No. | Sequence |
|---|---|---|---|---|---|---|
| | | | | | | ASPTSSTAKPSSTSTASNPSGTGAAHWAQCGGIGFSGPTT CPEPYTCAKDHDIYSQCV (SEQ ID NO: 68) |
| 32 | Fungi | Trichoderma viride | Cbh1 | exo | AY368686 | MYRKLAVISAFLATARAQSACTLQSETHPPLTWQKCSSG GTCTQQTGSVVIDANWRWTHATNSSTNCYDGNTWSSTL CPDNETCAKNCCLDGAAYASTYGVTTSGNSLSIGFVTQS AQKNVGARLYLMASDTTYQEFTLLGNEFSFDVDVSQLP CGLNGALYFVSMDADGGVSKYPTNTAGAKYGTGYCDS QCPRDLKFINGQANVEGWEPSSNNANTGIGGHGSCCSEM DIWEANSISEALTPHPCTTVGQEICEGDGCGGTYSDNRY GGTCDPDGCDWDPYRLGNTSFYGPGSSFTLDTTKKLTV VTQFETSGAINRYYVQNGVTFQQPNAELGSYSGNGLND DYCTAEEAEFGGSSFSDKGGLTQFKKATSGGMVLVMSL WDDYYANMLWLDSTYPTNETSSTPGAVRGSCSTSSGVP AQVESQSPNAKVTFSNIKFGPIGSTGDPSGGNPPGGNPPG TTTTRRPATTTGSSPGPTQSHYGQCGGIGYSGPTVCASGT TCQVLNPYYSQCL (SEQ ID NO: 69) |
| 34 | Fungi | Humicola grisea | Cbh1 | exo | X17258 | MRTAKFATLAALVASAAAQQACSLTTERHPSLSWNKCT AGGQCQTVQASITLDSNWRWTHQVSGSTNCYTGNKWD TSICTDAKSCAQNCCVDGADYTSTYGITTNGDSLSLKFV TKGQHSTNVGSRTYLMDGEDKYQTFELLGNEFTFDVDV SNIGCGLNGALYFVSMDADGGLSRYPGNKAGAKYGTGY CDAQCPRDIKFINGEANIEGWTGSTNDPNAGAGRYGTCC SEMDIWEANNMATAFTPHPCTIIGQSRCEGDSCGGTYSN ERYAGVCDPDGCDFNSYRQGNKTFYGKGMTVDTTKKIT VVTQFLKDANGDLGEIKRFYVQDGKIIPNSESTIPGVEGN SITQDWCDRQKVAFGDIDDFNRKGGMKQMGKALAGPM VLVMSIWDDHASNMLWLDSTFPVDAAGKPGAERGACP TTSGVPAEVEAEAPNSVVVFSNIRFGPIGSTVAGLPGAGN GGNNGGNPPPPTTTTSSAPATTTTASAGPKAGRWQQCG GIGFTGPTQCEEPYICTKLNDWYSQCL (SEQ ID NO: 70) |
| 35 | Fungi | Thermoascus aurantiacus | CBH | exo | AF421954 | MYQRALLFSFFLAAARAHEAGTVTAENHPSLTWQQCSS GGSCTTQNGKVVIDANWRWVHTTSGYTNCYTGNTWDT SICPDDVTCAQNCALDGADYSGTYGVTTSGNALRLNFVT QSSGKNIGSRLYLLQDDTTYQIFKLLGQEFTFDVDVSNLP CGLNGALYFVAMDADGNLSKYPGNKAGAKYGTGYCDS QCPRDLKFINGQANVEGWQPSANDPNAGVGNHGSSCAE MDVWEANSISTAVTPHPCDTPGQTMCQGDDCGGTYSST RYAGTCDTDGCDFNPYQPGNHSFYGPGKIVDTSSKFTVV TQFITDDGTPSGTLTEIKRFYVQNGKVIPQSESTISGVTGN SITTEYCTAQKAAFDNTGFFTHGGLQKISQALAQGMVL MSLWDDHAANMLWLDSTYPTDADPDTPGVARGTCPTT SGVPADVESQNPNSYVIYSNIKVGPINSTFTAN (SEQ ID NO: 71) |
| 36 | Fungi | Talaromyces emersonii | Cbh1 | exo | AAL89553 | mlrralllss sailavkaqq agtataenhp pltwqectap gscttqngav vldanwrwvhdvngytncyt gntwdptycp ddetcaqnca ldgadyegty gvtssgsslk lnfvtgsnvgsrlyllqdds tyqifkllnr efsfdvdvsn lpcglngaly fvamdadggv skypnnkagakygtgycdsq cprdlkfidg eanvegwqps snnantgigd hgsccaemdv weansisnavtphpcdtpgq tmcsgddcgg tysndryagt cdpdgcdfnp yrmgntsfyg pgkiidttkpftvvtqfltd dgtdtgtlse ikrfyiqnsn vipqpnsdis gvtgnsitte fctaqkqafgdtddfsqhgg lakmgaamqq gmvlvmslwd dyaaqmlwld sdyptdadpt tpgiargtcptdsgvpsdve sqspnsyvty snikfgpins tftas (SEQ ID NO: 72) |
| 38 | Fungi | Trichoderma reesei | Cbh1 | exo | P62694 | myrklavisa flataraqsa ctlqsethpp ltwqkcssgg tctqqtgsvv idanwrwthatnsstncydg ntwssticpd netcaknccl dgaayastyg vttsgnslsi gfvtqsaqknvgarlylmas dttyqeftll gnefsfdvdv sqlpcglnga lyfvsmdadg gvskyptntagakygtgycd sqcprdlkfi ngqanvegwe pssnnantgi gghgsccsem diweansisealtphpcttv gqeicegdgc |

TABLE 5-continued

| Cell # | Family | Organism | Protein | Activity | Genbank Acc. No. | Sequence |
|---|---|---|---|---|---|---|
| | | | | | | ggtysdnryg gtcdpdgcdw npyrlgntsf ygpgssftldttkkltvvtq fetsgainry yvqngvtfqq pnaelgsysg nelnddycta eeaefggssfsdkggltqfk katsggmvlv mslwddyyan mlwldstypt netsstpgav rgscstssgvpaqvesqspn akvtfsnikf gpigstgnps ggnppggnrg ttttrrpatt tgsspgptqshygqcggigy sgptvcasgt tcqvinpyys qcl (SEQ ID NO: 73) |
| 39 | Fungi | Phanerochaete chrysosporium | Cbh1 | exo | Z29653 | MFRAAALLAFTCLAMVSGQQAGTNTAENHPQLQSQQCT TSGGCKPLSTKVVLDSNWRWVHSTSGYTNCYTGNEWD TSLCPDGKTCAANCALDGADYSGTYGITSTGTALTLKFV TGSNVGSRVYLMADDTHYQLLKLLNQEFTFDVDMSNLP CGLNGALYLSAMDADGGMSKYPGNKAGAKYGTGYCDS QCPKDIKFINGEANVGNWTETGSNTGTGSYGTCCSEMDI WEANNDAAAFTPHPCTTTGQTRCSGDDCARNTGLCDGD GCDFNSFRMGDKTFLGKGMTVDTSKPFTVVTQFLTNDN TSTGTLSEIRRIYIQNGKVIQNSVANIPGVDPVNSITDNFC AQQKTAFGDTNWFAQKGGLKQMGEALGNGMVLALSIW DDHAANMLWLDSDYPTDKDPSAPGVARGTCATTSGVPS DVESQVPNSQVVFSNIKFGDIGSTFSGTSSPNPPGGSTTSS PVTTSPTPPPTGPTVPQWGQCGGIGYSGSTTCASPYTCHV LNPCESILSLQRSSNADQYLQTTRSATKRRLDTALQPRK (SEQ ID NO: 74) |
| 40 | Fungi | Aspergillus niger | CBHA | exo | XM_001391971 | MHQRALLFSALLTAVRAQQAGTLTEEVHPSLTWQKCTS EGSCTEQSGSVVIDSNWRWTHSVNDSTNCYTGNTWDAT LCPDDETCATNCALDGADYESTYGVTTDGDSLTLKFVT GSNVGSRLYLMDTSDEGYQTFNLLDAEFTFDVDVSNLPC GLNGALYFTAMDADGGASKYPANKAGAKYGTGYCDSQ CPRDLKFIDGQANVDGWEPSSNNDNTGIGNHGSCCPEM DIWEANKISTALTPHPCDSSEQTMCEGNDCGGTYSDDRY GGTCDPDGCDFNPYRMGNDSFYGPGKTIDTGSKMTVVT QFITDGSGSLSEIKRYYVQNGNVIANADSNISGVTGNSITT DFCTAQKKAFGDDDIFAEHNGLAGISDAMSSMVLILSLW DDYYASMEWLDSDYPENATATDPGVARGTCDSESGVPA TVEGAHPDSSVTFSNIKFGPINSTFSASA (SEQ ID NO: 75) |
| 41 | Fungi | Aspergillus niger | CBHB | exo | XM_001389539 | MSSFQVYRAALLLSILATANAQQVGTYTTETHPSLTWQT CTSDGSCTTNDGEVVIDANWRWVHSTSSATNCYTGNEW DTSICTDDVTCAANCALDGATYEATYGVTTSGSELRLNF VTQGSSICNIGSRLYLMSDDSNYELFKLLGQEFTFDVDVS NLPCGLNGALYFVAMDADGGTSEYSGNKAGAKYGTGY CDSQCPRDLKFINGEANCDGWEPSSNNVNTGVGDHGSC CAEMDVWEANSISNAFTAHPCDSVSQTMCDGDSCGGTY SASGDRYSGTCDPDGCDYNPYRLGNTDFYGPGLTVDTN SPFTVVTQFITDDGTSSGTLTEIKRLYVQNGEVIANGAST YSSVNGSSITSAFCESEKTLFGDENVFDKHGGLEGMGEA MAKGMVLVLSLWDDYAADMLWLDSDYPVNSSASTPGV ARGTCSTDSGVPATVEAESPNAYVTYSNIKFGPIGSTYSS GSSSGSGSSSSSSSTTTKATSTTLKTTSTTSSGSSSTSAAQA YGQCGGQGWTGPTTCVSGYTCTYENAYYSQCL (SEQ ID NO: 76) |

The thirty four degenerate primers designed to have homology to conservative regions of the fungal and protist Cbh's list above are presented in Table 6 below. These primers were ordered from Integrated DNA Technologies (IDT) and utilized to clone the cbh1 gene as discussed further below.

TABLE 6

| Primer No. | Primer Sequence* | Conservative Motif | IDT Ref. No. |
|---|---|---|---|
| 1 | gaa atg gat atY tgg gaR gcc (SEQ ID NO: 79) | Protozoa EMDIWEA (SEQ ID NO: 38) forward | 32980956 |
| 2 | ggc Ytc cca Rat atc cat ttc (SEQ ID NO: 80) | Protozoa EMDIWEA (SEQ ID NO: 38) reverse | 32980957 |
| 3 | gag atg gaY atc tgg gag gcK (SEQ ID NO: 81) | Fungi EMDIWEA (SEQ ID NO: 38) forward | 32980958 |
| 4 | Mgc ctc cca gat Rtc cat ctc (SEQ ID NO: 82) | Fungi EMDIWEA (SEQ ID NO: 38) reverse | 32980959 |

TABLE 6-continued

| Primer No. | Primer Sequence* | Conservative Motif | IDT Ref. No. |
|---|---|---|---|
| 5 | gaR atg gaY atY tgg gaR gcN (SEQ ID NO: 8) | EMDIWEA (SEQ ID NO: 38) forward | 32980960 |
| 6 | Ngc Ytc cca Rat Rtc cat Ytc (SEQ ID NO: 9) | EMDIWEA (SEQ ID NO: 38) reverse | 32980961 |
| 7 | gaR atg gaY atH tgg gaR gcN (SEQ ID NO: 10) | EMDIWEA (SEQ ID NO: 38) forward | 32980962 |
| 8 | Ngc Ytc cca Dat Rtc cat Ytc (SEQ ID NO: 11) | EMDIWEA (SEQ ID NO: 38) reverse | 32980963 |
| 9 | gcY ggW gcc aag tac ggt act (SEQ ID NO: 12) | Fungi AGAKYGT (SEQ ID NO: 39) forward | 32980964 |
| 10 | agt acc gta ctt ggc Wcc Rgc (SEQ ID NO: 13) | Fungi AGAKYGT (SEQ ID NO: 39) reverse | 32980965 |
| 11 | gcN ggN gcN aaR taY ggN can (SEQ ID NO: 14) | Fungi AGAKYGT (SEQ ID NO: 39) forward | 32980966 |
| 12 | Ngt Ncc Rta Ytt Ngc Ncc Ngc (SEQ ID NO: 15) | Fungi AGAKYGT (SEQ ID NO: 39) reverse | 32980967 |
| 13 | ggt tac tgt gaY gcc cag tgc (SEQ ID NO: 16) | Fungi GYCDAQC (SEQ ID NO: 40) forward | 32980968 |
| 14 | gca ctg ggc Rtc aca gta acc (SEQ ID NO: 17) | Fungi GYCDAQC (SEQ ID NO: 40) reverse | 32980969 |
| 15 | ggN taY tgY gaY gcN caR tgY (SEQ ID NO: 18) | GYCDAQC (SEQ ID NO: 40) forward | 32980970 |
| 16 | Rca Ytg Ngc Rtc Rca Rta Ncc (SEQ ID NO: 19) | GYCDAQC (SEQ ID NO: 40) reverse | 32980971 |
| 17 | ggt tac tgt gaY tct cag tgc (SEQ ID NO: 20) | Fungi GYCDSQC (SEQ ID NO: 41) forward | 32980972 |
| 18 | gca ctg aga Rtc aca gta acc (SEQ ID NO: 21) | Fungi GYCDSQC (SEQ ID NO: 41) reverse | 32980973 |
| 19 | ggN taY tgY gaY tcN caR tgY (SEQ ID NO: 22) | GYCDSQC (SEQ ID NO: 41) forward | 32980974 |
| 20 | Rca Ytg Nga Rtc Rca Rta Ncc (SEQ ID NO: 23) | GYCDSQC (SEQ ID NO: 41) reverse | 32980975 |
| 21 | gga tat tgt gat gcN caR tgY (SEQ ID NO: 24) | Protozoa GYCDAQC (SEQ ID NO: 40) forward | 32980976 |
| 22 | Rca Ytg Ngc atc aca ata tcc (SEQ ID NO: 25) | Protozoa GYCDAQC (SEQ ID NO: 40) reverse | 32980977 |
| 23 | acc gtc gtc acY cag ttc atc (SEQ ID NO: 26) | Fungal TVVTQFI (SEQ ID NO: 42) forward | 32980978 |
| 24 | gat gaa ctg Rgt gac gac ggt (SEQ ID NO: 27) | Fungal TVVTQFI (SEQ ID NO: 42) reverse | 32980979 |
| 25 | acN gtN gtN can caR ttY atH (SEQ ID NO: 28) | TVVTQFI (SEQ ID NO: 42) forward | 32980980 |
| 26 | Dat Raa Ytg Ngt Nac Nac Ngt (SEQ ID NO: 29) | TVVTQFI (SEQ ID NO: 42) reverse | 32980981 |
| 27 | acN gtN gtN can caR ttY ctN (SEQ ID NO: 30) | TVVTQFL (SEQ ID NO: 43) forward | 32980982 |
| 28 | Nag Raa Ytg Ngt Nac Nac Ngt (SEQ ID NO: 31) | TVVTQFL (SEQ ID NO: 43) reverse | 32980983 |
| 29 | acN gtN gtN can caR ttY caY (SEQ ID NO: 32) | TVVTQFH (SEQ ID NO: 44) forward | 32980984 |
| 30 | Rtg Raa Ytg Ngt Nac Nac Ngt (SEQ ID NO: 33) | TVVTQFH (SEQ ID NO: 44) reverse | 32980985 |
| 31 | acN gtN gtN can caR ttY gaR (SEQ ID NO: 34) | TVVTQFE (SEQ ID NO: 45) forward | 32980986 |
| 32 | Ytc Raa Ytg Ngt Nac Nac Ngt (SEQ ID NO: 35) | TVVTQFE (SEQ ID NO: 45) reverse | 32980987 |
| 33 | acN gtN gtN can caR ttY gtN (SEQ ID NO: 36) | TVVTQFV (SEQ ID NO: 46) forward | 32980988 |
| 34 | Nac Raa Ytg Ngt Nac Nac Ngt (SEQ ID NO: 37) | TVVTQFV (SEQ ID NO: 46) reverse | 32980989 |

*R = a, g; Y = c, t; M = a, c; K = g, t; S = g, c; W = a, t; H = a, c, t; B = g, t, c; V = g, c, a; D = g, a, t; and N = a, c, g, t Next, genomic DNA from *Schizochytrium aggregatum* was isolated as follows: *Schizochytrium aggregatum* was grown in 25 ml of cultivation media (as described above) in shaker flasks for 5-10 days. After 5-10 days, *S. aggregatum* culture was harvested and centrifuged to isolate the cells. The cells were washed with $H_2O$ and resuspended in 1 volume of "Smash and Grab" buffer. The "Smash and Grab" buffer contains 1% SDS (10% stock), 2% Triton X-100 (20% stock); 100 mM NaCl (4M stock); 1 mM EDTA (0.5M stock); and 10 mM Tris-Hl pH 8.0 (1M stock).

An equal volume of phenol-chloroform mix with glass beads was then added (2.5 ml cell pellet+2.5 ml buffer+5 ml phenol/chloroform+3 g beads). The resuspended cells were vortexed for 7 minutes, and then spun at 13,200 rpm in a 1.5 ml tubes for 10 minutes. The supernatant was then transferred to eppendorf tubes (450 µl/tube). 1 ml of cold ethanol was added to the supernatant, and this mixture was then spun down for 15 minutes. After this spinning step, the supernatant was discarded and 100 µl of TE was added to the pellet in each tube.

The resuspended pellets were combined and 1 µl RNAase (QIAGEN®) was added. This solution was next incubated at 37° C. for 5 minutes. After this, 1 µl of 4M NaCl, 10 µl of proteinase K, 20 µl of 10% SDS were added, and the mixture further incubated at 37° C. for 30 minutes. 400 µl of phenol-chloroform mix was then added, the mixture vortexed, and then spun down for 5 minutes. The resulting supernatant was transferred into new tubes, after which 400 µl of phenol-chloroform mix was again added, the mixture vortexed, and spun again for 5 minutes. To this final supernatant was added 40 µA 3M sodium acetate and 1 ml of cold ethanol. This final mixture was vortexed, spun for 15 minutes, and the supernatant discarded. The resulting pellet was washed with 70% ethanol twice and the pellet air-dried. The air-dried pellet was resuspended in 200 µl TE.

A GenomeWalker kit (Clontech) and protocol were used according to the manufacturer's instructions to perform PCR amplification using the *Schizochytrium aggregatum* genomic DNA as template. PCR amplification was performed using primer pairs, where each primer pair included one primer from Table 1 in combination with a primer homologous to the adapters that were used to make the template library according to the GenomeWalker kit manufacturer's protocol. Primers #4, 6, 8 (reverse primers for conservative region EMDI-WEA (SEQ ID NO: 38)) and #22 (reverse primer for conservative region GYCDAQC (SEQ ID NO: 40)) yielded PCR products that had homology to fungal Cbh1s, as described infra (Example 2). The corresponding forward primers were primers #3, 5, 7, and 21. The sequencing analysis of the generated PCR products revealed that all of the isolated products were fragments of the same gene. The full length gene sequence including coding and flanking regions was obtained as described herein. First, a PCR fragment was isolated from a library (with reverse primer #4) corresponding to a fragment containing the 5' flanking region and a portion of the 5' end of the *Schizochytrium aggregatum* cbh1 gene. Based on the sequence of this PCR fragment, *Schizochytrium aggregatum* cbh1-specific primers were designed (as indicated below):

Each of the primer pairs generated a PCR product about 2.5 to about 4 kb in length using the library template (four library templates were prepared according manufacture instructions). PCR products obtained with primers 39 and 40 were sequenced. The PCR fragment from primer 39 contained a portion of the 3' end of the *Schizochytrium aggregatum* cbh1 gene and additional 3' flanking region. The PCR fragment from primer 40 contained a portion of the 5' end of the *Schizochytrium aggregatum* cbh1 gene and additional 5' flanking region. The two sequences described above (the 5' and 3' portions of cbh1) were combined into one sequence about 7400 base pairs in length. This sequence containing the *Schizochytrium aggregatum* cbh1 is presented above and corresponds to SEQ ID NO:1.

As described above, the start codon, ATG, begins at position 3872 of SEQ ID NO: 1, followed by exon 1 (extending from position 3872 to 4345 of SEQ ID NO:1), intron 1 (extending from position 4346 to 4488 of SEQ ID NO:1), exon 2 (extending from position 4489 to 5542 of SEQ ID NO:1), intron 2 (extending from position 5543 to 5593 of SEQ ID NO:1), exon 3 (extending from position 5594 to 5626 of SEQ ID NO:1), and the termination codon TAG, ending at position 5626 of SEQ ID NO:1.

The cDNA was isolated as described further herein. Total RNA was isolated from *Schizochytrium aggregatum* as follows: 50-100 µl of cells or tissue were collected in a 2 ml tube with screw cap. 200 µl acid-washed 0.45-0.55 mm glass beads were added (beads were soaked in nitric acid for 1 hour, washed with water, and dried in a baking oven before utilization). 1 ml of TRIzol reagent (Invitrogen cat #15596-018) was added and the mixture homogenized in a homogenizer (Precellys 24, Bertin Technologies) for 2-3 minutes. The mixture was then incubated at room temperature for 5 minutes. Next, 0.2 ml of chloroform was added, the mixture shaken and then spun down for 10 minutes at 12,000 g at 2-8° C. The clear supernatant was removed into a new tube and 1 volume of 70% ethanol was added. The final sample was applied to a column from the RNaesy kit (Qiagen cat #74104). The yeast protocol from the kit manual was followed starting with the column step. cDNA was prepared using the Invitrogen TermoScript RT-PCR System (cat #11146-016).

The prepared cDNA was utilized to isolate the cbh1 cDNA. A DNA fragment containing the coding sequence of *Schizochytrium aggregatum* cbh1 cDNA was obtained by PCR with *Schizochytrium aggregatum* cDNA as a template

| Primer# | X# | Sequence | Note | IDT ref.# |
|---|---|---|---|---|
| 39 | X01379 | Cggaacaggatattgtgatgctcag (SEQ ID NO: 84) | *S. aggregatum* Cell1GTGYCDAQ for (SEQ ID NO: 85) | 34128302 |
| 40 | X01380 | Ctgagcatcacaatatcctgttccg (SEQ ID NO: 86) | *S. aggregatum* Cell1GTGYCDAQ rev (SEQ ID NO: 87) | 34128303 |
| 41 | X01381 | Tgcaacgagatggacatttgggaagcg (SEQ ID NO: 88) | *S. aggregatum* Cell1 CNEMDIWEA for (SEQ ID NO: 89) | 34128304 |
| 42 | X01382 | Cgcttcccaaatgtccatctcgttgca (SEQ ID NO: 90) | *S. aggregatum* Cell1 CNEMDIWEA rev (SEQ ID NO: 91) | 34128305 |

Primers 39 and 40 are complementary to each other as well as primers 41 and 42 are complementary to each other. Primers 39 and 40 generated distinct and abundant PCR products.

and primers specific for the *Schizochytrium aggregatum* cbh1 gene (forward primer: 5' acttaattaaaATGTCTGCCATTAC-CCTCGCCC (SEQ ID NO: 92), where the lower case letters represent the restriction enzyme sites; reverse primer: 5' acg-gcgcgccCTACAAGCACTGCGAGTAGTAGTC (SEQ ID NO: 93)). Sequence analysis of the DNA fragment yielded the complete cDNA sequence of the *Schizochytrium aggregatum* cbh1 gene, corresponding to SEQ ID NO:2. The cDNA sequence encodes for the *Schizochytrium aggregatum* Cbh1 polypeptide, also presented above, and corresponding to SEQ ID NO:3.

Example 2

Homology and Proteomics Analysis of *Schizochytrium Aggregatum* Cbh1

The isolated *Schizochytrium aggregatum* Cbh1 is novel. No identical sequences can be found in the public protein databases (PubMed). The translated sequence, based on sequence homology, belongs to the Glycosyl Hydrolase Family 7 (GHF7) of proteins and contains tunnel forming loops. Therefore, the sequence was predicted to encode a exoglucanase type I or Cbh1 based on previous data demonstrating that exoglucanases have tunnel forming loops, whereas endoglucanases do not (see Zhou X et al., *Gene* 395:29-39 (2007). The isolated cbh1 gene is predicted to contain a N-terminal 19 amino acid signal sequence, and thus encodes a secreted protein. A schematic diagram of *Schizochytrium aggregatum* Cbh1 is shown in FIG. 1, depicting the presence of a catalytic domain (CD) and a cellulose binding domain (CBD).

Results of BLAST analysis between PCR products obtained from reactions using Primers #39 and 40 as described supra (Example 1) and other fungal Cbh1's indicates that *Schizochytrium aggregatum* Cbh1 has substantial homology to these fungal sequences. The alignment between these sequences is shown in FIG. 3.

A comparison of the full translated Cbh1 sequence with other fungal Cbh1 s reveals that the novel Cbh1 contains an N-terminal exogluconase catalytic domain and C-terminal cellulose binding domain. Alignment between the predicted amino acid sequence of *Schizochytrium aggregatum* and the Cbh1 amino acid sequences of various Cbh1 source organisms is shown in FIG. 3. The percent identity between *Schizochytrium aggregatum* Cbh1 and these homologous Cbh1 sequences is summarized below in Table 7:

TABLE 7

| Cbh1 source organism | % Identity with *S. aggregatum* Cbh1 | |
|---|---|---|
| | Full length protein | Catalytic domain |
| *Trichoderma reesei* (SEQ ID NO: 73) | 52 | 55 |
| *Humicola grisea* (SEQ ID NO: 70) | 53 | 56 |
| *Thermoascus aurantiacus*\* (SEQ ID NO: 71) | 48 | 48 |
| *Talaromyces emersonii*\* (SEQ ID NO: 72) | 51 | 61 |
| *Botryotinia fuckeliana* (SEQ ID NO: 77) | 57 | 62 |
| *Phanerochaete chrysosporium* (SEQ ID NO: 74) | 56 | 59 |
| *Chaetomidium pingungium* | 56 | 59 |

*Note:
The Cbh1 sequences of these organisms do not contain a cellulose binding domain (CBD), as does *Schizochytrium aggregatum* Cbh1.

Genes encoding cellobiohydrolases in T. reseei (cbh1 and cbh2), *A. niger* (cbhA and cbhB) and *P. chrysosporium* (cbh1-4) have been cloned and described. The proteins encoded for by these genes are all modular enzymes containing a catalytic domain linked via a flexible liner sequence to a cellulose-binding molecule, similar to the isolated *Schizochytrium aggregatum* cbh1 gene described above. Cbh1, CbhB and Cbh1-4 are family 7 glycosyl hydrolases (GHF7) and have at least 50 to 60% homology at the amino acid level, but the homology between any of these enzymes and the glycosyl hydrolase family 6 CBH2 is less than 15%.

As shown above, the *Schizochytrium aggregatum* Cbh1 full length polypeptide sequence shares a 52% identity with the *T. reesei* Cbh1, and a 56% identity with the P. chrysosporium Cbh1, both of which have been previously identified and characterized. In addition, as shown above in Table 7, there is a higher percent identity shared between the individual domains of the *Schizochytrium aggregatum* Cbh1, and the corresponding domains in each of the various organisms identified in the table above. For example, the *Schizochytrium aggregatum* Cbh1 catalytic domain shares about 55% identity with the *T. reesei* Cbh1 catalytic domain. The *Schizochytrium aggregatum* Cbh1 shares the highest percent identity with the full length *Botryotinia fuckeliana* Cbh1, and shares about 62% identity with the *Botryotinia fuckeliana* Cbh1 catalytic domain.

Thus, based on the percent identity between the full length sequence of *S. aggregatum* Cbh1 and several GHF7 family members discussed above, the *S. aggregatum* Cbh1 is predicted to be a novel cellobiohydrolase I (Cbh1) of the GHF7 group, and is predicted to function similarly to the Cbh1 proteins of the organisms discussed above.

Example 3

Functional Expression of *Schizochytrium Aggregatum* Cbh1 in *Saccharomyces Cerevisiae*

To evaluate expression and activity of the novel *Schizochytrium aggregatum* Cbh1, the cbh1 cDNA, with its native signal sequence, was inserted into an episomal yeast expression vector under control of the ENO1 promoter and terminator to generate the pMU506 construct. The pMU506 construct is depicted in FIG. 4.

Yeast Transformation

A lithium acetate transformation (LiOAc) protocol was utilized for transformation of yeast with episomal plasmids containing the cbh1 sequence. Yeast were grown in 2 ml YPD media at 30° C. overnight. In the morning, 50 ml of YPD were inoculated with 0.5 ml of the overnight culture. This 50 ml culture was grown at 30° C. with shaking. After 4-5 hours, the yeast cells were spun down in a clinical centrifuge at 13,200 rpm for 5 minutes. The cells were suspended in sterile water and spun again. The cells were then suspended in 1 ml 100 mL LiOAc and transferred to a microfuge tube. The microfuge tube was spun at top speed for 15 seconds. The LiOAc was pipetted off. The remaining pellet was suspended in a tranformation mix, where 150 µl of the transformation mix was added to each sample. The 150 µl transformation mix contained 15 µl water, 15 µl 1M LiOAc, 20 µl DNA carrier (Ambion, cat #AM9680) and 100 µl 50% PEG 3350.

For the transformation, 1 µl of the DNA sample (the plasmid containing the cbh1 gene) was placed into a microfuge tube. 150 µl of the cells resuspended in transformation mix was added to the DNA sample. This sample with the DNA was incubated at 30° C. for 30 minutes in an incubator. Subsequently, the sample was heat-shocked in a water bath at 42° C. for 15 minutes. The cells were next spun down for 15 seconds and the transformation mix was pipetted off. Then 50 µl of sterile water was added to the cells, the cells were resuspended and then plated on selective plates. The plates were incubated at 30° C. for 2-3 days. In this way, cells transformed with the *S. aggregatum* cbh1 expression vector were generated.

Initially, the Y294 yeast strain (genotype: α leu2-3,112 ura3-52 his3 trp1-289; ATCC No. 201160), also referred to as MO013, was transformed with *Saccharomyces cerevisiae* His3 and Trp1 polymerase chain reaction (PCR) products to rescue the His3 and Trp1 auxotrophies. This rescued yeast strain is referred to as MO375. The pMU506 vector construct containing the *S. aggregatum* cbh1 sequence was then transformed into the MO375 yeast strain to generate the MO430 yeast strain.

Measurement of Cellulase Activity

Studies to determine the cellulase activity of the transformed MO430 yeast strain were next conducted. The MO430 strain and a Y294-derived control strain (MO375) transformed with empty vector (MO419) were inoculated in 50 ml YPD media and grown with shaking for three days.

After three days, cell supernatants were concentrated 100-fold by incubating with the cellulosic substrate phosphoric acid swollen cellulose (PASC). For each 50 ml of supernatant, 100 μl of 2.4% PASC was added. The supernatant-PASC combination was mixed with a stir bar for five to six hours at 4° C. The PASC and attached cellulose was then collected by centrifugation, washed with 50 mM NaAc pH 5.0, using microspin columns with filters for the final spin, and resuspended in 0.5 ml of 50 mM NaAc pH 5.0 in 1.5 ml tubes. The mixture in the 1.5 ml tubes was then incubated with shaking at 35° C. for 24-48 hours.

The accumulation of reducing sugars was measured at 0, 20 and 44 hours with 1% Dinitrosalicylic Acid Reagent Solution (DNS). The DNS includes the following: (1) 3,5-dinitrosalicylic acid: 10 g; (2) Sodium sulfite: 0.5 g; (3) Sodium hydroxide: 10 g; (4) Water to 1 liter total volume. The DNS was calibrated by glucose (using glucose samples with a concentration of 0, 1, 2, 3, 4, 5, 6, 7, 8, 9, and 10 g/l. Samples, 100 ul, were spun down at highest speed for 1 min, 50 ul of supernatant was then mixed with 100 ul DNS in PCR tubes, heated at 99° C. for 5 min and cooled down to 4° C. in a PCR machine. Next, 50 μl from each well of the cooled supernatant-DNS mixture was transferred to a microtiter plate. The absorbance of each sample was measured at 565 nm by a plate reader and reducing sugars concentration was calculated based on DNS glucose calibration slope.

As shown in FIG. 5, the *S. aggregatum* Cbh1 exhibited significant levels of cellulase activity after both 20 and 44 hours.

Example 4

Functional Expression of Codon-Optimized *Schizochytrium Aggregatum* Cbh1 in *Saccharomyces Cerevisiae*

The above-described experiments were also performed utilizing yeast strains (e.g., *Saccharomyces cerevisiae*) transformed with a vector containing the *Schizochytrium aggregatum* cbh1 that has been codon-optimized for *Saccharomyces cerevisiae*.

The codon-optimized *Schizochytrium aggregatum* CBH1 gene having an *Saccharomyces cerevisiae* alpha mating factor pre signal sequence (SEQ ID NO:4) was inserted into PacI/AscI sites of pMU451 episomal yeast expression vector (FIG. 6). In parallel, several fungal codon optimized CBH1 genes (Table 8) with the same signal sequence were inserted into PacI/AscI sites of pMU451. All of the expression constructs with the exception of the construct having the codon-optimized *Schizochytrium aggregatum* CBH1 were transformed into MO375. The construct with codon-optimized *Schizochytrium aggregatum* CBH1 was transformed into yeast strain Y294 (MO013). Strains MO375 and MO013 have a similar genetic background and demonstrate the same protein expression level for heterologous proteins.

The resulting strains are summarized in Table 8 below. The strains from Table 8 were inoculated in 10 ml YPD in 50 ml tubes and were grown with shaking for 2 days. Secreted cellulase activity in culture supernatants was analyzed by the Avicel conversion assay (as described above). The results of the assay are shown in FIG. 7. The expression level of the native *Schizochytrium aggregatum* Cbh1 (strain MO430) was not sufficient to be detected by the Avicel assay. It was, however, detectable using phosphoric acid swollen cellulose (PASC), an amorphous cellulose, as a substrate when the supernatant was concentrated 100-fold. Secreted activity on Avicel of codon-optimized *Schizochytrium aggregatum* Cbh1 with *Saccharomyces cerevisiae* alpha mating factor pre signal sequence (strain MO556) was detected above background (strain MO419) and was comparable with secreted activities of other fungal Cbh 1s (strains MO445, MO456, MO457 and MO458).

The expression level of *Schizochytrium aggregatum* Cbh1 is further optimized by screening for optimal signal sequence and/or mutagenesis of the protein sequence. Additional codon-optimized sequences that are utilized include those corresponding to SEQ ID NOs: 5-7.

The construct used to transform *Saccharomyces cerevisiae* and express *Schizochytrium aggregatum* Cbh1 can also include a variant, fragment or derivative thereof of a native or codon-optimized version of *Schizochytrium aggregatum* cbh1. A fragment of cbh1 includes a sequence encoding any domain of the *Schizochytrium aggregatum* Cbh1, e.g., the CD. The expression construct is optionally constructed to include an anchoring or tethering domain.

Additional gene sequences for one or more saccharolytic enzymes can optionally be included in a cbh1 vector construct using techniques well known in the art. For example, constructs for expressing two or three cellulases simultaneously (*Schizochytrium aggregatum* Cbh1, Eg1, Bgl1, and/or Cbh2) are constructed.

TABLE 8

Description of Strains Utilized for the Avicel Conversion Assay (FIG. 7)

| Strain # | Cellulase | Family | Organism | Gene | Signal Sequence |
| --- | --- | --- | --- | --- | --- |
| MO419 | None | | | | |
| MO430 | Cbh1 | Fungi/Protozoa | *Schizochytrium aggregatum* | Native | Native |
| MO445 | Cbh1 | Fungi | *Neosartorya fischeri* | Codon optimized | S.cer.αMFpre |
| MO456 | Cbh1 | Fungi | *Chaetomium thermophilum* | Codon optimized | S.cer.αMFpre |

TABLE 8-continued

Description of Strains Utilized for the Avicel Conversion Assay (FIG. 7)

| Strain # | Cellulase | Family | Organism | Gene | Signal Sequence |
|---|---|---|---|---|---|
| MO457 | Cbh1 | Fungi | *Aspergillus terreus* | Codon optimized | S.cer.αMFpre |
| MO458 | Cbh1 | Fungi | *Penicillium chrysogenum* | Codon optimized | S.cer.αMFpre |
| MO556 | Cbh1 | Fungi/Protozoa | *Schizochytrium aggregatum* | Codon optimized | S.cer.αMFpre |

Example 5

Construction of a Yeast Integrative Expression Vector Containing *Schizochytrium Aggregatum* cbh1

To further evaluate expression and activity of the novel *Schizochytrium aggregatum* Cbh1, the cbh1 cDNA is inserted into an yeast integrative expression vector. The yeast integrative expression vector, pMU562 is depicted in FIG. 8. Yeast cells are transformed with the pMU562 vector containing the *Schizochytrium aggregatum* cbh1 sequence and assayed for cellulase activity as described above in Example 5.

These examples illustrate possible embodiments of the present invention. While the invention has been particularly shown and described with reference to some embodiments thereof, it will be understood by those skilled in the art that they have been presented by way of example only, and not limitation, and various changes in form and details can be made therein without departing from the spirit and scope of the invention. Thus, the breadth and scope of the present invention should not be limited by any of the above-described exemplary embodiments, but should be defined only in accordance with the following claims and their equivalents.

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

What is claimed is:

1. An isolated polypeptide comprising an amino acid sequence having at least 95% identity to amino acids 20 to 456 of SEQ ID NO:3, wherein said polypeptide has cellobiohydrolase activity.

2. The polypeptide of claim 1, said polypeptide comprising amino acids 20 to 456 of SEQ ID NO: 3.

3. The polypeptide of claim 1, said polypeptide comprising amino acids 20-546 of SEQ ID NO: 3.

4. An isolated polypeptide comprising an amino acid sequence having at least 95% identity to amino acids 457 to 546 of SEQ ID NO: 3 or to amino acids 507 to 546 of SEQ ID NO:3, wherein said polypeptide has cellulose binding activity.

5. The polypeptide of claim 4, said polypeptide comprising amino acids 507 to 546 of SEQ ID NO: 3.

6. The polypeptide of claim 4, said polypeptide comprising amino acids 457 to 546 of SEQ ID NO: 3.

7. An isolated polypeptide comprising at least 50 contiguous amino acids within amino acids 20 to 456 of SEQ ID NO:3, wherein said polypeptide has cellobiohydrolase activity.

8. A host cell comprising the polypeptide of claim 7.

9. The host cell of claim 8, wherein the host cell is of a yeast organism.

10. The host cell of claim 8, wherein the host cell is a thermophilic or mesophilic bacterial organism.

11. The host cell of claim 8, said host cell further comprising at least one or more heterologously expressed endoglucanase polypeptides and/or at least one or more heterologously expressed β-glucosidase polypeptides and/or at least one or more heterologously expressed exoglucanase polypeptides.

12. The host cell of claim 11, wherein said endoglucanase polypeptide is selected from the group consisting of Eg1, Eg2, Eg3, Eg4 and Eg5.

13. The host cell of claim 11, wherein said μ-glucosidase polypeptide is selected from the group consisting of *S. fibuligera* Bgl1 and Bgl2.

14. The host cell of claim 11, wherein said exogluconase polypeptide is selected from the group consisting of *T. emersonii* cellobiohydrolase I (Cbh1), *T. reesei* cellobiohydrolase I (Cbh1), *T. reesei* cellobiohydrolase II (Cbh2), *Chaetomium thermophilum* cellobiohydrolase I (Cbh1), and *Neosartorya fischeri* cellobiohydrolase I (Cbh1).

15. A process for converting lignocellulosic biomass to ethanol, comprising contacting lignocellulosic biomass with the host cell of claim 8.

16. A process for digesting as cellulosic substrate, comprising contacting said cellulosic substrate with the host cell of claim 8.

17. An isolated polypeptide comprising at least 50 contiguous amino acids within amino acids 457 to 546 of SEQ ID NO: 3, wherein said polypeptide has cellulose binding activity.

18. An isolated polynucleotide comprising a nucleic acid sequence encoding a polypeptide having at least 95% identity to amino acids 20 to 456 of SEQ ID NO: 3, wherein said polypeptide has cellobiohydrolase activity.

19. The polynucleotide of claim 18, wherein said nucleic acid sequence is codon optimized for expression in *Saccharomyces cerevisiae* and encodes for a polypeptide comprising amino acids 20 to 456 of SEQ ID NO:3.

20. A vector comprising the polynucleotide of claim 18.

21. An isolated polynucleotide comprising a nucleic acid sequence encoding amino acids 457 to 546 of SEQ ID NO:3 or amino acids 507 to 546 of SEQ ID NO:3, wherein said polypeptide has cellulose binding activity.

* * * * *

```
SEQUENCE LISTING

<160> NUMBER OF SEQ ID NOS: 93

<210> SEQ ID NO 1
<211> LENGTH: 7422
<212> TYPE: DNA
<213> ORGANISM: Schizochytrium aggregatum

<400> SEQUENCE: 1
gtaatacgac tcactatagg gcacgcgtgg tcgacggccc gggctggtat cttgctggag      60
gcgttgcgac aggcctcaca gcaggacttg ccgcttgtgg agtaggacgc ggtctcttgt     120
tgcctggctc ttttccagga ggcgcatcct gatagcttcg cttcgatggc cgttcatcac     180
tgtcttcgct ccatggcttg gagccttttt gagactggct gtatgggttc catctcgcat     240
attcgtccct ttttcgtttc atgcctacct ggacctttc gtaccctct ctttgccgtt      300 tccacttctc tgccctccgt ttcttttctt ctttctcggt ggcgttggtg cgttcttgct     360
cggcggcgtc ggttcgttct ttctcggcgg cttttggcctg tgcctcctgg taccactttc     420
tttcctgtct ctctcttgat gccttccgct ccatctcttc ctctttcgaa gtgacatgta     480
tctcatccct gactccatgg aactgcgggc aaccagctcg ctcacaattg gttttggctt      540
cttcgaacga cgctgacttc gtagcagatt tctgtttggc cgcttcgagt ttggcttcag     600
cttccttgag cagagcgtct tgctcgcgaa ggccaatttc tgcattgcta aggtcttttg     660
agagcaacag atctccttcc ttggccgctt gggagaggtt gttaaaagcc gtgttcgcct     720
tgttcctggc tttgatgcgc tcctccaaca gatattctgc cataccctca gccttggaag     780
cgagatgcat gttttttgcga gcgtctagga acaccttgtg aaaaatgtca tggcgaccgg     840
tcccgctagg acgactcttg gctttcgtgt tgggaggcat cttgcggtgt tcgtcttgga     900
tgcgatgatg ttcgaggaat cgtcttgttg cacgcggga gtatatgtgg ttttcgaca      960 caggcgtacg agtttgtcgt gtagctcggt cggcacaatt tccgaagaat gacttcgtgg    1020
```

```
acctttgtc gcgtctattt ggcgatggct ggcgcttgac gcgggttgcc agtgactttc    1080
taccagtgaa taaagggctt gtctagctag cctttgttct cggtccatat tcatgaccat    1140
aattcacggg ttatctgcca tccaacatgt taatgtgagc actgcagata atttgcttcc    1200
gttaattagt tgtgtgagtg ctatcgctgg gtcaagattt agctcaatta ttctttggta    1260
cccgggtgtt ctcaaagctg gtgagcttca aggggcaacg cgcttgtgac actgccatcg    1320
aagggaggaa tttctgtatg ctcataatcc atgagtactc tttatatgct tctcgtaaac    1380
atgtatgcat gtcagcgttc tggttgttct ctcatccact tgcaactgcg aatcactctt    1440
ctcccgggac agcgacattc gatatgtctc ggcatatctt catcagctcc tcttgttttt    1500
taacattgtc ggctgctcca tgcggagcct gttcaccacc agtggtgaag aatgctccgg    1560
aggccagttt ggcggcgaat ccttcaccag gaccactc tgtcaaaacc tgggatgact    1620
tgtctgtggt tccaggagca gacgaaccgc ccatctttgt tttcagccag ccaggatgca    1680
tgctgacgct ctgcacatca gtccagcgtc tcgcgaaagc cttcgagagc atggtgtcct    1740
gcagtttgct attggcgtac gagaaagaag ttgtacagtt cttgagggat tcgtcacccc    1800
caaagtgact gtcagagctc atgaagagaa tcctggactt cggtttgttc atgagacatg    1860
tcaagatgta tggtgcaagt gtgttgacgg cgaagacggc ggaaactccg tctgaagtga    1920
tctcctgcga agatgtagca ccgtagccga tgccggcatt gtctgcaaaa gtatatgtat    1980
cagcatagca tctagcatga cctatacatg gtgacttacg aatgatggca tcgaaggtac    2040
cagtcttgtt tgcctcttcg gccaatcgtt tagtctcgtt gatcgaagag agatttccaa    2100
tcaagcatcc ttcagctttg ggcacagcct tgctggcctg ctttgctcgc tctgagttac    2160
gtgcgtgaag agtgacttgg tgcccctttt cggaaagcgc cttggctgcg gccaaaccaa    2220
taccgtcgct ggatcctgtg atgaagacgc gcaccatctt ggaaagtaag gtgtatgtac    2280
aaggacgtga tgtagctaca atggtcgaag aactacaaat gctcagaaat catgagaacg    2340
aggagcaagc acagctgtcg ttgctagagt ggacatgagg ccatccggtt gtcggttatg    2400
cgttctcgcc tcgacagatg gagcaaaaga aatggagatg ttcgtgatga cgtcattgga    2460
cgtaaacatt ccaaggaggc agaatgccct gttcgatgtt tacgtgtata tgtttcgatg    2520
tatgttcgaa accaaattgc tagtggtgaa catatccgat gatggctgca gcatttccat    2580
gtttcgtctg cgttctcaat cgttctcaat cgcccaggtt tctgcgcgtg tgacacgtga    2640
tcctagatcc gtgaccttcg gcaagggag ccgttcttgt taactgggga tggtgttgac    2700
acgaacgaag aaatggtttg aaagagatgg aaagccagga aagctgacga agctgatagg    2760
tggaagatac gattctctcc tgccttcaat cttacagtat ggtcacctt ccaggacagc    2820 tggatctgag gaccgtaatg cccgtcgtcg cggatcgtat gcggctcttc cagccaaatg    2880
cacgcccaaa ctacactgcc tccgtggaag gtctccattc tcatgccttt gagttgcagc    2940
gctagctatc agaaacacca aagggaagtt tatccggttg taccacgaga ccacaaaggc    3000
gtccggagcc acaggcgaga ttggaccgcg tccaggaacc tggtaatttg aaggttgcag    3060
cagtgcgaac attgctcgct gtaaaagcta cgtctgctcg acttcggaat gtcatcgata    3120
tgtgcagttt gccgcaatcg tcactcatct tggcggtggt tcttcgaatt atcgcttcac    3180
gccaactcca gatctaccat ctagtgcaga aggtattgct ggtggtaagc ccaaagagtg    3240
gcgaggactc cgaggaggct ggaggcaaac gttgcatggc tttggtacaa aggaaaattg    3300
attaattatg cagggcaagc tgcacgggga agagcttggc gacgccttac cattctggcc    3360
cggactcttg acttctttgg ctaacaacat gtgctgctcc gggctacttt ctgctatatt    3420
```

```
gctcgttaaa ccaggaggct taagctatac ccacaaattg cttcatgtgt tcattgtcca   3480
gcacttccct gcatgtccgc gtgtcaccag gacataccac aagccagacc ggaccatgag   3540
caggatactg gcatacatcg gcaactgctg gcgtagatct tgactcgtcg tgcgacgacg   3600
ggctcagccc tccgtagccc acaatctgcc taagcaggac agaacatctt ctgtccgtcg   3660
gaccgtccaa cgagggcaat cagtggatcc cacaatgctg gacaggcctc agaacagcca   3720
tgagcaagat ttgtgttttg cgcgaaggcc atgattgcaa gtggaagtga ggatgacgaa   3780
ctatataacg acgaagacgc catccacagt tcattctcat caaccaacaa agcaagcagt   3840
ttaaatctac cttacagaac aacctgcaag catgtctgcc attaccctcg ccctgggtgc   3900
tcttgccctc agctctgttg tcaacgctca gcaggctgga acccttactc ctgaaaaaca   3960
ccctgctttt tctgtgtcta cttgctctgc cggcggcact gcacgtcca agacccagag    4020
cattgtgctc gatggcaact ggcgctggct ccactctact tccggctcca ccaactgcta   4080
cacaggtaac accttcgaca agactttgtg ccctgatgga gtgacttgcg ccgcaaactg   4140
cgccctcgat ggtgctgact acaccggcac ttacggtatc aaggcatccg gcaactctct   4200
gagccttcag ctcaagactg gcagcaacgt tggctccaga gtctacctca tggacgagca   4260
ggacaagaac taccagctct tcaacctgaa gaaccaggag tttacgttcg acgtcgacgt   4320
cagcaagatc ggatgtaagt actctacatg acagggcagt agattaaatg ctaagcaaag   4380
gcaataggtg gtctcaacgg cgctctgtac ttcgtgtcca tgcccgcaga tggtggactt   4440
tctaccacta acaaggccgg caccaagttc ggaacaggat attgtgatgc tcagtgtcct   4500
aaagacatca agtttatcaa gggcaaggca acagcgatg gctggacagc atcttccaac    4560
aacgcaaaca ccggtttcgg tacgaccggc tcctgctgca acgagatgga tatctgggag   4620
gcaaacggga tctccaacgc tgtgactcct cactcctgca gtcccggcaa cgccgcttgc   4680
acttctgaca caacttgtgg ctctggcgac ggtaaccgct acaaaggcta ctgtgacaag   4740
gacggttgcg atttcaaccc cttcaggatg ggcaaccaga ccttctacgg ccccggcaag   4800
actatcgaca ccaccaagcc tctcactgtg gtcacccaat tcattacctc tgacaacact   4860
gctagtggcg atcttgttga gatccgtcgc aagtacgtcc agggcggcaa ggtcttcgat   4920
cagcccacat ccaacgttgc tggcgttagc ggcaactcga tcaccgacac cttctgcaaa   4980
aaccagaagt ccgtcttcgg tgacactaac gacttcgctg cgaagggtgg cttgaaggct   5040
atgggcgacg ccttcgctga tggcatggtc cttgtcatgt ctctgtggga tgattacgat   5100
gtcaacatgc actggctcaa ctctccttac ccaactgacg ccgacccaac aaagcctggt   5160
gttgcccgtg gaacttgctc tatcacctct ggtaagcccg ccgacgtcga gagccagact   5220
cctggtgcca ccgttgtcta ctcgaacatc aagactggtc ccattggctc caccttctct   5280
ggcgcccaac agcccggtgg ccccggcagt ggttcttcat cttccagctc agcgggaggc   5340
tcaagcacca cctccaggtc ttcttctacc acctccaggg ctaccaccac gagtgtcggg   5400
accactacca ccaccactag ctctcgcacg accacaacca gcgctgctgg cggcgtcgtc   5460
cagaagtacg gacagtgcgg tgtaagtgtt ccctatctgt ccaattttta ctactctcca   5520
tgtatactga ctcgcgtgac agggcctgac atacactggt cctactactt gtgtgagcgg   5580
aaccacttgc accaaggcca acgactacta ctcgcagtgc ttgtagatac agttacttgg   5640
cggcacgacc aacatgacgt gaaaacgatg acgaacacac gtgctaggca ggaaaaggac   5700
gttgcagctg tctggagaac tttgatagtt acattcgtta accgacaatt tgaattacca   5760
cgtttgtaga tcctcatggt ttcccactga cttctcgtgg tgaggttgcg tgacctgcag   5820
```

```
attcgtgcaa cttcttctcg tggtgttaac ggtgcaacgg ctgagtcgca aattttcgg      5880 tccttgtacg agcactattg gcaacaccac cgacaccaag aaagctagag acgccaatca     5940
tgtttcagat cgatgcaacg atcatccgtc gccaggcgtc cagcgatcac gatatcacag     6000
ctatagtagg cgacgaccac gccgtgggaa ccgagaacat ggggattagc aaccaaaatc     6060
agacagtatg cttaccttgt taagcggata gctatctaat gcttgcatga acggtcgtca     6120
ctataggaca attaatggtt cattatggaa cctgctgcaa tagaacatgg gcacgctatt     6180
ggcgggagca agcgcggcga tctcgcggcg atgtagaatt caccttttgac ttcaaccagg    6240 acccgctggt tctcgcctag ctaaaggata agatggggga ataaaccagt cgttccggac     6300
tcaccaacgg ccaggacgac atgactctca cgtccgacaa tactccgtta caatatcata     6360
aacgagagtt caagaccagc aattttgcaa catgggacat cgatggctga tttcagctta    6420
caatttgaag catgctcagg gctcacaagc ccggaatgaa ccatttatgc gattgacgga     6480
gtcgttgtcc gatagccaaa ctgccctgag acgctttggt gtggctaaca cgttctacag     6540
tgcagatcct tagcgggtct tcgggcaaag ccctgattgg gacaaacttc atctgtcacg     6600
actagacccg aactcacctg ctccgacttc cacacacgct cgcccgtacc tggccccgg     6660 taccgatatt atgcaggaac ttctgtgata tagaatccac actgagcttg atcaaactgc     6720
ccgccacggg gcacgatatg tcctagccgc gtctgacttg ggttgcatgt tgggtattac     6780
ggcacagcat ccatggaggg ttactgctca accatgctga cgcaatgaaa aaagtcctgg     6840
ccgagaccag ggtgcttgcg tgtgacaagc aataacgcca ccgcattggt cacatcgcgt     6900
gtcttcacac cttctttgag ccggctcaac gtgtgccgcg tatctcaaac acgcgatgcc     6960
ctgcgcgagg aaacgcctag agaaatacta ccgtcacaaa ccctggatca tcgatactag     7020
gctggcttaa gtaattagtg taaggccacc gaccgacccg ttcacccctg accatctgga     7080
gtgcatggag aatcactcca tgtgtagatc atcgttgccg gcgcatgtta gatcgattat     7140
ggcgcgctgc attatgcact aatgacttga gctgccctct ctccttaccg ggcgcgtgaa     7200
cgggttcctc agggccggtt actacaagtg cccatcgtcg tgcacatttg ctgcgctctt     7260
tgccgtgcgc tttgcgggtc gttcttgcgt cctgtacagt tgttgaggag acgactatat     7320
accattaccg ccaacatgga aggcacgttt gaaggcatca atcttgctga taggaccagc     7380
ccgggccgtc gaccacgcgt gccctatagt gagtcgtatt ac                        7422

<210> SEQ ID NO 2
<211> LENGTH: 1638
<212> TYPE: DNA
<213> ORGANISM: Artificial
<220> FEATURE:
<223> OTHER INFORMATION: cDNA of Schizochytrium aggregatum cbh1

<400> SEQUENCE: 2
atgtctgcca ttaccctcgc cctgggtgct cttgccctca gctctgttgt caacgctcag       60
caggctggaa cccttactcc tgaaaaacac cctgcttttt ctgtgtctac ttgctctgcc      120
ggcggcactt gcacgtccaa gacccagagc attgtgctcg atggcaactg cgctggctc       180 cactctactt ccggctccac caactgctac acaggtaaca ccttcgacaa gactttgtgc      240
cctgatggag tgacttgcgc cgcaaactgc gccctcgatg tgctgactac accggcact      300 tacggtatca aggcatccgg caactctctg agccttcagc tcaagactgg cagcaacgtt     360
ggctccgaga tctacctcat ggacgagcag gacaagaact accagctctt caacctgaag      420
aaccaggagt ttacgttcga cgtcgacgtc agcaagatcg gatgtggtct caacggcgct     480
```

```
ctgtacttcg tgtccatgcc cgcagatggt ggactttcta ccactaacaa ggccggcacc    540
aagttcggaa caggatattg tgatgctcag tgtcctaaag acatcaagtt tatcaagggc    600
aaggcaaaca gcgatggctg gacagcatct tccaacaacg caaacaccgg tttcggtacg    660
accggctcct gctgcaacga gatggatatc tgggaggcaa acgggatctc caacgctgtg    720
actcctcact cctgcagtcc cggcaacgcc gcttgcactt ctgacacaac ttgtggctct    780
ggcgacggta accgctacaa aggctactgt gacaaggacg gttgcgattt caaccccttc    840
aggatgggca accagacctt ctacggcccc ggcaagacta tcgacaccac caagcctctc    900
actgtggtca cccaattcat tacctctgac aacactgcta gtggcgatct tgttgagatc    960
cgtcgcaagt acgtccaggg cggcaaggtc ttcgatcagc ccacatccaa cgttgctggc   1020
gttagcggca actcgatcac cgacaccttc tgcaaaaacc agaagtccgt cttcggtgac   1080
actaacgact cgctgcgaa gggtggcttg aaggctatgg cgacgccctt cgctgatggc   1140
atggtccttg tcatgtctct gtgggatgat acgatgtca acatgcactg gctcaactct   1200
ccttacccaa ctgacgccga cccaacaaag cctggtgttg cccgtggaac ttgctctatc   1260
acctctggta agcccgccga cgtcgagagc cagactcctg gtgccaccgt tgtctactcg   1320
aacatcaaga ctggtcccat ggctccacc ttctctggcg cccaacagcc cggtggcccc   1380
ggcagtggtt cttcatcttc cagctcagcg ggaggctcaa gcaccacctc caggtcttct   1440
tctaccacct ccagggctac caccacgagt gtcgggacca ctaccaccac cactagctct   1500
cgcacgacca caaccagcgc tgctggcggc gtcgtccaga agtacggaca gtgcggtggc   1560
ctgacataca ctggtcctac tacttgtgtg agcggaacca cttgcaccaa ggccaacgac   1620
tactactcgc agtgcttg                                                  1638
```

<210> SEQ ID NO 3
<211> LENGTH: 546
<212> TYPE: PRT
<213> ORGANISM: Schizochytrium aggregatum

<400> SEQUENCE: 3

```
Met Ser Ala Ile Thr Leu Ala Leu Gly Ala Leu Ala Leu Ser Ser Val
1               5                  10                  15

Val Asn Ala Gln Gln Ala Gly Thr Leu Thr Pro Glu Lys His Pro Ala
            20                  25                  30

Phe Ser Val Ser Thr Cys Ser Ala Gly Gly Thr Cys Thr Ser Lys Thr
        35                  40                  45

Gln Ser Ile Val Leu Asp Gly Asn Trp Arg Trp Leu His Ser Thr Ser
    50                  55                  60

Gly Ser Thr Asn Cys Tyr Thr Gly Asn Thr Phe Asp Lys Thr Leu Cys
65                  70                  75                  80

Pro Asp Gly Val Thr Cys Ala Ala Asn Cys Ala Leu Asp Gly Ala Asp
                85                  90                  95

Tyr Thr Gly Thr Tyr Gly Ile Lys Ala Ser Gly Asn Ser Leu Ser Leu
            100                 105                 110

Gln Leu Lys Thr Gly Ser Asn Val Gly Ser Arg Val Tyr Leu Met Asp
        115                 120                 125

Glu Gln Asp Lys Asn Tyr Gln Leu Phe Asn Leu Lys Asn Gln Glu Phe
    130                 135                 140

Thr Phe Asp Val Asp Val Ser Lys Ile Gly Cys Gly Leu Asn Gly Ala
145                 150                 155                 160

Leu Tyr Phe Val Ser Met Pro Ala Asp Gly Gly Leu Ser Thr Thr Asn
```

```
                        165                 170                 175
Lys Ala Gly Thr Lys Phe Gly Thr Gly Tyr Cys Asp Ala Gln Cys Pro
                180                 185                 190

Lys Asp Ile Lys Phe Ile Lys Gly Lys Ala Asn Ser Asp Gly Trp Thr
            195                 200                 205

Ala Ser Ser Asn Asn Ala Asn Thr Gly Phe Gly Thr Thr Gly Ser Cys
        210                 215                 220

Cys Asn Glu Met Asp Ile Trp Glu Ala Asn Gly Ile Ser Asn Ala Val
225                 230                 235                 240

Thr Pro His Ser Cys Ser Pro Gly Asn Ala Ala Cys Thr Ser Asp Thr
                245                 250                 255

Thr Cys Gly Ser Gly Asp Gly Asn Arg Tyr Lys Gly Tyr Cys Asp Lys
                260                 265                 270

Asp Gly Cys Asp Phe Asn Pro Phe Arg Met Gly Asn Gln Thr Phe Tyr
            275                 280                 285

Gly Pro Gly Lys Thr Ile Asp Thr Thr Lys Pro Leu Thr Val Val Thr
        290                 295                 300

Gln Phe Ile Thr Ser Asp Asn Thr Ala Ser Gly Asp Leu Val Glu Ile
305                 310                 315                 320

Arg Arg Lys Tyr Val Gln Gly Gly Lys Val Phe Asp Gln Pro Thr Ser
                325                 330                 335

Asn Val Ala Gly Val Ser Gly Asn Ser Ile Thr Asp Thr Phe Cys Lys
                340                 345                 350

Asn Gln Lys Ser Val Phe Gly Asp Thr Asn Asp Phe Ala Ala Lys Gly
            355                 360                 365

Gly Leu Lys Ala Met Gly Asp Ala Phe Ala Asp Gly Met Val Leu Val
        370                 375                 380

Met Ser Leu Trp Asp Asp Tyr Asp Val Asn Met His Trp Leu Asn Ser
385                 390                 395                 400

Pro Tyr Pro Thr Asp Ala Asp Pro Thr Lys Pro Gly Val Ala Arg Gly
                405                 410                 415

Thr Cys Ser Ile Thr Ser Gly Lys Pro Ala Asp Val Glu Ser Gln Thr
                420                 425                 430

Pro Gly Ala Thr Val Val Tyr Ser Asn Ile Lys Thr Gly Pro Ile Gly
            435                 440                 445

Ser Thr Phe Ser Gly Ala Gln Gln Pro Gly Gly Pro Gly Ser Gly Ser
        450                 455                 460

Ser Ser Ser Ser Ser Ala Gly Gly Ser Ser Thr Thr Ser Arg Ser Ser
465                 470                 475                 480

Ser Thr Thr Ser Arg Ala Thr Thr Thr Ser Val Gly Thr Thr Thr Thr
                485                 490                 495

Thr Thr Ser Ser Arg Thr Thr Thr Thr Ser Ala Ala Gly Gly Val Val
                500                 505                 510

Gln Lys Tyr Gly Gln Cys Gly Gly Leu Thr Tyr Thr Gly Pro Thr Thr
            515                 520                 525

Cys Val Ser Gly Thr Thr Cys Thr Lys Ala Asn Asp Tyr Tyr Ser Gln
        530                 535                 540

Cys Leu
545

<210> SEQ ID NO 4
<211> LENGTH: 1641
<212> TYPE: DNA
<213> ORGANISM: Artificial
<220> FEATURE:
```

<223> OTHER INFORMATION: Schizochytrium aggregatum cbh1 optimized for
Saccharomyces cerevisiae

<400> SEQUENCE: 4

| | |
|---|---|
| atgagatttc catctatttt cactgctgtt ttgttcgcag cctcatcgag tctagctcaa | 60 |
| caggccggta ctctaacgcc tgagaaacat cccgccttct ccgttagtac atgttccgct | 120 |
| ggaggcacgt gcactagtaa gacacaaagc atagtcttag atggcaactg agatggctt | 180 |
| cacagcacat ccggttcaac gaactgttat actggcaata cattcgacaa gacgctttgt | 240 |
| cccgatggtg tcacttgtgc cgctaattgt gctttggacg gtgcagacta taccggaacg | 300 |
| tatggcataa aggcttcagg aaattcctta tccctacagc ttaaaactgg aagtaatgtg | 360 |
| ggttctagag tttacttgat ggacgagcaa gataagaatt atcaattatt caacttgaag | 420 |
| aatcaggagt tcacttttga tgtagacgtg tcaaagatcg gctgtggttt aaacggcgcc | 480 |
| ttgtacttcg tgtccatgcc agcagacgga ggtttgtcca aactaacaa agctggtacg | 540 |
| aagttcggca cgggatattg tgacgcccaa tgcccaaaag atattaagtt catcaaagga | 600 |
| aaggcaaatt ctgatggctg acagcttcc tcaaataatg ccaacacagg attcggcaca | 660 |
| accggtagtt gttgcaatga aatggatata tgggaagcaa acggaattag taatgctgtt | 720 |
| acacctcatt catgttctcc tggaaatgcc gcatgtacgt ccgatacgac ttgcggtagt | 780 |
| ggtgacggaa acagatacaa aggctattgc gataaggatg gatgcgactt taatccattc | 840 |
| agaatgggaa atcaaacttt ctacggcccc ggaaagacga tagatactac gaagccacta | 900 |
| acggtggtga cacagttcat aacgtcagac aatacagctt ctggcgactt agttgaaatt | 960 |
| agaagaaagt atgtgcaagg aggtaaagtg tttgatcagc ccaccagcaa cgtagccggt | 1020 |
| gtcagtggca attcaattac agacactttt tgcaagaacc agaaatctgt gtttggagat | 1080 |
| acgaatgact tcgcagctaa gggcggatta aaagcaatgg gagatgcatt tgctgatggt | 1140 |
| atggtcctag taatgtcctt atgggacgat tacgacgtca atatgcattg gcttaattca | 1200 |
| ccttatccaa ccgatgccga ccctacaaag ccaggtgttg ctagaggtac atgcagtatc | 1260 |
| actagtggaa agcccgctga tgtgggagag caaaccccctg gtgctacagt tgtatactca | 1320 |
| aacattaaga ctggtccaat ggctctacg ttcagtggag cccagcaacc tggaggcccc | 1380 |
| ggatctggtt cctcaagtag ttcatccgca ggcggttcat ccactacgtc aaggtccagt | 1440 |
| agcactacct ctagagctac aactaccagc gtcggaacaa ccactacgac aacctctagt | 1500 |
| aggacgacca ctacaagcgc cgcaggcggt gtagttcaga aatatggcca gtgtggaggt | 1560 |
| ctaacttaca caggaccaac gacttgcgta tctggtacaa cgtgcacgaa ggctaatgat | 1620 |
| tattactccc aatgtttata a | 1641 |

<210> SEQ ID NO 5
<211> LENGTH: 1638
<212> TYPE: DNA
<213> ORGANISM: Artificial
<220> FEATURE:
<223> OTHER INFORMATION: Codon-optimized Schizochytrium aggregatum cbh1
nucleotide sequence

<400> SEQUENCE: 5

| | |
|---|---|
| atgtcagcca ttactcttgc cttaggtgct ttagcccttt cctctgttgt aaatgctcaa | 60 |
| caggcaggta ccttgacacc agagaaacat ccagctttta gcgtatctac ctgtagtgca | 120 |
| ggtggaactt gtacttctaa gacccaaagc attgtgttgg acggaaattg gagatggtta | 180 |
| cactctacaa gtggttctac aaattgttac actggtaaca cttttgacaa gactctatgc | 240 |

```
cccgatggtg taacttgcgc agctaattgc gcattagacg gagccgacta cacaggtaca      300
tatggcataa aggcttcagg caattctctg agtctacaac ttaagacagg tagcaacgtt      360
ggctccagag tttatttaat ggacgaacaa gataaaaact accaactatt caatctgaaa      420
aatcaagaat tcacatttga tgtcgatgtt tccaaaatcg gctgtggttt gaacggtgca      480
ttatattttg tttcaatgcc cgcagatgga ggtttatcca ctacaaataa ggctggaacc      540
aaatttggaa cgggatattg tgacgctcaa tgtcctaagg atattaaatt tataaaagga      600
aaggctaact ctgatggttg gacagcctcc agtaacaatg ctaatacggg cttcggtacc      660
acaggatcct gttgcaatga aatggatatt tgggaagcaa acggtatcag taacgcagta      720
acgccacatt cgtgctctcc tggtaatgct gcctgcacct ctgatacaac ttgtggttct      780
ggcgacggta acaggtataa aggttattgt gataaggacg ttgtgatttt caatcctttc      840
aggatgggca atcagacctt ctatggtccc ggtaaaacaa ttgatactac gaaaccttta      900
actgtcgtaa cgcaatttat aacatctgat aataccgcct caggcgatct ggttgagatt      960
cgtagaaaat atgtccaagg aggtaaagtg tttgatcaac caaccagcaa cgtcgcaggt     1020
gtgagcggca actctataac tgatactttt tgtaagaacc aaaaatcggt tttcggtgat     1080
actaatgatt tcgcagctaa gggtggcttg aaagctatgg gtgatgcatt tgctgatggt     1140
atggtcctag ttatgtcctt gtgggatgac tacgatgtca atatgcattg gttaaattca     1200
ccatacccta cagacgctga cccaacaaag ccaggtgttg ctagaggaac atgctctatt     1260
accagcggta agccagctga tgttgaatcc caaactccag gagcaactgt ggtttatagc     1320
aatatcaaaa caggtcctat cggatcaact tttttcaggtg cccagcaacc aggtggccca     1380
ggaagtggtt cctcttcatc ttcgtcagct ggtggctctt cgactacatc aagatcgtcc     1440
tcaacgacta gtagagccac gacaacctca gttggtacca ctacgaccac tacatcaagt     1500
agaacaacta ccactagtgc tgctggaggc gtggtacaga aatacggtca gtgcggtggt     1560
ttgacgtata ctggtccaac cacatgtgtg agtggtacga cttgtaccaa agctaacgac     1620
tactactcgc agtgtttg                                                   1638
```

<210> SEQ ID NO 6
<211> LENGTH: 1638
<212> TYPE: DNA
<213> ORGANISM: Artificial
<220> FEATURE:
<223> OTHER INFORMATION: Codon-optimized Schizochytrium aggregatum cbh1
      nucleotide sequence

<400> SEQUENCE: 6

```
atgtcagcca ttactcttgc cttaggtgct ttagcccttt cctctgttgt aaatgctcaa       60
caggcaggta ccttgacacc agagaaacat ccagctttta gcgtatctac ctgtagtgca      120
ggtggaactt gtacttctaa gacccaaagc attgtgttgg acggaaattg gagatggtta      180
cactctacaa gtgttctac aaattgttac actggtaaca cttttgacaa gactctatgc      240
cccgatggtg taacttgcgc agctaattgc gcattagacg gagccgacta cacaggtaca      300
tatggcataa aggcttcagg caattctctg agtctacaac ttaagacagg tagcaacgtt      360
ggctccagag tttatttaat ggacgaacaa gataaaaact accaactatt caatctgaaa      420
aatcaagaat tcacatttga tgtcgatgtt tccaaaatcg gctgtggttt gaacggtgca      480
ttatattttg tttcaatgcc cgcagatgga ggtttatcca ctacaaataa ggctggaacc      540
aaatttggaa cgggatattg tgacgctcaa tgtcctaagg atattaaatt tataaaagga      600
aaggctaact ctgatggttg gacagcctcc agtaacaatg ctaatacggg cttcggtacc      660
```

```
acaggatcct gttgcaatga aatggatatt tgggaagcaa acggtatcag taacgcagta    720
acgccacatt cgtgctctcc tggtaatgct gcctgcacct ctgatacaac ttgtggttct    780
ggcgacggta acaggtataa aggttattgt gataaggacg gttgtgattt caatcctttc    840
aggatgggca atcagacctt ctatggtccc ggtaaaacaa ttgatactac gaaacctta     900 actgtcgtaa cgcaatttat aacatctgat aataccgcct caggcgatct ggttgagatt    960
cgtagaaaat atgtccaagg aggtaaagtg tttgatcaac caaccagcaa cgtcgcaggt   1020
gtgagcggca actctataac tgatactttt tgtaagaacc aaaaatcggt tttcggtgat   1080
actaatgatt tcgcagctaa gggtggcttg aaagctatgg gtgatgcatt tgctgatggt   1140
atggtcctag ttatgtcctt gtgggatgac tacgatgtca atatgcattg gttaaattca   1200
ccatacccta cagacgctga cccaacaaag ccaggtgttg ctagaggaac atgctctatt   1260
accagcggta agccagctga tgttgaatcc caaactccag agcaactgt ggtttatagc    1320 aatatcaaaa caggtcctat cggatcaact ttttcaggtg cccagcaacc aggtggccca   1380
ggaagtggtt cctcttcatc ttcgtcagct ggtggctctt cgactacatc aagatcgtcc   1440
tcaacgacta gtagagccac gacaacctca gttggtacca ctacgaccac tacatcaagt   1500
agaacaacta ccactagtgc tgctggaggc gtggtacaga aatacggtca gtgcggtggt   1560
ttgacgtata ctggtccaac cacatgtgtg agtggtacga cttgtaccaa agctaacgac   1620
tactactcgc agtgtttg                                                  1638

<210> SEQ ID NO 7
<211> LENGTH: 1638
<212> TYPE: DNA
<213> ORGANISM: Artificial
<220> FEATURE:
<223> OTHER INFORMATION: Codon-optimized Saccharomyces cerevisiae cbh1
      nucleotide sequence

<400> SEQUENCE: 7
atgtcagcca ttactcttgc cttaggtgct ttagcccttt cctctgttgt aaatgctcaa     60
caggcaggta ccttgacacc agagaaacat ccagcttta gcgtatctac ctgtagtgca    120
ggtggaactt gtacttctaa gacccaaagc attgtgttgg acggaaattg agatggtta    180 cactctacaa gtggttctac aaattgttac actggtaaca cttttgacaa gactctatgc    240
cccgatggtg taacttgcgc agctaattgc gcattagacg gagccgacta cacaggtaca    300
tatggcataa aggcttcagg caattctctg agtctacaac ttaagacagg tagcaacgtt    360
ggctccagag tttatttaat ggacgaacaa gataaaaaact accaactatt caatctgaaa    420
aatcaagaat tcacatttga tgtcgatgtt tccaaaatcg gctgtggttt gaacggtgca    480
ttatattttg tttcaatgcc cgcagatgga gggtttatcca ctacaaataa ggctggaacc    540
aaatttggaa cgggatattg tgacgctcaa tgtcctaagg atattaaatt tataaaagga    600
aaggctaact ctgatggttg gacagcctcc agtaacaatg ctaatacggg cttcggtacc    660
acaggatcct gttgcaatga aatggatatt tgggaagcaa acggtatcag taacgcagta    720
acgccacatt cgtgctctcc tggtaatgct gcctgcacct ctgatacaac ttgtggttct    780
ggcgacggta acaggtataa aggttattgt gataaggacg gttgtgattt caatcctttc    840
aggatgggca atcagacctt ctatggtccc ggtaaaacaa ttgatactac gaaacctta     900 actgtcgtaa cgcaatttat aacatctgat aataccgcct caggcgatct ggttgagatt    960
cgtagaaaat atgtccaagg aggtaaagtg tttgatcaac caaccagcaa cgtcgcaggt   1020
```

```
gtgagcggca actctataac tgatactttt tgtaagaacc aaaaatcggt tttcggtgat    1080
actaatgatt tcgcagctaa gggtggcttg aaagctatgg gtgatgcatt tgctgatggt    1140
atggtcctag ttatgtcctt gtgggatgac tacgatgtca atatgcattg gttaaattca    1200
ccatacccta cagacgctga cccaacaaag ccaggtgttg ctagaggaac atgctctatt    1260
accagcggta agccagctga tgttgaatcc caaactccag gagcaactgt ggtttatagc    1320
aatatcaaaa caggtcctat cggatcaact ttttcaggtg cccagcaacc aggtggccca    1380
ggaagtggtt cctcttcatc ttcgtcagct ggtggctctt cgactacatc aagatcgtcc    1440
tcaacgacta gtagagccac gacaacctca gttggtacca ctacgaccac tacatcaagt    1500
agaacaacta ccactagtgc tgctggaggc gtggtacaga aatacggtca gtgcggtggt    1560
ttgacgtata ctggtccaac cacatgtgtg agtggtacga cttgtaccaa agctaacgac    1620
tactactcgc agtgtttg                                                   1638
```

<210> SEQ ID NO 8
<211> LENGTH: 21
<212> TYPE: DNA
<213> ORGANISM: Artificial
<220> FEATURE:
<223> OTHER INFORMATION: Synthetic primer
<220> FEATURE:
<221> NAME/KEY: misc_feature
<222> LOCATION: (21)..(21)
<223> OTHER INFORMATION: n is a, c, g, or t

<400> SEQUENCE: 8
garatggaya tytgggargc n                                              21

<210> SEQ ID NO 9
<211> LENGTH: 21
<212> TYPE: DNA
<213> ORGANISM: Artificial
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: n is a, c, g, or t

<400> SEQUENCE: 9
ngcytcccar atrtccatyt c                                              21

<210> SEQ ID NO 10
<211> LENGTH: 21
<212> TYPE: DNA
<213> ORGANISM: Artificial
<220> FEATURE:
<223> OTHER INFORMATION: Synthetic primer
<220> FEATURE:
<221> NAME/KEY: misc_feature
<222> LOCATION: (21)..(21)
<223> OTHER INFORMATION: n is a, c, g, or t

<400> SEQUENCE: 10
garatggaya thtgggargc n                                              21

<210> SEQ ID NO 11
<211> LENGTH: 21
<212> TYPE: DNA
<213> ORGANISM: Artificial
<220> FEATURE:
<223> OTHER INFORMATION: Synthetic primer
<220> FEATURE:
<221> NAME/KEY: misc_feature
<222> LOCATION: (1)..(1)

<223> OTHER INFORMATION: n is a, c, g, or t

<400> SEQUENCE: 11
ngcytcccad atrtccatyt c                                              21

<210> SEQ ID NO 12
<211> LENGTH: 21
<212> TYPE: DNA
<213> ORGANISM: Artificial
<220> FEATURE:
<223> OTHER INFORMATION: Synthetic primer

<400> SEQUENCE: 12
gcyggwgcca agtacggtac t                                              21

<210> SEQ ID NO 13
<211> LENGTH: 21
<212> TYPE: DNA
<213> ORGANISM: Artificial
<220> FEATURE:
<223> OTHER INFORMATION: Synthetic primer

<400> SEQUENCE: 13
agtaccgtac ttggcwccrg c                                              21

<210> SEQ ID NO 14
<211> LENGTH: 21
<212> TYPE: DNA
<213> ORGANISM: Artificial
<220> FEATURE:
<223> OTHER INFORMATION: Synthetic primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 14
gcnggngcna artayggnca n                                              21

<210> SEQ ID NO 15
<211> LENGTH: 21
<212> TYPE: DNA
<213> ORGANISM: Artificial
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (13)..(13)

<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 15
ngtnccrtay ttngcnccng c                                          21

<210> SEQ ID NO 16
<211> LENGTH: 21
<212> TYPE: DNA
<213> ORGANISM: Artificial
<220> FEATURE:
<223> OTHER INFORMATION: Synthetic primer

<400> SEQUENCE: 16
ggttactgtg aygcccagtg c                                          21

<210> SEQ ID NO 17
<211> LENGTH: 21
<212> TYPE: DNA
<213> ORGANISM: Artificial
<220> FEATURE:
<223> OTHER INFORMATION: Synthetic primer

<400> SEQUENCE: 17
gcactgggcr tcacagtaac c                                          21

<210> SEQ ID NO 18
<211> LENGTH: 21
<212> TYPE: DNA
<213> ORGANISM: Artificial
<220> FEATURE:
<223> OTHER INFORMATION: Synthetic primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 18
ggntaytgyg aygcncartg y                                          21

<210> SEQ ID NO 19
<211> LENGTH: 21
<212> TYPE: DNA
<213> ORGANISM: Artificial
<220> FEATURE:
<223> OTHER INFORMATION: Synthetic primer
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 19
rcaytgngcr tcrcartanc c                                          21

<210> SEQ ID NO 20

```
<211> LENGTH: 21
<212> TYPE: DNA
<213> ORGANISM: Artificial
<220> FEATURE:
<223> OTHER INFORMATION: Synthetic primer

<400> SEQUENCE: 20
ggttactgtg aytctcagtg c                                              21

<210> SEQ ID NO 21
<211> LENGTH: 21
<212> TYPE: DNA
<213> ORGANISM: Artificial
<220> FEATURE:
<223> OTHER INFORMATION: Synthetic primer

<400> SEQUENCE: 21
gcactgagar tcacagtaac c                                              21

<210> SEQ ID NO 22
<211> LENGTH: 21
<212> TYPE: DNA
<213> ORGANISM: Artificial
<220> FEATURE:
<223> OTHER INFORMATION: Synthetic primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 22
ggntaytgyg aytcncartg y                                              21

<210> SEQ ID NO 23
<211> LENGTH: 21
<212> TYPE: DNA
<213> ORGANISM: Artificial
<220> FEATURE:
<223> OTHER INFORMATION: Synthetic primer
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 23
rcaytgngar tcrcartanc c                                              21

<210> SEQ ID NO 24
<211> LENGTH: 21
<212> TYPE: DNA
<213> ORGANISM: Artificial
<220> FEATURE:
<223> OTHER INFORMATION: Synthetic primer
<220> FEATURE:
<221> NAME/KEY: misc_feature
<222> LOCATION: (15)..(15)
<223> OTHER INFORMATION: n is a, c, g, or t

<400> SEQUENCE: 24
ggatattgtg atgcncartg y                                              21

<210> SEQ ID NO 25
```

```
<211> LENGTH: 21
<212> TYPE: DNA
<213> ORGANISM: Artificial
<220> FEATURE:
<223> OTHER INFORMATION: Synthetic primer
<220> FEATURE:
<221> NAME/KEY: misc_feature
<222> LOCATION: (7)..(7)
<223> OTHER INFORMATION: n is a, c, g, or t

<400> SEQUENCE: 25
rcaytgngca tcacaatatc c                                              21

<210> SEQ ID NO 26
<211> LENGTH: 21
<212> TYPE: DNA
<213> ORGANISM: Artificial
<220> FEATURE:
<223> OTHER INFORMATION: Synthetic primer

<400> SEQUENCE: 26
accgtcgtca cycagttcat c                                              21

<210> SEQ ID NO 27
<211> LENGTH: 21
<212> TYPE: DNA
<213> ORGANISM: Artificial
<220> FEATURE:
<223> OTHER INFORMATION: Synthetic primer

<400> SEQUENCE: 27
gatgaactgr gtgacgacgg t                                              21

<210> SEQ ID NO 28
<211> LENGTH: 21
<212> TYPE: DNA
<213> ORGANISM: Artificial
<220> FEATURE:
<223> OTHER INFORMATION: Synthetic primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 28
acngtngtnc ancarttyat h                                              21

<210> SEQ ID NO 29
<211> LENGTH: 21
<212> TYPE: DNA
<213> ORGANISM: Artificial
<220> FEATURE:
<223> OTHER INFORMATION: Synthetic primer
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
```

```
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 29
datraaytgn gtnacnacng t                                              21

<210> SEQ ID NO 30
<211> LENGTH: 21
<212> TYPE: DNA
<213> ORGANISM: Artificial
<220> FEATURE:
<223> OTHER INFORMATION: Synthetic primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 30
acngtngtnc ancarttyct n                                              21

<210> SEQ ID NO 31
<211> LENGTH: 21
<212> TYPE: DNA
<213> ORGANISM: Artificial
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 31
nagraaytgn gtnacnacng t                                              21

<210> SEQ ID NO 32
```

```
<211> LENGTH: 21
<212> TYPE: DNA
<213> ORGANISM: Artificial
<220> FEATURE:
<223> OTHER INFORMATION: Synthetic primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 32
acngtngtnc ancarttyca y                                          21

<210> SEQ ID NO 33
<211> LENGTH: 21
<212> TYPE: DNA
<213> ORGANISM: Artificial
<220> FEATURE:
<223> OTHER INFORMATION: Synthetic primer
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 33
rtgraaytgn gtnacnacng t                                          21

<210> SEQ ID NO 34
<211> LENGTH: 21
<212> TYPE: DNA
<213> ORGANISM: Artificial
<220> FEATURE:
<223> OTHER INFORMATION: Synthetic primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 34
```
acngtngtnc ancarttyga r          21

<210> SEQ ID NO 35
<211> LENGTH: 21
<212> TYPE: DNA
<213> ORGANISM: Artificial
<220> FEATURE:
<223> OTHER INFORMATION: Synthetic primer
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 35
ytcraaytgn gtnacnacng t          21

<210> SEQ ID NO 36
<211> LENGTH: 21
<212> TYPE: DNA
<213> ORGANISM: Artificial
<220> FEATURE:
<223> OTHER INFORMATION: Synthetic primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 36
acngtngtnc ancarttygt n          21

<210> SEQ ID NO 37
<211> LENGTH: 21
<212> TYPE: DNA
<213> ORGANISM: Artificial
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)

```
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 37
nacraaytgn gtnacnacng t                                              21

<210> SEQ ID NO 38
<211> LENGTH: 7
<212> TYPE: PRT
<213> ORGANISM: Artificial
<220> FEATURE:
<223> OTHER INFORMATION: Synthetic primer

<400> SEQUENCE: 38

Glu Met Asp Ile Trp Glu Ala
1               5

<210> SEQ ID NO 39
<211> LENGTH: 7
<212> TYPE: PRT
<213> ORGANISM: Artificial
<220> FEATURE:
<223> OTHER INFORMATION: Synthetic primer

<400> SEQUENCE: 39

Ala Gly Ala Lys Tyr Gly Thr
1               5

<210> SEQ ID NO 40
<211> LENGTH: 7
<212> TYPE: PRT
<213> ORGANISM: Artificial
<220> FEATURE:
<223> OTHER INFORMATION: Synthetic primer

<400> SEQUENCE: 40

Gly Tyr Cys Asp Ala Gln Cys
1               5

<210> SEQ ID NO 41
<211> LENGTH: 7
<212> TYPE: PRT
<213> ORGANISM: Artificial
<220> FEATURE:
<223> OTHER INFORMATION: Synthetic primer

<400> SEQUENCE: 41

Gly Tyr Cys Asp Ser Gln Cys
1               5

<210> SEQ ID NO 42
<211> LENGTH: 7
<212> TYPE: PRT
<213> ORGANISM: Artificial
<220> FEATURE:
<223> OTHER INFORMATION: Synthetic primer

<400> SEQUENCE: 42

Thr Val Val Thr Gln Phe Ile
1               5
```

```
<210> SEQ ID NO 43
<211> LENGTH: 7
<212> TYPE: PRT
<213> ORGANISM: Artificial
<220> FEATURE:
<223> OTHER INFORMATION: Synthetic primer

<400> SEQUENCE: 43

Thr Val Val Thr Gln Phe Leu
1               5

<210> SEQ ID NO 44
<211> LENGTH: 7
<212> TYPE: PRT
<213> ORGANISM: Artificial
<220> FEATURE:
<223> OTHER INFORMATION: Synthetic primer

<400> SEQUENCE: 44

Thr Val Val Thr Gln Phe His
1               5

<210> SEQ ID NO 45
<211> LENGTH: 7
<212> TYPE: PRT
<213> ORGANISM: Artificial
<220> FEATURE:
<223> OTHER INFORMATION: Synthetic primer

<400> SEQUENCE: 45

Thr Val Val Thr Gln Phe Glu
1               5

<210> SEQ ID NO 46
<211> LENGTH: 7
<212> TYPE: PRT
<213> ORGANISM: Artificial
<220> FEATURE:
<223> OTHER INFORMATION: Synthetic primer

<400> SEQUENCE: 46

Thr Val Val Thr Gln Phe Val
1               5

<210> SEQ ID NO 47
<211> LENGTH: 1590
<212> TYPE: DNA
<213> ORGANISM: Artificial
<220> FEATURE:
<223> OTHER INFORMATION: Synthetic Humicoloa grisea cbh1

<400> SEQUENCE: 47
gaattcatga gaaccgctaa gttcgctacc ttggctgcct tggttgcctc tgctgctgct      60
caacaagcct gttccttgac tactgaacgt cacccatctt tgtcttggaa caagtgtact     120
gctggtggtc aatgtcaaac tgtccaagcc tccatcactt tggactctaa ttggagatgg     180
acccaccaag tctctggtag tactaactgt acaccggta ataagtggga cacttctatt      240
tgtactgacg ctaagtcttg tgctcaaaat tgttgtgttg atggtgctga ttacccctcc     300
acttatggta ttaccaccaa cggtgactct ttgtccttga agttcgttac taaaggtcaa     360
cattccacca acgtcggttc tagaacctac ttaatggacg tgaagacaa gtaccaaacc     420 ttcgaattgt tgggtaatga atttaccttc gatgtcgatg tgtctaacat cggttgtggt     480
ttgaacggtg ctttatactt cgtttctatg gacgccgacg gtggtttgtc tcgttaccca     540
ggtaataagg ctggtgccaa gtatggtacc ggttactgtg atgctcaatg cccaagagac     600
```

```
attaagttca tcaacggtga agctaacatt gaaggttgga ctggttctac caacgaccca      660
aacgctggcg ccggtagata cggtacctgt tgttccgaaa tggacatttg ggaagccaac      720
aacatggcta ctgctttttac tccacaccca tgtaccatca ttggtcaatc cagatgtgaa     780
ggtgactcct gtggcggtac ctactccaac gaaagatacg ctggtgtttg tgatccagac      840
ggttgtgact tcaactccta cagacaaggt aacaagactt tctatggtaa gggtatgact      900
gtcgatacca ccaagaagat caccgtcgtc acccaattct tgaaggacgc taacggtgat      960
ttaggtgaaa ttaaaagatt ctacgtccaa gatggtaaga tcatcccaaa ctctgaatct     1020
accattccag gtgttgaagg taattccatc actcaagact ggtgtgacag acaaaaggtt     1080
gccttcggtg atattgacga cttcaacaga aagggtggta tgaagcaaat gggtaaggct     1140
ttggccggtc caatggtctt ggttatgtct atttgggacg atcacgcttc caacatgttg     1200
tggttggact ccaccttccc agttgatgct gctggtaagc aggtgccga aagaggtgct      1260 tgtccaacta cttccggtgt cccagctgaa gttgaagccg aagctccaaa ttctaacgtt     1320
gtcttctcta acatcagatt cggtccaatc ggttccacag tcgctggttt gccaggtgct     1380
ggtaatggtg gtaataacgg tggtaaccca ccaccaccaa ccactaccac ttcttctgcc     1440
ccagctacta ccaccaccgc ttctgctggt ccaaaggctg gtagatggca acaatgtggt     1500
ggtattggtt tcaccggtcc aacccaatgt gaagaaccat acatctgtac caagttgaac     1560
gactggtact ctcaatgttt ataactcgag                                       1590

<210> SEQ ID NO 48
<211> LENGTH: 1383
<212> TYPE: DNA
<213> ORGANISM: Artificial
<220> FEATURE:
<223> OTHER INFORMATION: Synthetic Thermoascus aurantiacus cbh1

<400> SEQUENCE: 48
gaattcatgt accaaagagc tctattgttc tccttcttct tggccgccgc tagagctcat       60
gaagccggta ctgtcaccgc cgaaaaccac ccatccttga cttggcaaca atgttcctct      120
ggtggttctt gtactactca aaacgggaag gttgttattg acgctaactg gagatgggtt      180
cacactacct ccggttacac caactgttac actggtaaca cttgggatac ttccatctgt      240
ccagacgacg ttacctgtgc tcaaaactgt gctttggacg gtgctgacta ctccggtact      300
tacggtgtca ctacctctgg caacgcgttg agattgaact tcgtcaccca atcttctggt      360
aagaacatcg gttctagatt gtacttgttg caagacgata ctacttacca aatcttcaag      420
ttgttgggtc aagagttcac tttcgacgtt gatgtttcca acttgccttg tggttttgaac    480 ggtgctttgt acttcgttgc tatggacgcc gacggtaact tatccaagta cccaggtaac      540
aaggccggtg ccaagtacgg taccggttac tgtgattctc aatgtccaag agacctaaaa      600
ttcattaacg gtcaagctaa cgtcgaaggt tggcaaccat ctgctaacga tccaaacgcc      660
ggtgtcggta tcacggttc ctcctgtgct gaaatggacg tttgggaagc taactctatc       720
tccaccgccg tcactccaca tccatgtgat accccaggtc aaaccatgtg tcaaggtgat      780
gattgtggtg gtacctactc ttccactaga tacgctggta cctgtgacac cgacggttgt      840
gatttcaacc cataccaacc aggtaaccac tctttctacg gtccaggtaa gattgtcgat      900
acttcttcta gttcactgt tgtcactcaa ttcattaccg acgatggtac cccatctggt      960
accctaactg aaattaagag attctacgtc caaaacggta agtcattcc acaatccgaa      1020 agcaccattt ccggtgttac cggtaactcc atcaccactg aatactgtac cgctcaaaag     1080
```

| | |
|---|---|
| gccgcctttg acaacaccgg tttcttcacc catggtggtt tgcaaaagat ttctcaagcc | 1140 |
| ttggctcaag gtatggtttt ggtcatgtcc ttgtgggatg accacgctgc taacatgttg | 1200 |
| tggttggatt ctacttaccc aactgacgct gatccagaca ccccaggtgt tgctagaggt | 1260 |
| acttgtccaa ccacttctgg tgttccagct gacgtcgaat ctcaaaaccc taactcttac | 1320 |
| gttatctact ctaacatcaa ggtgggtcca attaactcca ccttcactgc taactaactc | 1380 |
| gag | 1383 |

<210> SEQ ID NO 49
<211> LENGTH: 1379
<212> TYPE: DNA
<213> ORGANISM: Artificial
<220> FEATURE:
<223> OTHER INFORMATION: Synthetic Talaromyces emersonii cbh1

<400> SEQUENCE: 49

| | |
|---|---|
| gaattcatgc taagaagagc tttactattg agctcttctg ctatcttggc cgttaaggct | 60 |
| caacaagccg gtaccgctac tgctgaaaac caccctccat tgacctggca agaatgtacc | 120 |
| gctccaggtt cttgtaccac ccaaaacggt gctgtcgtct ggacgctaa ctggagatgg | 180 |
| gtccacgacg tcaacggtta cactaactgt acaccggta acacctggga cccaacttac | 240 |
| tgtccagacg acgaaacttg cgctcaaaac tgtgccttgg acggtgctga ctacgaaggt | 300 |
| acttacggtg ttacctcctc tggttcttcc ttgaagttga acttcgtcac tggttctaac | 360 |
| gtcggttcca gattgtattt gttgcaagat gactccactt accaaatctt caagttgttg | 420 |
| aacagagaat ttctttcga cgtcgatgtg tccaacttgc cttgtggttt gaacggtgct | 480 |
| ctatacttcg ttgctatgga cgctgatggt ggtgttccca agtacccaaa caacaaggct | 540 |
| ggtgccaaat acggtactgg ttactgtgac tctcaatgtc cacgtgactt gaagtttatt | 600 |
| gatggtgaag ctaatgtcga aggttggcaa ccatcttcta caacgctaa cactggcatc | 660 |
| ggtgaccacg gttcttgctg tgccgaaatg gacgtttggg aagccaactc catttccaac | 720 |
| gccgtcactc cacacccatg tgacactcca ggtcaaacta tgtgttccgg cgatgactgt | 780 |
| ggtggtactt actctaacga tagatacgct ggtacctgtg atccagacgg ttgcgacttc | 840 |
| aatccataca gaatgggtaa cacttccttt tacggtccag caagatcat cgacactact | 900 |
| aagccattca ctgttgtcac ccaattcttg accgacgatg gtactgatac cggtactttg | 960 |
| tccgaaatca agagattcta catccaaaac tctaacgtca tcccacaacc aaattccgac | 1020 |
| atctctggtg tcactggtaa ctccattacc accgaatttt gtaccgccca aaagcaagct | 1080 |
| ttcggtgaca ccgacgactt ctctcaacac ggtggtttgg ctaagatggg tgctgctatg | 1140 |
| caacaaggta tggttttggt catgtctttg tgggacgact acgctgctca aatgttgtgg | 1200 |
| ttggactccg attacccaac cgatgccgac ccaaccaccc ctggtatcgc tagaggtacc | 1260 |
| tgtccaactg actctggtgt tccatctgac gtcgaatccc aatctccaaa ctcctacgtc | 1320 |
| acttactcca acattaaatt ggtccaatca actccacttt cactgcttct taactcgag | 1379 |

<210> SEQ ID NO 50
<211> LENGTH: 1392
<212> TYPE: DNA
<213> ORGANISM: Artificial
<220> FEATURE:
<223> OTHER INFORMATION: Synthetic Talaromyces emersonii cbh2

<400> SEQUENCE: 50

| | |
|---|---|
| gaattcatgc gtaacttgtt ggccttggct ccagccgctt tgttggttgg tgctgccgaa | 60 |

```
gctcaacaat ccttgtgggg tcaatgcggt ggttcctcct ggactggtgc aacttcctgt      120
gccgctggtg ccacctgttc caccattaac ccatactacg ctcaatgtgt tccagccact      180
gccactccaa ctaccttgac taccaccact aagccaacct ccaccggtgg tgctgctcca      240
accactccac caccaactac taccggtact accacctctc cagtcgtcac cagacctgcc      300
tccgcctccg gtaatccatt cgaaggttat caattgtacg ctaaccctta ctacgcttct      360
gaagtcattt ccttggctat cccatctttg agctccgagt tggtcccaaa ggcctccgaa      420
gttgctaagg tcccttcatt tgtctggtta gatcaagctg ccaaggttcc atctatgggt      480
gattacttga aggatattca atctcaaaac gctgctggtg ctgatccacc aatcgccggt      540
attttcgttg tttacgattt gccagataga gactgtgccg ccgctgcttc taacggtgaa      600
ttttctatcg ccaacaacgg tgtcgcttta tacaaacaat atatcgattc cattagagaa      660
caattaacca cttactccga cgtccatacc atcttggtta tcgaaccaga ctctttggct      720
aacgttgtca ctaacttgaa cgttccaaaa tgtgctaacg ctcaagatgc ttacttggaa      780
tgtatcaact acgctattac ccaattggac ttgccaaacg ttgctatgta cttggacgct      840
ggtcacgccg ttggttggg ttggcaagcc aacttggccc cagctgctca attattcgct      900
tctgtttaca agaacgcctc ttccccagcc tctgttagag gtttggctac caacgtggct      960
aactacaacg cctggtccat ttctagatgt ccatcctaca ctcaaggtga cgctaactgt      1020
gatgaagaag attacgttaa cgctttgggt ccattgttcc aagaacaagg tttcccagct      1080
tacttcatca tcgacactta ccgtaacggt gtcagaccaa ctaagcaatc tcaatgggt      1140 gactggtgta acgttattgg taccggtttc ggtgttagac aaccaccga cactggtaac      1200 ccattggaag acgctttcgt ttgggtcaag ccaggtggtg aatccgacgg tacctccaac      1260
actactagcc cacgttacga ttaccactgt ggtttgtctg acgctttgca accagctcca      1320
gaagctggta cctggttcca agcctacttc gaacaattgt tgactaacgc caacccattg      1380
ttctaactcg ag                                                         1392
```

<210> SEQ ID NO 51  
<211> LENGTH: 1608  
<212> TYPE: DNA  
<213> ORGANISM: Artificial  
<220> FEATURE:  
<223> OTHER INFORMATION: Synthetic Trichoderma reesei cbh1

<400> SEQUENCE: 51

```
atggtctcct tcacctccct gctggccggc gttgccgcta tctctggtgt cctagcagcc       60
cctgccgcag aagttgaacc tgtcgcagtt gagaaacgtg aggccgaagc agaagctcaa      120
tccgcttgta ccctacaatc cgaaactcac ccaccattga cctggcaaaa gtgttctagc      180
ggtggaactt gtactcaaca aactggttct gttgttatcg acgctaactg gagatggaca     240
cacgccacta actcttctac caactgttac gacggtaaca cttggtcttc cacttatgt     300 ccagataacg aaacttgtgc taagaattgc tgtttggacg gtgccgccta cgcttctacc     360
tacggtgtta ccaccttccgg taactccttg tctattggtt tcgtcactca atccgctcaa     420
aagaacgttg gtgctagatt gtacttgatg gcttctgaca ctacttatca agaatttact     480
ttgttgggta acgaatttttc tttcgatgtt gacgtttccc aattgccatg tggcttgaac     540
ggtgctttgt actttgtctc tatggatgct gacggtggtg tttctaagta cccaactaac     600
actgccggtg ctaagtacgg tactggttac tgtgattctc aatgtccacg tgacttgaag     660
ttcattaacg gtcaagccaa cgtcgaaggt tgggaaccat cctccaacaa cgctaacacc     720
```

```
ggtatcggtg gtcacggttc ctgttgttcc gaaatggaca tctgggaagc taacagtatt      780
tctgaagctt tgacaccaca cccatgcacc actgtcggtc aagaaatttg tgaaggtgat      840
ggatgtggtg gaacctactc tgataacaga tacggtggta cttgtgaccc agacggttgt      900
gactggaacc catacagatt gggtaacact tctttctatg gtccaggttc ttctttcacc      960
ttggatacca ccaagaagtt gactgttgtt acccaattcg aaacttctgg tgctatcaac     1020
agatactacg ttcaaaacgg tgtcaccttc aacaaccaa cgctgaatt gggttcttac      1080 tctggtaatg aattgaacga cgactactgt accgctgaag aagctgaatt tggtggttcc     1140
tctttctccg acaagggtgg tttgacccaa ttcaagaagg ctacctccgg tggtatggtt     1200
ttggttatgt ccttgtggga tgattactac gcaaacatgt tatggttaga cagtacttac     1260
ccaactaacg aaacctcctc tactccaggt gctgtcagag gttcctgttc tacctcttct     1320
ggtgttccag ctcaagttga atctcaatct ccaaacgcta aggtcacttt ctccaacatc     1380
aagttcggtc caatcggttc cactggtaat ccatctggtg aaaccctcc aggtggtaac     1440 agaggtacta ccactactcg taggccagct actacaactg ttcttcccc aggcccaacc     1500 caatcccact acggtcaatg tggtggtatc ggttactctg gtccaaccgt ctgtgcttct     1560
ggtactacct gtcaagtttt aaacccatac tactctcaat gtttgtaa              1608
```

<210> SEQ ID NO 52
<211> LENGTH: 1479
<212> TYPE: DNA
<213> ORGANISM: Artificial
<220> FEATURE:
<223> OTHER INFORMATION: Synthetic Trichoderma reesei cbh2

<400> SEQUENCE: 52

```
atggtctcct tcacctcct gctggccggc gttgccgcta tctctggtgt cctagcagcc       60
cctgccgcag aagttgaacc tgtcgcagtt gagaaacgtg aggccgaagc agaagctgtc      120
ccattagaag aaagacaagc ctgctcctct gtttgggggtc aatgtggtgg tcaaaactgg      180
tctggtccaa cttgttgtgc ttccggttct acctgtgttt actccaacga ctactattcc      240
caatgtttgc aggtgctgc ttcctcttcc tcttcaacta gagctgcttc tacaacttct      300
agggtctccc caaccactc cagatcctct tctgctactc caccaccagg ttctactacc      360
actagagttc caccagtcgg ttccggtact gctacttact ctggtaaccc tttcgtcggt      420
gttactccat gggctaacgc ttactacgct tctgaagttt cttctttggc tatcccatct      480
ttgactggtg ctatggctac cgctgctgct gctgtcgcca agttccatc cttcatgtgg      540 ttggacacct tggacaaaac tccattaatg aacaaacct tggcagacat aaggactgct      600
aacaagaacg gcggtaacta cgctggtcaa tttgttgtgt acgacttgcc agacagagac      660
tgtgctgctt tggcttccaa cggtgaatac tccatcgctg acggtggtgt cgccaagtac      720
aagaactaca ttgataccat tagacaaatc gttgtcgaat actctgacat cagaaccttg      780
ttagtcatcg aaccagattc tttagccaat ttagtcacca acttgggtac tccaaagtgt      840
gctaacgctc aatctgccta cttagaatgt atcaattatg cagttaccca attgaacttg      900
ccaaacgttg ctatgtactt ggacgctggt cacgccggtt ggttgggttg gccagctaac      960
caagacccag ccgctcaatt attcgccaac gtttacaaga tgcctcttc tcctagagcc     1020 ttgcgtggtt tggctactaa cgtcgctaac tacaacggtt ggaacatcac ttctccacca     1080
tcttacaccc aaggtaacgc tgtttacaac gaaaagttgt acattcacgc tatcggtcca     1140
ttattggcta accatggttg gtctaacgcc ttcttcatca ccgaccaagg tagatccggt     1200
```

```
aaacaaccaa ctggtcaaca acaatggggt gattggtgta acgtcatcgg tactggtttc    1260
ggtatcagac catccgctaa cactggtgat tccttgttgg attccttcgt ctgggttaag    1320
ccaggtggtg aatgtgatgg cacctctgat tcctctgctc caagattcga ttccactgc    1380 gccttgccag acgctttgca accagcccca caagctggtg catggttcca agcttacttt    1440
gtccaattgt tgaccaacgc taacccatct ttcttgtaa                           1479
```

<210> SEQ ID NO 53
<211> LENGTH: 525
<212> TYPE: PRT
<213> ORGANISM: Artificial
<220> FEATURE:
<223> OTHER INFORMATION: Synthetic Humicola grisea cbh1

<400> SEQUENCE: 53

```
Met Arg Thr Ala Lys Phe Ala Thr Leu Ala Ala Leu Val Ala Ser Ala
1               5                   10                  15

Ala Ala Gln Gln Ala Cys Ser Leu Thr Thr Glu Arg His Pro Ser Leu
            20                  25                  30

Ser Trp Asn Lys Cys Thr Ala Gly Gly Gln Cys Gln Thr Val Gln Ala
        35                  40                  45

Ser Ile Thr Leu Asp Ser Asn Trp Arg Trp Thr His Gln Val Ser Gly
    50                  55                  60

Ser Thr Asn Cys Tyr Thr Gly Asn Lys Trp Asp Thr Ser Ile Cys Thr
65                  70                  75                  80

Asp Ala Lys Ser Cys Ala Gln Asn Cys Cys Val Asp Gly Ala Asp Tyr
                85                  90                  95

Thr Ser Thr Tyr Gly Ile Thr Thr Asn Gly Asp Ser Leu Ser Leu Lys
            100                 105                 110

Phe Val Thr Lys Gly Gln His Ser Thr Asn Val Gly Ser Arg Thr Tyr
        115                 120                 125

Leu Met Asp Gly Glu Asp Lys Tyr Gln Thr Phe Glu Leu Leu Gly Asn
    130                 135                 140

Glu Phe Thr Phe Asp Val Asp Val Ser Asn Ile Gly Cys Gly Leu Asn
145                 150                 155                 160

Gly Ala Leu Tyr Phe Val Ser Met Asp Ala Asp Gly Gly Leu Ser Arg
                165                 170                 175

Tyr Pro Gly Asn Lys Ala Gly Ala Lys Tyr Gly Thr Gly Tyr Cys Asp
            180                 185                 190

Ala Gln Cys Pro Arg Asp Ile Lys Phe Ile Asn Gly Glu Ala Asn Ile
        195                 200                 205

Glu Gly Trp Thr Gly Ser Thr Asn Asp Pro Asn Ala Gly Ala Gly Arg
    210                 215                 220

Tyr Gly Thr Cys Cys Ser Glu Met Asp Ile Trp Glu Ala Asn Asn Met
225                 230                 235                 240

Ala Thr Ala Phe Thr Pro His Pro Cys Thr Ile Ile Gly Gln Ser Arg
                245                 250                 255

Cys Glu Gly Asp Ser Cys Gly Gly Thr Tyr Ser Asn Glu Arg Tyr Ala
            260                 265                 270

Gly Val Cys Asp Pro Asp Gly Cys Asp Phe Asn Ser Tyr Arg Gln Gly
        275                 280                 285

Asn Lys Thr Phe Tyr Gly Lys Gly Met Thr Val Asp Thr Thr Lys Lys
    290                 295                 300

Ile Thr Val Val Thr Gln Phe Leu Lys Asp Ala Asn Gly Asp Leu Gly
305                 310                 315                 320
```

```
Glu Ile Lys Arg Phe Tyr Val Gln Asp Gly Lys Ile Ile Pro Asn Ser
            325                 330                 335

Glu Ser Thr Ile Pro Gly Val Glu Gly Asn Ser Ile Thr Gln Asp Trp
        340                 345                 350

Cys Asp Arg Gln Lys Val Ala Phe Gly Asp Ile Asp Asp Phe Asn Arg
    355                 360                 365

Lys Gly Gly Met Lys Gln Met Gly Lys Ala Leu Ala Gly Pro Met Val
370                 375                 380

Leu Val Met Ser Ile Trp Asp Asp His Ala Ser Asn Met Leu Trp Leu
385                 390                 395                 400

Asp Ser Thr Phe Pro Val Asp Ala Ala Gly Lys Pro Gly Ala Glu Arg
                405                 410                 415

Gly Ala Cys Pro Thr Thr Ser Gly Val Pro Ala Glu Val Glu Ala Glu
            420                 425                 430

Ala Pro Asn Ser Asn Val Val Phe Ser Asn Ile Arg Phe Gly Pro Ile
        435                 440                 445

Gly Ser Thr Val Ala Gly Leu Pro Gly Ala Gly Asn Gly Asn Asn
    450                 455                 460

Gly Gly Asn Pro Pro Pro Thr Thr Thr Thr Ser Ser Ala Pro Ala
465                 470                 475                 480

Thr Thr Thr Thr Ala Ser Ala Gly Pro Lys Ala Gly Arg Trp Gln Gln
                485                 490                 495

Cys Gly Gly Ile Gly Phe Thr Gly Pro Thr Gln Cys Glu Glu Pro Tyr
            500                 505                 510

Ile Cys Thr Lys Leu Asn Asp Trp Tyr Ser Gln Cys Leu
        515                 520                 525

<210> SEQ ID NO 54
<211> LENGTH: 456
<212> TYPE: PRT
<213> ORGANISM: Artificial
<220> FEATURE:
<223> OTHER INFORMATION: Synthetic Thermoascus aurantiacus cbh1

<400> SEQUENCE: 54

Met Tyr Gln Arg Ala Leu Leu Phe Ser Phe Phe Leu Ala Ala Ala Arg
1               5                   10                  15

Ala His Glu Ala Gly Thr Val Thr Ala Glu Asn His Pro Ser Leu Thr
            20                  25                  30

Trp Gln Gln Cys Ser Ser Gly Gly Ser Cys Thr Thr Gln Asn Gly Lys
        35                  40                  45

Val Val Ile Asp Ala Asn Trp Arg Trp Val His Thr Thr Ser Gly Tyr
    50                  55                  60

Thr Asn Cys Tyr Thr Gly Asn Thr Trp Asp Thr Ser Ile Cys Pro Asp
65                  70                  75                  80

Asp Val Thr Cys Ala Gln Asn Cys Ala Leu Asp Gly Ala Asp Tyr Ser
                85                  90                  95

Gly Thr Tyr Gly Val Thr Thr Ser Gly Asn Ala Leu Arg Leu Asn Phe
            100                 105                 110

Val Thr Gln Ser Ser Gly Lys Asn Ile Gly Ser Arg Leu Tyr Leu Leu
        115                 120                 125

Gln Asp Asp Thr Thr Tyr Gln Ile Phe Lys Leu Leu Gly Gln Glu Phe
    130                 135                 140

Thr Phe Asp Val Asp Val Ser Asn Leu Pro Cys Gly Leu Asn Gly Ala
145                 150                 155                 160
```

```
Leu Tyr Phe Val Ala Met Asp Ala Asp Gly Asn Leu Ser Lys Tyr Pro
                165                 170                 175

Gly Asn Lys Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
        195                 200                 205

Trp Gln Pro Ser Ala Asn Asp Pro Asn Ala Gly Val Gly Asn His Gly
210                 215                 220

Ser Ser Cys Ala Glu Met Asp Val Trp Glu Ala Asn Ser Ile Ser Thr
225                 230                 235                 240

Ala Val Thr Pro His Pro Cys Asp Thr Pro Gly Gln Thr Met Cys Gln
                245                 250                 255

Gly Asp Asp Cys Gly Gly Thr Tyr Ser Ser Thr Arg Tyr Ala Gly Thr
            260                 265                 270

Cys Asp Thr Asp Gly Cys Asp Phe Asn Pro Tyr Gln Pro Gly Asn His
        275                 280                 285

Ser Phe Tyr Gly Pro Gly Lys Ile Val Asp Thr Ser Ser Lys Phe Thr
290                 295                 300

Val Val Thr Gln Phe Ile Thr Asp Asp Gly Thr Pro Ser Gly Thr Leu
305                 310                 315                 320

Thr Glu Ile Lys Arg Phe Tyr Val Gln Asn Gly Lys Val Ile Pro Gln
                325                 330                 335

Ser Glu Ser Thr Ile Ser Gly Val Thr Gly Asn Ser Ile Thr Thr Glu
            340                 345                 350

Tyr Cys Thr Ala Gln Lys Ala Ala Phe Asp Asn Thr Gly Phe Phe Thr
        355                 360                 365

His Gly Gly Leu Gln Lys Ile Ser Gln Ala Leu Ala Gln Gly Met Val
370                 375                 380

Leu Val Met Ser Leu Trp Asp Asp His Ala Ala Asn Met Leu Trp Leu
385                 390                 395                 400

Asp Ser Thr Tyr Pro Thr Asp Ala Asp Pro Asp Thr Pro Gly Val Ala
                405                 410                 415

Arg Gly Thr Cys Pro Thr Thr Ser Gly Val Pro Ala Asp Val Glu Ser
            420                 425                 430

Gln Asn Pro Asn Ser Tyr Val Ile Tyr Ser Asn Ile Lys Val Gly Pro
        435                 440                 445

Ile Asn Ser Thr Phe Thr Ala Asn
450                 455

<210> SEQ ID NO 55
<211> LENGTH: 455
<212> TYPE: PRT
<213> ORGANISM: Artificial
<220> FEATURE:
<223> OTHER INFORMATION: Synthetic Talaromyces emersonii cbh1

<400> SEQUENCE: 55

Met Leu Arg Arg Ala Leu Leu Ser Ser Ser Ala Ile Leu Ala Val
1               5                   10                  15

Lys Ala Gln Gln Ala Gly Thr Ala Thr Ala Glu Asn His Pro Pro Leu
            20                  25                  30

Thr Trp Gln Glu Cys Thr Ala Pro Gly Ser Cys Thr Thr Gln Asn Gly
        35                  40                  45

Ala Val Val Leu Asp Ala Asn Trp Arg Trp Val His Asp Val Asn Gly
50                  55                  60

Tyr Thr Asn Cys Tyr Thr Gly Asn Thr Trp Asp Pro Thr Tyr Cys Pro
```

```
                65                  70                  75                  80
Asp Asp Glu Thr Cys Ala Gln Asn Cys Ala Leu Asp Gly Ala Asp Tyr
                    85                  90                  95
Glu Gly Thr Tyr Gly Val Thr Ser Ser Gly Ser Leu Lys Leu Asn
               100                 105                 110
Phe Val Thr Gly Ser Asn Val Gly Ser Arg Leu Tyr Leu Leu Gln Asp
           115                 120                 125
Asp Ser Thr Tyr Gln Ile Phe Lys Leu Leu Asn Arg Glu Phe Ser Phe
145    130                 135                 140
Asp Val Asp Val Ser Asn Leu Pro Cys Gly Leu Asn Gly Ala Leu Tyr
145                150                 155                 160
Phe Val Ala Met Asp Ala Asp Gly Gly Val Ser Lys Tyr Pro Asn Asn
               165                 170                 175
Lys Ala Gly Ala Lys Tyr Gly Thr Gly Tyr Cys Asp Ser Gln Cys Pro
               180                 185                 190
Arg Asp Leu Lys Phe Ile Asp Gly Glu Ala Asn Val Glu Gly Trp Gln
               195                 200                 205
Pro Ser Ser Asn Asn Ala Asn Thr Gly Ile Gly Asp His Gly Ser Cys
    210                 215                 220
Cys Ala Glu Met Asp Val Trp Glu Ala Asn Ser Ile Ser Asn Ala Val
225                 230                 235                 240
Thr Pro His Pro Cys Asp Thr Pro Gly Gln Thr Met Cys Ser Gly Asp
               245                 250                 255
Asp Cys Gly Gly Thr Tyr Ser Asn Asp Arg Tyr Ala Gly Thr Cys Asp
               260                 265                 270
Pro Asp Gly Cys Asp Phe Asn Pro Tyr Arg Met Gly Asn Thr Ser Phe
           275                 280                 285
Tyr Gly Pro Gly Lys Ile Ile Asp Thr Thr Lys Pro Phe Thr Val Val
    290                 295                 300
Thr Gln Phe Leu Thr Asp Asp Gly Thr Asp Thr Gly Thr Leu Ser Glu
305                 310                 315                 320
Ile Lys Arg Phe Tyr Ile Gln Asn Ser Asn Val Ile Pro Gln Pro Asn
               325                 330                 335
Ser Asp Ile Ser Gly Val Thr Gly Asn Ser Ile Thr Thr Glu Phe Cys
           340                 345                 350
Thr Ala Gln Lys Gln Ala Phe Gly Asp Thr Asp Asp Phe Ser Gln His
           355                 360                 365
Gly Gly Leu Ala Lys Met Gly Ala Ala Met Gln Gln Gly Met Val Leu
    370                 375                 380
Val Met Ser Leu Trp Asp Asp Tyr Ala Ala Gln Met Leu Trp Leu Asp
385                 390                 395                 400
Ser Asp Tyr Pro Thr Asp Ala Asp Pro Thr Thr Pro Gly Ile Ala Arg
               405                 410                 415
Gly Thr Cys Pro Thr Asp Ser Gly Val Pro Ser Asp Val Glu Ser Gln
               420                 425                 430
Ser Pro Asn Ser Tyr Val Thr Tyr Ser Asn Ile Lys Phe Gly Pro Ile
           435                 440                 445
Asn Ser Thr Phe Thr Ala Ser
    450                 455

<210> SEQ ID NO 56
<211> LENGTH: 459
<212> TYPE: PRT
<213> ORGANISM: Artificial
<220> FEATURE:
```

<223> OTHER INFORMATION: Talaromyces emersonii cbh2

<400> SEQUENCE: 56

```
Met Arg Asn Leu Leu Ala Leu Ala Pro Ala Leu Leu Val Gly Ala
1               5                   10                  15

Ala Glu Ala Gln Gln Ser Leu Trp Gly Gln Cys Gly Gly Ser Ser Trp
            20                  25                  30

Thr Gly Ala Thr Ser Cys Ala Ala Gly Ala Thr Cys Ser Thr Ile Asn
            35                  40                  45

Pro Tyr Tyr Ala Gln Cys Val Pro Ala Thr Ala Thr Pro Thr Thr Leu
        50                  55                  60

Thr Thr Thr Thr Lys Pro Thr Ser Thr Gly Gly Ala Ala Pro Thr Thr
65              70                  75                  80

Pro Pro Pro Thr Thr Thr Gly Thr Thr Thr Ser Pro Val Val Thr Arg
                85                  90                  95

Pro Ala Ser Ala Ser Gly Asn Pro Phe Glu Gly Tyr Gln Leu Tyr Ala
            100                 105                 110

Asn Pro Tyr Tyr Ala Ser Glu Val Ile Ser Leu Ala Ile Pro Ser Leu
        115                 120                 125

Ser Ser Glu Leu Val Pro Lys Ala Ser Glu Val Ala Lys Val Pro Ser
130             135                 140

Phe Val Trp Leu Asp Gln Ala Ala Lys Val Pro Ser Met Gly Asp Tyr
145                 150                 155                 160

Leu Lys Asp Ile Gln Ser Gln Asn Ala Ala Gly Ala Asp Pro Pro Ile
                165                 170                 175

Ala Gly Ile Phe Val Val Tyr Asp Leu Pro Asp Arg Asp Cys Ala Ala
            180                 185                 190

Ala Ala Ser Asn Gly Glu Phe Ser Ile Ala Asn Asn Gly Val Ala Leu
        195                 200                 205

Tyr Lys Gln Tyr Ile Asp Ser Ile Arg Glu Gln Leu Thr Thr Tyr Ser
210                 215                 220

Asp Val His Thr Ile Leu Val Ile Glu Pro Asp Ser Leu Ala Asn Val
225                 230                 235                 240

Val Thr Asn Leu Asn Val Pro Lys Cys Ala Asn Ala Gln Asp Ala Tyr
                245                 250                 255

Leu Glu Cys Ile Asn Tyr Ala Ile Thr Gln Leu Asp Leu Pro Asn Val
            260                 265                 270

Ala Met Tyr Leu Asp Ala Gly His Ala Gly Trp Leu Gly Trp Gln Ala
        275                 280                 285

Asn Leu Ala Pro Ala Ala Gln Leu Phe Ala Ser Val Tyr Lys Asn Ala
290                 295                 300

Ser Ser Pro Ala Ser Val Arg Gly Leu Ala Thr Asn Val Ala Asn Tyr
305                 310                 315                 320

Asn Ala Trp Ser Ile Ser Arg Cys Pro Ser Tyr Thr Gln Gly Asp Ala
                325                 330                 335

Asn Cys Asp Glu Glu Asp Tyr Val Asn Ala Leu Gly Pro Leu Phe Gln
            340                 345                 350

Glu Gln Gly Phe Pro Ala Tyr Phe Ile Ile Asp Thr Ser Arg Asn Gly
        355                 360                 365

Val Arg Pro Thr Lys Gln Ser Gln Trp Gly Asp Trp Cys Asn Val Ile
370                 375                 380

Gly Thr Gly Phe Gly Val Arg Pro Thr Thr Thr Gly Asn Pro Leu
385                 390                 395                 400

Glu Asp Ala Phe Val Trp Val Lys Pro Gly Gly Glu Ser Asp Gly Thr
```

```
                     405                 410                 415
Ser Asn Thr Thr Ser Pro Arg Tyr Asp Tyr His Cys Gly Leu Ser Asp
            420                 425                 430

Ala Leu Gln Pro Ala Pro Glu Ala Gly Thr Trp Phe Gln Ala Tyr Phe
            435                 440                 445

Glu Gln Leu Leu Thr Asn Ala Asn Pro Leu Phe
            450                 455

<210> SEQ ID NO 57
<211> LENGTH: 535
<212> TYPE: PRT
<213> ORGANISM: Artificial
<220> FEATURE:
<223> OTHER INFORMATION: Synthetic Trichoderma reesei cbh1

<400> SEQUENCE: 57

Met Val Ser Phe Thr Ser Leu Leu Ala Gly Val Ala Ala Ile Ser Gly
1               5                   10                  15

Val Leu Ala Ala Pro Ala Ala Glu Val Glu Pro Val Ala Val Glu Lys
            20                  25                  30

Arg Glu Ala Glu Ala Glu Ala Gln Ser Ala Cys Thr Leu Gln Ser Glu
        35                  40                  45

Thr His Pro Pro Leu Thr Trp Gln Lys Cys Ser Ser Gly Gly Thr Cys
    50                  55                  60

Thr Gln Gln Thr Gly Ser Val Val Ile Asp Ala Asn Trp Arg Trp Thr
65                  70                  75                  80

His Ala Thr Asn Ser Ser Thr Asn Cys Tyr Asp Gly Asn Thr Trp Ser
                85                  90                  95

Ser Thr Leu Cys Pro Asp Asn Glu Thr Cys Ala Lys Asn Cys Cys Leu
            100                 105                 110

Asp Gly Ala Ala Tyr Ala Ser Thr Tyr Gly Val Thr Thr Ser Gly Asn
        115                 120                 125

Ser Leu Ser Ile Gly Phe Val Thr Gln Ser Ala Gln Lys Asn Val Gly
    130                 135                 140

Ala Arg Leu Tyr Leu Met Ala Ser Asp Thr Thr Tyr Gln Glu Phe Thr
145                 150                 155                 160

Leu Leu Gly Asn Glu Phe Ser Phe Asp Val Asp Val Ser Gln Leu Pro
                165                 170                 175

Cys Gly Leu Asn Gly Ala Leu Tyr Phe Val Ser Met Asp Ala Asp Gly
            180                 185                 190

Gly Val Ser Lys Tyr Pro Thr Asn Thr Ala Gly Ala Lys Tyr Gly Thr
        195                 200                 205

Gly Tyr Cys Asp Ser Gln Cys Pro Arg Asp Leu Lys Phe Ile Asn Gly
    210                 215                 220

Gln Ala Asn Val Glu Gly Trp Glu Pro Ser Ser Asn Asn Ala Asn Thr
225                 230                 235                 240

Gly Ile Gly Gly His Gly Ser Cys Cys Ser Glu Met Asp Ile Trp Glu
                245                 250                 255

Ala Asn Ser Ile Ser Glu Ala Leu Thr Pro His Pro Cys Thr Thr Val
            260                 265                 270

Gly Gln Glu Ile Cys Glu Gly Asp Gly Cys Gly Gly Thr Tyr Ser Asp
        275                 280                 285

Asn Arg Tyr Gly Gly Thr Cys Asp Pro Asp Gly Cys Asp Trp Asn Pro
    290                 295                 300

Tyr Arg Leu Gly Asn Thr Ser Phe Tyr Gly Pro Gly Ser Ser Phe Thr
305                 310                 315                 320
```

-continued

Leu Asp Thr Thr Lys Lys Leu Thr Val Thr Gln Phe Glu Thr Ser
                325                 330                 335

Gly Ala Ile Asn Arg Tyr Tyr Val Gln Asn Gly Val Thr Phe Gln Gln
            340                 345                 350

Pro Asn Ala Glu Leu Gly Ser Tyr Ser Gly Asn Glu Leu Asn Asp Asp
        355                 360                 365

Tyr Cys Thr Ala Glu Glu Ala Glu Phe Gly Ser Ser Phe Ser Asp
    370                 375                 380

Lys Gly Gly Leu Thr Gln Phe Lys Lys Ala Thr Ser Gly Gly Met Val
385                 390                 395                 400

Leu Val Met Ser Leu Trp Asp Asp Tyr Tyr Ala Asn Met Leu Trp Leu
                405                 410                 415

Asp Ser Thr Tyr Pro Thr Asn Glu Thr Ser Ser Thr Pro Gly Ala Val
            420                 425                 430

Arg Gly Ser Cys Ser Thr Ser Ser Gly Val Pro Ala Gln Val Glu Ser
        435                 440                 445

Gln Ser Pro Asn Ala Lys Val Thr Phe Ser Asn Ile Lys Phe Gly Pro
    450                 455                 460

Ile Gly Ser Thr Gly Asn Pro Ser Gly Gly Asn Pro Pro Gly Gly Asn
465                 470                 475                 480

Arg Gly Thr Thr Thr Thr Arg Arg Pro Ala Thr Thr Thr Gly Ser Ser
                485                 490                 495

Pro Gly Pro Thr Gln Ser His Tyr Gly Gln Cys Gly Gly Ile Gly Tyr
            500                 505                 510

Ser Gly Pro Thr Val Cys Ala Ser Gly Thr Thr Cys Gln Val Leu Asn
        515                 520                 525

Pro Tyr Tyr Ser Gln Cys Leu
    530                 535

<210> SEQ ID NO 58
<211> LENGTH: 471
<212> TYPE: PRT
<213> ORGANISM: Artificial
<220> FEATURE:
<223> OTHER INFORMATION: Synthetic Trichoderma reesei cbh2

<400> SEQUENCE: 58

Met Ile Val Gly Ile Leu Thr Thr Leu Ala Thr Leu Ala Thr Leu Ala
1               5                   10                  15

Ala Ser Val Pro Leu Glu Glu Arg Gln Ala Cys Ser Ser Val Trp Gly
            20                  25                  30

Gln Cys Gly Gly Gln Asn Trp Ser Gly Pro Thr Cys Cys Ala Ser Gly
        35                  40                  45

Ser Thr Cys Val Tyr Ser Asn Asp Tyr Tyr Ser Gln Cys Leu Pro Gly
    50                  55                  60

Ala Ala Ser Ser Ser Ser Ser Thr Arg Ala Ala Ser Thr Thr Ser Arg
65                  70                  75                  80

Val Ser Pro Thr Thr Ser Arg Ser Ser Ser Ala Thr Pro Pro Pro Gly
                85                  90                  95

Ser Thr Thr Thr Arg Val Pro Pro Val Gly Ser Gly Thr Ala Thr Tyr
            100                 105                 110

Ser Gly Asn Pro Phe Val Gly Val Thr Pro Trp Ala Asn Ala Tyr Tyr
        115                 120                 125

Ala Ser Glu Val Ser Ser Leu Ala Ile Pro Ser Leu Thr Gly Ala Met
    130                 135                 140

Ala Thr Ala Ala Ala Ala Val Ala Lys Val Pro Ser Phe Met Trp Leu
145                 150                 155                 160

Asp Thr Leu Asp Lys Thr Pro Leu Met Glu Gln Thr Leu Ala Asp Ile
            165                 170                 175

Arg Thr Ala Asn Lys Asn Gly Asn Tyr Ala Gly Gln Phe Val Val
            180                 185                 190

Tyr Asp Leu Pro Asp Arg Asp Cys Ala Ala Leu Ala Ser Asn Gly Glu
        195                 200                 205

Tyr Ser Ile Ala Asp Gly Gly Val Ala Lys Tyr Lys Asn Tyr Ile Asp
        210                 215                 220

Thr Ile Arg Gln Ile Val Val Glu Tyr Ser Asp Ile Arg Thr Leu Leu
225                 230                 235                 240

Val Ile Glu Pro Asp Ser Leu Ala Asn Leu Val Thr Asn Leu Gly Thr
                245                 250                 255

Pro Lys Cys Ala Asn Ala Gln Ser Ala Tyr Leu Glu Cys Ile Asn Tyr
            260                 265                 270

Ala Val Thr Gln Leu Asn Leu Pro Asn Val Ala Met Tyr Leu Asp Ala
            275                 280                 285

Gly His Ala Gly Trp Leu Gly Trp Pro Ala Asn Gln Asp Pro Ala Ala
290                 295                 300

Gln Leu Phe Ala Asn Val Tyr Lys Asn Ala Ser Ser Pro Arg Ala Leu
305                 310                 315                 320

Arg Gly Leu Ala Thr Asn Val Ala Asn Tyr Asn Gly Trp Asn Ile Thr
                325                 330                 335

Ser Pro Pro Ser Tyr Thr Gln Gly Asn Ala Val Tyr Asn Glu Lys Leu
            340                 345                 350

Tyr Ile His Ala Ile Gly Arg Leu Leu Ala Asn His Gly Trp Ser Asn
            355                 360                 365

Ala Phe Phe Ile Thr Asp Gln Gly Arg Ser Gly Lys Gln Pro Thr Gly
370                 375                 380

Gln Gln Gln Trp Gly Asp Trp Cys Asn Val Ile Gly Thr Gly Phe Gly
385                 390                 395                 400

Ile Arg Pro Ser Ala Asn Thr Gly Asp Ser Leu Leu Asp Ser Phe Val
                405                 410                 415

Trp Val Lys Pro Gly Gly Glu Cys Asp Gly Thr Ser Asp Ser Ser Ala
            420                 425                 430

Pro Arg Phe Asp Ser His Cys Ala Leu Pro Asp Ala Leu Gln Pro Ala
            435                 440                 445

Ala Gln Ala Gly Ala Trp Phe Gln Ala Tyr Phe Val Gln Leu Leu Thr
450                 455                 460

Asn Ala Asn Pro Ser Phe Leu
465                 470

<210> SEQ ID NO 59
<211> LENGTH: 459
<212> TYPE: PRT
<213> ORGANISM: Trichoderma reesei

<400> SEQUENCE: 59

Met Ala Pro Ser Val Thr Leu Pro Leu Thr Thr Ala Ile Leu Ala Ile
1               5                   10                  15

Ala Arg Leu Val Ala Ala Gln Gln Pro Gly Thr Ser Thr Pro Glu Val
                20                  25                  30

His Pro Lys Leu Thr Thr Tyr Lys Cys Thr Lys Ser Gly Gly Cys Val
            35                  40                  45

```
Ala Gln Asp Thr Ser Val Val Leu Asp Trp Asn Tyr Arg Trp Met His
 50                  55                  60

Asp Ala Asn Tyr Asn Ser Cys Thr Val Asn Gly Gly Val Asn Thr Thr
 65                  70                  75                  80

Leu Cys Pro Asp Glu Ala Thr Cys Gly Lys Asn Cys Phe Ile Glu Gly
                 85                  90                  95

Val Asp Tyr Ala Ala Ser Gly Val Thr Thr Ser Gly Ser Ser Leu Thr
                100                 105                 110

Met Asn Gln Tyr Met Pro Ser Ser Gly Gly Tyr Ser Ser Val Ser
                115                 120                 125

Pro Arg Leu Tyr Leu Leu Asp Ser Asp Gly Glu Tyr Val Met Leu Lys
            130                 135                 140

Leu Asn Gly Gln Glu Leu Ser Phe Asp Val Asp Leu Ser Ala Leu Pro
145                 150                 155                 160

Cys Gly Glu Asn Gly Ser Leu Tyr Leu Ser Gln Met Asp Glu Asn Gly
                165                 170                 175

Gly Ala Asn Gln Tyr Asn Thr Ala Gly Ala Asn Tyr Gly Ser Gly Tyr
                180                 185                 190

Cys Asp Ala Gln Cys Pro Val Gln Thr Trp Arg Asn Gly Thr Leu Asn
            195                 200                 205

Thr Ser His Gln Gly Phe Cys Cys Asn Glu Met Asp Ile Leu Glu Gly
            210                 215                 220

Asn Ser Arg Ala Asn Ala Leu Thr Pro His Ser Cys Thr Ala Thr Ala
225                 230                 235                 240

Cys Asp Ser Ala Gly Cys Gly Phe Asn Pro Tyr Gly Ser Gly Tyr Lys
                245                 250                 255

Ser Tyr Tyr Gly Pro Gly Asp Thr Val Asp Thr Ser Lys Thr Phe Thr
                260                 265                 270

Ile Ile Thr Gln Phe Asn Thr Asp Asn Gly Ser Pro Ser Gly Asn Leu
                275                 280                 285

Val Ser Ile Thr Arg Lys Tyr Gln Gln Asn Gly Val Asp Ile Pro Ser
            290                 295                 300

Ala Gln Pro Gly Gly Asp Thr Ile Ser Ser Cys Pro Ser Ala Ser Ala
305                 310                 315                 320

Tyr Gly Gly Leu Ala Thr Met Gly Lys Ala Leu Ser Ser Gly Met Val
                325                 330                 335

Leu Val Phe Ser Ile Trp Asn Asp Asn Ser Gln Tyr Met Asn Trp Leu
                340                 345                 350

Asp Ser Gly Asn Ala Gly Pro Cys Ser Ser Thr Glu Gly Asn Pro Ser
            355                 360                 365

Asn Ile Leu Ala Asn Asn Pro Asn Thr His Val Val Phe Ser Asn Ile
            370                 375                 380

Arg Trp Gly Asp Ile Gly Ser Thr Thr Asn Ser Thr Ala Pro Pro Pro
385                 390                 395                 400

Pro Pro Ala Ser Ser Thr Thr Phe Ser Thr Thr Arg Arg Ser Ser Thr
                405                 410                 415

Thr Ser Ser Ser Pro Ser Cys Thr Gln Thr His Trp Gly Gln Cys Gly
                420                 425                 430

Gly Ile Gly Tyr Ser Gly Cys Lys Thr Cys Thr Ser Gly Thr Thr Cys
            435                 440                 445

Gln Tyr Ser Asn Asp Tyr Tyr Ser Gln Cys Leu
            450                 455

<210> SEQ ID NO 60
```

```
<211> LENGTH: 875
<212> TYPE: PRT
<213> ORGANISM: Artificial
<220> FEATURE:
<223> OTHER INFORMATION: Recombinant beta-glucanase I from a
      Saccharomycopsis fibuligera source

<400> SEQUENCE: 60
```

| Met | Leu | Met | Ile | Val | Gln | Leu | Leu | Val | Phe | Ala | Leu | Gly | Leu | Ala | Val |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Ala Val Pro Ile Gln Asn Tyr Thr Gln Ser Pro Ser Gln Arg Asp Glu
            20                  25                  30

Ser Ser Gln Trp Val Ser Pro His Tyr Tyr Pro Thr Pro Gln Gly Gly
            35                  40                  45

Arg Leu Gln Asp Val Trp Gln Glu Ala Tyr Ala Arg Ala Lys Ala Ile
        50                  55                  60

Val Gly Gln Met Thr Ile Val Glu Lys Val Asn Leu Thr Thr Gly Thr
65                  70                  75                  80

Gly Trp Gln Leu Asp Pro Cys Val Gly Asn Thr Gly Ser Val Pro Arg
                85                  90                  95

Phe Gly Ile Pro Asn Leu Cys Leu Gln Asp Gly Pro Leu Gly Val Arg
            100                 105                 110

Phe Ala Asp Phe Val Thr Gly Tyr Pro Ser Gly Leu Ala Thr Gly Ala
        115                 120                 125

Thr Phe Asn Lys Asp Leu Phe Leu Gln Arg Gly Gln Ala Leu Gly His
130                 135                 140

Glu Phe Asn Ser Lys Gly Val His Ile Ala Leu Gly Pro Ala Val Gly
145                 150                 155                 160

Pro Leu Gly Val Lys Ala Arg Gly Gly Arg Asn Phe Glu Ala Gly Ser
                165                 170                 175

Asp Pro Tyr Leu Gln Gly Thr Ala Ala Ala Thr Ile Lys Gly Leu
            180                 185                 190

Gln Glu Asn Asn Val Met Ala Cys Val Lys His Phe Ile Gly Asn Glu
        195                 200                 205

Gln Glu Lys Tyr Arg Gln Pro Asp Asp Ile Asn Pro Ala Thr Asn Gln
    210                 215                 220

Thr Thr Lys Glu Ala Ile Ser Ala Asn Ile Pro Asp Arg Ala Met His
225                 230                 235                 240

Ala Leu Tyr Leu Trp Pro Phe Ala Asp Ser Val Arg Ala Gly Val Gly
                245                 250                 255

Ser Val Met Cys Ser Tyr Asn Arg Val Asn Asn Thr Tyr Ala Cys Glu
                260                 265                 270

Asn Ser Tyr Met Met Asn His Leu Leu Lys Glu Glu Leu Gly Phe Gln
            275                 280                 285

Gly Phe Val Val Ser Asp Trp Gly Ala Gln Leu Ser Gly Val Tyr Ser
        290                 295                 300

Ala Ile Ser Gly Leu Asp Met Ser Met Pro Gly Glu Val Tyr Gly Gly
305                 310                 315                 320

Trp Asn Thr Gly Thr Ser Phe Trp Gly Gln Asn Leu Thr Lys Ala Ile
                325                 330                 335

Tyr Asn Glu Thr Val Pro Ile Glu Arg Leu Asp Asp Met Ala Thr Arg
                340                 345                 350

Ile Leu Ala Ala Leu Tyr Ala Thr Asn Ser Phe Pro Thr Glu Asp His
            355                 360                 365

Leu Pro Asn Phe Ser Ser Trp Thr Thr Lys Glu Tyr Gly Asn Lys Tyr
        370                 375                 380

```
Tyr Ala Asp Asn Thr Thr Glu Ile Val Lys Val Asn Tyr Asn Val Asp
385                 390                 395                 400

Pro Ser Asn Asp Phe Thr Glu Asp Thr Ala Leu Lys Val Ala Glu Glu
            405                 410                 415

Ser Ile Val Leu Leu Lys Asn Glu Asn Asn Thr Leu Pro Ile Ser Pro
            420                 425                 430

Glu Lys Ala Lys Arg Leu Leu Leu Ser Gly Ile Ala Ala Gly Pro Asp
            435                 440                 445

Pro Ile Gly Tyr Gln Cys Glu Asp Gln Ser Cys Thr Asn Gly Ala Leu
            450                 455                 460

Phe Gln Gly Trp Gly Ser Gly Ser Val Gly Ser Pro Lys Tyr Gln Val
465                 470                 475                 480

Thr Pro Phe Glu Glu Ile Ser Tyr Leu Ala Arg Lys Asn Lys Met Gln
            485                 490                 495

Phe Asp Tyr Ile Arg Glu Ser Tyr Asp Leu Ala Gln Val Thr Lys Val
            500                 505                 510

Ala Ser Asp Ala His Leu Ser Ile Val Val Ser Ala Ala Ser Gly
            515                 520                 525

Glu Gly Tyr Ile Thr Val Asp Gly Asn Gln Gly Asp Arg Lys Asn Leu
530                 535                 540

Thr Leu Trp Asn Asn Gly Asp Lys Leu Ile Glu Thr Val Ala Glu Asn
545                 550                 555                 560

Cys Ala Asn Thr Val Val Val Thr Ser Thr Gly Gln Ile Asn Phe
            565                 570                 575

Glu Gly Phe Ala Asp His Pro Asn Val Thr Ala Ile Val Trp Ala Gly
            580                 585                 590

Pro Leu Gly Asp Arg Ser Gly Thr Ala Ile Ala Asn Ile Leu Phe Gly
            595                 600                 605

Lys Ala Asn Pro Ser Gly His Leu Pro Phe Thr Ile Ala Lys Thr Asp
            610                 615                 620

Asp Asp Tyr Ile Pro Ile Glu Thr Tyr Ser Pro Ser Ser Gly Glu Pro
625                 630                 635                 640

Glu Asp Asn His Leu Val Glu Asn Asp Leu Leu Val Asp Tyr Arg Tyr
            645                 650                 655

Phe Glu Glu Lys Asn Ile Glu Pro Arg Tyr Ala Phe Gly Tyr Gly Leu
            660                 665                 670

Ser Tyr Asn Glu Tyr Glu Val Ser Asn Ala Lys Val Ser Ala Ala Lys
            675                 680                 685

Lys Val Asp Glu Glu Leu Pro Glu Pro Ala Thr Tyr Leu Ser Glu Phe
            690                 695                 700

Ser Tyr Gln Asn Ala Lys Asp Ser Lys Asn Pro Ser Asp Ala Phe Ala
705                 710                 715                 720

Pro Ala Asp Leu Asn Arg Val Asn Glu Tyr Leu Tyr Pro Tyr Leu Asp
            725                 730                 735

Ser Asn Val Thr Leu Lys Asp Gly Asn Tyr Glu Tyr Pro Asp Gly Tyr
            740                 745                 750

Ser Thr Glu Gln Arg Thr Thr Pro Asn Gln Pro Gly Gly Leu Gly
            755                 760                 765

Gly Asn Asp Ala Leu Trp Glu Val Ala Tyr Asn Ser Thr Asp Lys Phe
770                 775                 780

Val Pro Gln Gly Asn Ser Thr Asp Lys Phe Val Pro Gln Leu Tyr Leu
785                 790                 795                 800

Lys His Pro Glu Asp Gly Lys Phe Glu Thr Pro Ile Gln Leu Arg Gly
```

-continued

```
                    805                 810                 815
Phe Glu Lys Val Glu Leu Ser Pro Gly Glu Lys Lys Thr Val Asp Leu
                820                 825                 830

Arg Leu Leu Arg Arg Asp Leu Ser Val Trp Asp Thr Thr Arg Gln Ser
            835                 840                 845

Trp Ile Val Glu Ser Gly Thr Tyr Glu Ala Leu Ile Gly Val Ala Val
        850                 855                 860

Asn Asp Ile Lys Thr Ser Val Leu Phe Thr Ile
865                 870                 875

<210> SEQ ID NO 61
<211> LENGTH: 529
<212> TYPE: PRT
<213> ORGANISM: Artificial
<220> FEATURE:
<223> OTHER INFORMATION: Synthetic Neosartorya fischeri cbh

<400> SEQUENCE: 61

Met Leu Ala Ser Thr Phe Ser Tyr Arg Met Tyr Lys Thr Ala Leu Ile
1               5                   10                  15

Leu Ala Ala Leu Leu Gly Ser Gly Gln Ala Gln Gln Val Gly Thr Ser
            20                  25                  30

Gln Ala Glu Val His Pro Ser Met Thr Trp Gln Ser Cys Thr Ala Gly
        35                  40                  45

Gly Ser Cys Thr Thr Asn Asn Gly Lys Val Val Ile Asp Ala Asn Trp
    50                  55                  60

Arg Trp Val His Lys Val Gly Asp Tyr Thr Asn Cys Tyr Thr Gly Asn
65                  70                  75                  80

Thr Trp Asp Lys Thr Leu Cys Pro Asp Asp Ala Thr Cys Ala Ser Asn
                85                  90                  95

Cys Ala Leu Glu Gly Ala Asn Tyr Gln Ser Thr Tyr Gly Ala Thr Thr
            100                 105                 110

Ser Gly Asp Ser Leu Arg Leu Asn Phe Val Thr Thr Ser Gln Gln Lys
        115                 120                 125

Asn Ile Gly Ser Arg Leu Tyr Met Met Lys Asp Asp Thr Thr Tyr Glu
    130                 135                 140

Met Phe Lys Leu Leu Gln Glu Phe Thr Phe Asp Val Asp Val Ser Asn
145                 150                 155                 160

Leu Pro Cys Gly Leu Asn Gly Ala Leu Tyr Phe Val Ala Met Asp Ala
                165                 170                 175

Asp Gly Gly Met Ser Lys Tyr Pro Thr Asn Lys Ala Gly Ala Lys Tyr
            180                 185                 190

Gly Thr Gly Tyr Cys Asp Ser Gln Cys Pro Arg Asp Leu Lys Phe Ile
        195                 200                 205

Asn Gly Gln Ala Asn Val Glu Gly Trp Gln Pro Ser Ser Asn Asp Ala
    210                 215                 220

Asn Ala Gly Thr Gly Asn His Gly Ser Cys Cys Ala Glu Met Asp Ile
225                 230                 235                 240

Trp Glu Ala Asn Ser Ile Ser Thr Ala Phe Thr Pro His Pro Cys Asp
                245                 250                 255

Thr Pro Gly Gln Val Met Cys Thr Gly Asp Ala Cys Gly Gly Thr Tyr
            260                 265                 270

Ser Ser Asp Arg Tyr Gly Gly Thr Cys Asp Pro Asp Gly Cys Asp Phe
        275                 280                 285

Asn Ser Phe Arg Gln Gly Asn Lys Thr Phe Tyr Gly Pro Gly Met Thr
    290                 295                 300
```

```
Val Asp Thr Lys Ser Lys Phe Thr Val Val Thr Gln Phe Ile Thr Asp
305                 310                 315                 320

Asp Gly Thr Ala Ser Gly Thr Leu Lys Glu Ile Lys Arg Phe Tyr Val
            325                 330                 335

Gln Asn Gly Lys Val Ile Pro Asn Ser Glu Ser Thr Trp Ser Gly Val
            340                 345                 350

Gly Gly Asn Ser Ile Thr Asn Asp Tyr Cys Thr Ala Gln Lys Ser Leu
            355                 360                 365

Phe Lys Asp Gln Asn Val Phe Ala Lys His Gly Gly Met Glu Gly Met
            370                 375                 380

Gly Ala Ala Leu Ala Gln Gly Met Val Leu Val Met Ser Leu Trp Asp
385                 390                 395                 400

Asp His Ala Ala Asn Met Leu Trp Leu Asp Ser Asn Tyr Pro Thr Thr
                405                 410                 415

Ala Ser Ser Ser Thr Pro Gly Val Ala Arg Gly Thr Cys Asp Ile Ser
            420                 425                 430

Ser Gly Val Pro Ala Asp Val Glu Ala Asn His Pro Asp Ala Ser Val
            435                 440                 445

Val Tyr Ser Asn Ile Lys Val Gly Pro Ile Gly Ser Thr Phe Asn Ser
            450                 455                 460

Gly Gly Ser Asn Pro Gly Gly Thr Thr Thr Ala Lys Pro Thr
465                 470                 475                 480

Thr Thr Thr Thr Thr Ala Gly Ser Pro Gly Gly Thr Gly Val Ala Gln
                485                 490                 495

His Tyr Gly Gln Cys Gly Gly Asn Gly Trp Gln Gly Pro Thr Thr Cys
            500                 505                 510

Ala Ser Pro Tyr Thr Cys Gln Lys Leu Asn Asp Phe Tyr Ser Gln Cys
            515                 520                 525

Leu

<210> SEQ ID NO 62
<211> LENGTH: 512
<212> TYPE: PRT
<213> ORGANISM: Artificial
<220> FEATURE:
<223> OTHER INFORMATION: Synthetic Gibberella zeae cbh

<400> SEQUENCE: 62

Met Tyr Arg Ala Ile Ala Thr Ala Ser Ala Leu Ile Ala Ala Val Arg
1               5                   10                  15

Ala Gln Gln Val Cys Ser Leu Thr Gln Glu Ser Lys Pro Ser Leu Asn
            20                  25                  30

Trp Ser Lys Cys Thr Ser Ser Gly Cys Ser Asn Val Lys Gly Ser Val
        35                  40                  45

Thr Ile Asp Ala Asn Trp Arg Trp Thr His Gln Val Ser Gly Ser Thr
    50                  55                  60

Asn Cys Tyr Thr Gly Asn Lys Trp Asp Thr Ser Val Cys Thr Ser Gly
65                  70                  75                  80

Lys Val Cys Ala Glu Lys Cys Cys Leu Asp Gly Ala Asp Tyr Ala Ser
                85                  90                  95

Thr Tyr Gly Ile Thr Ser Ser Gly Asp Gln Leu Ser Leu Ser Phe Val
            100                 105                 110

Thr Lys Gly Pro Tyr Ser Thr Asn Ile Gly Ser Arg Thr Tyr Leu Met
        115                 120                 125

Glu Asp Glu Asn Thr Tyr Gln Met Phe Gln Leu Leu Gly Asn Glu Phe
```

```
                130                 135                 140
Thr Phe Asp Val Asp Val Ser Asn Ile Gly Cys Gly Leu Asn Gly Ala
145                 150                 155                 160
Leu Tyr Phe Val Ser Met Asp Ala Asp Gly Gly Lys Ala Lys Tyr Pro
                165                 170                 175
Gly Asn Lys Ala Gly Ala Lys Tyr Gly Thr Gly Tyr Cys Asp Ala Gln
                180                 185                 190
Cys Pro Arg Asp Val Lys Phe Ile Asn Gly Gln Ala Asn Ser Asp Gly
                195                 200                 205
Trp Gln Pro Ser Asp Ser Asp Val Asn Gly Gly Ile Gly Asn Leu Gly
210                 215                 220
Thr Cys Cys Pro Glu Met Asp Ile Trp Glu Ala Asn Ser Ile Ser Thr
225                 230                 235                 240
Ala Tyr Thr Pro His Pro Cys Thr Lys Leu Thr Gln His Ser Cys Thr
                245                 250                 255
Gly Asp Ser Cys Gly Gly Thr Tyr Ser Asn Asp Arg Tyr Gly Gly Thr
                260                 265                 270
Cys Asp Ala Asp Gly Cys Asp Phe Asn Ser Tyr Arg Gln Gly Asn Lys
                275                 280                 285
Thr Phe Tyr Gly Pro Gly Ser Gly Phe Asn Val Asp Thr Thr Lys Lys
                290                 295                 300
Val Thr Val Val Thr Gln Phe His Lys Gly Ser Asn Gly Arg Leu Ser
305                 310                 315                 320
Glu Ile Thr Arg Leu Tyr Val Gln Asn Gly Lys Val Ile Ala Asn Ser
                325                 330                 335
Glu Ser Lys Ile Ala Gly Val Pro Gly Asn Ser Leu Thr Ala Asp Phe
                340                 345                 350
Cys Thr Lys Gln Lys Lys Val Phe Asn Asp Pro Asp Phe Thr Lys
                355                 360                 365
Lys Gly Ala Trp Ser Gly Met Ser Asp Ala Leu Glu Ala Pro Met Val
370                 375                 380
Leu Val Met Ser Leu Trp His Asp His His Ser Asn Met Leu Trp Leu
385                 390                 395                 400
Asp Ser Thr Tyr Pro Thr Asp Ser Thr Lys Leu Gly Ser Gln Arg Gly
                405                 410                 415
Ser Cys Ser Thr Ser Ser Gly Val Pro Ala Asp Leu Glu Lys Asn Val
                420                 425                 430
Pro Asn Ser Lys Val Ala Phe Ser Asn Ile Lys Phe Gly Pro Ile Gly
                435                 440                 445
Ser Thr Tyr Lys Ser Asp Gly Thr Thr Pro Thr Asn Pro Thr Asn Pro
450                 455                 460
Ser Glu Pro Ser Asn Thr Ala Asn Pro Asn Pro Gly Thr Val Asp Gln
465                 470                 475                 480
Trp Gly Gln Cys Gly Gly Ser Asn Tyr Ser Gly Pro Thr Ala Cys Lys
                485                 490                 495
Ser Gly Phe Thr Cys Lys Lys Ile Asn Asp Phe Tyr Ser Gln Cys Gln
                500                 505                 510

<210> SEQ ID NO 63
<211> LENGTH: 537
<212> TYPE: PRT
<213> ORGANISM: Artificial
<220> FEATURE:
<223> OTHER INFORMATION: Synthetic Penicillium janthinellum cbh
<220> FEATURE:
<221> NAME/KEY: misc_feature
```

```
<222> LOCATION: (48)..(48)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid

<400> SEQUENCE: 63
```

| | | | | | | | | | | | | | | |
|---|---|---|---|---|---|---|---|---|---|---|---|---|---|---|
| Met | Lys | Gly | Ser | Ile | Ser | Tyr | Gln | Ile | Tyr | Lys | Gly | Ala | Leu | Leu |
| 1 | | | | 5 | | | | | 10 | | | | | 15 |
| Ser | Ala | Leu | Leu | Asn | Ser | Val | Ser | Ala | Gln | Gln | Val | Gly | Thr | Leu | Thr |
| | | | 20 | | | | | 25 | | | | | 30 | | |
| Ala | Glu | Thr | His | Pro | Ala | Leu | Thr | Trp | Ser | Lys | Cys | Thr | Ala | Gly | Xaa |
| | | 35 | | | | | 40 | | | | | 45 | | | |
| Cys | Ser | Gln | Val | Ser | Gly | Ser | Val | Val | Ile | Asp | Ala | Asn | Trp | Pro | Xaa |
| | 50 | | | | | 55 | | | | | 60 | | | | |
| Val | His | Ser | Thr | Ser | Gly | Ser | Thr | Asn | Cys | Tyr | Thr | Gly | Asn | Thr | Trp |
| 65 | | | | | 70 | | | | | 75 | | | | | 80 |
| Asp | Ala | Thr | Leu | Cys | Pro | Asp | Asp | Val | Thr | Cys | Ala | Ala | Asn | Cys | Ala |
| | | | | 85 | | | | | 90 | | | | | 95 | |
| Val | Asp | Gly | Ala | Arg | Arg | Gln | His | Leu | Arg | Val | Thr | Thr | Ser | Gly | Asn |
| | | | 100 | | | | | 105 | | | | | 110 | | |
| Ser | Leu | Arg | Ile | Asn | Phe | Val | Thr | Thr | Ala | Ser | Gln | Lys | Asn | Ile | Gly |
| | | 115 | | | | | 120 | | | | | 125 | | | |
| Ser | Arg | Leu | Tyr | Leu | Leu | Glu | Asn | Asp | Thr | Thr | Tyr | Gln | Lys | Phe | Asn |
| | 130 | | | | | 135 | | | | | 140 | | | | |
| Leu | Leu | Asn | Gln | Glu | Phe | Thr | Phe | Asp | Val | Asp | Val | Ser | Asn | Leu | Pro |
| 145 | | | | | 150 | | | | | 155 | | | | | 160 |
| Cys | Gly | Leu | Asn | Gly | Ala | Leu | Tyr | Phe | Val | Asp | Met | Asp | Ala | Asp | Gly |
| | | | | 165 | | | | | 170 | | | | | 175 | |
| Gly | Met | Ala | Lys | Tyr | Pro | Thr | Asn | Lys | Ala | Gly | Ala | Lys | Tyr | Gly | Thr |
| | | | 180 | | | | | 185 | | | | | 190 | | |
| Gly | Tyr | Cys | Asp | Ser | Gln | Cys | Pro | Arg | Asp | Leu | Lys | Phe | Ile | Asn | Gly |
| | | 195 | | | | | 200 | | | | | 205 | | | |
| Gln | Ala | Asn | Val | Asp | Gly | Trp | Thr | Pro | Ser | Lys | Asn | Asp | Val | Asn | Ser |
| | 210 | | | | | 215 | | | | | 220 | | | | |
| Gly | Ile | Gly | Asn | His | Gly | Ser | Cys | Cys | Ala | Glu | Met | Asp | Ile | Trp | Glu |
| 225 | | | | | 230 | | | | | 235 | | | | | 240 |
| Ala | Asn | Ser | Ile | Ser | Asn | Ala | Val | Thr | Pro | His | Pro | Cys | Asp | Thr | Pro |
| | | | | 245 | | | | | 250 | | | | | 255 | |
| Ser | Gln | Thr | Met | Cys | Thr | Gly | Gln | Arg | Cys | Gly | Gly | Thr | Tyr | Ser | Thr |
| | | | 260 | | | | | 265 | | | | | 270 | | |
| Asp | Arg | Tyr | Gly | Gly | Thr | Cys | Asp | Pro | Asp | Gly | Cys | Asp | Phe | Asn | Pro |
| | | 275 | | | | | 280 | | | | | 285 | | | |
| Tyr | Arg | Met | Gly | Val | Thr | Asn | Phe | Tyr | Gly | Pro | Gly | Glu | Thr | Ile | Asp |
| | 290 | | | | | 295 | | | | | 300 | | | | |
| Thr | Lys | Ser | Pro | Phe | Thr | Val | Val | Thr | Gln | Phe | Leu | Thr | Asn | Asp | Gly |
| 305 | | | | | 310 | | | | | 315 | | | | | 320 |
| Thr | Ser | Thr | Gly | Thr | Leu | Ser | Glu | Ile | Lys | Arg | Phe | Tyr | Val | Gln | Gly |
| | | | | 325 | | | | | 330 | | | | | 335 | |
| Gly | Lys | Val | Ile | Gly | Asn | Pro | Gln | Ser | Thr | Ile | Val | Gly | Val | Ser | Gly |
| | | | 340 | | | | | 345 | | | | | 350 | | |
| Asn | Ser | Ile | Thr | Asp | Ser | Trp | Cys | Asn | Ala | Gln | Lys | Ser | Ala | Phe | Gly |
| | | 355 | | | | | 360 | | | | | 365 | | | |
| Asp | Thr | Asn | Glu | Phe | Ser | Lys | His | Gly | Gly | Met | Ala | Gly | Met | Gly | Ala |
| | 370 | | | | | 375 | | | | | 380 | | | | |

```
Gly Leu Ala Asp Gly Met Val Leu Val Met Ser Leu Trp Asp Asp His
385                 390                 395                 400

Ala Ser Asp Met Leu Trp Leu Asp Ser Thr Tyr Pro Thr Asn Ala Thr
                405                 410                 415

Ser Thr Thr Pro Gly Ala Lys Arg Gly Thr Cys Asp Ile Ser Arg Arg
            420                 425                 430

Pro Asn Thr Val Glu Ser Thr Tyr Pro Asn Ala Tyr Val Ile Tyr Ser
            435                 440                 445

Asn Ile Lys Thr Gly Pro Leu Asn Ser Thr Phe Thr Gly Gly Thr Thr
        450                 455                 460

Ser Ser Ser Ser Thr Thr Thr Thr Ser Lys Ser Thr Ser Thr Thr Ser
465                 470                 475                 480

Ser Ser Ser Lys Thr Thr Thr Thr Val Thr Thr Thr Thr Thr Ser Ser
                485                 490                 495

Gly Ser Ser Gly Thr Gly Ala Arg Asp Trp Ala Gln Cys Gly Gly Asn
            500                 505                 510

Gly Trp Thr Gly Pro Thr Thr Cys Val Ser Pro Tyr Thr Cys Thr Lys
        515                 520                 525

Gln Asn Asp Trp Tyr Ser Gln Cys Leu
        530                 535

<210> SEQ ID NO 64
<211> LENGTH: 511
<212> TYPE: PRT
<213> ORGANISM: Artificial
<220> FEATURE:
<223> OTHER INFORMATION: Synthetic Fusarium poae cbh

<400> SEQUENCE: 64

Met Tyr Arg Ala Ile Ala Thr Ala Ser Ala Leu Ile Ala Ala Val Arg
1               5                   10                  15

Ala Gln Gln Val Cys Ser Leu Thr Thr Glu Thr Lys Pro Ala Le

```
Trp Glu Pro Ser Lys Ser Asp Val Asn Gly Ile Gly Asn Leu Gly
    210                 215                 220

Thr Cys Cys Pro Glu Met Asp Ile Trp Glu Ala Asn Ser Ile Ser Thr
225                 230                 235                 240

Ala Tyr Thr Pro His Pro Cys Thr Lys Leu Thr Gln His Ala Cys Thr
                245                 250                 255

Gly Asp Ser Cys Gly Gly Thr Tyr Ser Asn Asp Arg Tyr Gly Gly Thr
                260                 265                 270

Cys Asp Ala Asp Gly Cys Asp Phe Asn Ala Tyr Arg Gln Gly Asn Lys
        275                 280                 285

Thr Phe Tyr Gly Pro Gly Ser Gly Phe Asn Val Asp Thr Lys Lys
    290                 295                 300

Val Thr Val Val Thr Gln Phe His Lys Gly Ser Asn Gly Arg Leu Ser
305                 310                 315                 320

Glu Ile Thr Arg Leu Tyr Val Gln Asn Gly Lys Val Ile Ala Asn Ser
                325                 330                 335

Glu Ser Lys Ile Ala Gly Asn Pro Gly Ser Ser Leu Thr Ser Asp Phe
                340                 345                 350

Cys Thr Thr Gln Lys Lys Val Phe Gly Asp Ile Asp Asp Phe Ala Lys
        355                 360                 365

Lys Gly Ala Trp Asn Gly Met Ser Asp Ala Leu Glu Ala Pro Met Val
    370                 375                 380

Leu Val Met Ser Leu Trp His Asp His His Ser Asn Met Leu Trp Leu
385                 390                 395                 400

Asp Ser Thr Tyr Pro Thr Asp Ser Thr Ala Leu Gly Ser Gln Arg Gly
                405                 410                 415

Ser Cys Ser Thr Ser Ser Gly Val Pro Ala Asp Leu Glu Lys Asn Val
                420                 425                 430

Pro Asn Ser Lys Val Ala Phe Ser Asn Ile Lys Phe Gly Pro Ile Gly
        435                 440                 445

Ser Thr Tyr Asn Lys Glu Gly Thr Gln Pro Gln Pro Thr Asn Pro Thr
    450                 455                 460

Asn Pro Asn Pro Thr Asn Pro Thr Asn Pro Gly Thr Val Asp Gln Trp
465                 470                 475                 480

Gly Gln Cys Gly Gly Thr Asn Tyr Ser Gly Pro Thr Ala Cys Lys Ser
                485                 490                 495

Pro Phe Thr Cys Lys Lys Ile Asn Asp Phe Tyr Ser Gln Cys Gln
                500                 505                 510

<210> SEQ ID NO 65
<211> LENGTH: 530
<212> TYPE: PRT
<213> ORGANISM: Artificial
<220> FEATURE:
<223> OTHER INFORMATION: Synthetic Chaetomium thermophilum cbh

<400> SEQUENCE: 65

Met Met Tyr Lys Lys Phe Ala Ala Leu Ala Ala Leu Val Ala Gly Ala
1               5                   10                  15

Ala Ala Gln Gln Ala Cys Ser Leu Thr Thr Glu Thr His Pro Arg Leu
                20                  25                  30

Thr Trp Lys Arg Cys Thr Ser Gly Gly Asn Cys Ser Thr Val Asn Gly
            35                  40                  45

Ala Val Thr Ile Asp Ala Asn Trp Arg Trp Thr His Thr Val Ser Gly
        50                  55                  60

Ser Thr Asn Cys Tyr Thr Gly Asn Glu Trp Asp Thr Ser Ile Cys Ser
```

```
                65                  70                  75                  80
Asp Gly Lys Ser Cys Ala Gln Thr Cys Cys Val Asp Gly Ala Asp Tyr
                        85                  90                  95
Ser Ser Thr Tyr Gly Ile Thr Thr Ser Gly Asp Ser Leu Asn Leu Lys
                100                 105                 110
Phe Val Thr Lys His Gln His Gly Thr Asn Val Gly Ser Arg Val Tyr
            115                 120                 125
Leu Met Glu Asn Asp Thr Lys Tyr Gln Met Phe Glu Leu Leu Gly Asn
        130                 135                 140
Glu Phe Thr Phe Asp Val Asp Val Ser Asn Leu Gly Cys Gly Leu Asn
145                 150                 155                 160
Gly Ala Leu Tyr Phe Val Ser Met Asp Ala Asp Gly Gly Met Ser Lys
                165                 170                 175
Tyr Ser Gly Asn Lys Ala Gly Ala Lys Tyr Gly Thr Gly Tyr Cys Asp
                180                 185                 190
Ala Gln Cys Pro Arg Asp Leu Lys Phe Ile Asn Gly Glu Ala Asn Ile
            195                 200                 205
Glu Asn Trp Thr Pro Ser Thr Asn Asp Ala Asn Ala Gly Phe Gly Arg
        210                 215                 220
Tyr Gly Ser Cys Cys Ser Glu Met Asp Ile Trp Asp Ala Asn Asn Met
225                 230                 235                 240
Ala Thr Ala Phe Thr Pro His Pro Cys Thr Ile Ile Gly Gln Ser Arg
                245                 250                 255
Cys Glu Gly Asn Ser Cys Gly Gly Thr Tyr Ser Ser Glu Arg Tyr Ala
                260                 265                 270
Gly Val Cys Asp Pro Asp Gly Cys Asp Phe Asn Ala Tyr Arg Gln Gly
            275                 280                 285
Asp Lys Thr Phe Tyr Gly Lys Gly Met Thr Val Asp Thr Thr Lys Lys
        290                 295                 300
Met Thr Val Val Thr Gln Phe His Lys Asn Ser Ala Gly Val Leu Ser
305                 310                 315                 320
Glu Ile Lys Arg Phe Tyr Val Gln Asp Gly Lys Ile Ile Ala Asn Ala
                325                 330                 335
Glu Ser Lys Ile Pro Gly Asn Pro Gly Asn Ser Ile Thr Gln Glu Trp
                340                 345                 350
Cys Asp Ala Gln Lys Val Ala Phe Gly Asp Ile Asp Asp Phe Asn Arg
            355                 360                 365
Lys Gly Gly Met Ala Gln Met Ser Lys Ala Leu Glu Gly Pro Met Val
        370                 375                 380
Leu Val Met Ser Val Trp Asp Asp His Tyr Ala Asn Met Leu Trp Leu
385                 390                 395                 400
Asp Ser Thr Tyr Pro Ile Asp Lys Ala Gly Thr Pro Gly Ala Glu Arg
                405                 410                 415
Gly Ala Cys Pro Thr Thr Ser Gly Val Pro Ala Glu Ile Glu Ala Gln
                420                 425                 430
Val Pro Asn Ser Asn Val Ile Phe Ser Asn Ile Arg Phe Gly Pro Ile
            435                 440                 445
Gly Ser Thr Val Pro Gly Leu Asp Gly Ser Thr Pro Ser Asn Pro Thr
        450                 455                 460
Ala Thr Val Ala Pro Pro Thr Ser Thr Thr Thr Ser Val Arg Ser Ser
465                 470                 475                 480
Thr Thr Gln Ile Ser Thr Pro Thr Ser Gln Pro Gly Gly Cys Thr Thr
                485                 490                 495
```

Gln Lys Trp Gly Gln Cys Gly Gly Ile Gly Tyr Thr Gly Cys Thr Asn
                500                 505                 510

Cys Val Ala Gly Thr Thr Cys Thr Glu Leu Asn Pro Trp Tyr Ser Gln
            515                 520                 525

Cys Leu
    530

<210> SEQ ID NO 66
<211> LENGTH: 541
<212> TYPE: PRT
<213> ORGANISM: Artificial
<220> FEATURE:
<223> OTHER INFORMATION: Synthetic Aspergillus terreus cbh

<400> SEQUENCE: 66

Met Pro Ser Thr Tyr Asp Ile Tyr Lys Lys Leu Leu Leu Ala Ser
1               5                   10                  15

Phe Leu Ser Ala Ser Gln Ala Gln Val Gly Thr Ser Lys Ala Glu
            20                  25                  30

Val His Pro Ser Leu Thr Trp Gln Thr Cys Thr Ser Gly Gly Ser Cys
            35                  40                  45

Thr Thr Val Asn Gly Lys Val Val Asp Ala Asn Trp Arg Trp Val
    50                  55                  60

His Asn Val Asp Gly Tyr Asn Asn Cys Tyr Thr Gly Asn Thr Trp Asp
65                  70                  75                  80

Thr Thr Leu Cys Pro Asp Asp Glu Thr Cys Ala Ser Asn Cys Ala Leu
                85                  90                  95

Glu Gly Ala Asp Tyr Ser Gly Thr Tyr Gly Val Thr Thr Ser Gly Asn
            100                 105                 110

Ser Leu Arg Leu Asn Phe Val Thr Gln Ala Ser Gln Lys Asn Ile Gly
        115                 120                 125

Ser Arg Leu Tyr Leu Met Glu Asp Asp Ser Thr Tyr Lys Met Phe Lys
    130                 135                 140

Leu Leu Asn Gln Glu Phe Thr Phe Asp Val Asp Val Ser Asn Leu Pro
145                 150                 155                 160

Cys Gly Leu Asn Gly Ala Val Tyr Phe Val Ser Met Asp Ala Asp Gly
                165                 170                 175

Gly Met Ala Lys Tyr Pro Ala Asn Lys Ala Gly Ala Lys Tyr Gly Thr
            180                 185                 190

Gly Tyr Cys Asp Ser Gln Cys Pro Arg Asp Leu Lys Phe Ile Asn Gly
        195                 200                 205

Met Ala Asn Val Glu Gly Trp Glu Pro Ser Ala Asn Asp Ala Asn Ala
    210                 215                 220

Gly Thr Gly Asn His Gly Ser Cys Cys Ala Glu Met Asp Ile Trp Glu
225                 230                 235                 240

Ala Asn Ser Ile Ser Thr Ala Tyr Thr Pro His Pro Cys Asp Thr Pro
                245                 250                 255

Gly Gln Val Met Cys Thr Gly Asp Ser Cys Gly Gly Thr Tyr Ser Ser
            260                 265                 270

Asp Arg Tyr Gly Gly Thr Cys Asp Pro Asp Gly Cys Asp Phe Asn Ser
        275                 280                 285

Tyr Arg Gln Gly Asn Lys Thr Phe Tyr Gly Pro Gly Met Thr Val Asp
    290                 295                 300

Thr Lys Ser Lys Ile Thr Val Val Thr Gln Phe Leu Thr Asn Asp Gly
305                 310                 315                 320

Thr Ala Ser Gly Thr Leu Ser Glu Ile Lys Arg Phe Tyr Val Gln Asn

```
                    325                 330                 335
Gly Lys Val Ile Pro Asn Ser Glu Ser Thr Trp Ser Gly Val Ser Gly
            340                 345                 350

Asn Ser Ile Thr Thr Ala Tyr Cys Asn Ala Gln Lys Thr Leu Phe Gly
            355                 360                 365

Asp Thr Asp Val Phe Thr Lys His Gly Gly Met Glu Gly Met Gly Ala
            370                 375                 380

Ala Leu Ala Glu Gly Met Val Leu Val Leu Ser Leu Trp Asp Asp His
385                 390                 395                 400

Asn Ser Asn Met Leu Trp Leu Asp Ser Asn Tyr Pro Thr Asp Lys Pro
            405                 410                 415

Ser Thr Thr Pro Gly Val Ala Arg Gly Ser Cys Asp Ile Ser Ser Gly
            420                 425                 430

Asp Pro Lys Asp Val Glu Ala Asn Asp Ala Asn Ala Tyr Val Val Tyr
            435                 440                 445

Ser Asn Ile Lys Val Gly Pro Ile Gly Ser Thr Phe Ser Gly Ser Thr
            450                 455                 460

Gly Gly Gly Ser Ser Ser Thr Thr Ala Thr Ser Lys Thr Thr Thr Thr
465                 470                 475                 480

Thr Ser Ala Thr Lys Thr Thr Thr Thr Thr Lys Thr Thr Thr Thr Thr
            485                 490                 495

Thr Ser Ala Ser Ser Thr Ser Thr Gly Gly Ala Gln His Trp Ala Gln
            500                 505                 510

Cys Gly Gly Ile Gly Trp Thr Gly Pro Thr Thr Cys Val Ala Pro Tyr
            515                 520                 525

Thr Cys Gln Lys Gln Asn Asp Tyr Tyr Ser Gln Cys Leu
            530                 535                 540

<210> SEQ ID NO 67
<211> LENGTH: 529
<212> TYPE: PRT
<213> ORGANISM: Artificial
<220> FEATURE:
<223> OTHER INFORMATION: Synthetic Penicillium chrysogenum cbh

<400> SEQUENCE: 67

Met Ala Ser Thr Leu Ser Phe Lys Ile Tyr Lys Asn Ala Leu Leu Leu
1               5                   10                  15

Ala Ala Phe Leu Gly Ala Ala Gln Ala Gln Gln Val Gly Thr Ser Thr
            20                  25                  30

Ala Glu Val His Pro Ser Leu Thr Trp Gln Lys Cys Thr Ala Gly Gly
            35                  40                  45

Ser Cys Thr Ser Gln Ser Gly Lys Val Val Ile Asp Ser Asn Trp Arg
    50                  55                  60

Trp Val His Asn Thr Gly Gly Tyr Thr Asn Cys Tyr Thr Gly Asn Asp
65                  70                  75                  80

Trp Asp Arg Thr Leu Cys Pro Asp Asp Val Thr Cys Ala Thr Asn Cys
            85                  90                  95

Ala Leu Asp Gly Ala Asp Tyr Lys Gly Thr Tyr Gly Val Thr Ala Ser
            100                 105                 110

Gly Ser Ser Leu Arg Leu Asn Phe Val Thr Gln Ala Ser Gln Lys Asn
            115                 120                 125

Ile Gly Ser Arg Leu Tyr Leu Met Ala Asp Asp Ser Lys Tyr Glu Met
            130                 135                 140

Phe Gln Leu Leu Asn Gln Glu Phe Thr Phe Asp Val Asp Val Ser Asn
145                 150                 155                 160
```

Leu Pro Cys Gly Leu Asn Gly Ala Leu Tyr Phe Val Ala Met Asp Glu
                165                 170                 175

Asp Gly Gly Met Ala Arg Tyr Pro Thr Asn Lys Ala Gly Ala Lys Tyr
            180                 185                 190

Gly Thr Gly Tyr Cys Asp Ala Gln Cys Pro Arg Asp Leu Lys Phe Ile
        195                 200                 205

Asn Gly Gln Ala Asn Val Glu Gly Trp Glu Pro Ser Ser Ser Asp Val
210                 215                 220

Asn Gly Gly Thr Gly Asn Tyr Gly Ser Cys Cys Ala Glu Met Asp Ile
225                 230                 235                 240

Trp Glu Ala Asn Ser Ile Ser Thr Ala Phe Thr Pro His Pro Cys Asp
                245                 250                 255

Asp Pro Ala Gln Thr Arg Cys Thr Gly Asp Ser Cys Gly Gly Thr Tyr
            260                 265                 270

Ser Ser Asp Arg Tyr Gly Gly Thr Cys Asp Pro Asp Gly Cys Asp Phe
        275                 280                 285

Asn Pro Tyr Arg Met Gly Asn Gln Ser Phe Tyr Gly Pro Ser Lys Ile
290                 295                 300

Val Asp Thr Glu Ser Pro Phe Thr Val Val Thr Gln Phe Ile Thr Asn
305                 310                 315                 320

Asp Gly Thr Ser Thr Gly Thr Leu Ser Glu Ile Lys Arg Phe Tyr Val
                325                 330                 335

Gln Asn Gly Lys Val Ile Pro Gln Ser Val Ser Thr Ile Ser Ala Val
            340                 345                 350

Thr Gly Asn Ser Ile Thr Asp Ser Phe Cys Ser Ala Gln Lys Thr Ala
        355                 360                 365

Phe Lys Asp Thr Asp Val Phe Ala Lys His Gly Gly Met Ala Gly Met
370                 375                 380

Gly Ala Gly Leu Ala Glu Gly Met Val Leu Val Met Ser Leu Trp Asp
385                 390                 395                 400

Asp His Ala Ala Asn Met Leu Trp Leu Asp Ser Thr Tyr Pro Thr Ser
                405                 410                 415

Ala Ser Ser Thr Thr Pro Gly Ala Ala Arg Gly Ser Cys Asp Ile Ser
            420                 425                 430

Ser Gly Glu Pro Ser Asp Val Glu Ala Asn His Ser Asn Ala Tyr Val
        435                 440                 445

Val Tyr Ser Asn Ile Lys Val Gly Pro Leu Gly Ser Thr Phe Gly Ser
450                 455                 460

Thr Asp Ser Gly Ser Gly Thr Thr Thr Lys Val Thr Thr Thr Thr
465                 470                 475                 480

Ala Thr Lys Thr Thr Thr Thr Thr Gly Pro Ser Thr Thr Gly Ala Ala
                485                 490                 495

His Tyr Ala Gln Cys Gly Gly Gln Asn Trp Thr Gly Pro Thr Thr Cys
            500                 505                 510

Ala Ser Pro Tyr Thr Cys Gln Arg Gln Gly Asp Tyr Tyr Ser Gln Cys
        515                 520                 525

Leu

<210> SEQ ID NO 68
<211> LENGTH: 516
<212> TYPE: PRT
<213> ORGANISM: Artificial
<220> FEATURE:
<223> OTHER INFORMATION: Synthetic Neurospora crassa cbh

<400> SEQUENCE: 68

```
Met Arg Ala Ser Leu Leu Ala Phe Ser Leu Ala Ala Val Ala Gly
1               5                   10                  15

Gly Gln Gln Ala Gly Thr Leu Thr Ala Lys Arg His Pro Ser Leu Thr
                20                  25                  30

Trp Gln Lys Cys Thr Arg Gly Gly Cys Pro Thr Leu Asn Thr Thr Met
            35                  40                  45

Val Leu Asp Ala Asn Trp Arg Trp Thr His Ala Thr Ser Gly Ser Thr
50                  55                  60

Lys Cys Tyr Thr Gly Asn Lys Trp Gln Ala Thr Leu Cys Pro Asp Gly
65                  70                  75                  80

Lys Ser Cys Ala Ala Asn Cys Ala Leu Asp Gly Ala Asp Tyr Thr Gly
                85                  90                  95

Thr Tyr Gly Ile Thr Gly Ser Gly Trp Ser Leu Thr Leu Gln Phe Val
            100                 105                 110

Thr Asp Asn Val Gly Ala Arg Ala Tyr Leu Met Ala Asp Asp Thr Gln
        115                 120                 125

Tyr Gln Met Leu Glu Leu Leu Asn Gln Glu Leu Trp Phe Asp Val Asp
130                 135                 140

Met Ser Asn Ile Pro Cys Gly Leu Asn Gly Ala Leu Tyr Leu Ser Ala
145                 150                 155                 160

Met Asp Ala Asp Gly Gly Met Arg Lys Tyr Pro Thr Asn Lys Ala Gly
                165                 170                 175

Ala Lys Tyr Ala Thr Gly Tyr Cys Asp Ala Gln Cys Pro Arg Asp Leu
            180                 185                 190

Lys Tyr Ile Asn Gly Ile Ala Asn Val Glu Gly Trp Thr Pro Ser Thr
        195                 200                 205

Asn Asp Ala Asn Gly Ile Gly Asp His Gly Ser Cys Cys Ser Glu Met
210                 215                 220

Asp Ile Trp Glu Ala Asn Lys Val Ser Thr Ala Phe Thr Pro His Pro
225                 230                 235                 240

Cys Thr Thr Ile Glu Gln His Met Cys Glu Gly Asp Ser Cys Gly Gly
                245                 250                 255

Thr Tyr Ser Asp Asp Arg Tyr Gly Val Leu Cys Asp Ala Asp Gly Cys
            260                 265                 270

Asp Phe Asn Ser Tyr Arg Met Gly Asn Thr Thr Phe Tyr Gly Glu Gly
        275                 280                 285

Lys Thr Val Asp Thr Ser Ser Lys Phe Thr Val Thr Gln Phe Ile
290                 295                 300

Lys Asp Ser Ala Gly Asp Leu Ala Glu Ile Lys Ala Phe Tyr Val Gln
305                 310                 315                 320

Asn Gly Lys Val Ile Glu Asn Ser Gln Ser Asn Val Asp Gly Val Ser
                325                 330                 335

Gly Asn Ser Ile Thr Gln Ser Phe Cys Lys Ser Gln Lys Thr Ala Phe
            340                 345                 350

Gly Asp Ile Asp Asp Phe Asn Lys Lys Gly Gly Leu Lys Gln Met Gly
        355                 360                 365

Lys Ala Leu Ala Gln Ala Met Val Leu Val Met Ser Ile Trp Asp Asp
370                 375                 380

His Ala Ala Asn Met Leu Trp Leu Asp Ser Thr Tyr Pro Val Pro Lys
385                 390                 395                 400

Val Pro Gly Ala Tyr Arg Gly Ser Gly Pro Thr Thr Ser Gly Val Pro
                405                 410                 415
```

```
Ala Glu Val Asp Ala Asn Ala Pro Asn Ser Lys Val Ala Phe Ser Asn
            420                 425                 430

Ile Lys Phe Gly His Leu Gly Ile Ser Pro Phe Ser Gly Gly Ser Ser
            435                 440                 445

Gly Thr Pro Pro Ser Asn Pro Ser Ser Ser Ala Ser Pro Thr Ser Ser
450                 455                 460

Thr Ala Lys Pro Ser Ser Thr Ser Thr Ala Ser Asn Pro Ser Gly Thr
465                 470                 475                 480

Gly Ala Ala His Trp Ala Gln Cys Gly Gly Ile Gly Phe Ser Gly Pro
                485                 490                 495

Thr Thr Cys Pro Glu Pro Tyr Thr Cys Ala Lys Asp His Asp Ile Tyr
            500                 505                 510

Ser Gln Cys Val
        515

<210> SEQ ID NO 69
<211> LENGTH: 514
<212> TYPE: PRT
<213> ORGANISM: Artificial
<220> FEATURE:
<223> OTHER INFORMATION: Synthetic Trichoderma viride cbh

<400> SEQUENCE: 69

Met Tyr Arg Lys Leu Ala Val Ile Ser Ala Phe Leu Ala Thr Ala Arg
1               5                   10                  15

Ala Gln Ser Ala Cys Thr Leu Gln Ser Glu Thr His Pro Pro Leu Thr
            20                  25                  30

Trp Gln Lys Cys Ser Ser Gly Gly Thr Cys Thr Gln Gln Thr Gly Ser
        35                  40                  45

Val Val Ile Asp Ala Asn Trp Arg Trp Thr His Ala Thr Asn Ser Ser
    50                  55                  60

Thr Asn Cys Tyr Asp Gly Asn Thr Trp Ser Ser Thr Leu Cys Pro Asp
65                  70                  75                  80

Asn Glu Thr Cys Ala Lys Asn Cys Cys Leu Asp Gly Ala Ala Tyr Ala
                85                  90                  95

Ser Thr Tyr Gly Val Thr Thr Ser Gly Asn Ser Leu Ser Ile Gly Phe
            100                 105                 110

Val Thr Gln Ser Ala Gln Lys Asn Val Gly Ala Arg Leu Tyr Leu Met
        115                 120                 125

Ala Ser Asp Thr Thr Tyr Gln Glu Phe Thr Leu Leu Gly Asn Glu Phe
    130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Ser Lys Tyr Pro
                165                 170                 175

Thr Asn Thr Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
        195                 200                 205

Trp Glu Pro Ser Ser Asn Asn Ala Asn Thr Gly Ile Gly Gly His Gly
    210                 215                 220

Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Glu
                245                 250                 255

Gly Asp Gly Cys Gly Gly Thr Tyr Ser Asp Asn Arg Tyr Gly Gly Thr
```

Cys Asp Pro Asp Gly Cys Asp Trp Asp Pro Tyr Arg Leu Gly Asn Thr
            275                 280                 285

Ser Phe Tyr Gly Pro Gly Ser Ser Phe Thr Leu Asp Thr Thr Lys Lys
        290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
                325                 330                 335

Ser Tyr Ser Gly Asn Gly Leu Asn Asp Asp Tyr Cys Thr Ala Glu Glu
            340                 345                 350

Ala Glu Phe Gly Gly Ser Ser Phe Ser Asp Lys Gly Gly Leu Thr Gln
        355                 360                 365

Phe Lys Lys Ala Thr Ser Gly Gly Met Val Leu Val Met Ser Leu Trp
    370                 375                 380

Asp Asp Tyr Tyr Ala Asn Met Leu Trp Leu Asp Ser Thr Tyr Pro Thr
385                 390                 395                 400

Asn Glu Thr Ser Ser Thr Pro Gly Ala Val Arg Gly Ser Cys Ser Thr
                405                 410                 415

Ser Ser Gly Val Pro Ala Gln Val Glu Ser Gln Ser Pro Asn Ala Lys
            420                 425                 430

Val Thr Phe Ser Asn Ile Lys Phe Gly Pro Ile Gly Ser Thr Gly Asp
        435                 440                 445

Pro Ser Gly Gly Asn Pro Pro Gly Gly Asn Pro Pro Gly Thr Thr Thr
    450                 455                 460

Thr Arg Arg Pro Ala Thr Thr Thr Gly Ser Ser Pro Gly Pro Thr Gln
465                 470                 475                 480

Ser His Tyr Gly Gln Cys Gly Gly Ile Gly Tyr Ser Gly Pro Thr Val
                485                 490                 495

Cys Ala Ser Gly Thr Thr Cys Gln Val Leu Asn Pro Tyr Tyr Ser Gln
            500                 505                 510

Cys Leu

<210> SEQ ID NO 70
<211> LENGTH: 525
<212> TYPE: PRT
<213> ORGANISM: Artificial
<220> FEATURE:
<223> OTHER INFORMATION: Synthetic Humicola grisea cbh

<400> SEQUENCE: 70

Met Arg Thr Ala Lys Phe Ala Thr Leu Ala Ala Leu Val Ala Ser Ala
1               5                   10                  15

Ala Ala Gln Gln Ala Cys Ser Leu Thr Thr Glu Arg His Pro Ser Leu
            20                  25                  30

Ser Trp Asn Lys Cys Thr Ala Gly Gly Gln Cys Gln Thr Val Gln Ala
        35                  40                  45

Ser Ile Thr Leu Asp Ser Asn Trp Arg Trp Thr His Gln Val Ser Gly
    50                  55                  60

Ser Thr Asn Cys Tyr Thr Gly Asn Lys Trp Asp Thr Ser Ile Cys Thr
65                  70                  75                  80

Asp Ala Lys Ser Cys Ala Gln Asn Cys Cys Val Asp Gly Ala Asp Tyr
                85                  90                  95

Thr Ser Thr Tyr Gly Ile Thr Thr Asn Gly Asp Ser Leu Ser Leu Lys
            100                 105                 110

-continued

Phe Val Thr Lys Gly Gln His Ser Thr Asn Val Gly Ser Arg Thr Tyr
    115                 120                 125

Leu Met Asp Gly Glu Asp Lys Tyr Gln Thr Phe Glu Leu Leu Gly Asn
130                 135                 140

Glu Phe Thr Phe Asp Val Asp Val Ser Asn Ile Gly Cys Gly Leu Asn
145                 150                 155                 160

Gly Ala Leu Tyr Phe Val Ser Met Asp Ala Asp Gly Gly Leu Ser Arg
                165                 170                 175

Tyr Pro Gly Asn Lys Ala Gly Ala Lys Tyr Gly Thr Gly Tyr Cys Asp
                180                 185                 190

Ala Gln Cys Pro Arg Asp Ile Lys Phe Ile Asn Gly Glu Ala Asn Ile
                195                 200                 205

Glu Gly Trp Thr Gly Ser Thr Asn Asp Pro Asn Ala Gly Ala Gly Arg
210                 215                 220

Tyr Gly Thr Cys Cys Ser Glu Met Asp Ile Trp Glu Ala Asn Asn Met
225                 230                 235                 240

Ala Thr Ala Phe Thr Pro His Pro Cys Thr Ile Ile Gly Gln Ser Arg
                245                 250                 255

Cys Glu Gly Asp Ser Cys Gly Gly Thr Tyr Ser Asn Glu Arg Tyr Ala
                260                 265                 270

Gly Val Cys Asp Pro Asp Gly Cys Asp Phe Asn Ser Tyr Arg Gln Gly
                275                 280                 285

Asn Lys Thr Phe Tyr Gly Lys Gly Met Thr Val Asp Thr Thr Lys Lys
                290                 295                 300

Ile Thr Val Val Thr Gln Phe Leu Lys Asp Ala Asn Gly Asp Leu Gly
305                 310                 315                 320

Glu Ile Lys Arg Phe Tyr Val Gln Asp Gly Lys Ile Ile Pro Asn Ser
                325                 330                 335

Glu Ser Thr Ile Pro Gly Val Glu Gly Asn Ser Ile Thr Gln Asp Trp
                340                 345                 350

Cys Asp Arg Gln Lys Val Ala Phe Gly Asp Ile Asp Asp Phe Asn Arg
                355                 360                 365

Lys Gly Gly Met Lys Gln Met Gly Lys Ala Leu Ala Gly Pro Met Val
370                 375                 380

Leu Val Met Ser Ile Trp Asp Asp His Ala Ser Asn Met Leu Trp Leu
385                 390                 395                 400

Asp Ser Thr Phe Pro Val Asp Ala Ala Gly Lys Pro Gly Ala Glu Arg
                405                 410                 415

Gly Ala Cys Pro Thr Thr Ser Gly Val Pro Ala Glu Val Glu Ala Glu
                420                 425                 430

Ala Pro Asn Ser Asn Val Val Phe Ser Asn Ile Arg Phe Gly Pro Ile
                435                 440                 445

Gly Ser Thr Val Ala Gly Leu Pro Gly Ala Gly Asn Gly Gly Asn Asn
                450                 455                 460

Gly Gly Asn Pro Pro Pro Thr Thr Thr Thr Ser Ser Ala Pro Ala
465                 470                 475                 480

Thr Thr Thr Thr Ala Ser Ala Gly Pro Lys Ala Gly Arg Trp Gln Gln
                485                 490                 495

Cys Gly Gly Ile Gly Phe Thr Gly Pro Thr Gln Cys Glu Glu Pro Tyr
                500                 505                 510

Ile Cys Thr Lys Leu Asn Asp Trp Tyr Ser Gln Cys Leu
                515                 520                 525

<210> SEQ ID NO 71

```
<211> LENGTH: 456
<212> TYPE: PRT
<213> ORGANISM: Artificial
<220> FEATURE:
<223> OTHER INFORMATION: Synthetic Thermoascus aurantiacus cbh

<400> SEQUENCE: 71

Met Tyr Gln Arg Ala Leu Leu Phe Ser Phe Leu Ala Ala Arg
1               5                   10                  15

Ala His Glu Ala Gly Thr Val Thr Ala Glu Asn His Pro Ser Leu Thr
                20                  25                  30

Trp Gln Gln Cys Ser Ser Gly Gly Ser Cys Thr Thr Gln Asn Gly Lys
            35                  40                  45

Val Val Ile Asp Ala Asn Trp Arg Trp Val His Thr Thr Ser Gly Tyr
        50                  55                  60

Thr Asn Cys Tyr Thr Gly Asn Thr Trp Asp Thr Ser Ile Cys Pro Asp
65                  70                  75                  80

Asp Val Thr Cys Ala Gln Asn Cys Ala Leu Asp Gly Ala Asp Tyr Ser
                85                  90                  95

Gly Thr Tyr Gly Val Thr Thr Ser Gly Asn Ala Leu Arg Leu Asn Phe
            100                 105                 110

Val Thr Gln Ser Ser Gly Lys Asn Ile Gly Ser Arg Leu Tyr Leu Leu
        115                 120                 125

Gln Asp Asp Thr Thr Tyr Gln Ile Phe Lys Leu Leu Gly Gln Glu Phe
130                 135                 140

Thr Phe Asp Val Asp Val Ser Asn Leu Pro Cys Gly Leu Asn Gly Ala
145                 150                 155                 160

Leu Tyr Phe Val Ala Met Asp Ala Asp Gly Asn Leu Ser Lys Tyr Pro
                165                 170                 175

Gly Asn Lys Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
        195                 200                 205

Trp Gln Pro Ser Ala Asn Asp Pro Asn Ala Gly Val Gly Asn His Gly
    210                 215                 220

Ser Ser Cys Ala Glu Met Asp Val Trp Glu Ala Asn Ser Ile Ser Thr
225                 230                 235                 240

Ala Val Thr Pro His Pro Cys Asp Thr Pro Gly Gln Thr Met Cys Gln
                245                 250                 255

Gly Asp Asp Cys Gly Gly Thr Tyr Ser Ser Thr Arg Tyr Ala Gly Thr
            260                 265                 270

Cys Asp Thr Asp Gly Cys Asp Phe Asn Pro Tyr Gln Pro Gly Asn His
        275                 280                 285

Ser Phe Tyr Gly Pro Gly Lys Ile Val Asp Thr Ser Ser Lys Phe Thr
    290                 295                 300

Val Val Thr Gln Phe Ile Thr Asp Gly Thr Pro Ser Gly Thr Leu
305                 310                 315                 320

Thr Glu Ile Lys Arg Phe Tyr Val Gln Asn Gly Lys Val Ile Pro Gln
                325                 330                 335

Ser Glu Ser Thr Ile Ser Gly Val Thr Gly Asn Ser Ile Thr Thr Glu
            340                 345                 350

Tyr Cys Thr Ala Gln Lys Ala Ala Phe Asp Asn Thr Gly Phe Phe Thr
        355                 360                 365

His Gly Gly Leu Gln Lys Ile Ser Gln Ala Leu Ala Gln Gly Met Val
    370                 375                 380
```

```
Leu Val Met Ser Leu Trp Asp Asp His Ala Ala Asn Met Leu Trp Leu
385                 390                 395                 400

Asp Ser Thr Tyr Pro Thr Asp Ala Asp Pro Asp Thr Pro Gly Val Ala
            405                 410                 415

Arg Gly Thr Cys Pro Thr Thr Ser Gly Val Pro Ala Asp Val Glu Ser
            420                 425                 430

Gln Asn Pro Asn Ser Tyr Val Ile Tyr Ser Asn Ile Lys Val Gly Pro
            435                 440                 445

Ile Asn Ser Thr Phe Thr Ala Asn
            450                 455

<210> SEQ ID NO 72
<211> LENGTH: 455
<212> TYPE: PRT
<213> ORGANISM: Artificial
<220> FEATURE:
<223> OTHER INFORMATION: Synthetic Talaromyces emersonii cbh

<400> SEQUENCE: 72

Met Leu Arg Arg Ala Leu Leu Leu Ser Ser Ala Ile Leu Ala Val
1               5                   10                  15

Lys Ala Gln Gln Ala Gly Thr Ala Thr Ala Glu Asn His Pro Pro Leu
                20                  25                  30

Thr Trp Gln Glu Cys Thr Ala Pro Gly Ser Cys Thr Thr Gln Asn Gly
            35                  40                  45

Ala Val Val Leu Asp Ala Asn Trp Arg Trp Val His Asp Val Asn Gly
        50                  55                  60

Tyr Thr Asn Cys Tyr Thr Gly Asn Thr Trp Asp Pro Thr Tyr Cys Pro
65                  70                  75                  80

Asp Asp Glu Thr Cys Ala Gln Asn Cys Ala Leu Asp Gly Ala Asp Tyr
                85                  90                  95

Glu Gly Thr Tyr Gly Val Thr Ser Ser Gly Ser Ser Leu Lys Leu Asn
            100                 105                 110

Phe Val Thr Gly Ser Asn Val Gly Ser Arg Leu Tyr Leu Leu Gln Asp
        115                 120                 125

Asp Ser Thr Tyr Gln Ile Phe Lys Leu Leu Asn Arg Glu Phe Ser Phe
130                 135                 140

Asp Val Asp Val Ser Asn Leu Pro Cys Gly Leu Asn Gly Ala Leu Tyr
145                 150                 155                 160

Phe Val Ala Met Asp Ala Asp Gly Gly Val Ser Lys Tyr Pro Asn Asn
                165                 170                 175

Lys Ala Gly Ala Lys Tyr Gly Thr Gly Tyr Cys Asp Ser Gln Cys Pro
            180                 185                 190

Arg Asp Leu Lys Phe Ile Asp Gly Glu Ala Asn Val Glu Gly Trp Gln
        195                 200                 205

Pro Ser Ser Asn Asn Ala Asn Thr Gly Ile Gly Asp His Gly Ser Cys
210                 215                 220

Cys Ala Glu Met Asp Val Trp Glu Ala Asn Ser Ile Ser Asn Ala Val
225                 230                 235                 240

Thr Pro His Pro Cys Asp Thr Pro Gly Gln Thr Met Cys Ser Gly Asp
                245                 250                 255

Asp Cys Gly Gly Thr Tyr Ser Asn Asp Arg Tyr Ala Gly Thr Cys Asp
            260                 265                 270

Pro Asp Gly Cys Asp Phe Asn Pro Tyr Arg Met Gly Asn Thr Ser Phe
        275                 280                 285

Tyr Gly Pro Gly Lys Ile Ile Asp Thr Thr Lys Pro Phe Thr Val Val
```

```
                290                 295                 300
Thr Gln Phe Leu Thr Asp Asp Gly Thr Asp Thr Gly Thr Leu Ser Glu
305                 310                 315                 320

Ile Lys Arg Phe Tyr Ile Gln Asn Ser Asn Val Ile Pro Gln Pro Asn
                325                 330                 335

Ser Asp Ile Ser Gly Val Thr Gly Asn Ser Ile Thr Thr Glu Phe Cys
                340                 345                 350

Thr Ala Gln Lys Gln Ala Phe Gly Asp Thr Asp Phe Ser Gln His
                355                 360                 365

Gly Gly Leu Ala Lys Met Gly Ala Ala Met Gln Gln Gly Met Val Leu
370                 375                 380

Val Met Ser Leu Trp Asp Asp Tyr Ala Ala Gln Met Leu Trp Leu Asp
385                 390                 395                 400

Ser Asp Tyr Pro Thr Asp Ala Asp Pro Thr Thr Pro Gly Ile Ala Arg
                405                 410                 415

Gly Thr Cys Pro Thr Asp Ser Gly Val Pro Ser Asp Val Glu Ser Gln
                420                 425                 430

Ser Pro Asn Ser Tyr Val Thr Tyr Ser Asn Ile Lys Phe Gly Pro Ile
                435                 440                 445

Asn Ser Thr Phe Thr Ala Ser
                450                 455

<210> SEQ ID NO 73
<211> LENGTH: 513
<212> TYPE: PRT
<213> ORGANISM: Artificial
<220> FEATURE:
<223> OTHER INFORMATION: Synthetic Trichoderma reesei cbh

<400> SEQUENCE: 73

Met Tyr Arg Lys Leu Ala Val Ile Ser Ala Phe Leu Ala Thr Ala Arg
1               5                   10                  15

Ala Gln Ser Ala Cys Thr Leu Gln Ser Glu Thr His Pro Pro Leu Thr
                20                  25                  30

Trp Gln Lys Cys Ser Ser Gly Gly Thr Cys Thr Gln Gln Thr Gly Ser
            35                  40                  45

Val Val Ile Asp Ala Asn Trp Arg Trp Thr His Ala Thr Asn Ser Ser
50                  55                  60

Thr Asn Cys Tyr Asp Gly Asn Thr Trp Ser Ser Thr Leu Cys Pro Asp
65                  70                  75                  80

Asn Glu Thr Cys Ala Lys Asn Cys Cys Leu Asp Gly Ala Ala Tyr Ala
                85                  90                  95

Ser Thr Tyr Gly Val Thr Thr Ser Gly Asn Ser Leu Ser Ile Gly Phe
                100                 105                 110

Val Thr Gln Ser Ala Gln Lys Asn Val Gly Ala Arg Leu Tyr Leu Met
            115                 120                 125

Ala Ser Asp Thr Thr Tyr Gln Glu Phe Thr Leu Leu Gly Asn Glu Phe
130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Ser Lys Tyr Pro
                165                 170                 175

Thr Asn Thr Ala Gly Ala Lys Tyr Gly Thr Gly Tyr Cys Asp Ser Gln
                180                 185                 190

Cys Pro Arg Asp Leu Lys Phe Ile Asn Gly Gln Ala Asn Val Glu Gly
            195                 200                 205
```

Trp Glu Pro Ser Ser Asn Asn Ala Asn Thr Gly Ile Gly Gly His Gly
    210                 215                 220

Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Glu
                245                 250                 255

Gly Asp Gly Cys Gly Gly Thr Tyr Ser Asp Asn Arg Tyr Gly Gly Thr
            260                 265                 270

Cys Asp Pro Asp Gly Cys Asp Trp Asn Pro Tyr Arg Leu Gly Asn Thr
        275                 280                 285

Ser Phe Tyr Gly Pro Gly Ser Ser Phe Thr Leu Asp Thr Lys Lys
    290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
                325                 330                 335

Ser Tyr Ser Gly Asn Glu Leu Asn Asp Asp Tyr Cys Thr Ala Glu Glu
            340                 345                 350

Ala Glu Phe Gly Gly Ser Ser Phe Ser Asp Lys Gly Gly Leu Thr Gln
        355                 360                 365

Phe Lys Lys Ala Thr Ser Gly Gly Met Val Leu Val Met Ser Leu Trp
    370                 375                 380

Asp Asp Tyr Tyr Ala Asn Met Leu Trp Leu Asp Ser Thr Tyr Pro Thr
385                 390                 395                 400

Asn Glu Thr Ser Ser Thr Pro Gly Ala Val Arg Gly Ser Cys Ser Thr
                405                 410                 415

Ser Ser Gly Val Pro Ala Gln Val Glu Ser Gln Ser Pro Asn Ala Lys
            420                 425                 430

Val Thr Phe Ser Asn Ile Lys Phe Gly Pro Ile Gly Ser Thr Gly Asn
        435                 440                 445

Pro Ser Gly Gly Asn Pro Pro Gly Gly Asn Arg Gly Thr Thr Thr Thr
    450                 455                 460

Arg Arg Pro Ala Thr Thr Thr Gly Ser Ser Pro Gly Pro Thr Gln Ser
465                 470                 475                 480

His Tyr Gly Gln Cys Gly Gly Ile Gly Tyr Ser Gly Pro Thr Val Cys
                485                 490                 495

Ala Ser Gly Thr Thr Cys Gln Val Leu Asn Pro Tyr Tyr Ser Gln Cys
            500                 505                 510

Leu

<210> SEQ ID NO 74
<211> LENGTH: 540
<212> TYPE: PRT
<213> ORGANISM: Artificial
<220> FEATURE:
<223> OTHER INFORMATION: Synthetic Phanerochaete chrysosporium cbh

<400> SEQUENCE: 74

Met Phe Arg Ala Ala Ala Leu Leu Ala Phe Thr Cys Leu Ala Met Val
1               5                   10                  15

Ser Gly Gln Gln Ala Gly Thr Asn Thr Ala Glu Asn His Pro Gln Leu
                20                  25                  30

Gln Ser Gln Gln Cys Thr Thr Ser Gly Gly Cys Lys Pro Leu Ser Thr
            35                  40                  45

Lys Val Val Leu Asp Ser Asn Trp Arg Trp Val His Ser Thr Ser Gly

```
                50               55                 60
Tyr Thr Asn Cys Tyr Thr Gly Asn Glu Trp Asp Thr Ser Leu Cys Pro
65                   70                  75                  80

Asp Gly Lys Thr Cys Ala Ala Asn Cys Ala Leu Asp Gly Ala Asp Tyr
                85                  90                  95

Ser Gly Thr Tyr Gly Ile Thr Ser Thr Gly Thr Ala Leu Thr Leu Lys
                100                 105                 110

Phe Val Thr Gly Ser Asn Val Gly Ser Arg Val Tyr Leu Met Ala Asp
                115                 120                 125

Asp Thr His Tyr Gln Leu Leu Lys Leu Leu Asn Gln Glu Phe Thr Phe
130                 135                 140

Asp Val Asp Met Ser Asn Leu Pro Cys Gly Leu Asn Gly Ala Leu Tyr
145                 150                 155                 160

Leu Ser Ala Met Asp Ala Asp Gly Gly Met Ser Lys Tyr Pro Gly Asn
                165                 170                 175

Lys Ala Gly Ala Lys Tyr Gly Thr Gly Tyr Cys Asp Ser Gln Cys Pro
                180                 185                 190

Lys Asp Ile Lys Phe Ile Asn Gly Glu Ala Asn Val Gly Asn Trp Thr
                195                 200                 205

Glu Thr Gly Ser Asn Thr Gly Thr Gly Ser Tyr Gly Thr Cys Cys Ser
210                 215                 220

Glu Met Asp Ile Trp Glu Ala Asn Asn Asp Ala Ala Ala Phe Thr Pro
225                 230                 235                 240

His Pro Cys Thr Thr Thr Gly Gln Thr Arg Cys Ser Gly Asp Asp Cys
                245                 250                 255

Ala Arg Asn Thr Gly Leu Cys Asp Gly Asp Gly Cys Asp Phe Asn Ser
                260                 265                 270

Phe Arg Met Gly Asp Lys Thr Phe Leu Gly Lys Gly Met Thr Val Asp
                275                 280                 285

Thr Ser Lys Pro Phe Thr Val Val Thr Gln Phe Leu Thr Asn Asp Asn
                290                 295                 300

Thr Ser Thr Gly Thr Leu Ser Glu Ile Arg Arg Ile Tyr Ile Gln Asn
305                 310                 315                 320

Gly Lys Val Ile Gln Asn Ser Val Ala Asn Ile Pro Gly Val Asp Pro
                325                 330                 335

Val Asn Ser Ile Thr Asp Asn Phe Cys Ala Gln Lys Thr Ala Phe
                340                 345                 350

Gly Asp Thr Asn Trp Phe Ala Gln Lys Gly Gly Leu Lys Gln Met Gly
                355                 360                 365

Glu Ala Leu Gly Asn Gly Met Val Leu Ala Leu Ser Ile Trp Asp Asp
370                 375                 380

His Ala Ala Asn Met Leu Trp Leu Asp Ser Asp Tyr Pro Thr Asp Lys
385                 390                 395                 400

Asp Pro Ser Ala Pro Gly Val Ala Arg Gly Thr Cys Ala Thr Thr Ser
                405                 410                 415

Gly Val Pro Ser Asp Val Glu Ser Gln Val Pro Asn Ser Gln Val Val
                420                 425                 430

Phe Ser Asn Ile Lys Phe Gly Asp Ile Gly Ser Thr Phe Ser Gly Thr
                435                 440                 445

Ser Ser Pro Asn Pro Gly Gly Ser Thr Thr Ser Ser Pro Val Thr
                450                 455                 460

Thr Ser Pro Thr Pro Pro Thr Gly Pro Thr Val Pro Gln Trp Gly
465                 470                 475                 480
```

```
Gln Cys Gly Gly Ile Gly Tyr Ser Gly Ser Thr Cys Ala Ser Pro
                485                 490                 495

Tyr Thr Cys His Val Leu Asn Pro Cys Glu Ser Ile Leu Ser Leu Gln
            500                 505                 510

Arg Ser Ser Asn Ala Asp Gln Tyr Leu Gln Thr Thr Arg Ser Ala Thr
            515                 520                 525

Lys Arg Arg Leu Asp Thr Ala Leu Gln Pro Arg Lys
            530                 535                 540

<210> SEQ ID NO 75
<211> LENGTH: 452
<212> TYPE: PRT
<213> ORGANISM: Artificial
<220> FEATURE:
<223> OTHER INFORMATION: Synthetic Aspergillus niger cbh

<400> SEQUENCE: 75

Met His Gln Arg Ala Leu Leu Phe Ser Ala Leu Leu Thr Ala Val Arg
1               5                   10                  15

Ala Gln Gln Ala Gly Thr Leu Thr Glu Glu Val His Pro Ser Leu Thr
                20                  25                  30

Trp Gln Lys Cys Thr Ser Glu Gly Ser Cys Thr Glu Gln Ser Gly Ser
            35                  40                  45

Val Val Ile Asp Ser Asn Trp Arg Trp Thr His Ser Val Asn Asp Ser
        50                  55                  60

Thr Asn Cys Tyr Thr Gly Asn Thr Trp Asp Ala Thr Leu Cys Pro Asp
65                  70                  75                  80

Asp Glu Thr Cys Ala Thr Asn Cys Ala Leu Asp Gly Ala Asp Tyr Glu
                85                  90                  95

Ser Thr Tyr Gly Val Thr Asp Gly Asp Ser Leu Thr Leu Lys Phe
                100                 105                 110

Val Thr Gly Ser Asn Val Gly Ser Arg Leu Tyr Leu Met Asp Thr Ser
            115                 120                 125

Asp Glu Gly Tyr Gln Thr Phe Asn Leu Leu Asp Ala Glu Phe Thr Phe
        130                 135                 140

Asp Val Asp Val Ser Asn Leu Pro Cys Gly Leu Asn Gly Ala Leu Tyr
145                 150                 155                 160

Phe Thr Ala Met Asp Ala Asp Gly Gly Ala Ser Lys Tyr Pro Ala Asn
                165                 170                 175

Lys Ala Gly Ala Lys Tyr Gly Thr Gly Tyr Cys Asp Ser Gln Cys Pro
            180                 185                 190

Arg Asp Leu Lys Phe Ile Asp Gly Gln Ala Asn Val Asp Gly Trp Glu
        195                 200                 205

Pro Ser Ser Asn Asn Asp Asn Thr Gly Ile Gly Asn His Gly Ser Cys
    210                 215                 220

Cys Pro Glu Met Asp Ile Trp Glu Ala Asn Lys Ile Ser Thr Ala Leu
225                 230                 235                 240

Thr Pro His Pro Cys Asp Ser Ser Glu Gln Thr Met Cys Glu Gly Asn
                245                 250                 255

Asp Cys Gly Gly Thr Tyr Ser Asp Asp Arg Tyr Gly Gly Thr Cys Asp
            260                 265                 270

Pro Asp Gly Cys Asp Phe Asn Pro Tyr Arg Met Gly Asn Asp Ser Phe
        275                 280                 285

Tyr Gly Pro Gly Lys Thr Ile Asp Thr Gly Ser Lys Met Thr Val Val
    290                 295                 300

Thr Gln Phe Ile Thr Asp Gly Ser Gly Ser Leu Ser Glu Ile Lys Arg
```

```
                    305                 310                 315                 320
Tyr Tyr Val Gln Asn Gly Asn Val Ile Ala Asn Ala Asp Ser Asn Ile
                325                 330                 335

Ser Gly Val Thr Gly Asn Ser Ile Thr Thr Asp Phe Cys Thr Ala Gln
                340                 345                 350

Lys Lys Ala Phe Gly Asp Asp Ile Phe Ala Glu His Asn Gly Leu
                355                 360                 365

Ala Gly Ile Ser Asp Ala Met Ser Ser Met Val Leu Ile Leu Ser Leu
            370                 375                 380

Trp Asp Asp Tyr Tyr Ala Ser Met Glu Trp Leu Asp Ser Asp Tyr Pro
385                 390                 395                 400

Glu Asn Ala Thr Ala Thr Asp Pro Gly Val Ala Arg Gly Thr Cys Asp
                405                 410                 415

Ser Glu Ser Gly Val Pro Ala Thr Val Glu Gly Ala His Pro Asp Ser
                420                 425                 430

Ser Val Thr Phe Ser Asn Ile Lys Phe Gly Pro Ile Asn Ser Thr Phe
                435                 440                 445

Ser Ala Ser Ala
            450

<210> SEQ ID NO 76
<211> LENGTH: 536
<212> TYPE: PRT
<213> ORGANISM: Artificial
<220> FEATURE:
<223> OTHER INFORMATION: Synthetic Aspergillus niger cbh

<400> SEQUENCE: 76

Met Ser Ser Phe Gln Val Tyr Arg Ala Ala Leu Leu Leu Ser Ile Leu
1               5                   10                  15

Ala Thr Ala Asn Ala Gln Gln Val Gly Thr Tyr Thr Thr Glu Thr His
                20                  25                  30

Pro Ser Leu Thr Trp Gln Thr Cys Thr Ser Asp Gly Ser Cys Thr Thr
            35                  40                  45

Asn Asp Gly Glu Val Val Ile Asp Ala Asn Trp Arg Trp Val His Ser
        50                  55                  60

Thr Ser Ser Ala Thr Asn Cys Tyr Thr Gly Asn Glu Trp Asp Thr Ser
65                  70                  75                  80

Ile Cys Thr Asp Asp Val Thr Cys Ala Ala Asn Cys Ala Leu Asp Gly
                85                  90                  95

Ala Thr Tyr Glu Ala Thr Tyr Gly Val Thr Thr Ser Gly Ser Glu Leu
                100                 105                 110

Arg Leu Asn Phe Val Thr Gln Gly Ser Ser Lys Asn Ile Gly Ser Arg
            115                 120                 125

Leu Tyr Leu Met Ser Asp Asp Ser Asn Tyr Glu Leu Phe Lys Leu Leu
        130                 135                 140

Gly Gln Glu Phe Thr Phe Asp Val Asp Val Ser Asn Leu Pro Cys Gly
145                 150                 155                 160

Leu Asn Gly Ala Leu Tyr Phe Val Ala Met Asp Ala Asp Gly Gly Thr
                165                 170                 175

Ser Glu Tyr Ser Gly Asn Lys Ala Gly Ala Lys Tyr Gly Thr Gly Tyr
                180                 185                 190

Cys Asp Ser Gln Cys Pro Arg Asp Leu Lys Phe Ile Asn Gly Glu Ala
            195                 200                 205

Asn Cys Asp Gly Trp Glu Pro Ser Ser Asn Asn Val Asn Thr Gly Val
        210                 215                 220
```

```
Gly Asp His Gly Ser Cys Cys Ala Glu Met Asp Val Trp Glu Ala Asn
225                 230                 235                 240

Ser Ile Ser Asn Ala Phe Thr Ala His Pro Cys Asp Ser Val Ser Gln
                245                 250                 255

Thr Met Cys Asp Gly Asp Ser Cys Gly Gly Thr Tyr Ser Ala Ser Gly
            260                 265                 270

Asp Arg Tyr Ser Gly Thr Cys Asp Pro Asp Gly Cys Asp Tyr Asn Pro
        275                 280                 285

Tyr Arg Leu Gly Asn Thr Asp Phe Tyr Gly Pro Gly Leu Thr Val Asp
290                 295                 300

Thr Asn Ser Pro Phe Thr Val Val Thr Gln Phe Ile Thr Asp Asp Gly
305                 310                 315                 320

Thr Ser Ser Gly Thr Leu Thr Glu Ile Lys Arg Leu Tyr Val Gln Asn
                325                 330                 335

Gly Glu Val Ile Ala Asn Gly Ala Ser Thr Tyr Ser Ser Val Asn Gly
            340                 345                 350

Ser Ser Ile Thr Ser Ala Phe Cys Glu Ser Glu Lys Thr Leu Phe Gly
        355                 360                 365

Asp Glu Asn Val Phe Asp Lys His Gly Gly Leu Gly Met Gly Glu
370                 375                 380

Ala Met Ala Lys Gly Met Val Leu Val Leu Ser Leu Trp Asp Asp Tyr
385                 390                 395                 400

Ala Ala Asp Met Leu Trp Leu Asp Ser Asp Tyr Pro Val Asn Ser Ser
                405                 410                 415

Ala Ser Thr Pro Gly Val Ala Arg Gly Thr Cys Ser Thr Asp Ser Gly
            420                 425                 430

Val Pro Ala Thr Val Glu Ala Glu Ser Pro Asn Ala Tyr Val Thr Tyr
        435                 440                 445

Ser Asn Ile Lys Phe Gly Pro Ile Gly Ser Thr Tyr Ser Ser Gly Ser
450                 455                 460

Ser Ser Gly Ser Gly Ser Ser Ser Ser Ser Ser Thr Thr Thr Lys
465                 470                 475                 480

Ala Thr Ser Thr Thr Leu Lys Thr Thr Ser Thr Thr Ser Ser Gly Ser
                485                 490                 495

Ser Ser Thr Ser Ala Ala Gln Ala Tyr Gly Gln Cys Gly Gly Gln Gly
            500                 505                 510

Trp Thr Gly Pro Thr Thr Cys Val Ser Gly Tyr Thr Cys Thr Tyr Glu
        515                 520                 525

Asn Ala Tyr Tyr Ser Gln Cys Leu
530                 535

<210> SEQ ID NO 77
<211> LENGTH: 516
<212> TYPE: PRT
<213> ORGANISM: Botryotinia fuckeliana

<400> SEQUENCE: 77

Met Ile Ser Lys Val Leu Ala Phe Thr Ser Leu Leu Ala Ala Ala Arg
1               5                   10                  15

Ala Gln Gln Ala Gly Thr Leu Thr Thr Glu Thr His Pro Pro Leu Ser
                20                  25                  30

Val Ser Gln Cys Thr Ala Ser Gly Cys Thr Thr Ser Ala Gln Ser Ile
            35                  40                  45

Val Val Asp Ala Asn Trp Arg Trp Leu His Ser Thr Thr Gly Ser Thr
        50                  55                  60
```

```
Asn Cys Tyr Thr Gly Asn Thr Trp Asp Lys Thr Leu Cys Pro Asp Gly
 65                  70                  75                  80

Ala Thr Cys Ala Ala Asn Cys Ala Leu Asp Gly Ala Asp Tyr Ser Gly
                 85                  90                  95

Val Tyr Gly Ile Thr Thr Ser Gly Asn Ser Ile Lys Leu Asn Phe Val
            100                 105                 110

Thr Lys Gly Ala Asn Thr Asn Val Gly Ser Arg Thr Tyr Leu Met Ala
            115                 120                 125

Ala Gly Ser Thr Thr Gln Tyr Gln Met Leu Lys Leu Leu Asn Gln Glu
        130                 135                 140

Phe Thr Phe Asp Val Asp Val Ser Asn Leu Pro Cys Gly Leu Asn Gly
145                 150                 155                 160

Ala Leu Tyr Phe Ala Ala Met Asp Ala Asp Gly Gly Leu Ser Arg Phe
                165                 170                 175

Pro Thr Asn Lys Ala Gly Ala Lys Tyr Gly Thr Gly Tyr Cys Asp Ala
            180                 185                 190

Gln Cys Pro Gln Asp Ile Lys Phe Ile Asn Gly Val Ala Asn Ser Val
            195                 200                 205

Gly Trp Thr Pro Ser Ser Asn Asp Val Asn Ala Gly Ala Gly Gln Tyr
        210                 215                 220

Gly Ser Cys Cys Ser Glu Met Asp Ile Trp Glu Ala Asn Lys Ile Ser
225                 230                 235                 240

Ala Ala Tyr Thr Pro His Pro Cys Ser Val Asp Thr Gln Thr Arg Cys
                245                 250                 255

Thr Gly Thr Asp Cys Gly Ile Gly Ala Arg Tyr Ser Ser Leu Cys Asp
            260                 265                 270

Ala Asp Gly Cys Asp Phe Asn Ser Tyr Arg Gln Gly Asn Thr Ser Phe
            275                 280                 285

Tyr Gly Ala Gly Leu Thr Val Asn Thr Asn Lys Val Phe Thr Val Val
        290                 295                 300

Thr Gln Phe Ile Thr Asn Asp Gly Thr Ala Ser Gly Thr Leu Lys Glu
305                 310                 315                 320

Ile Arg Arg Phe Tyr Val Gln Asn Gly Val Val Ile Pro Asn Ser Gln
                325                 330                 335

Ser Thr Ile Ala Gly Val Pro Gly Asn Ser Ile Thr Asp Ser Phe Cys
            340                 345                 350

Ala Ala Gln Lys Thr Ala Phe Gly Asp Thr Asn Glu Phe Ala Thr Lys
            355                 360                 365

Gly Gly Leu Ala Thr Met Ser Lys Ala Leu Ala Lys Gly Met Val Leu
        370                 375                 380

Val Met Ser Ile Trp Asp Asp His Thr Ala Asn Met Leu Trp Leu Asp
385                 390                 395                 400

Ala Pro Tyr Pro Ala Thr Lys Ser Pro Ser Ala Pro Gly Val Thr Arg
                405                 410                 415

Gly Ser Cys Ser Ala Thr Ser Gly Asn Pro Val Asp Val Glu Ala Asn
            420                 425                 430

Ser Pro Gly Ser Ser Val Thr Phe Ser Asn Ile Lys Trp Gly Pro Ile
            435                 440                 445

Asn Ser Thr Tyr Thr Gly Ser Gly Ala Ala Pro Ser Val Pro Gly Thr
        450                 455                 460

Thr Thr Val Ser Ser Ala Pro Ala Ser Thr Ala Thr Ser Gly Ala Gly
465                 470                 475                 480

Gly Val Ala Lys Tyr Ala Gln Cys Gly Gly Ser Gly Tyr Ser Gly Ala
```

```
                        485                 490                 495
Thr Ala Cys Val Ser Gly Ser Thr Cys Val Ala Leu Asn Pro Tyr Tyr
                    500                 505                 510
Ser Gln Cys Gln
        515

<210> SEQ ID NO 78
<211> LENGTH: 448
<212> TYPE: PRT
<213> ORGANISM: Coptotermes formosanus

<400> SEQUENCE: 78

Met Arg Val Phe Val Cys Leu Leu Ser Ala Leu Ala Leu Cys Gln Ala
1               5                   10                  15

Ala Tyr Asp Tyr Lys Thr Val Leu Lys Asn Ser Leu Leu Phe Tyr Glu
            20                  25                  30

Ala Gln Arg Ser Gly Lys Leu Pro Ala Asp Gln Lys Val Thr Trp Arg
        35                  40                  45

Lys Asp Ser Ala Leu Asn Asp Lys Gly Gln Lys Gly Glu Asp Leu Thr
    50                  55                  60

Gly Gly Tyr Tyr Asp Ala Gly Asp Phe Val Lys Phe Gly Phe Pro Met
65                  70                  75                  80

Ala Tyr Thr Val Thr Val Leu Ala Trp Gly Leu Val Asp Tyr Glu Ser
                85                  90                  95

Ala Tyr Ser Thr Ala Gly Ala Leu Asp Asp Gly Arg Lys Ala Leu Lys
            100                 105                 110

Trp Gly Thr Asp Tyr Phe Leu Lys Ala His Thr Ala Ala Asn Glu Phe
        115                 120                 125

Tyr Gly Gln Val Gly Gln Gly Asp Val Asp His Ala Tyr Trp Gly Arg
    130                 135                 140

Pro Glu Asp Met Thr Met Ser Arg Pro Ala Tyr Lys Ile Asp Thr Ser
145                 150                 155                 160

Lys Pro Gly Ser Asp Leu Ala Ala Glu Thr Ala Ala Ala Leu Ala Ala
                165                 170                 175

Thr Ala Ile Ala Tyr Lys Ser Ala Asp Ser Thr Tyr Ser Asn Asn Leu
            180                 185                 190

Ile Thr His Ala Lys Gln Leu Phe Asp Phe Ala Asn Asn Tyr Arg Gly
        195                 200                 205

Lys Tyr Ser Asp Ser Ile Thr Asp Ala Lys Asn Phe Tyr Ala Ser Gly
    210                 215                 220

Asp Tyr Lys Asp Glu Leu Val Trp Ala Ala Trp Leu Tyr Arg Ala
225                 230                 235                 240

Thr Asn Asp Asn Thr Tyr Leu Thr Lys Ala Glu Ser Leu Tyr Asn Glu
                245                 250                 255

Phe Gly Leu Gly Ser Trp Asn Gly Ala Phe Asn Trp Asp Asn Lys Ile
            260                 265                 270

Ser Gly Val Gln Val Leu Leu Ala Lys Leu Thr Ser Lys Gln Ala Tyr
        275                 280                 285

Lys Asp Lys Val Gln Gly Tyr Val Asp Tyr Leu Val Ser Ser Gln Lys
    290                 295                 300

Lys Thr Pro Lys Gly Leu Val Tyr Ile Asp Gln Trp Gly Thr Leu Arg
305                 310                 315                 320

His Ala Ala Asn Ser Ala Leu Ile Ala Leu Gln Ala Ala Asp Leu Gly
                325                 330                 335

Ile Asn Ala Ala Ser Tyr Arg Gln Tyr Ala Lys Lys Gln Ile Asp Tyr
```

```
                    340             345             350
Ala Leu Gly Asp Gly Gly Arg Ser Tyr Val Val Gly Phe Gly Thr Asn
        355                 360                 365

Pro Pro Val Arg Pro His His Arg Ser Ser Cys Pro Asp Ala Pro
    370                 375                 380

Ala Ala Cys Asp Trp Asn Thr Tyr Asn Ser Ala Gly Pro Asn Ala His
385                 390                 395                 400

Val Leu Thr Gly Ala Leu Val Gly Gly Pro Asp Ser Asn Asp Ser Tyr
                405                 410                 415

Thr Asp Ser Arg Ser Asp Tyr Ile Ser Asn Glu Val Ala Thr Asp Tyr
                420                 425                 430

Asn Ala Gly Phe Gln Ser Ala Val Ala Gly Leu Leu Lys Ala Gly Val
        435                 440                 445

<210> SEQ ID NO 79
<211> LENGTH: 21
<212> TYPE: DNA
<213> ORGANISM: Artificial
<220> FEATURE:
<223> OTHER INFORMATION: Synthetic primer

<400> SEQUENCE: 79
gaaatggata tytgggargc c                                       21

<210> SEQ ID NO 80
<211> LENGTH: 21
<212> TYPE: DNA
<213> ORGANISM: Artificial
<220> FEATURE:
<223> OTHER INFORMATION: Synthetic primer

<400> SEQUENCE: 80
ggcytcccar atatccattt c                                       21

<210> SEQ ID NO 81
<211> LENGTH: 21
<212> TYPE: DNA
<213> ORGANISM: Artificial
<220> FEATURE:
<223> OTHER INFORMATION: Synthetic primer

<400> SEQUENCE: 81
gagatggaya tctgggaggc k                                       21

<210> SEQ ID NO 82
<211> LENGTH: 21
<212> TYPE: DNA
<213> ORGANISM: Artificial
<220> FEATURE:
<223> OTHER INFORMATION: Synthetic primer

<400> SEQUENCE: 82
mgcctcccag atrtccatct c                                       21

<210> SEQ ID NO 83
<211> LENGTH: 508
<212> TYPE: PRT
<213> ORGANISM: Artificial
<220> FEATURE:
<223> OTHER INFORMATION: Synthetic Nectria haematococca cbh

<400> SEQUENCE: 83

Met Tyr Arg Ala Ile Ala Thr Ala Ser Ala Leu Leu Ala Thr Ala Arg
1               5                   10                  15
```

```
Ala Gln Gln Val Cys Thr Leu Asn Thr Glu Asn Lys Pro Ala Leu Thr
            20                  25                  30

Trp Ala Lys Cys Thr Ser Ser Gly Cys Ser Asn Val Arg Gly Ser Val
        35                  40                  45

Val Val Asp Ala Asn Trp Arg Trp Ala His Ser Thr Ser Ser Ser Thr
 50                  55                  60

Asn Cys Tyr Thr Gly Asn Thr Trp Asp Lys Thr Leu Cys Pro Asp Gly
 65                  70                  75                  80

Lys Thr Cys Ala Asp Lys Cys Cys Leu Asp Gly Ala Asp Tyr Ser Gly
                85                  90                  95

Thr Tyr Gly Val Thr Ser Ser Gly Asn Gln Leu Asn Leu Lys Phe Val
            100                 105                 110

Thr Val Gly Pro Tyr Ser Thr Asn Val Gly Ser Arg Leu Tyr Leu Met
            115                 120                 125

Glu Asp Glu Asn Asn Tyr Gln Met Phe Asp Leu Leu Gly Asn Glu Phe
130                 135                 140

Thr Phe Asp Val Asp Val Asn Asn Ile Gly Cys Gly Leu Asn Gly Ala
145                 150                 155                 160

Leu Tyr Phe Val Ser Met Asp Lys Asp Gly Lys Ser Arg Phe Ser
                165                 170                 175

Thr Asn Lys Ala Gly Ala Lys Tyr Gly Thr Gly Tyr Cys Asp Ala Gln
                180                 185                 190

Cys Pro Arg Asp Val Lys Phe Ile Asn Gly Val Ala Asn Ser Asp Glu
            195                 200                 205

Trp Lys Pro Ser Asp Ser Asp Lys Asn Ala Gly Val Gly Lys Tyr Gly
            210                 215                 220

Thr Cys Cys Pro Glu Met Asp Ile Trp Glu Ala Asn Lys Ile Ser Thr
225                 230                 235                 240

Ala Tyr Thr Pro His Pro Cys Lys Ser Leu Thr Gln Gln Ser Cys Glu
                245                 250                 255

Gly Asp Ala Cys Gly Gly Thr Tyr Ser Ala Thr Arg Tyr Ala Gly Thr
                260                 265                 270

Cys Asp Pro Asp Gly Cys Asp Phe Asn Pro Tyr Arg Gln Gly Asn Lys
            275                 280                 285

Thr Phe Tyr Gly Pro Gly Ser Gly Phe Asn Val Asp Thr Thr Lys Lys
            290                 295                 300

Val Thr Val Val Thr Gln Phe Ile Lys Gly Ser Asp Gly Lys Leu Ser
305                 310                 315                 320

Glu Ile Lys Arg Leu Tyr Val Gln Asn Gly Lys Val Ile Gly Asn Pro
                325                 330                 335

Gln Ser Glu Ile Ala Asn Asn Pro Gly Ser Ser Val Thr Asp Ser Phe
            340                 345                 350

Cys Lys Ala Gln Lys Val Ala Phe Asn Asp Pro Asp Phe Asn Lys
            355                 360                 365

Lys Gly Gly Trp Ser Gly Met Ser Asp Ala Leu Ala Lys Pro Met Val
            370                 375                 380

Leu Val Met Ser Leu Trp His Asp His Tyr Ala Asn Met Leu Trp Leu
385                 390                 395                 400

Asp Ser Thr Tyr Pro Lys Gly Ser Lys Thr Pro Gly Ser Ala Arg Gly
                405                 410                 415

Ser Cys Pro Glu Asp Ser Gly Asp Pro Asp Thr Leu Glu Lys Glu Val
            420                 425                 430

Pro Asn Ser Gly Val Ser Phe Ser Asn Ile Lys Phe Gly Pro Ile Gly
```

```
                435                 440                 445
Ser Thr Tyr Thr Gly Thr Gly Gly Ser Asn Pro Asp Pro Glu Glu Pro
    450                 455                 460

Glu Glu Pro Glu Glu Pro Val Gly Thr Val Pro Gln Tyr Gln Cys
465                 470                 475                 480

Gly Gly Ile Asn Tyr Ser Gly Pro Thr Ala Cys Val Ser Pro Tyr Lys
                485                 490                 495

Cys Asn Lys Ile Asn Asp Phe Tyr Ser Gln Cys Gln
            500                 505

<210> SEQ ID NO 84
<211> LENGTH: 25
<212> TYPE: DNA
<213> ORGANISM: Artificial
<220> FEATURE:
<223> OTHER INFORMATION: Synthetic Schizochytrium aggregatrum cbh1
      primer

<400> SEQUENCE: 84
cggaacagga tattgtgatg ctcag                                         25

<210> SEQ ID NO 85
<211> LENGTH: 8
<212> TYPE: PRT
<213> ORGANISM: Artificial
<220> FEATURE:
<223> OTHER INFORMATION: Synthetic Schizochytrium aggregatrum cbh1
      primer

<400> SEQUENCE: 85

Gly Thr Gly Tyr Cys Asp Ala Gln
1               5

<210> SEQ ID NO 86
<211> LENGTH: 25
<212> TYPE: DNA
<213> ORGANISM: Artificial
<220> FEATURE:
<223> OTHER INFORMATION: Synthetic Schizochytrium aggregatrum cbh1
      primer

<400> SEQUENCE: 86
ctgagcatca caatatcctg ttccg                                         25

<210> SEQ ID NO 87
<211> LENGTH: 8
<212> TYPE: PRT
<213> ORGANISM: Artificial
<220> FEATURE:
<223> OTHER INFORMATION: Synthetic Schizochytrium aggregatrum cbh1
      primer

<400> SEQUENCE: 87

Gly Thr Gly Tyr Cys Asp Ala Gln
1               5

<210> SEQ ID NO 88
<211> LENGTH: 27
<212> TYPE: DNA
<213> ORGANISM: Artificial
<220> FEATURE:
<223> OTHER INFORMATION: Synthetic Schizochytrium aggregatrum cbh1
      primer

<400> SEQUENCE: 88
tgcaacgaga tggacatttg ggaagcg                                       27
```

```
<210> SEQ ID NO 89
<211> LENGTH: 9
<212> TYPE: PRT
<213> ORGANISM: Artificial
<220> FEATURE:
<223> OTHER INFORMATION: Synthetic Schizochytrium aggregatrum cbh1
      primer

<400> SEQUENCE: 89

Cys Asn Glu Met Asp Ile Trp Glu Ala
1               5

<210> SEQ ID NO 90
<211> LENGTH: 27
<212> TYPE: DNA
<213> ORGANISM: Artificial
<220> FEATURE:
<223> OTHER INFORMATION: Synthetic Schizochytrium aggregatrum cbh1
      primer

<400> SEQUENCE: 90
cgcttcccaa atgtccatct cgttgca                                            27

<210> SEQ ID NO 91
<211> LENGTH: 9
<212> TYPE: PRT
<213> ORGANISM: Artificial
<220> FEATURE:
<223> OTHER INFORMATION: Synthetic Schizochytrium aggregatrum cbh1
      primer

<400> SEQUENCE: 91

Cys Asn Glu Met Asp Ile Trp Glu Ala
1               5

<210> SEQ ID NO 92
<211> LENGTH: 22
<212> TYPE: DNA
<213> ORGANISM: Artificial
<220> FEATURE:
<223> OTHER INFORMATION: Synthetic Schizochytrium aggregatrum cbh1
      primer

<400> SEQUENCE: 92
atgtctgcca ttaccctcgc cc                                                 22

<210> SEQ ID NO 93
<211> LENGTH: 24
<212> TYPE: DNA
<213> ORGANISM: Artificial
<220> FEATURE:
<223> OTHER INFORMATION: Synthetic Schizochytrium aggregatrum cbh1
      primer

<400> SEQUENCE: 93
ctacaagcac tgcgagtagt agtc                                               24
```